(12) United States Patent
Veiby et al.

(10) Patent No.: US 8,323,906 B2
(45) Date of Patent: Dec. 4, 2012

(54) COMPOSITIONS, KITS, AND METHODS FOR IDENTIFICATION, ASSESSMENT, PREVENTION AND THERAPY OF BREAST AND OVARIAN CANCER

(75) Inventors: Ole Petter Veiby, Westborough, MA (US); Robert C. Bast, Jr., Houston, TX (US); Gordon B. Mills, Houston, TX (US); Gabriel N. Hortobagyi, Bellaire, TX (US)

(73) Assignees: Millennium Pharmaceuticals, Inc., Cambridge, MA (US); Board of Regents, The University of Texas System, Austin, TX (US)

( * ) Notice: Subject to any disclaimer, the term of this patent is extended or adjusted under 35 U.S.C. 154(b) by 302 days.

(21) Appl. No.: 12/317,003

(22) Filed: Dec. 17, 2008

(65) Prior Publication Data

US 2010/0003682 A1    Jan. 7, 2010

Related U.S. Application Data

(63) Continuation of application No. 11/080,991, filed on Mar. 11, 2005, now Pat. No. 7,494,775, which is a continuation of application No. 10/176,847, filed on Jun. 21, 2002, now abandoned.

(60) Provisional application No. 60/300,159, filed on Jun. 21, 2001, provisional application No. 60/301,351, filed on Jun. 27, 2001.

(51) Int. Cl.
*G01N 33/53* (2006.01)
*G01N 33/574* (2006.01)
*C12Q 1/68* (2006.01)

(52) U.S. Cl. ............................ 435/7.1; 435/6; 435/7.23

(58) Field of Classification Search ......................... None
See application file for complete search history.

(56) References Cited

U.S. PATENT DOCUMENTS

| 6,762,020 B1 * | 7/2004 | Mack et al. | 435/6.16 |
| 7,285,382 B2 * | 10/2007 | de Sauvage et al. | 435/5 |
| 2003/0064385 A1 * | 4/2003 | Dressman et al. | 435/6 |
| 2003/0166047 A1 | 9/2003 | Gu | |

FOREIGN PATENT DOCUMENTS

| EP | 1002862 A1 | 5/2000 |
| WO | WO-00/12139 A1 | 3/2000 |
| WO | WO 01/55178 A2 * | 8/2001 |

OTHER PUBLICATIONS

NCBI GenBank: AAA96258.2, printed Jul. 26, 2011.*
NCBI GenBank:AAA96258.1, printed Jul. 30, 2011.*
Taylor et al (IUBMB Life, 2000, 49:249-253).*
Knowlden et al (Clinical Cancer Research, 1997, 3:2165-2172).*
Manning et al (Acta Oncologica, 1995, 34:641-646).*
Tockman et al (Cancer Res., 1992, 52:2711s-2718s).*
Hsu, Sheau Yu et al., "The Three Subfamilies of Leucine-Rich Repeat-Containing G Protein-Coupled Receptors (LGR): Identification of LGR6 and LGR7 and the Signaling Mechanism for LGR7," *Molecular Endocrinology*, vol. 14(8):1257-1271 (2000).
Wolman, Sandra R. et al., "Genetic Markers as Prognostic Indicators in Breast Cancer," *Cancer*, vol. 70:1765 1774 (1992).
European Search Report for Application No. 02759097.5-2405, dated Sep. 30, 2005.
International Search Report for Application No. PCT/US02/19773, dated Dec. 30, 2002.
GenBank Accession No. AAA96258.

* cited by examiner

*Primary Examiner* — Laura B Goddard
(74) *Attorney, Agent, or Firm* — McCarter & English, LLP; Maria Laccotripe Zacharakis; Deborah L. Nagle

(57) ABSTRACT

The invention relates to newly discovered nucleic acid molecules and proteins associated with breast or ovarian cancer. Compositions, kits, and methods for detecting, characterizing, preventing, and treating human breast or ovarian cancers are provided.

14 Claims, No Drawings

COMPOSITIONS, KITS, AND METHODS FOR IDENTIFICATION, ASSESSMENT, PREVENTION AND THERAPY OF BREAST AND OVARIAN CANCER

RELATED APPLICATIONS

The present application is a continuation application of U.S. utility application Ser. No. 11/080,991, filed on Mar. 11, 2005; which is a continuation application of U.S. utility application Ser. No. 10/176,847, filed on Jun. 21, 2002; which claims priority from U.S. provisional patent application Ser. No. 60/300,159, filed on Jun. 21, 2001, which was abandoned on Jun. 25, 2001; and which claims priority from U.S. provisional patent application Ser. No. 60/301,351, filed on Jun. 27, 2001. The entire contents of each of the foregoing applications are expressly incorporated by reference.

FIELD OF THE INVENTION

The field of the invention is cancer, particularly breast and ovarian cancers, including diagnosis, characterization, management, and therapy of breast and ovarian cancers.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. In order to be most effective, these treatments require not only an early detection of the malignancy, but a reliable assessment of the severity of the malignancy.

The incidence of breast cancer, a leading cause of death in women, has been gradually increasing in the United States over the last thirty years. In 1997, it was estimated that 181,000 new cases were reported in the U.S., and that 44,000 people would die of breast cancer (Parker et al, 1997, *CA Cancer J. Clin.* 47:5-27; Chu et al, 1996, *J. Nat. Cancer Inst.* 88:1571-1579). While the pathogenesis of breast cancer is unclear, transformation of normal breast epithelium to a malignant phenotype may be the result of genetic factors, especially in women under 30 (Miki et al., 1994, *Science*, 266:66-71). The discovery and characterization of BRCA1 and BRCA2 has recently expanded our knowledge of genetic factors which can contribute to familial breast cancer. Germline mutations within these two loci are associated with a 50 to 85% lifetime risk of breast and/or ovarian cancer (Casey, 1997, *Curr. Opin. Oncol.* 9:88-93; Marcus et al, 1996, *Cancer* 77:697-709). However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods (Jatoi, 1999, *Am. J. Surg.* 177:518-524). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

Ovarian cancer is also responsible for significant morbidity and mortality in populations around the world. Ovarian cancer is classified, on the basis of clinical and pathological features, in three groups, namely epithelial ovarian cancer (EOC; >90% of ovarian cancer in Western countries), germ cell tumors (circa 2-3% of ovarian cancer), and stromal ovarian cancer (circa 5% of ovarian cancer; Ozols et al., 1997, *Cancer Principles and Practice of Oncology*, 5th ed., DeVita et al., Eds. pp. 1502). Relative to EOC, germ cell tumors and stromal ovarian cancers are more easily detected and treated at an early stage, translating into higher/better survival rates for patients afflicted with these two types of ovarian cancer.

There are numerous types of ovarian tumors, some of which are benign, and others of which are malignant. Treatment (including non-treatment) options and predictions of patient outcome depend on accurate classification of the ovarian cancer. Ovarian cancers are named according to the type of cells from which the cancer is derived and whether the ovarian cancer is benign or malignant. Recognized histological tumor types include, for example, serous, mucinous, endometrioid, and clear cell tumors. In addition, ovarian cancers are classified according to recognized grade and stage scales.

In grade I, the tumor tissue is well differentiated from normal ovarian tissue. In grade II, tumor tissue is moderately well differentiated. In grade III, the tumor tissue is poorly differentiated from normal tissue, and this grade correlates with a less favorable prognosis than grades I and II. Stage I is generally confined within the capsule surrounding one (stage IA) or both (stage IB) ovaries, although in some stage I (i.e. stage IC) cancers, malignant cells may be detected in ascites, in peritoneal rinse fluid, or on the surface of the ovaries. Stage II involves extension or metastasis of the tumor from one or both ovaries to other pelvic structures. In stage IIA, the tumor extends or has metastasized to the uterus, the fallopian tubes, or both. Stage IIB involves extension of the tumor to the pelvis. Stage IIC is stage IIA or IIB in which malignant cells may be detected in ascites, in peritoneal rinse fluid, or on the surface of the ovaries. In stage III, the tumor comprises at least one malignant extension to the small bowel or the omentum, has formed extrapelvic peritoneal implants of microscopic (stage IIIA) or macroscopic (<2 centimeter diameter, stage IIIB; >2 centimeter diameter, stage IIIC) size, or has metastasized to a retroperitoneal or inguinal lymph node (an alternate indicator of stage IIIC). In stage IV, distant (i.e. non-peritoneal) metastases of the tumor can be detected.

The durations of the various stages of ovarian cancer are not presently known, but are believed to be at least about a year each (Richart et al., 1969, *Am. J. Obstet. Gynecol.* 105: 386). Prognosis declines with increasing stage designation. For example, 5-year survival rates for patients diagnosed with stage I, II, III, and IV ovarian cancer are 80%, 57%, 25%, and 8%, respectively.

Despite being the third most prevalent gynecological cancer, ovarian cancer is the leading cause of death among those afflicted with gynecological cancers. The disproportionate mortality of ovarian cancer is attributable to a substantial absence of symptoms among those afflicted with early-stage ovarian cancer and to difficulty diagnosing ovarian cancer at an early stage. Patients afflicted with ovarian cancer most often present with non-specific complaints, such as abnormal vaginal bleeding, gastrointestinal symptoms, urinary tract symptoms, lower abdominal pain, and generalized abdominal distension. These patients rarely present with paraneoplastic symptoms or with symptoms which clearly indicate their affliction. Presently, less than about 40% of patients afflicted with ovarian cancer present with stage I or stage II. Management of ovarian cancer would be significantly enhanced if the disease could be detected at an earlier stage, when treatments are much more generally efficacious.

Ovarian cancer may be diagnosed, in part, by collecting a routine medical history from a patient and by performing physical examination, x-ray examination, and chemical and hematological studies on the patient. Hematological tests which may be indicative of ovarian cancer in a patient include analyses of serum levels of proteins designated CA125 and DF3 and plasma levels of lysophosphatidic acid (LPA). Palpation of the ovaries and ultrasound techniques (particularly including endovaginal ultrasound and color Doppler flow ultrasound techniques) can aid detection of ovarian tumors and differentiation of ovarian cancer from benign ovarian cysts. However, a definitive diagnosis of ovarian cancer typically requires performing exploratory laparotomy of the patient.

Potential tests for the detection of ovarian cancer (e.g., screening, reflex or monitoring) may be characterized by a number of factors. The "sensitivity" of an assay refers to the probability that the test will yield a positive result in an individual afflicted with ovarian cancer. The "specificity" of an assay refers to the probability that the test will yield a negative result in an individual not afflicted with ovarian cancer. The "positive predictive value" (PPV) of an assay is the ratio of true positive results (i.e. positive assay results for patients afflicted with ovarian cancer) to all positive results (i.e. positive assay results for patients afflicted with ovarian cancer+positive assay results for patients not afflicted with ovarian cancer). It has been estimated that in order for an assay to be an appropriate population-wide screening tool for ovarian cancer the assay must have a PPV of at least about 10% (Rosenthal et al., 1998, *Sem. Oncol.* 25:315-325). It would thus be desirable for a screening assay for detecting ovarian cancer in patients to have a high sensitivity and a high PPV. Monitoring and reflex tests would also require appropriate specifications.

Owing to the cost, limited sensitivity, and limited specificity of known methods of detecting ovarian cancer, screening is not presently performed for the general population. In addition, the need to perform laparotomy in order to diagnose ovarian cancer in patients who screen positive for indications of ovarian cancer limits the desirability of population-wide screening, such that a PPV even greater than 10% would be desirable.

Prior use of serum CA125 level as a diagnostic marker for ovarian cancer indicated that this method exhibited insufficient specificity for use as a general screening method. Use of a refined algorithm for interpreting CA125 levels in serial retrospective samples obtained from patients improved the specificity of the method without shifting detection of ovarian cancer to an earlier stage (Skakes, 1995, *Cancer* 76:2004). Screening for LPA to detect gynecological cancers including ovarian cancer exhibited a sensitivity of about 96% and a specificity of about 89%. However, CA125-based screening methods and LPA-based screening methods are hampered by the presence of CA125 and LPA, respectively, in the serum of patients afflicted with conditions other than ovarian cancer. For example, serum CA125 levels are known to be associated with menstruation, pregnancy, gastrointestinal and hepatic conditions such as colitis and cirrhosis, pericarditis, renal disease, and various non-ovarian malignancies. Serum LPA is known, for example, to be affected by the presence of non-ovarian gynecological malignancies. A screening method having a greater specificity for ovarian cancer than the current screening methods for CA125 and LPA could provide a population-wide screening for early stage ovarian cancer.

Presently greater than about 60% of ovarian cancers diagnosed in patients are stage III or stage IV cancers. Treatment at these stages is largely limited to cytoreductive surgery (when feasible) and chemotherapy, both of which aim to slow the spread and development of metastasized tumor. Substantially all late stage ovarian cancer patients currently undergo combination chemotherapy as primary treatment, usually a combination of a platinum compound and a taxane. Median survival for responding patients is about one year. Combination chemotherapy involving agents such as doxorubicin, cyclophosphamide, cisplatin, hexamethylmelamine, paclitaxel, and methotrexate may improve survival rates in these groups, relative to single-agent therapies. Various recently-developed chemotherapeutic agents and treatment regimens have also demonstrated usefulness for treatment of advanced ovarian cancer. For example, use of the topoisomerase I inhibitor topectan, use of amifostine to minimize chemotherapeutic side effects, and use of intraperitoneal chemotherapy for patients having peritoneally implanted tumors have demonstrated at least limited utility. Presently, however, the 5-year survival rate for patients afflicted with stage III ovarian cancer is 25%, and the survival rate for patients afflicted with stage IV ovarian cancer is 8%.

It would therefore be beneficial to provide specific methods and reagents for the diagnosis, staging, prognosis, monitoring, and treatment of diseases associated with breast and/or ovarian cancer, or to indicate a predisposition to such for preventative measures. The present invention is directed towards these needs.

SUMMARY OF THE INVENTION

The invention relates to breast and/or ovarian cancer markers (hereinafter "markers" or "markers of the invention"), which are listed in Tables 1-5. The invention provides nucleic acids and proteins that are encoded by or correspond to the markers (hereinafter "marker nucleic acids" and "marker proteins," respectively). Table 1 provides the sequence identifiers of the sequences of such marker nucleic acids and proteins listed in the accompanying Sequence Listing. The invention further provides antibodies, antibody derivatives and antibody fragments which bind specifically with such proteins and/or fragments of the proteins.

The invention also relates to various methods, reagents and kits for diagnosing, staging, prognosing, monitoring and treating cancers, particularly breast and ovarian cancers. "Breast cancer" and "ovarian cancer" as used herein include carcinomas, (e.g., carcinoma in situ, invasive carcinoma, metastatic carcinoma) and pre-malignant conditions. In one embodiment, the invention provides a diagnostic method of assessing whether a patient has breast or ovarian cancer or has higher than normal risk for developing breast or ovarian cancer, comprising the steps of comparing the level of expression of a marker of the invention in a patient sample and the normal level of expression of the marker in a control, e.g., a sample from a patient without breast or ovarian cancer. A significantly higher level of expression of the marker in the patient sample as compared to the normal level is an indication that the patient is afflicted with breast or ovarian cancer or has higher than normal risk for developing breast or ovarian cancer.

According to the invention, the markers are selected such that the positive predictive value of the methods of the invention is at least about 10%, preferably about 25%, more preferably about 50% and most preferably about 90%. Also preferred for use in the methods of the invention are markers that are differentially expressed, as compared to normal breast cells, by at least two-fold in at least about 20%, more preferably about 50% and most preferably about 75% of any of the following conditions: stage 0 breast cancer patients, stage I breast cancer patients, stage IIA breast cancer patients, stage IIB breast cancer patients, stage IIIA breast cancer patients, stage IIIB breast cancer patients, stage IV breast cancer patients, grade I breast cancer patients, grade II breast cancer patients, grade III breast cancer patients, malignant breast cancer patients, ductal carcinoma breast cancer patients, and lobular carcinoma breast cancer patients. Further preferred for use in the methods of the invention are markers that are differentially expressed, as compared to normal ovarian cells, by at least two-fold in at least about 20%, more preferably about 50%, and most preferably about 75% of any of the following conditions: stage I ovarian cancer patients, stage II ovarian cancer patients, stage III ovarian cancer patients, stage IV ovarian cancer patients, grade I ovarian cancer patients, grade II ovarian cancer patients, grade III ovarian cancer patients, epithelial ovarian cancer patients, stromal ovarian cancer patients, germ cell ovarian cancer patients, malignant ovarian cancer patients, benign ovarian cancer patients, serous neoplasm ovarian cancer patients, mucinous neoplasm ovarian cancer patients, endometrioid neoplasm ovarian cancer patients and/or clear cell neoplasm ovarian cancer patients.

In a preferred diagnostic method of assessing whether a patient is afflicted with breast or ovarian cancer (e.g., new detection ("screening"), detection of recurrence, reflex testing), the method comprises comparing:
 a) the level of expression of a marker of the invention in a patient sample, and
 b) the normal level of expression of the marker in a control non-cancerous breast or non-cancerous ovarian cancer sample.

A significantly higher level of expression of the marker in the patient sample as compared to the normal level is an indication that the patient is afflicted with breast or ovarian cancer. In a preferred diagnostic method for breast cancer, the marker is selected from the markers in Table 2. In a preferred diagnostic method for ovarian cancer, the marker is selected from the markers in Table 3.

The invention also provides methods for assessing the efficacy of a therapy for inhibiting breast or ovarian cancer in a patient. Such methods comprise comparing:
 a) expression of a marker of the invention in a first sample obtained from the patient prior to providing at least a portion of the therapy to the patient, and
 b) expression of the marker in a second sample obtained from the patient following provision of the portion of the therapy.

A significantly lower level of expression of the marker in the second sample relative to that in the first sample is an indication that the therapy is efficacious for inhibiting breast or ovarian cancer in the patient. In a preferred method for breast cancer, the marker is selected from the markers in Table 2. In a preferred method for ovarian cancer, the marker is selected from the markers in Table 3.

It will be appreciated that in these methods the "therapy" may be any therapy for treating breast or ovarian cancer including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In a preferred embodiment, the methods are directed to therapy using a chemical or biologic agent. These methods comprise comparing:
 a) expression of a marker of the invention in a first sample obtained from the patient and maintained in the presence of the chemical or biologic agent, and
 b) expression of the marker in a second sample obtained from the patient and maintained in the absence of the agent.

A significantly lower level of expression of the marker in the second sample relative to that in the first sample is an indication that the agent is efficacious for inhibiting breast or ovarian cancer, in the patient. In one embodiment, the first and second samples can be portions of a single sample obtained from the patient or portions of pooled samples obtained from the patient. In a preferred embodiment, the methods are directed to therapy for treating breast cancer and the marker is selected from the markers in Table 2.

In another preferred embodiment, the methods are directed to therapy for treating ovarian cancer and the marker is selected from the markers in Table 3.

The invention additionally provides a monitoring method for assessing the progression of breast or ovarian cancer in a patient, the method comprising:
 a) detecting in a patient sample at a first time point, the expression of a marker of the invention;
 b) repeating step a) at a subsequent time point in time; and
 c) comparing the level of expression detected in steps a) and b), and therefrom monitoring the progression of breast or ovarian cancer in the patient.

A significantly higher level of expression of the marker in the sample at the subsequent time point from that of the sample at the first time point is an indication that the breast or ovarian cancer has progressed, whereas a significantly lower level of expression is an indication that the breast or ovarian cancer has regressed. In a preferred embodiment for breast cancer, the marker is selected from the markers in Table 2. In a preferred embodiment for ovarian cancer, the marker is selected from the markers in Table 3.

The invention further provides a diagnostic method for determining whether breast or ovarian cancer has metastasized or is likely to metastasize, the method comprising comparing:
 a) the level of expression of a marker of the invention in a patient sample, and
 b) the normal level (or non-metastatic level) of expression of the marker in a control sample.

A significantly higher level of expression in the patient sample as compared to the normal level (or non-metastatic level) is an indication that the breast or ovarian cancer has metastasized or is likely to metastasize. In a preferred diagnostic method for breast cancer, the marker is selected from the markers in Table 2. In a preferred diagnostic method for ovarian cancer, the marker is selected from the markers in Table 3.

The invention moreover provides a test method for selecting a composition for inhibiting breast or ovarian cancer in a patient. This method comprises the steps of:
a) obtaining a sample comprising cancer cells from the patient;
b) separately maintaining aliquots of the sample in the presence of a plurality of test compositions;
c) comparing expression of a marker of the invention in each of the aliquots; and
d) selecting one of the test compositions which significantly reduces the level of expression of the marker in the aliquot containing that test composition, relative to the levels of expression of the marker in the presence of the other test compositions.

In a preferred method for selecting a composition for inhibiting breast cancer, the marker is selected from the markers in Table 2. In a preferred method for selecting a composition for inhibiting ovarian cancer, the marker is selected from the markers in Table 3.

The invention additionally provides a test method of assessing the breast or ovarian carcinogenic potential of a compound. This method comprises the steps of:
a) maintaining separate aliquots of breast or ovarian cells in the presence and absence of the compound; and
b) comparing expression of a marker of the invention in each of the aliquots.

A significantly higher level of expression of the marker in the aliquot maintained in the presence of the compound, relative to that of the aliquot maintained in the absence of the compound, is an indication that the compound possesses breast or ovarian carcinogenic potential. In a preferred method for assessing breast carcinogenic potential, the marker is selected from the markers in Table 2. In a preferred method for assessing ovarian carcinogenic potential, the marker is selected from the markers in Table 3.

In addition, the invention further provides a method of inhibiting breast or ovarian cancer in a patient. This method comprises the steps of:
a) obtaining a sample comprising cancer cells from the patient;
b) separately maintaining aliquots of the sample in the presence of a plurality of compositions;
c) comparing expression of a marker of the invention in each of the aliquots; and
d) administering to the patient at least one of the compositions which significantly lowers the level of expression of the marker in the aliquot containing that composition, relative to the levels of expression of the marker in the presence of the other compositions.

In a preferred method for breast cancer, the marker is selected from the markers in Table 2. In a preferred method for ovarian cancer, the marker is selected from the markers in Table 3.

In the aforementioned methods, the samples or patient samples can comprise a breast- or ovary-associated body fluid. Breast-associated fluids include, for example, blood fluids, lymph and cystic fluids, as well as nipple aspirates. Ovary-associated body fluids include, for example, blood fluids, lymph, ascites fluids, gynecological fluids, cystic fluids, urine, and fluids collected by peritoneal rinsing. The cells may be found in an ovarian or breast tissue sample collected, for example, by an ovarian or breast tissue biopsy or histology section. In another embodiment, the sample comprises cells obtained from the patient. In another embodiment, the patient sample is in vivo.

According to the invention, the level of expression of a marker of the invention in a sample can be assessed, for example, by detecting the presence in the sample of:
the corresponding marker protein (e.g., a protein having one of the sequences of the even numbered SEQ ID NOs. such as SEQ ID NOs: 2, 4, 6, 8, etc.) or a fragment of the protein (e.g. by using a reagent, such as an antibody, an antibody derivative, an antibody fragment or single-chain antibody, which binds specifically with the protein or protein fragment)
the corresponding marker nucleic acid (e.g. a nucleotide transcript having one of the sequences of the odd numbered SEQ ID NOs. such as SEQ ID NOs: 1, 3, 5, 7, etc., or a complement thereof), or a fragment of the nucleic acid (e.g. by contacting transcribed polynucleotides obtained from the sample with a substrate having affixed thereto one or more nucleic acids having the entire or a segment of the sequence of any of the odd numbered SEQ ID NOs., or a complement thereof)
a metabolite which is produced directly (i.e., catalyzed) or indirectly by the corresponding marker protein.

According to the invention, any of the aforementioned methods may be performed using a plurality (e.g. 2, 3, 5, or 10 or more) of breast or ovarian cancer markers, including breast or ovarian cancer markers known in the art. In such methods, the level of expression in the sample of each of a plurality of markers, at least one of which is a marker of the invention, is compared with the normal level of expression of each of the plurality of markers in samples of the same type obtained from control humans not afflicted with breast or ovarian cancer. A significantly altered (i.e., increased or decreased as specified in the above-described methods using a single marker) level of expression in the sample of one or more markers of the invention, or some combination thereof, relative to that marker's corresponding normal levels, is an indication that the patient is afflicted with breast or ovarian cancer. For all of the aforementioned methods, the marker(s) are preferably selected such that the positive predictive value of the method is at least about 10%.

In a further aspect, the invention provides an antibody, an antibody derivative, or an antibody fragment, which binds specifically with a marker protein (e.g., a protein having the sequence of any of the even numbered SEQ ID NOs.) or a fragment of the protein. The invention also provides methods for making such antibody, antibody derivative, and antibody fragment. Such methods may comprise immunizing a mammal with a protein or peptide comprising the entirety, or a segment of 10 or more amino acids, of a marker protein (e.g., a protein having the sequence of any of the even numbered SEQ ID NOs.), wherein the protein or peptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker protein or a fragment of the protein.

The markers of the invention are predicted to code for secreted or extracellular proteins, as well as for other types of transmembrane proteins (e.g., integral membrane proteins, type I and type II transmembrane proteins, multi-transmembrane proteins), and are therefore attractive targets for anti-cancer therapy and detection techniques, e.g., using antibodies and derivatives. Thus, markers of Table 2 are useful targets for detecting and treating breast cancer cancers and markers of Table 3 are useful targets for detecting and treating ovarian cancer. Further, certain markers of the invention (listed in Table 4) are selectively expressed in multiple types of cancers and thus are useful targets for detecting and treating several types of cancers. Table 4 indicates the usefulness of a marker as a target for a specific type of cancer with a plus sign in that cancer's column. In one embodiment, Markers 1, 2, 3, 26 and 32 each can be used as a target for diagnosis and treatment of breast and lung cancers. In another embodiment, Markers 6, 23, 43 and 47 each can be used as a target for diagnosis and treatment of ovarian, breast, lung and colon cancers. In a further embodiment, Markers 5 and 7 each can be used as a target for diagnosis and treatment of ovarian, breast, lung, colon and prostate cancers. In a further embodiment, Markers 5 and 7 each can be used as a target for diagnosis and treatment of ovarian, breast, lung, colon and prostate cancers. In yet another embodiment, Marker 22 can be used as a target for diagnosis and treatment of breast, lung and colon cancers. In another embodiment, Marker 36 can be used as a target for diagnosis and treatment of ovarian, breast and lung, cancers. In a further additional embodiment, Marker 39 can be used as a target for diagnosis and treatment of ovarian and lung cancers. In yet a further embodiment, Marker 45 can be used as a target for diagnosis and treatment of ovarian and colon cancers. In another additional embodiment, Marker 56 can be used as a target for diagnosis and treatment of ovarian lung and colon cancers. In a preferred embodiment of the invention, Marker 7 and Marker 32 can be used as targets for inhibiting angiogenenis associated with tumor growth. Antibodies, antibody derivatives, and antibody fragments which bind specifically with a marker protein of the invention (i.e., a protein comprising the sequence of any of the even numbered) or a fragment of the protein, may thus be used to treat a cancer of which the corresponding marker is a target.

In another aspect, the invention relates to various diagnostic and test kits. In one embodiment, the invention provides a kit for assessing whether a patient is afflicted with breast or ovarian cancer. The kit comprises a reagent for assessing expression of a marker of the invention. In another embodiment, the invention provides a kit for assessing the suitability of a chemical or biologic agent for inhibiting an breast or ovarian cancer in a patient. Such kit comprises a reagent for assessing expression of a marker of the invention, and may also comprise one or more of such agents. In a further embodiment, the invention provides kits for assessing the presence of breast or ovarian cancer cells or treating breast or ovarian cancers. Such kits comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In an additional embodiment, the invention also provides a kit for assessing the presence of breast or ovarian cancer cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

In a further aspect, the invention relates to methods for treating a patient afflicted with cancer, particularly breast or ovarian cancer or at risk of developing such a cancer. The methods may comprise reducing the expression and/or interfering with the biological function of a marker of the invention so as to treat a cancer of which the marker has been identified herein as a useful diagnosis and therapeutic target. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an anti-sense polynucleotide of a marker nucleic acid or a fragment thereof. In another embodiment, the method comprises providing to the patient an antibody, an antibody derivative, or antibody fragment, which binds specifically with a marker protein or a fragment of the protein. In a preferred embodiment, the antibody, antibody derivative or antibody fragment binds specifically with a protein having the sequence of an even numbered SEQ ID NO., or a fragment of the protein.

It will be appreciated that the methods and kits of the present invention may also include known cancer markers including known breast or ovarian cancer markers. It will further be appreciated that the methods and kits may be used to identify cancers other than breast or ovarian cancer.

DETAILED DESCRIPTION OF THE INVENTION

The invention relates to newly discovered Markers 1-56 (Table 1) associated with cancer and more particularly the cancerous state of breast and/or ovarian cells. Table 1 lists the markers of the invention, which are over-expressed in breast and/or ovarian cancer cells compared to normal (i.e., non-cancerous) cells and provides the sequence listing identifiers of the cDNA sequence of a nucleotide transcript and the amino acid sequence of a protein encoded by or corresponding to each marker. It has been discovered that higher than normal level of expression of any of Markers 1-33 (Table 2) or a combination of these markers correlates with the presence of cancer, particularly breast cancer in a patient. Likewise, it has been discovered that higher than normal level of expression of any of Markers 34-56 (Table 3) or a combination of these markers correlates with the presence of cancer, particularly ovarian cancer in a patient. Methods are provided for detecting the presence of cancer, particularly breast or ovarian cancer in a sample, the absence of breast or ovarian cancer in a sample, the stage of a breast or ovarian cancer, and with other characteristics of breast or ovarian cancer that are relevant to prevention, diagnosis, characterization, and therapy of breast or ovarian cancer in a patient. Methods of treating cancer, particularly breast or ovarian cancer are also provided.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the odd number SEQ ID NOs. or the complement of such a sequence. The marker nucleic acids also include RNA comprising the entire or a partial sequence of any odd number SEQ ID NO. or the complement of such a sequence, wherein all thymidine residues are replaced with uridine residues. A "marker protein" is a protein encoded by or corresponding to a marker of the invention. A marker protein comprises the entire or a partial sequence of any of the even numbered SEQ ID NOs. The terms "protein" and "polypeptide" are used interchangeably.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

A "breast-associated" body fluid is a fluid which, when in the body of a patient, contacts or passes through breast cells or into which cells or proteins shed from breast cells are capable of passing. Exemplary breast-associated body fluids include, for example, blood fluids, lymph and cystic fluids, as well as nipple aspirates.

An "ovarian-associated" body fluid is a fluid which, when in the body of a patient contacts or passes through ovarian cells or into which cells or proteins shed from ovarian cells are capable of passing. Ovary-associated body fluids include, for example, fluids include blood fluids (e.g. whole blood, blood serum, blood having platelets removed therefrom, etc.), lymph, ascitic fluids, gynecological fluids (e.g. ovarian, fallopian, and uterine secretions, menses, vaginal douching fluids, fluids used to rinse ovarian cell samples, etc.), cystic fluid, urine, fluids collected by peritoneal rinsing (e.g. fluids applied and collected during laparoscopy or fluids instilled into and withdrawn from the peritoneal cavity of a human patient), a fluid collected by uterine rinsing, a uterine fluid, a uterine exudate or menses, a pleural fluid, or an ovarian exudate.

The "normal" level of expression of a marker is the level of expression of the marker in breast or ovarian cells of a human subject or patient not afflicted with breast or ovarian cancer An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subjects not having the marker associated disease) and preferably, the average expression level of the marker in several control samples.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

A cancer is "inhibited" if at least one symptom of the cancer is alleviated, terminated, slowed, or prevented. As used herein, breast or ovarian cancer is also "inhibited" if recurrence or metastasis of the cancer is reduced, slowed, delayed, or prevented.

A kit is any manufacture (e.g. a package or container) comprising at least one reagent, e.g. a probe, for specifically detecting the expression of a marker of the invention. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody moiety.

DESCRIPTION

The present invention is based, in part, on newly identified markers which are over-expressed in breast or ovarian cancer cells as compared to their expression in normal (i.e. non-cancerous) breast or ovarian cells. The enhanced expression of one or more of these markers in breast or ovarian cells is herein correlated with the cancerous state of the tissue. The invention provides compositions, kits, and methods for assessing the cancerous state of breast or ovarian cells (e.g. cells obtained from a human, cultured human cells, archived or preserved human cells and in vivo cells) as well as treating patients afflicted with breast or ovarian cancer.

The compositions, kits, and methods of the invention have the following uses, among others:
1) assessing whether a patient is afflicted with breast or ovarian cancer;
2) assessing the stage of breast or ovarian cancer in a human patient;
3) assessing the grade of breast or ovarian cancer in a patient;
4) assessing the benign or malignant nature of breast or ovarian cancer in a patient;
5) assessing the metastatic potential of breast or ovarian cancer in a patient;
6) assessing the histological type of neoplasm associated with breast or ovarian cancer in a patient;
7) making antibodies, antibody fragments or antibody derivatives that are useful for treating breast or ovarian cancer and/or assessing whether a patient is afflicted with breast or ovarian cancer;
8) assessing the presence of breast or ovarian cancer cells;
9) assessing the efficacy of one or more test compounds for inhibiting breast or ovarian cancer in a patient;
10) assessing the efficacy of a therapy for inhibiting breast or ovarian cancer in a patient;
11) monitoring the progression of breast or ovarian cancer in a patient;
12) selecting a composition or therapy for inhibiting breast or ovarian cancer in a patient;
13) treating a patient afflicted with breast or ovarian cancer;
14) inhibiting breast or ovarian cancer in a patient;
15) assessing the breast or ovarian carcinogenic potential of a test compound; and
16) preventing the onset of breast or ovarian cancer in a patient at risk for developing breast or ovarian cancer.

The invention thus includes a method of assessing whether a patient is afflicted with breast or ovarian cancer which includes assessing whether the patient has pre-metastasized breast or ovarian cancer. This method comprises comparing the level of expression of a marker of the invention in a patient sample and the normal level of expression of the marker in a control, e.g., a non-cancerous breast or ovarian sample. A significantly higher level of expression of the marker in the patient sample as compared to the normal level is an indication that the patient is afflicted with breast or ovarian cancer.

Gene delivery vehicles, host cells and compositions (all described herein) containing nucleic acids comprising the entirety, or a segment of 15 or more nucleotides, of any of the sequences of the odd numbered SEQ ID NOs. or the complement of such sequences, and polypeptides comprising the entirety, or a segment of 10 or more amino acids, of any of the sequences of the even numbered SEQ ID NOs. are also provided by this invention.

As described herein, breast or ovarian cancer in patients is associated with an increased level of expression of one or more markers of the invention. While, as discussed above, some of these changes in expression level result from occurrence of the breast or ovarian cancer, others of these changes induce, maintain, and promote the cancerous state of breast or ovarian cancer cells. Thus, breast or ovarian cancer characterized by an increase in the level of expression of one or more markers of the invention can be inhibited by reducing and/or interfering with the expression of the markers and/or function of the proteins encoded by those markers.

Expression of a marker of the invention can be inhibited in a number of ways generally known in the art. For example, an antisense oligonucleotide can be provided to the breast or ovarian cancer cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the breast or ovarian cancer cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit breast or ovarian cancer cells of the patient.

Any marker or combination of markers of the invention, as well as any known markers in combination with the markers of the invention, may be used in the compositions, kits, and methods of the present invention. In general, it is preferable to use markers for which the difference between the level of expression of the marker in breast or ovarian cancer cells and the level of expression of the same marker in normal breast or ovarian cells is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the level of expression of the same marker in normal breast or ovarian tissue.

The marker proteins of the present invention are transmembrane proteins and are therefore extremely useful in the compositions, kits, and methods of the invention, owing to the fact that the such marker proteins can be detected in a breast or ovary-associated body fluid sample, which may be more easily collected from a human patient than a tissue biopsy sample. In addition, preferred in vivo techniques for detection of a marker protein include introducing into a subject a labeled antibody directed against the protein. For example, the antibody can be labeled with a radioactive marker whose presence and location in a subject can be detected by standard imaging techniques. Anti-cancer therapy utilizing antibodies directed against the marker proteins of the present invention is also provided. In particular, it has been found that Markers 7 and 32 are attractive targets for inhibiting breast, ovary, lung and colon tumors, as well as for inhibiting angiogenesis associated with tumor growth.

It will be appreciated that patient samples containing breast or ovarian cells may be used in the methods of the present invention. In these embodiments, the level of expression of the marker can be assessed by assessing the amount (e.g. absolute amount or concentration) of the marker in a breast or ovarian cell sample, e.g., breast or ovarian tissue biopsy obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker nucleic acid. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal breast or ovarian cells and cancerous breast or ovarian cells.

It is understood that by routine screening of additional patient samples using one or more of the markers of the invention, it will be realized that certain of the markers are over-expressed in cancers of various types, including specific breast or ovarian cancers, as well as other cancers such as lung cancer, colon cancer, etc. For example, it will be confirmed that some of the markers of the invention are over-expressed in most (i.e. 50% or more) or substantially all (i.e. 80% or more) of breast or ovarian cancers. Furthermore, it will be confirmed that certain of the markers of the invention are associated with breast cancer of various stages (i.e. stage 0, I, II, III, and IV breast cancers, as well as subclassifications IIA, IIB, IIIA, and IIIB, using the FIGO Stage Grouping system for primary carcinoma of the breast; (see Breast, In: *American Joint Committee on Cancer: AJCC Cancer Staging Manual*. Lippincott-Raven Publishers, 5th ed., 1997, pp. 171-180), or stage I, II, III, and IV ovarian cancers, as well as subclassifications IA, IB, IC, IIA, IIB, IIC, IIIA, IIIB, and IIIC, using the FIGO Stage Grouping system for primary carcinoma of the ovary; 1987, *Am. J. Obstet. Gynecol.* 156:236, of various histologic subtypes (e.g. serous, mucinous, endometroid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal (Müllerian) mixed tumor, mesonephroid tumor, malignant carcinoma, Brenner tumor, mixed epithelial tumor, and undifferentiated carcinoma, using the WHO/FIGO system for classification of malignant breast and ovarian tumors; Scully, *Atlas of Tumor Pathology*, 3d series, Washington D.C.), and various grades (i.e. grade I {well differentiated}, grade II {moderately well differentiated}, and grade III {poorly differentiated from surrounding normal tissue})). In addition, as a greater number of patient samples are assessed for expression of the markers of the invention and the outcomes of the individual patients from whom the samples were obtained are correlated, it will also be confirmed that altered expression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of breast or ovarian cancer in patients.

When the compositions, kits, and methods of the invention are used for characterizing one or more of the stage, grade, histological type, and benign/malignant nature of breast or ovarian cancer in a patient, it is preferred that the marker or panel of markers of the invention is selected such that a positive result is obtained in at least about 20%, and preferably at least about 40%, 60%, or 80%, and more preferably in substantially all patients afflicted with a breast or ovarian cancer of the corresponding stage, grade, histological type, or benign/malignant nature. Preferably, the marker or panel of markers of the invention is selected such that a positive predictive value (PPV) of greater than about 10% is obtained for the general population (more preferably coupled with an assay specificity greater than 80%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with breast or ovarian cancer. When a plurality of markers is used, it is preferred that 2, 3, 4, 5, 8, 10, 12, 15, 20, 30, or 50 or more individual markers be used, wherein fewer markers are preferred.

In order to maximize the sensitivity of the compositions, kits, and methods of the invention (i.e. by interference attributable to cells of non-breast or ovarian origin in a patient sample), it is preferable that the marker of the invention used therein be a marker which has a restricted tissue distribution, e.g., normally not expressed in a non-breast or ovarian tissue.

Only a small number of markers are known to be associated with breast or ovarian cancers (e.g., for breast: BRCA1 and BRCA2; and, for ovarian: AKT2, Ki-RAS, ERBB2, c-MYC, RB1, and TP53). These markers are not, of course, included among the markers of the invention, although they may be used together with one or more markers of the invention in a panel of markers, for example. It is well known that certain types of genes, such as oncogenes, tumor suppressor genes, growth factor-like genes, protease-like genes, and protein kinase-like genes are often involved with development of cancers of various types. Thus, among the markers of the invention, use of those which correspond to proteins which resemble known proteins encoded by known oncogenes and tumor suppressor genes, and those which correspond to proteins which resemble growth factors, proteases, and protein kinases are preferred.

It is recognized that the compositions, kits, and methods of the invention will be of particular utility to patients having an enhanced risk of developing breast or ovarian cancer and their medical advisors. Patients recognized as having an enhanced risk of developing breast or ovarian cancer include, for example, patients having a familial history of breast or ovarian cancer, patients identified as having a mutant oncogene (i.e. at least one allele), and patients of advancing age (i.e. women older than about 50 or 60 years).

The level of expression of a marker in normal (i.e. non-cancerous) human breast or ovarian tissue can be assessed in a variety of ways. In one embodiment, this normal level of expression is assessed by assessing the level of expression of the marker in a portion of breast or ovarian cells which appears to be non-cancerous and by comparing this normal level of expression with the level of expression in a portion of the breast or ovarian cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of breast or ovarian cancer in the patient, from archived patient samples, and the like.

The invention includes compositions, kits, and methods for assessing the presence of breast or ovarian cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of breast or ovarian cancer cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal breast or ovarian cells, a sample of breast or ovarian cancer cells, and the like.

The invention also includes a method of making an isolated hybridoma which produces an antibody useful for assessing whether patient is afflicted with an breast or ovarian cancer. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro using known methods). A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting breast or ovarian cancer cells. As described above, differences in the level of expression of the markers of the invention correlate with the cancerous state of breast or ovarian cells. Although it is recognized that changes in the levels of expression of certain of the markers of the invention likely result from the cancerous state of breast or ovarian cells, it is likewise recognized that changes in the levels of expression of other of the markers of the invention induce, maintain, and promote the cancerous state of those cells. Thus, compounds which inhibit an breast or ovarian cancer in a patient will cause the level of expression of one or more of the markers of the invention to change to a level nearer the normal level of expression for that marker (i.e. the level of expression for the marker in non-cancerous breast or ovarian cells).

This method thus comprises comparing expression of a marker in a first breast or ovarian cell sample and maintained in the presence of the test compound and expression of the marker in a second breast or ovarian cell sample and maintained in the absence of the test compound. A significantly reduced expression of a marker of the invention in the presence of the test compound is an indication that the test compound inhibits breast or ovarian cancer. The breast or ovarian cell samples may, for example, be aliquots of a single sample of normal breast or ovarian cells obtained from a patient, pooled samples of normal breast or ovarian cells obtained from a patient, cells of a normal breast or ovarian cell line, aliquots of a single sample of breast or ovarian cancer cells obtained from a patient, pooled samples of breast or ovarian cancer cells obtained from a patient, cells of an breast or ovarian cancer cell line, or the like. In one embodiment, the samples are breast or ovarian cancer cells obtained from a patient and a plurality of compounds known to be effective for inhibiting various breast or ovarian cancers are tested in order to identify the compound which is likely to best inhibit the breast or ovarian cancer in the patient.

This method may likewise be used to assess the efficacy of a therapy for inhibiting breast or ovarian cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significantly lower level of expression of a marker of the invention then the therapy is efficacious for inhibiting breast or ovarian cancer. As above, if samples from a selected patient are used in this method, then alternative therapies can be assessed in vitro in order to select a therapy most likely to be efficacious for inhibiting breast or ovarian cancer in the patient. As described above, the cancerous state of human breast or ovarian cells is correlated with changes in the levels of expression of the markers of the invention.

The invention includes a method for assessing the human breast or ovarian cell carcinogenic potential of a test compound. This method comprises maintaining separate aliquots of human breast or ovarian cells in the presence and absence of the test compound. Expression of a marker of the invention in each of the aliquots is compared.

A significantly higher level of expression of a marker of the invention in the aliquot maintained in the presence of the test compound (relative to the aliquot maintained in the absence of the test compound) is an indication that the test compound possesses human breast or ovarian cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

I. Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein (e.g., protein having the sequence of the even numbered SEQ ID NOs.), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 95%, or 98% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a breast- or ovary-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996,

*Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

II. Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising the sequence of any of the even numbered SEQ ID NOs. Other useful proteins are substantially identical (e.g., at least about 40%, preferably 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLASTN and BLASTX programs of Altschul, et al. (1990) J. Mol. Biol. 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) Nucleic Acids Res. 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See ncbi.nlm.nih.gov on the world wide web. Another preferred, non-limiting example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448.

When using the FASTA algorithm for comparing nucleotide or amino acid sequences, a PAM 120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other. The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of single polypeptides. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625, 126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, Bio/technology 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of expression of the marker. The antibodies can also be used diagnostically to monitor protein levels in tissues or body fluids (e.g. in a breast- or ovary-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention may also be used as therapeutic agents in treating cancers. In a preferred embodiment, completely human antibodies of the invention are used for therapeutic treatment of human cancer patients, particularly those having breast or ovarian cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention. In one embodiment, the pharmaceutical composition comprises an antibody of the invention, a therapeutic moiety, and a pharmaceutically acceptable carrier.

III. Recombinant Expression Vectors and Host Cells

Another aspect of the invention pertains to vectors, preferably expression vectors, containing a nucleic acid encoding a marker protein (or a portion of such a protein). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a marker protein or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology:. Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY 88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokaryotic or eukaryotic host cell in culture, can be used to produce a marker protein or a segment thereof. Accordingly, the invention further provides methods for producing a marker protein or a segment thereof using the host cells of the invention. In one embodiment, the method comprises culturing the host cell of the invention (into which a recombinant expression vector encoding a marker protein or a segment thereof has been introduced) in a suitable medium such that the is produced. In another embodiment, the method further comprises isolating the a marker protein or a segment thereof from the medium or the host cell.

The host cells of the invention can also be used to produce nonhuman transgenic animals. For example, in one embodiment, a host cell of the invention is a fertilized oocyte or an embryonic stem cell into which a sequences encoding a marker protein or a segment thereof have been introduced.

Such host cells can then be used to create non-human transgenic animals in which exogenous sequences encoding a marker protein of the invention have been introduced into their genome or homologous recombinant animals in which endogenous gene(s) encoding a marker protein have been altered. Such animals are useful for studying the function and/or activity of the marker protein and for identifying and/or evaluating modulators of marker protein. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a marker protein into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a marker protein into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a marker nucleic acid or protein. Such methods comprise formulating a pharmaceutically acceptable carrier with an agent which modulates expression or activity of a marker nucleic acid or protein. Such compositions can further include additional active agents. Thus, the invention further includes methods for preparing a pharmaceutical composition by formulating a pharmaceutically acceptable carrier with an agent which modulates expression or activity of a marker nucleic acid or protein and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker. The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a protein encoded by or corresponding to a marker or biologically active portion thereof. In another embodiment, the invention provides assays for screening candidate or test compounds which bind to a protein encoded by or corresponding to a marker or biologically active portion thereof. Determining the ability of the test compound to directly bind to a protein can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}$I, $^{35}$S, $^{14}$C, or $^3$H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker or the activity of a protein encoded by or corresponding to a marker, or a biologically active portion thereof. In all likelihood, the protein encoded by or corresponding to the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of a protein encoded by or corresponding to marker to identify the protein's natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283, 317; Zervos et al, 1993, *Cell* 72:223-232; Madura et al, 1993, *J. Biol. Chem.* 268:12046-12054; Bartel et al, 1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker protein or downstream elements of a marker protein-mediated signaling pathway. Alternatively, such marker protein binding partners may also be found to be inhibitors of the marker protein.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker protein and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is a breast or ovarian cancer marker protein identified herein, the known binding partner and/or substrate of same, and the test compound. Test compounds can be supplied from any source.

The basic principle of the assay systems used to identify compounds that interfere with the interaction between the marker protein and its binding partner involves preparing a reaction mixture containing the marker protein and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker protein and its binding partner. Control reaction mixtures are incubated without the test compound or with a placebo. The formation of any complexes between the marker protein and its binding partner is then detected. The formation of a complex in the control reaction, but less or no such formation in the reaction mixture containing the test compound, indicates that the compound interferes with the interaction of the marker protein and its binding partner. Conversely, the formation of more complex in the presence of compound than in the control reaction indicates that the compound may enhance interaction of the marker protein and its binding partner.

The assay for compounds that interfere with the interaction of the marker protein with its binding partner may be conducted in a heterogeneous or homogeneous format. Heterogeneous assays involve anchoring either the marker protein or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the marker proteins and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker protein or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker protein or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker protein or a marker protein binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J. Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker protein and its binding partner.

Also within the scope of the present invention are methods for direct detection of interactions between the marker protein and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of marker mRNA or protein in the cell, is determined. The level of expression of marker mRNA or protein in the presence of the candidate compound is compared to the level of expression of marker mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration. A method for lipidation of antibodies is described by Cruikshank et al. (1997) *J. Acquired Immune Deficiency Syndromes and Human Retrovirology* 14:193.

The marker nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing breast or ovarian cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit breast or ovarian cancer or to treat or prevent any other disorder {i.e. in order to understand any breast or ovarian carcinogenic effects that such treatment may have}) on the expression or activity of a marker of the invention in clinical trials. These and other agents are described in further detail in the following sections.

A. Diagnostic Assays

An exemplary method for detecting the presence or absence of a marker protein or nucleic acid in a biological sample involves obtaining a biological sample (e.g. a breast- or ovary-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S, and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit. Winter* 11(1-6):141-8; Hage, D. S., and Tweed, S. A. *J. Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from breast or ovarian cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the breast or ovarian cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-breast or non-ovarian cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from breast or ovarian cancer or from non-breast or non-ovarian cancer cells of breast or ovarian tissue. The choice of the cell source is dependent on the use of the relative expression level. Using expression found in normal tissues as a mean expression score aids in validating whether the marker assayed is breast or ovarian specific (versus normal cells). In addition, as more data is accumulated, the mean expression value can be revised, providing improved relative expression values based on accumulated data. Expression data from breast or ovarian cells provides a means for grading the severity of the breast or ovarian cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from breast or ovarian cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether breast or ovarian cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from breast or ovarian cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample (e.g. a breast- or ovary-associated body fluid such as a urine sample). Such kits can be used to determine if a subject is suffering from or is at increased risk of developing breast or ovarian cancer. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

The marker of the invention are also useful as pharmacogenomic markers. As used herein, a "pharmacogenomic marker" is an objective biochemical marker whose expression level correlates with a specific clinical drug response or susceptibility in a patient (see, e.g., McLeod et al. (1999) *Eur. J. Cancer* 35(12):1650-1652). The presence or quantity of the pharmacogenomic marker expression is related to the predicted responsive of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific tumor markers in a patient, a drug or course of treatment may be selected that is optimized for the treatment of the specific tumor likely to be present in the patient. The use of pharmacogenomic markers therefore permits selecting or designing the most appropriate treatment for each cancer patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for breast or ovarian cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased of expression of the marker gene(s) during the course of treatment may indicate ineffective dosage and the desirability of increasing the dosage. Conversely, decreased expression of the marker gene(s) may indicate efficacious treatment and no need to change dosage.

D. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has breast or ovarian cancer or a pre-disposition to breast or ovarian cancer, wherein the method comprises the steps of determining the presence or absence of a marker and based on the presence or absence of the marker, determining whether the subject has breast or ovarian cancer or a pre-disposition to breast or ovarian cancer and/or recommending a particular treatment for breast or ovarian cancer or pre-breast or pre-ovarian cancer condition.

The present invention further provides in an electronic system and/or in a network, a method for determining whether a subject has breast or ovarian cancer or a pre-disposition to breast or ovarian cancer associated with a marker wherein the method comprises the steps of determining the presence or absence of the marker, and based on the presence or absence of the marker, determining whether the subject has breast or ovarian cancer or a pre-disposition to breast or ovarian cancer, and/or recommending a particular treatment for the breast or ovarian cancer or pre-breast or pre-ovarian cancer condition. The method may further comprise the step of receiving phenotypic information associated with the subject and/or acquiring from a network phenotypic information associated with the subject.

The present invention also provides in a network, a method for determining whether a subject has breast or ovarian cancer or a pre-disposition to breast or ovarian cancer associated with a marker, said method comprising the steps of receiving information associated with the marker receiving phenotypic information associated with the subject, acquiring information from the network corresponding to the marker and/or breast or pre-ovarian cancer, and based on one or more of the phenotypic information, the marker, and the acquired information, determining whether the subject has a breast or ovarian cancer or a pre-disposition to breast or ovarian cancer. The method may further comprise the step of recommending a particular treatment for the breast or ovarian cancer or pre-breast or pre-ovarian cancer condition.

The present invention also provides a business method for determining whether a subject has breast or ovarian cancer or a pre-disposition to breast or ovarian cancer, said method comprising the steps of receiving information associated with the marker, receiving phenotypic information associated with the subject, acquiring information from the network corresponding to the marker and/or breast or ovarian cancer, and based on one or more of the phenotypic information, the marker, and the acquired information, determining whether the subject has breast or ovarian cancer or a pre-disposition to breast or ovarian cancer. The method may further comprise the step of recommending a particular treatment for the breast or ovarian cancer or pre-breast or pre-ovarian cancer condition.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of breast or ovarian cancer, progression of breast or ovarian cancer, and processes, such a cellular transformation associated with breast or ovarian cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

E. Surrogate Markers

The markers of the invention may serve as surrogate markers for one or more disorders or disease states or for conditions leading up to disease states, and in particular, breast or ovarian cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

Experimental Protocol

A. Identification of Markers And Assembly of their Sequences

RNA from tumor and normal breast and ovarian tissue samples were extracted and amplified by poly-dT primed RT-PCR into cDNA using the SMART PCR kit from Clonetech. Amplified cDNA was then labeled using random priming PRIME-IT from Stratagene with a radioactive nucleotide. Labeled cDNA was hybridized to nylon filters spotted with purified PCR product from EST sequences representing known and unknown genes. Several thousand clones were spotted on each nylon filter. Duplicate independent hybridization experiments were performed to generate transcriptional profiling data (see Nature Genetics, 1999, 21). After repeated washings the nylon filters were scanned and the intensity of each spotted gene was converted electronically to indicate expression level in the sample from which the cDNA was derived. Tables were generated for each sample showing the expression level for each of the spotted ESTs. These tables were transferred to Microsoft Excel spreadsheets and the expression levels for each spotted EST was compared between samples. A total of 41 tumor samples representing both early and late stage breast cancer and 7 normal breast tissue samples were profiled on these EST arrays. Additionally, a total of 70 late stage ovarian tumor samples and 5 normal ovarian tissue samples were also profiled on the EST arrays. ESTs that displayed a 5-fold increase in the expression level over the average expression level in the normal samples in at least 30% of the tumor samples were exported to a separate data table.

The corresponding nucleotide sequences for each of these spots were imported and blasted against both public and proprietary sequence databases in order to identify other EST sequences with significant overlap. Thus, contiguous EST sequences were assembled into tentative full-length genes. Reblasting of the assembled sequences against databases of genes coding for known proteins was done to assess whether the assembled gene was a known or unknown protein. Genes in which the potential open reading frame was still open in the 5' end were experimentally extended by either 5'RACE PCR or extracted out from full length cDNA libraries by a simple PCR reaction between the vector and 5' end of the assembled electronic sequence. To predict whether an assembled gene encodes a potential integral membrane protein, hydropathy predictions of the predicted open reading frame was performed (Jones et al., 1994, *Biochemistry.* 33:3038-3049). If the open reading frame contained a predicted signal peptide in the N-terminal portion and a single membrane spanning domain, it was labeled as being a potential type I transmembrane protein. If the predicted amino acid sequence contained a transmembrane domain in the N-terminal portion of the protein, it was labeled as being a potential type II transmembrane protein. If the predicted amino acid sequence was a short hydrophobic protein (<50 amino acids) it was labeled as a potential integral membrane protein. If the predicted amino acid sequence contained multiple membrane spanning regions it was labeled as a multi-transmembrane (multi-TM) region protein B. Identification of Marker 7 and Marker 23 as Targets for Anti-Cancer Therapy Expression levels of Marker 7, a putative transmembrane protein was >5-fold higher in 25/56 breast, 17/20 colon and 26/58 ovarian cancer samples compared to normal tissues. The full-length gene was cloned and expressed and the protein found to be localized to the cell surface of transfected cells. Marker 7 does not belong to any known protein family and does not show significant homology to any protein in the public databases. Northern blots of various carcinoma cells lines reveal the presence of a single mRNA species at approximately 1.4 kb.

Expression of Marker 7 in normal and malignant human tissues was further evaluated by quantitative PCR analysis. Expression levels in breast, ovary, lung and colon tumor samples were 10-300 fold higher than corresponding normal tissues. In addition there was high expression of Marker 7 in in vitro cultured endothelial cells and Wilms tumors and hemangiomas, which are highly vascularized tumors. In situ hybridization (ISH) on tumor samples showed that Marker 7 is predominantly expressed within the tumor stroma and possibly localized to tumor vasculature. Analysis of normal human tissues, including aorta, by ISH suggested that Marker 7 is not expressed on cells within mature vessels. When human tumor cells are transplanted subcutaneously in immunodeficient mice, there is an induction of Marker 7 expression in the mouse stroma associated with tumor vasculature. Marker 7 is hence found expressed in many human cancers, (e.g. breast, ovary, colon, lung and prostate) and not in normal adult tissue.

A similar analysis of Marker 23 showed that this marker is stroma specific, and is upregulated in ovary, breast, lung and colon cancers. Marker 7 and Marker 23 are therefore attractive targets for inhibition of cancers as well as angiogenesis in general. Antibodies, antibody derivatives, and antibody fragments which bind, specifically with Marker 7 or Marker 32 protein (i.e., SEQ ID NOs: 14 and 64, respectively), or a fragment of the protein, may be used to treat cancer of the breast, ovary, lung, colon and prostate as well as generally inhibiting angiogenesis.

VII. Summary of the Data in the Tables:

Table 1 lists all of the markers of the invention.

Table 2 lists Markers 1-33 which were found to be upregulated (i.e., over-expressed) by transcription profiling (TP) in breast cancer. The markers were upregulated at least 5-fold in >30% of the tumors arrayed.

Table 3 lists Markers 34-56 which were found to be upregulated by TP in ovarian cancer. The markers were upregulated at least 5-fold in >30% of the tumors arrayed.

Table 4 lists markers in which additional expression analyses were done by either in situ hybridization (ISH), quantitative mRNA analysis (Taqman) or both. Table 5 lists markers whose encoded protein were heretofore unknown.

In Tables 1-3 and 5 the following definitions apply:

"Marker" corresponds to the arbitrary identifier used within this application to designate the marker of the invention.

"Gene Name" corresponds to the commonly used terminology for the marker gene, if it exists.

"Image Clone ID" corresponds to the cDNA clone number from the IMAGE Consortium (see, for example Lennon, G., et al., 1996, Genomics 33:151-152; and bio.llnl.gov/bbrp/image/image.html on the world wide web). All referenced IMAGE clone sequences are expressly incorporated herein by reference.

"SEQ ID NO (nts)" designates the entry number in the Sequence Listing that corresponds to the nucleotide sequence of the particular marker. "SEQ ID NO (AAs)" designates the entry number in the Sequence Listing that corresponds to the amino acid sequence of the particular marker. Each known sequence submitted to GenBank has a unique identifier number, also called the GenBank GI Accession Number, for a complete sequence record in the relevant database (see, e.g. "ncbi.nlm.nih.gov/genbank/query_form.html" on the world wide web and "derwent.com" on the world wide web for further information). "Acc # (NTS)" corresponds to the GenBank Accession Number for a nucleotide sequence, while "Acc # (AA)" corresponds to the GenBank Accession Number for a protein sequence. "GI # (NTS)" is the GI identification number assigned to the nucleotide sequence of the marker gene in the GenBank database (see supra). "GI # (AA)" corresponds to the GI sequence identification number assigned to that particular protein translation within a nucleotide sequence record in the GenBank database.

The following data is presented in Table 4:

"Gene" corresponds to the arbitrary identifier used within this application to designate the marker of the invention.

The "TaqMan" and "ISH" columns of Table 4, designate whether expression of this marker was analyzed using TaqMan technology or in situ hybridization, respectively. "Yes" indicates that such analysis was done, while "No" similarly indicates that such analysis was not done. "TaqMan" corresponds to the results of quantitative PCR analysis using the TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of taq polymerase digests the labeled primer, producing a free nucleotide labeled with 6-FAM, which is detected as a fluorescent signal. The PCR cycle where fluorescence is first released and detected is directly proportional to the starting amount of the gene of interest in the test sample, thus providing a way of quantitating the initial template concentration.

"Ovary", "Breast", "Lung", "Colon", and "Prostate" correspond to expression as detected by TaqMan analysis in ovarian, breast, lung, colon and prostate cancer respectively. Markers scored with a "+" were found to be upregulated by at least 3-fold in at least 20% of the tumors analyzed (n=>5) in the designated tumor type by Taqman analysis. Markers scored with a "−" were not found to be upregulated in the designated tumor type by Taqman analysis. Expression for markers scored with "ND" was not determined in the designated tumor type. In addition, ISH analysis confirmed that the genes were expressed by the carcinoma cells, except for Marker 23, which is stroma specific and Marker 7 which is expressed mostly in the stroma but can also be found on tumor cells. Evidence to support this includes Taqman RNA analysis from cancer cell lines (breast, ovary, lung, colon and prostate) and ISH.

The contents of all references, patents, published patent applications, and database records including GenBank, IMAGE consortium and Derwent cited throughout this application, are hereby incorporated by reference.

Other Embodiments

Those skilled in the art will recognize, or be able to ascertain using no more than routine experimentation, many equivalents to the specific embodiments of the invention described herein. Such equivalents are intended to be encompassed by the following claims:

TABLE 1

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 1 | KIAA0018 | 840878 | D13643 | 285996 | 1 | BAA02806 | 6630632 | 2 |
| Marker 2 | Nonspecific cross reacting antigen (NCA) | 509823 | M18728 | 189084 | 3 | AAA51739 | 178691 | 4 |
| Marker 3 | Unnamed protein product | 461336 | AK001105 | 7022160 | 5 | BAA91505 | 7022161 | 6 |
| Marker 4 | Net-6 | 416374 | AF120265 | 4325179 | 7 | AAD17294 | 4325180 | 8 |
| Marker 5 | DKFZp727C191 | 785703 | AL117474 | 5911946 | 9 | | | 10 |
| Marker 6 | Interferon-induced protein 6-16 | 782513 | Q28808 | N/A | 11 | BAA01980 | 218574 | 12 |
| Marker 7 | UNNAMED | 753428 | | | 13 | | | 14 |
| Marker 8 | Alphe 2,6-sialyltransferase | 823590 | AJ251053 | 6453383 | 15 | CAB61434 | 6453384 | 16 |
| Marker 9 | Programmed cell death 9 (PCD9) | 270558 | AL355715 | 7799103 | 17 | CAB90810 | 7799104 | 18 |
| Marker 10 | DKFZp564B1264 | 813730 | AL117612 | 5912188 | 19 | | | 20 |
| Marker 11 | receptor protein tyrosine phosphatase | 41647 | AF043644 | 5468530 | 21 | AAD09421 | 6554165 | 22 |

TABLE 1-continued

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 12 | MAT-8 | 511428 | Q14802 | N/A | 23 | CAA63604 | 1085026 | 24 |
| Marker 13 | Neuropeptide Y receptor, type I | 33045 | P25929 | N/A | 25 | CAA01819 | 1247453 | 26 |
| Marker 14 | Interferon-inducible protein 9-27 | 755599 | P13164 | N/A | 27 | CAA59337 | 1177476 | 28 |
| Marker 15 | UNNAMED | From subtracted library | | | 29 | | | 30 |
| Marker 16 | Vascular cell adhesion molecule (VCAM) | 44477 | M30257 | 179885 | 31 | AAA51917 | 179886 | 32 |
| Marker 17 | 8D6 antigen | 770879 | AF161254 | 7406951 | 33 | AAF61850 | 7406952 | 34 |
| Marker 18 | DKFZp564E1363 | 841067 | AL110137 | 5817032 | 35 | | | 36 |
| Marker 19 | clone 25242 mRNA | 795821 | AF131854 | 4406700 | 37 | | | 38 |
| Marker 20 | multiple mambrane spanning receptor (TRC8) | 812050 | AF064801 | 3395786 | 39 | AAC39930 | 3395787 | 40 |
| Marker 21 | hypothetical protein | From subtracted library | AL080097 | 5262519 | 41 | CAB45709 | 5262520 | 42 |
| Marker 22 | hypothetical protein | 34442 | AL121740 | 6012998 | 43 | CAB57330 | 6012999 | 44 |
| Marker 23 | OSF-2 | 897910 | D13665 | 393318 | 45 | BAA02836 | 393319 | 46 |
| Marker 24 | CTL1 protein | 838689 | AJ245620 | 6996441 | 47 | CAB75541 | 6996442 | 48 |
| Marker 25 | CEGP1 protein | 346321 | AJ400877 | 8052236 | 49 | CAB92285 | 8052237 | 50 |
| Marker 26 | LIV-1 | 52933 | U41060 | 1256000 | 51 | AAA96258 | 12711793 | 52 |
| Marker 27 | Adlican | 810224 | AF245505 | 9280404 | 53 | AAF86402 | 9280405 | 54 |
| Marker 28 | UNNAMED | 754126 | | | 55 | | | 56 |
| Marker 29 | p24B protein | 260628 | AJ132270 | 4583676 | 57 | CAB40416 | 4583677 | 58 |
| Marker 30 | Unnamed protein product | From subtracted library | AK001761 | 7023229 | 59 | BAA91890 | 7023230 | 60 |
| Marker 31 | Unnamed protein product | 266500 | AX084239 | 13185742 | 61 | CAC33425 | 13185743 | 62 |
| Marker 32 | ALCAM | 26617 | L38608 | 886257 | 63 | AAB59499 | 886258 | 64 |
| Marker 33 | sperm membrane protein | 290091 | S83157 | 1836034 | 65 | AAB46833 | 1836035 | 66 |
| Marker 34 | N-methyl-D-aspartate receptor | 179163 | U77783 | 2444025 | 67 | AAC15910 | 2444026 | 68 |
| Marker 35 | Claudin-4 | 770388 | AB000712 | 2570124 | 69 | BAA22984 | 2570125 | 70 |
| Marker 36 | Hypothetical Protein KIAA0247 | 292894 | D87434 | 1665762 | 71 | BAA13378 | 1665763 | 72 |
| Marker 37 | bumetanide-sensitive Na—K—Cl cotransporter | 685801 | U30246 | 903681 | 73 | AAC50561 | 903682 | 74 |
| Marker 38 | Glucose transporter, type I | 207358 | K03195 | 183302 | 75 | AAA52571 | 183303 | 76 |
| Marker 39 | coxsackie and adenovirus receptor protein | 265680 | Y07593 | 1881446 | 77 | CAA68868 | 1881447 | 78 |
| Marker 40 | connexin 26 | 288663 | BC002805 | 12803916 | 79 | AAH02805 | 12803917 | 80 |
| Marker 41 | Cadherin-6 | 739155 | D31784 | 974184 | 81 | BAA06562 | 974185 | 82 |
| Marker 42 | claudin-7 | 841645 | AJ011497 | 4128014 | 83 | CAA09626 | 4128015 | 84 |
| Marker 43 | Prostasin | 132636 | U33446 | 1143193 | 85 | AAB19071 | 1143194 | 86 |
| Marker 44 | MT3-MMP | 46916 | D85511 | 2424978 | 87 | BAA22226 | 2424979 | 88 |
| Marker 45 | UNNAMED | 771301 | | | 89 | | | 90 |
| Marker 46 | Cluadin-16 | 449034 | AF152101 | 5410526 | 91 | AAD43096 | 5410527 | 92 |
| Marker 47 | LR11, sortillin-related receptor | 279388 | U60975 | 1589775 | 93 | AAC50891 | 5030424 | 94 |
| Marker 48 | Myoferlin | 161992 | AF182316 | 6731234 | 95 | AAF27176 | 6731235 | 96 |
| Marker 49 | desmocollin type 3 | 544639 | X83929 | 1122882 | 97 | CAA58781 | 1122883 | 98 |
| Marker 50 | similar to D. melanogaster cadherin related tumor suppressor | 175103 | D87469 | 1665820 | 99 | BAA13407 | 1665821 | 100 |
| Marker 51 | protocadherin | 50114 | AF152304 | 5456893 | 101 | AAD43698 | 5456894 | 102 |
| Marker 52 | occludin | 243159 | U53823 | 1322281 | 103 | AAB00195 | 1322282 | 104 |
| Marker 53 | Unnamed protein | 12577 | BC004337 | 13279268 | 105 | AAH04337 | 13279269 | 106 |
| Marker 54 | Lutheran blood group protein | 160656 | X83425 | 603559 | 107 | CAA58449 | 603560 | 108 |
| Marker 55 | AC133 | 27544 | AF027208 | 2688948 | 109 | AAB92514 | 2688949 | 110 |
| Marker 56 | epithelial V-like antigen | 853998 | AF030455 | 3169829 | 111 | AAC39762 | 3169830 | 112 |

TABLE 2

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 1 | KIAA0018 | 840878 | D13643 | 285996 | 1 | BAA02806 | 6630632 | 2 |
| Marker 2 | Nonspecific cross reacting antigen (NCA) | 509823 | M18728 | 189084 | 3 | AAA51739 | 178691 | 4 |
| Marker 3 | Unnamed protein product | 461336 | AK001105 | 7022160 | 5 | BAA91505 | 7022161 | 6 |
| Marker 4 | Net-6 | 416374 | AF120265 | 4325179 | 7 | AAD17294 | 4325180 | 8 |
| Marker 5 | DKFZp727C191 | 785703 | AL117474 | 5911946 | 9 | | | 10 |
| Marker 6 | Interferon-induced protein 6-16 | 782513 | Q28808 | N/A | 11 | BAA01980 | 218574 | 12 |

TABLE 2-continued

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 7 | UNNAMED | 753428 | | | 13 | | | 14 |
| Marker 8 | Alphe 2,6-sialyltransferase | 823590 | AJ251053 | 6453383 | 15 | CAB61434 | 6453384 | 16 |
| Marker 9 | Programmed cell death 9 (PCD9) | 270558 | AL355715 | 7799103 | 17 | CAB90810 | 7799104 | 18 |
| Marker 10 | DKFZp564B1264 | 813730 | AL117612 | 5912188 | 19 | | | 20 |
| Marker 11 | receptor protein tyrosine phospatase | 41647 | AF043644 | 5468530 | 21 | AAD09421 | 6554165 | 22 |
| Marker 12 | MAT-8 | 511428 | Q14802 | N/A | 23 | CAA63604 | 1085026 | 24 |
| Marker 13 | Neuropeptide Y receptor, type I | 33045 | P25929 | N/A | 25 | CAA01819 | 1247453 | 26 |
| Marker 14 | Interferon-inducible protein 9-27 | 755599 | P13164 | N/A | 27 | CAA59337 | 1177476 | 28 |
| Marker 15 | UNNAMED | From subtracted library | | | 29 | | | 30 |
| Marker 16 | Vascular cell adhesion molecule (VCAM) | 44477 | M30257 | 179885 | 31 | AAA51917 | 179886 | 32 |
| Marker 17 | 8D6 antigen | 770879 | AF161254 | 7406951 | 33 | AAF61850 | 7406952 | 34 |
| Marker 18 | DKFZp564E1363 | 841067 | AL110137 | 5817032 | 35 | | | 36 |
| Marker 19 | clone 25242 mRNA | 795821 | AF131854 | 4406700 | 37 | | | 38 |
| Marker 20 | multiple mambrane spanning receptor (TRC8) | 812050 | AF064801 | 3395786 | 39 | AAC39930 | 3395787 | 40 |
| Marker 21 | hypothetical protein | From subtracted library | AL080097 | 5262519 | 41 | CAB45709 | 5262520 | 42 |
| Marker 22 | hypothetical protein | 34442 | AL121740 | 6012998 | 43 | CAB57330 | 6012999 | 44 |
| Marker 23 | OSF-2 | 897910 | D13665 | 393318 | 45 | BAA02836 | 393319 | 46 |
| Marker 24 | CTL1 protein | 838689 | AJ245620 | 6996441 | 47 | CAB75541 | 6996442 | 48 |
| Marker 25 | CEGP1 protein | 346321 | AJ400877 | 8052236 | 49 | CAB92285 | 8052237 | 50 |
| Marker 26 | LIV-1 | 52933 | U41060 | 1256000 | 51 | AAA96258 | 12711793 | 52 |
| Marker 27 | Adlican | 810224 | AF245505 | 9280404 | 53 | AAF86402 | 9280405 | 54 |
| Marker 28 | UNNAMED | 754126 | | | 55 | | | 56 |
| Marker 29 | p24B protein | 260628 | AJ132270 | 4583676 | 57 | CAB40416 | 4583677 | 58 |
| Marker 30 | Unnamed protein product | From subtracted library | AK001761 | 7023229 | 59 | BAA91890 | 7023230 | 60 |
| Marker 31 | Unnamed protein product | 266500 | AX084239 | 13185742 | 61 | CAC33425 | 13185743 | 62 |
| Marker 32 | ALCAM | 26617 | L38608 | 886257 | 63 | AAB59499 | 886258 | 64 |
| Marker 33 | sperm membrane protein | 290091 | S83157 | 1836034 | 65 | AAB46833 | 1836035 | 66 |

TABLE 3

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 34 | N-methyl-D-aspartate receptor | 179163 | U77783 | 2444025 | 67 | AAC15910 | 2444026 | 68 |
| Marker 35 | Claudin-4 | 770388 | AB000712 | 2570124 | 69 | BAA22984 | 2570125 | 70 |
| Marker 36 | Hypothetical Protein KIAA0247 | 292894 | D87434 | 1665762 | 71 | BAA13378 | 1665763 | 72 |
| Marker 37 | bumetanide-sensitive Na—K—Cl cotransporter | 685801 | U30246 | 903681 | 73 | AAC50561 | 903682 | 74 |
| Marker 38 | Glucose transporter, type I | 207358 | K03195 | 183302 | 75 | AAA52571 | 183303 | 76 |
| Marker 39 | coxsackie and adenovirus receptor protein | 265680 | Y07593 | 1881446 | 77 | CAA68868 | 1881447 | 78 |
| Marker 40 | connexin 26 | 288663 | BC002805 | 12803916 | 79 | AAH02805 | 12803917 | 80 |
| Marker 41 | Cadherin-6 | 739155 | D31784 | 974184 | 81 | BAA06562 | 974185 | 82 |
| Marker 42 | claudin-7 | 841645 | AJ011497 | 4128014 | 83 | CAA09626 | 4128015 | 84 |
| Marker 43 | Prostasin | 132636 | U33446 | 1143193 | 85 | AAB19071 | 1143194 | 86 |
| Marker 44 | MT3-MMP | 46916 | D85511 | 2424978 | 87 | BAA22226 | 2424979 | 88 |
| Marker 45 | UNNAMED | 771301 | | | 89 | | | 90 |
| Marker 46 | Cluadin-16 | 449034 | AF152101 | 5410526 | 91 | AAD43096 | 5410527 | 92 |
| Marker 47 | LR11, sortillin-related receptor | 279388 | U60975 | 1589775 | 93 | AAC50891 | 5030424 | 94 |
| Marker 48 | Myoferlin | 161992 | AF182316 | 6731234 | 95 | AAF27176 | 6731235 | 96 |
| Marker 49 | desmocollin type 3 | 544639 | X83929 | 1122882 | 97 | CAA58781 | 1122883 | 98 |
| Marker 50 | similar to D. melanogaster cadherin related tumor suppressor | 175103 | D87469 | 1665820 | 99 | BAA13407 | 1665821 | 100 |
| Marker 51 | protocadherin | 50114 | AF152304 | 5456893 | 101 | AAD43698 | 5456894 | 102 |
| Marker 52 | occludin | 243159 | U53823 | 1322281 | 103 | AAB00195 | 1322282 | 104 |
| Marker 53 | Unnamed protein | 12577 | BC004337 | 13279268 | 105 | AAH04337 | 13279269 | 106 |
| Marker 54 | Lutheran blood group protein | 160656 | X83425 | 603559 | 107 | CAA58449 | 603560 | 108 |
| Marker 55 | AC133 | 27544 | AF027208 | 2688948 | 109 | AAB92514 | 2688949 | 110 |
| Marker 56 | epithelial V-like antigen | 853998 | AF030455 | 3169829 | 111 | AAC39762 | 3169830 | 112 |

TABLE 4

| Gene | TaqMan | ISH | Ovary | Breast | Lung | Colon | Prostate |
|---|---|---|---|---|---|---|---|
| Marker 1 | Yes | Yes | − | + | + | − | ND |
| Marker 2 | Yes | Yes | − | + | + | − | − |
| Marker 3 | Yes | Yes | − | + | − | − | − |
| Marker 4 | Yes | Yes | + | + | + | + | + |
| Marker 6 | Yes | Yes | + | + | + | + | − |
| Marker 7 | Yes | Yes | + | + | + | + | + |
| Marker 22 | Yes | Yes | − | + | + | + | − |
| Marker 23 | Yes | Yes | + | + | + | + | ND |
| Marker 26 | Yes | Yes | − | + | + | − | + |

TABLE 4-continued

| Gene | TaqMan | ISH | Ovary | Breast | Lung | Colon | Prostate |
|---|---|---|---|---|---|---|---|
| Marker 32 | Yes | Yes | − | + | + | − | + |
| Marker 36 | Yes | No | + | + | + | − | ND |
| Marker 39 | Yes | No | + | − | + | − | ND |
| Marker 43 | Yes | No | + | + | + | + | ND |
| Marker 45 | Yes | Yes | + | − | − | + |  |
| Marker 47 | Yes | No | + | + | + | + |  |
| Marker 56 | Yes | No | + | − | + | + | − |

TABLE 5

| Marker | Gene Name | Image Clone ID | Acc # (NTS) | GI # (NTS) | SEQ ID NO (nts) | Acc # (AA) | GI # (AA) | SEQ ID NO (AAs) |
|---|---|---|---|---|---|---|---|---|
| Marker 5 | DKFZp727C191 | 785703 | AL117474 | 5911946 | 9 |  |  | 10 |
| Marker 7 | UNNAMED | 753428 |  |  | 13 |  |  | 14 |
| Marker 10 | DKFZp564B1264 | 813730 | AL117612 | 5912188 | 19 |  |  | 20 |
| Marker 15 | UNNAMED |  |  |  | 29 |  |  | 30 |
| Marker 18 | DKFZp564E1363 | 841067 | AL110137 | 5817032 | 35 |  |  | 36 |
| Marker 19 | clone 25242 mRNA | 795821 | AF131854 | 4406700 | 37 |  |  | 38 |
| Marker 28 | UNNAMED | 754126 |  |  | 55 |  |  | 56 |
| Marker 45 | UNNAMED | 771301 |  |  | 89 |  |  | 90 |

What is claimed:

1. A method of assessing whether a patient is afflicted with breast cancer, the method comprising:
   a) determining the level of expression of a LIV-1 marker in a patient sample, wherein the LIV-1 marker comprises SEQ ID NO:51 or SEQ ID NO:52, and
   b) determining the level of expression of the LIV-1 marker in a control non-breast cancer sample,
   c) comparing the level of expression of the LIV-1 marker in the patient sample and the level of expression of the marker in the control sample, wherein an increase in the level of expression of the LIV-1 marker in the patient sample as compared to the level of expression of the LIV-1 marker in the control sample is an indication that the patient is afflicted with breast cancer.

2. The method of claim 1, wherein the level of expression of the LIV-1 marker in the patient sample is assessed by detecting the presence of a LIV-1 marker protein in the sample.

3. The method of claim 2, wherein the presence of the LIV-1 marker is detected using a reagent which specifically binds to SEQ ID NO:52, wherein the reagent is selected from the group consisting of an antibody, an antibody derivative, an antigen-binding antibody fragment, and a non-antibody peptide which specifically binds the protein.

4. The method of claim 3, wherein the reagent is labelled.

5. The method of claim 4, wherein the label is selected from the group consisting of a radio-label, a chromophore-label, a fluorophore-label, an enzyme label, and a biotin-label.

6. The method of claim 3, wherein the antibody, antibody derivative or antigen-binding antibody fragment, is a monoclonal antibody or a polyclonal antibody.

7. The method of claim 1, wherein the LIV-1 marker comprises a transcribed polynucleotide or portion thereof.

8. The method of claim 7, wherein the transcribed polynucleotide or portion thereof is a mRNA or a cDNA.

9. The method of claim 7, wherein the step of detecting a transcribed polynucleotide further comprises amplifying the transcribed polynucleotide.

10. The method of claim 1, wherein the level of expression of the LIV-1 marker in the patient sample differs from the level of expression of the marker in the control sample by a factor selected from the group consisting of: a factor of at least about 2, a factor of at least about 3, a factor of at least about 4, and a factor of at least about 5.

11. The method of claim 1, wherein the level of expression of the LIV-1 marker in the patient sample is assessed using a technique selected from the group consisting of: Northern hybridization, polymerase chain reaction analysis, RT-PCR, probe array and in situ hybridization.

12. The method of claim 1, wherein the patient sample comprises a breast-associated body fluid.

13. The method of claim 12, wherein the breast-associated body fluid is selected from the group consisting of blood, breast fluid, lymph fluid, cystic fluid, nipple aspirates, and fluid collected from a lump biopsy.

14. The method of claim 1, wherein the level of expression of the marker in the patient sample is assessed using a technique selected from the group consisting of: enzyme immunoassay, radioimmunoassay, Western blot analysis, enzyme linked immunoabsorbant assay (ELISA) immunoprecipitation and immunoflourescence.

* * * * *

```
                        SEQUENCE LISTING

<160> NUMBER OF SEQ ID NOS: 112

<210> SEQ ID NO 1
<211> LENGTH: 4275
<212> TYPE: DNA
<213> ORGANISM: Homo sapiens
<220> FEATURE:
<221> NAME/KEY: misc_feature
<222> LOCATION: 4241, 4243, 4244, 4246, 4247, 4250, 4253, 4254, 4255,
      4259, 4260, 4261, 4262, 4263, 4266, 4270, 4271, 4272, 4273
<223> OTHER INFORMATION: n = A,T,C or G

<400> SEQUENCE: 1
ccgggccagg cgcggagctg gcggcagtga caggaggcgc gaacccgcag cgcttaccgc      60
gcggcgccgc accatggagc ccgccgtgtc gctggccgtg tgcgcgctgc tcttcctgct     120
gtgggtgcgc ctgaagggc tggagttcgt gctcatccac cagcgctggg tgttcgtgtg     180
cctcttcctc ctgccgctct cgcttatctt cgatatctac tactacgtgc gcgcctgggt     240
ggtgttcaag ctcagcagcg ctccgcgcct gcacgagcag cgcgtgcggg acatccagaa     300
gcaggtgcgg gaatggaagg agcagggtag caagaccttc atgtgcacgg ggcgccctgg     360
ctggctcact gtctcactac gtgtcgggaa gtacaagaag acacacaaaa acatcatgat     420
caacctgatg gacattctgg aagtggacac caagaaacag attgtccgtg tggagccctt     480
ggtgaccatg ggccaggtga ctgccctgct gacctccatt ggctggactc tccccgtgtt     540
gcctgagctt gatgacctca cagtgggggg cttgatcatg ggcacaggca tcgagtcatc     600
atcccacaag tacggcctgt tccaacacat ctgcactgct tacgagctgg tcctggctga     660
tggcagcttt gtgcgatgca ctccgtccga aaactcagac ctgttctatg ccgtaccctg     720
gtcctgtggg acgctgggtt tcctggtggc cgctgagatc cgcatcatcc ctgccaagaa     780
gtacgtcaag ctgcgtttcg agccagtgcg gggcctggag gctatctgtg ccaagttcac     840
ccacgagtcc cagcggcagg agaaccactt cgtggaaggg ctgctctact ccctggatga     900
ggctgtcatt atgacagggg tcatgacaga tgaggcagag cccagcaagc tgaatagcat     960
```

```
tggcaattac tacaagccgt ggttctttaa gcatgtggag aactatctga agacaaaccg   1020
agagggcctg gagtacattc ccttgagaca ctactaccac cgccacacgc gcagcatctt   1080
ttgggagctc caggacatca tcccctttgg caacaacccc atcttccgct acctctttgg   1140
ctggatggtg cctcccaaga tctccctcct gaagctgacc cagggtgaga ccctgcgcaa   1200
gctgtacgag cagcaccacg tggtgcagga catgctggtg cccatgaagt gcctgcagca   1260
ggccctgcac accttccaaa acgacatcca cgtctacccc atctggctgt gtccgttcat   1320
cctgcccagc cagccaggcc tagtgcaccc caaaggaaat gaggcagagc tctacatcga   1380
cattggagca tatggggagc cgcgtgtgaa acactttgaa gccaggtcct gcatgaggca   1440
gctggagaag tttgtccgca gcgtgcatgg cttccagatg ctgtatgccg actgctacat   1500
gaaccgggag gagttctggg agatgtttga tggctccttg taccacaagc tgcgagagaa   1560
gctgggttgc caggacgcct tccccgaggt gtacgacaag atctgcaagg ccgccaggca   1620
ctgagctgga gcccgcctgg agagacagac acgtgtgagt ggtcaggcat cttcccttca   1680
ctcaagcttg gctgctttcc tagatccaca cttcaaaga gaaaccctc cagaactccc    1740 accctgacag cccaacacca ccttcctcct ggcttccagg gggcagccca gtggaatgga   1800
aagaatgtgg gatttggagt cagacaagcc tgagtccagt tccccgttta gaactcatta   1860
gctgtgtgac tctgggtgag tcccttaacc cctctgagcc cgggtctctt cattagttga   1920
aagggatagt aatacctact gcaggttgt tgtcatctga gttgagcact ggtcacattg     1980
aaggtgctgg gtaagtggta gctcttgttg cttcccgttc agcgtcacat ctgcagtgga   2040
gcctgaaaag gctccacatt aggtcacctg tgcacagcca tggctggaat gatgaagggg   2100
atacgctgga gttgccctgc catcgcctcc atcagccaga cgaggtcctc acaggagaag   2160
gacagctctt ccccaccctg ggatctcagg agggcagcca cggagtgggg aggccccaga   2220
tgcgctgtgc caaagccagg tccgaggcca aagttctccc tgccatcctt ggtgccgtcc   2280
tgccccttcc tccttcatgc ctgggcctgc aggcccaccc cagccaccac tgagtccact   2340
cggagtgccc tgtgttcctg gagaaggcat tccagggttg aatcttgtcc cagcctcagc   2400
ctgggacacc taggtggaga gagtggtctc cgctctgaat tggatccagg ggacctgggc   2460
tcattcttct tggctcacca accctgcagg cctcatcttt cccaaaaccc actttgtctt   2520
ggtgggagtg ggtccgcgct gctctgcagc aggggctggg gagtggacag catcaggtgg   2580
gaaagtggag tccaccctca tgtttctgta ggattctcac cgtggggctg gaagaaaaga   2640
gcatcgactt gatttctcca accactcatc cctcttttc tttcttccac cactcccac     2700 cccagctgta gttaatttca gtgccttaca aatcctaagc tcagagaaag ttccatttcc   2760
gttccagagg gaagggaacc tccctaggtc cttccctggc ttgttataac gcaaagcttg   2820
gttgtttatg caactctatc ttaagaactg cccagcctca gctgaaaacc cgaatctgag   2880
aaggaattgc gtcatgtaag ggaagctgga attaagggag ctgagccagt catggttgtg   2940
gcgtgtgagt caggagacct aggtttcagc ccctctctac tgtcagcgag ctgtgcaacg   3000
tgggcaagtc attgtcctct gagctgcagt ttcctcatct gtcacatcgc tacagacaag   3060
acctccctgg aacccttctg attgtcttag acactgtggt tgcaaaccc acggaaagcc     3120 tcatttgtgt ggaaagtcag aggaaaaatg atccagtgga cacttgggga ttatctgtca   3180
ttcaagatcc ttccttcaac cccaaggtca gctcccatct catttccaga aaggctcata   3240
cctggcttgc agggaagcat ctgtcttgtc attccaggtg ccagaatcct ctcagagtca   3300
ttgaagggtg ttcacccatc ccacccaagg cttggcacac tgccagtgtc ttagcagggt   3360
```

```
cttgtgaggg ctgggggcat ccaggcactc agaaggcaaa ggaaccaccc tacccatttg   3420
gcctctggag ggggcagaag aaagaaagaa acctcatcct atattttaca aagcatgtga   3480
attctggcat tagctctcat aggagaccca tgtgcttcct tgctcagtgc aaaactgatg   3540
attctacttg ctgtagatga atggttaaca cgagctagtt aaacagtgcc attgttttgc   3600
cagtgaagcc tccaaccta agccactggg acggtggcca gagatgccag cagcctctgt    3660
```

```
cgcccttagt catataacca aaatccagac cttatccaca acccggggct tggaaaggaa   3720
ggtattttgg aatcacaccc tccggttatg ttgctccagt aaaatcttgc ctggaaagag   3780
gcagtcttct tagcatggtg agctgagttc atggcttttt tttgtagcca gtcctgtccc   3840
tggccatcca tgtgatggtt ttggatggag ttaaacttga tgccagtggg cagtgcatgt   3900
ggaaagtatc agagtaagcc tctcccctcc agagccctga gtttcttggc tgcatgaagg   3960
ttttctttag aatcagaatt gtagccagtt tctttggcca aaggatgaa tacttggata    4020 ttactgaaag ggaggggtgg agatgggtgt ggcagtgtat ggtgtgtgat ttttattttc   4080
ttctttggtc atgggggcca aggagaaagg catgaatctt ccctgtcagg ctcttacagc   4140
cacaggcact gtgtctactg tctggaagac atgtccccgt ggctgtgggg ccgctgcttc   4200
tgtttaaata aaagtggcct ggaaaaaaaa aaaaaaaaa ngnnannstn yknnnctknn   4260
nnngtnhgsn nnnts                                                    4275
```

<210> SEQ ID NO 2
<211> LENGTH: 516
<212> TYPE: PRT
<213> ORGANISM: Homo sapiens

<400> SEQUENCE: 2

Met Glu Pro Ala Val Ser Leu Ala Val Cys Ala Leu Leu Phe Leu Leu
1               5                   10                  15

Trp Val Arg Leu Lys Gly Leu Glu Phe Val Leu Ile His Gln Arg Trp
            20                  25                  30

Val Phe Val Cys Leu Phe Leu Leu Pro Leu Ser Leu Ile Phe Asp Ile
        35                  40                  45

Tyr Tyr Tyr Val Arg Ala Trp Val Val Phe Lys Leu Ser Ser Ala Pro
    50                  55                  60

Arg Leu His Glu Gln Arg Val Arg Asp Ile Lys Gln Val Arg Glu
65                  70                  75                  80

Trp Lys Glu Gln Gly Ser Lys Thr Phe Met Cys Thr Gly Arg Pro Gly
                85                  90                  95

Trp Leu Thr Val Ser Leu Arg Val Gly Lys Tyr Lys Thr His Lys
            100                 105                 110

Asn Ile Met Ile Asn Leu Met Asp Ile Leu Glu Val Asp Thr Lys Lys
        115                 120                 125

Gln Ile Val Arg Val Glu Pro Leu Val Thr Met Gly Gln Val Thr Ala
    130                 135                 140

Leu Leu Thr Ser Ile Gly Trp Thr Leu Pro Val Leu Pro Glu Leu Asp
145                 150                 155                 160

Asp Leu Thr Val Gly Gly Leu Ile Met Gly Thr Gly Ile Glu Ser Ser
                165                 170                 175

Ser His Lys Tyr Gly Leu Phe Gln His Ile Cys Thr Ala Tyr Glu Leu
            180                 185                 190

Val Leu Ala Asp Gly Ser Phe Val Arg Cys Thr Pro Ser Glu Asn Ser
        195                 200                 205

```
Asp Leu Phe Tyr Ala Val Pro Trp Ser Cys Gly Thr Leu Gly Phe Leu
        210                 215                 220
Val Ala Ala Glu Ile Arg Ile Ile Pro Ala Lys Lys Tyr Val Lys Leu
225                 230                 235                 240
Arg Phe Glu Pro Val Arg Gly Leu Glu Ala Ile Cys Ala Lys Phe Thr
                245                 250                 255
His Glu Ser Gln Arg Gln Glu Asn His Phe Val Glu Gly Leu Leu Tyr
            260                 265                 270
Ser Leu Asp Glu Ala Val Ile Met Thr Gly Val Met Thr Asp Glu Ala
        275                 280                 285
Glu Pro Ser Lys Leu Asn Ser Ile Gly Asn Tyr Tyr Lys Pro Trp Phe
290                 295                 300
Phe Lys His Val Glu Asn Tyr Leu Lys Thr Asn Arg Glu Gly Leu Glu
305                 310                 315                 320
Tyr Ile Pro Leu Arg His Tyr Tyr His Arg Thr Arg Ser Ile Phe
                325                 330                 335
Trp Glu Leu Gln Asp Ile Ile Pro Phe Gly Asn Asn Pro Ile Phe Arg
            340                 345                 350
Tyr Leu Phe Gly Trp Met Val Pro Pro Lys Ile Ser Leu Leu Lys Leu
        355                 360                 365
Thr Gln Gly Glu Thr Leu Arg Lys Leu Tyr Glu Gln His His Val Val
    370                 375                 380
Gln Asp Met Leu Val Pro Met Lys Cys Leu Gln Gln Ala Leu His Thr
385                 390                 395                 400
Phe Gln Asn Asp Ile His Val Tyr Pro Ile Trp Leu Cys Pro Phe Ile
                405                 410                 415
Leu Pro Ser Gln Pro Gly Leu Val His Pro Lys Gly Asn Glu Ala Glu
            420                 425                 430
Leu Tyr Ile Asp Ile Gly Ala Tyr Gly Glu Pro Arg Val Lys His Phe
        435                 440                 445
Glu Ala Arg Ser Cys Met Arg Gln Leu Glu Lys Phe Val Arg Ser Val
    450                 455                 460
His Gly Phe Gln Met Leu Tyr Ala Asp Cys Tyr Met Asn Arg Glu Glu
465                 470                 475                 480
Phe Trp Glu Met Phe Asp Gly Ser Leu Tyr His Lys Leu Arg Glu Lys
                485                 490                 495
Leu Gly Cys Gln Asp Ala Phe Pro Glu Val Tyr Asp Lys Ile Cys Lys
            500                 505                 510
Ala Ala Arg His
        515

<210> SEQ ID NO 3
<211> LENGTH: 2342
<212> TYPE: DNA
<213> ORGANISM: Homo sapiens

<400> SEQUENCE: 3
gtcgacccac gcgtccggca gggccaacag tcacagcagc cctgaccaga gcattcctgg      60
agctcaagct cctctacaaa gaggtggaca gagaagacag cagagaccat gggaccccc     120 tcagccctc cctgcagatt gcatgtcccc tggaaggagg tcctgctcac agcctcactt     180
ctaaccttct ggaacccacc caccactgcc aagctcacta ttgaatccac gccgttcaat     240
gtcgcagagg ggaaggaggt tcttctactc gcccacaacc tgccccagaa tcgtattggt     300
tacagctggt acaaaggcga aagagtggat ggcaacagtc taattgtagg atatgtaata     360
```

```
ggaactcaac aagctacccc agggcccgca tacagtggtc gagagacaat atacccccaat    420
gcatccctgc tgatccagaa cgtcacccag aatgacacag gattctatac cctacaagtc    480
ataaagtcag atcttgtgaa tgaagaagca accggacagt tccatgtata cccggagctg    540
cccaagccct ccatctccag caacaactcc aaccccgtgg aggacaagga tgctgtggcc    600
ttcacctgtg aacctgaggt tcagaacaca acctacctgt ggtgggtaaa tggtcagagc    660
ctcccggtca gtcccaggct gcagctgtcc aatggcaaca tgaccctcac tctactcagc    720
gtcaaaagga acgatgcagg atcctatgaa tgtgaaatac agaacccagc gagtgccaac    780
cgcagtgacc cagtcacccct gaatgtcctc tatggcccag atggcccccac catttccccc    840
tcaaaggcca attaccgtcc aggggaaaat ctgaacctct cctgccacgc agcctctaac    900
ccacctgcac agtactcttg gtttatcaat gggacgttcc agcaatccac acaagagctc    960
tttatcccca acatcactgt gaataatagc ggatcctata tgtgccaagc ccataactca    1020
gccactggcc tcaataggac cacagtcacg atgatcacag tctctggaag tgctcctgtc    1080
ctctcagctg tggccaccgt cggcatcacg attggagtgc tggccagggt ggctctgata    1140
tagcagccct ggtgtatttt cgatatttca ggaagactgg cagattggac cagaccctga    1200
attcttctag ctcctccaat cccatttat cccatggaac cactaaaaac aaggtctgct    1260
ctgctcctga agccctatat gctggagatg acaactcaa tgaaaattta aagggaaaac    1320
cctcaggcct gaggtgtgtg ccactcagag acttcaccta actagagaca gcaaactgc    1380
aaaccatggt gagaaattga cgacttcaca ctatggacag ctttccccaa gatgtcaaaa    1440
caagactcct catcatgata aggctcttac cccttttaa tttgtccttg cttatgcctg    1500
cctctttcgc ttggcaggat gatgctgtca ttagtatttc acaagaagta gcttcagagg    1560
gtaacttaac agagtatcag atctatcttg tcaatcccaa cgttttacat aaaataagag    1620
atcctttagt gcacccagtg actgacatta gcagcatctt taacacagcc gtgtgttcaa    1680
atgtacagtg gtccttttca gagttggact tctagactca cctgttctca ctccctgttt    1740
taattcaacc cagccatgca atgccaaata atagaattgc tccctaccag ctgaacaggg    1800
aggagtctgt gcagtttctg acacttgttg ttgaacatgg ctaaatacaa tgggtatcgc    1860
tgagactaag ttgtagaaat taacaaatgt gctgcttggt taaatggct acactcatct    1920
gactcattct ttattctatt ttagttggtt tgtatcttgc ctaaggtgcg tagtccaact    1980
cttggtatta ccctcctaat agtcatacta gtagtcatac tccctggtgt agtgtattct    2040
ctaaaagctt taaatgtctg catgcagcca gccatcaaat agtgaatggt ctctcttttgg    2100
ctggaattac aaaactcaga gaaatgtgtc atcaggagaa catcataacc catgaaggat    2160
aaaagcccca aatggtggta actgataata gcactaatgc tttaagattt ggtcacactc    2220
tcacctaggt gagcgcattg agccagtggt gctaaatgct acatactcca actgaaatgt    2280
taaggaagaa gatagatcca attaaaaaaa aaaaaaaaaa aaaaaaaaaa aagggcggcc    2340
gc                                                                  2342
```

```
<210> SEQ ID NO 4
<211> LENGTH: 344
<212> TYPE: PRT
<213> ORGANISM: Homo sapiens

<400> SEQUENCE: 4

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
```

```
            20                  25                  30
Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 5
<211> LENGTH: 2557
<212> TYPE: DNA
<213> ORGANISM: Homo sapiens
<220> FEATURE:
<221> NAME/KEY: misc_feature
<222> LOCATION: 47, 2120, 2127, 2131, 2135, 2143, 2144, 2162, 2166,
      2172, 2186, 2192, 2200, 2219, 2246, 2265, 2375, 2376, 2377, 2411,
      2439, 2456, 2457, 2458, 2461, 2462, 2552, 2553, 2554, 2555,
      2556, 2557
<223> OTHER INFORMATION: n = A,T,C or G

<400> SEQUENCE: 5
gggcgaaggg gcagccgcag cgcagaggcc cgccccgccc tccccntccg tcacagccca       60
gccttccggc ccttgggctg ctcgcggcct tttttttccg gctgggctcg ggctcagctc      120
```

```
gactgggctc ggcgggcggc ggcggcggcg ccggcggctg gcggaggagg gagggcgagg      180
gcgggcgcgg gccggcgggc gggcggaaga gggaggagag gcgcggggag ccaggcctcg      240
gggcctcgga gcaaccaccc gagcagacgg agtacacgga gcagcggccc cggccccgcc      300
aacgctgccg ccgggatgct ccagaccttg tatgattact tctggtggga acgtctgtgg      360
ctgcctgtga acttgacctg ggccgatcta gaagaccgag atggacgtgt ctacgccaaa      420
gcctcagatc tctatatcac gctgccctg gccttgctct tcctcatcgt tcgatacttc      480
tttgagctgt acgtgctac accactggct gccctcttga acataaagga gaaaactcgg      540
ctgcgggcac ctcccaacgc caccttggaa catttctacc tgaccagtgg caagcagccc      600
aagcaggtgg aagtagagct tttgtcccgg cagagcgggc tctctggccg ccaggtagag      660
cgttggttcc gtcgccgccg caaccaggac cggcccagtc cctcaagaa gttccgagaa      720 gccagctgga gattcacatt ttacctgatt gccttcattg ccggcatggc cgtcattgtg      780
gataaaccct ggttctatga catgaagaaa gtttgggagg gatatcccat acagagcact      840
atcccttccc agtattggta ctacatgatt gaactttcct tctactggtc cctgctcttc      900
agcattgcct ctgatgtcaa gcgaaggat ttcaaggaac agatcatcca ccatgtggcc      960
accatcattc tcatcagctt ttcctggttt gccaattaca tccgagctgg gactctaatc     1020
atggctctgc atgactcttc cgattacctg ctggagtcag ccaagatgtt taactacgcg     1080
ggatggaaga cacctgcaa caacatcttc atcgtcttcg ccattgtttt tatcatcacc     1140
cgactggtca tcctgccctt ctggatcctg cattgcaccc tggtgtaccc actggagctc     1200
tatcctgcct tctttggcta ttacttcttc aattccatga tgggagttct acagctgctg     1260
catatcttct gggcctacct cattttgcgc atggcccaca agttcataac tggaaagctg     1320
gtagaagatg aacgcagtga ccgggaagaa acagagagct cagaggggga ggaggctgca     1380
gctgggggag gagcaaagag ccggccccta gccaatggcc accccatcct caataacaac     1440
catcgtaaga atgactgaac cattattcca gctgcctccc agattaatgc ataaagccaa     1500
ggaactaccc cgctccctgc gctatagggt cactttaagc tctggggaaa aggagaaag     1560 tgagaggaga gttctctgca tcctccctcc ttgcttgtca cccagttgcc tttaaaccaa     1620
attctaacca gccatccccc aggtaggggg acgttggtta tattctgtta gaggggacg      1680 gtcgtatttt cctccctacc cgccaagtca tccttctac tgcttttgag gccctccctc      1740
agctctctgt gggtaggggt tacaattcac attccttatt ctgagaattt ggccccagct     1800
gtttgccttt gactccctga cctccagagc cagggttgtg ccttattgtc ccatctgtgg     1860
gcctcattct gccaaagctg gaccaaggct aaccttcta agctccctaa cttgggccag      1920
aaaccaaagc tgagctttta actttctccc tctatgacac aaatgaattg agggtaggag     1980
gagggtgcac ataaccctta ccctaccctct gccaaaaagt gggggctgta ctggggactg     2040
ctcggatgat ctttcttagt gctacttctt tcagctgtcc ctgtagcgac aggtctaaga     2100
tctgactgcc tcctcctctn ctctggncct ncttncccc ttnncctct tctcttcagc       2160 tnaggnctag cntggtttgg agtagnaatg gncaactaan ttctaattt tatttattna      2220 aatatttggg gttttggttt taaagnccag aattacggct agcancctag catttcagca     2280
gagggaccat tttagaccaa aatgtactgt taatgggttt tttttaaaa ttaaaagatt      2340 aaataaaaaa tattaaataa aaaaaaaaaa taagnnccag actattagga attgagaagg     2400
gggatcaact naaataaacg aagagagtct ttcttatgnm tgccttavma aaaaannncc     2460
nnacaaaaaa acggggggg ggccttacaa attttaaaaa aaaaccccc cccccccc        2520
```
cccggaaccg aaaaaaaaaa aaaagcccca annnnnn                                2557

<210> SEQ ID NO 6
<211> LENGTH: 380
<212> TYPE: PRT
<213> ORGANISM: Homo sapiens

<400> SEQUENCE: 6

Met Leu Gln Thr Leu Tyr Asp Tyr Phe Trp Trp Glu Arg Leu Trp Leu
 1               5                  10                  15

Pro Val Asn Leu Thr Trp Ala Asp Leu Glu Asp Arg Asp Gly Arg Val
            20                  25                  30

Tyr Ala Lys Ala Ser Asp Leu Tyr Ile Thr Leu Pro Leu Ala Leu Leu
        35                  40                  45

Phe Leu Ile Val Arg Tyr Phe Phe Glu Leu Tyr Val Ala Thr Pro Leu
    50                  55                  60

Ala Ala Leu Leu Asn Ile Lys Glu Lys Thr Arg Leu Arg Ala Pro Pro
65                  70                  75                  80

Asn Ala Thr Leu Glu His Phe Tyr Leu Thr Ser Gly Lys Gln Pro Lys
                85                  90                  95

Gln Val Glu Val Glu Leu Leu Ser Arg Gln Ser Gly Leu Ser Gly Arg
            100                 105                 110

Gln Val Glu Arg Trp Phe Arg Arg Arg Asn Gln Asp Arg Pro Ser
        115                 120                 125

Leu Leu Lys Lys Phe Arg Glu Ala Ser Trp Arg Phe Thr Phe Tyr Leu
    130                 135                 140

Ile Ala Phe Ile Ala Gly Met Ala Val Ile Val Asp Lys Pro Trp Phe
145                 150                 155                 160

Tyr Asp Met Lys Lys Val Trp Glu Gly Tyr Pro Ile Gln Ser Thr Ile
                165                 170                 175

Pro Ser Gln Tyr Trp Tyr Tyr Met Ile Glu Leu Ser Phe Tyr Trp Ser
            180                 185                 190

Leu Leu Phe Ser Ile Ala Ser Asp Val Lys Arg Lys Asp Phe Lys Glu
        195                 200                 205

Gln Ile Ile His His Val Ala Thr Ile Ile Leu Ile Ser Phe Ser Trp
    210                 215                 220

Phe Ala Asn Tyr Ile Arg Ala Gly Thr Leu Ile Met Ala Leu His Asp
225                 230                 235                 240

Ser Ser Asp Tyr Leu Leu Glu Ser Ala Lys Met Phe Asn Tyr Ala Gly
                245                 250                 255

Trp Lys Asn Thr Cys Asn Asn Ile Phe Ile Val Phe Ala Ile Val Phe
            260                 265                 270

Ile Ile Thr Arg Leu Val Ile Leu Pro Phe Trp Ile Leu His Cys Thr
        275                 280                 285

Leu Val Tyr Pro Leu Glu Leu Tyr Pro Ala Phe Gly Tyr Tyr Phe
    290                 295                 300

Phe Asn Ser Met Met Gly Val Leu Gln Leu Leu His Ile Phe Trp Ala
305                 310                 315                 320

Tyr Leu Ile Leu Arg Met Ala His Lys Phe Ile Thr Gly Lys Leu Val
                325                 330                 335

Glu Asp Glu Arg Ser Asp Arg Glu Glu Thr Glu Ser Ser Glu Gly Glu
            340                 345                 350

Glu Ala Ala Ala Gly Gly Gly Ala Lys Ser Arg Pro Leu Ala Asn Gly
        355                 360                 365

His Pro Ile Leu Asn Asn Asn His Arg Lys Asn Asp
       370                 375                 380

<210> SEQ ID NO 7
<211> LENGTH: 1861
<212> TYPE: DNA
<213> ORGANISM: Homo sapiens
<220> FEATURE:
<221> NAME/KEY: misc_feature
<222> LOCATION: 1249
<223> OTHER INFORMATION: n = A,T,C or G

<400> SEQUENCE: 7

| | | | | | |
|---|---|---|---|---|---|
| aagcgggcvc | gagccgccgc | gcgcgcgccg | cgcactgcag | ccccaggccc | cggccccccca | 60 |
| cccacgtctg | cgttgctgcc | ccgcctgggc | cgggccccaa | aggcaaggac | aaagcagctg | 120 |
| tcagggaacc | tccgccggag | tcgaatttac | gtgcagctgc | cggcaaccac | aggttccaag | 180 |
| atggtttgcg | ggggcttcgc | gtgttccaag | aactgcctgt | gcgccctcaa | cctgctttac | 240 |
| accttggtta | gtctgctgct | aattggaatt | gctgcgtggg | gcattggctt | cgggctgatt | 300 |
| tccagtctcc | gagtggtcgg | cgtggtcatt | gcagtgggca | tcttcttgtt | cctgattgct | 360 |
| ttagtgggtc | tgattggagc | tgtaaaacat | catcaggtgt | tgctatttt | ttatatgatt | 420 |
| attctgttac | ttgtatttat | tgttcagttt | tctgtatctt | gcgcttgttt | agccctgaac | 480 |
| caggagcaac | agggtcagct | tctggaggtt | ggttggaaca | atacggcaag | tgctcgaaat | 540 |
| gacatccaga | gaaatctaaa | ctgctgtggg | ttccgaagtg | ttaacccaaa | tgacacctgt | 600 |
| ctggctagct | gtgttaaaag | tgaccactcg | tgctcgccat | gtgctccaat | cataggagaa | 660 |
| tatgctggag | aggttttgag | atttgttggt | ggcattggcc | tgttcttcag | ttttacagag | 720 |
| atcctgggtg | tttggctgac | ctacagatac | aggaaccaga | aagaccccg | cgcgaatcct | 780 |
| agtgcattcc | tttgatgaga | aaacaaggaa | gatttccttt | cgtattatga | tcttgttcac | 840 |
| tttctgtaat | tttctgttaa | gctccatttg | ccagtttaag | gaaggaaaca | ctatctggaa | 900 |
| aagtacctta | ttgatagtgg | aattatatat | ttttactcta | tgtttctcta | catgtttttt | 960 |
| tctttccgtt | gctgaaaaat | atttgaaact | tgtggtctct | gaagctcggt | ggcacctgga | 1020 |
| atttactgta | ttcattgtcg | ggcactgtcc | actgtggcct | ttcttagcat | ttttacctgc | 1080 |
| agaaaaactt | tgtatggtac | cactgtgttg | gttatatggt | gaatctgaac | gtacatctca | 1140 |
| ctggtataat | tatatgtagc | actgtgctgt | gtagatagtt | cctactggaa | aaagagtgga | 1200 |
| aatttattaa | aatcagaaag | tatgagatcc | tgttatgtta | agggaaatnc | caaattccca | 1260 |
| attttttttg | gtcttttttag | gaaagatgtg | ttgtggtaaa | aagtgttagt | ataaaaatga | 1320 |
| taatttactt | gtagtctttt | atgattacac | caatgtattc | tagaaatagt | tatgtcttag | 1380 |
| gaaattgtgg | tttaattttt | gactttaca | ggtaagtgca | aaggaaaagt | ggtttcatga | 1440 |
| aatgttctaa | tgtataataa | catttaccct | cagcctccat | ccagaatgga | acggagtttt | 1500 |
| gagtaatcca | gggaagtata | tctatatgat | cttgatattg | ttttataata | atttgaagtc | 1560 |
| taaaagactg | cattttaaa | caagttagta | ttaatgcgtt | ggcccacgta | gcaaaaagat | 1620 |
| atttgattat | cttaaaaatt | gttaaatacc | gttttcatga | aakttctcag | tattgtaaca | 1680 |
| gcaacttgtc | aaacctaagc | gatatttgaa | tatgatctcc | cataatttga | aattgaaatc | 1740 |
| gtattgtgtg | gctctgtata | ttctgttaaa | aaattaaagg | acagaaacct | ttctttgtgt | 1800 |
| atgcatgttt | gaattaaaag | aaagtaatgg | aagaattgww | mrawraaaaa | aaaaaaaaaa | 1860 |
| a | | | | | | 1861 |

<210> SEQ ID NO 8
<211> LENGTH: 204
<212> TYPE: PRT
<213> ORGANISM: Homo sapiens

<400> SEQUENCE: 8

Met Val Cys Gly Gly Phe Ala Cys Ser Lys Asn Cys Leu Cys Ala Leu
 1               5                  10                  15

Asn Leu Leu Tyr Thr Leu Val Ser Leu Leu Ile Gly Ile Ala Ala
             20                  25                  30

Trp Gly Ile Gly Phe Gly Leu Ile Ser Ser Leu Arg Val Gly Val
         35                  40                  45

Val Ile Ala Val Gly Ile Phe Leu Phe Leu Ile Ala Leu Val Gly Leu
 50                  55                  60

Ile Gly Ala Val Lys His His Gln Val Leu Leu Phe Phe Tyr Met Ile
 65                  70                  75                  80

Ile Leu Leu Leu Val Phe Ile Val Gln Phe Ser Val Ser Cys Ala Cys
                 85                  90                  95

Leu Ala Leu Asn Gln Glu Gln Gly Gln Leu Leu Glu Val Gly Trp
            100                 105                 110

Asn Asn Thr Ala Ser Ala Arg Asn Asp Ile Gln Arg Asn Leu Asn Cys
            115                 120                 125

Cys Gly Phe Arg Ser Val Asn Pro Asn Asp Thr Cys Leu Ala Ser Cys
        130                 135                 140

Val Lys Ser Asp His Ser Cys Ser Pro Cys Ala Pro Ile Ile Gly Glu
145                 150                 155                 160

Tyr Ala Gly Glu Val Leu Arg Phe Val Gly Gly Ile Gly Leu Phe Phe
                165                 170                 175

Ser Phe Thr Glu Ile Leu Gly Val Trp Leu Thr Tyr Tyr Arg Asn
            180                 185                 190

Gln Lys Asp Pro Arg Ala Asn Pro Ser Ala Phe Leu
        195                 200

<210> SEQ ID NO 9
<211> LENGTH: 3579
<212> TYPE: DNA
<213> ORGANISM: Homo sapiens
<220> FEATURE:
<221> NAME/KEY: misc_feature
<222> LOCATION: 3350, 3546
<223> OTHER INFORMATION: n = A,T,C or G

<400> SEQUENCE: 9
ccgaaaaaat cttagtgtct gcaaaacagg tgggtttaag atttattgat attagggaaa      60
gtgaaattaa tgagctactc aagtttctgt ctttggtcat cactgagagt ctatttccat     120
aggaagaagt ctttgcagag gaaattgaat gctgtctgat gctacaattc atatggatcc     180
tttcctggat tgaagcctga cttttaaaaa aggtttcaat aaattgctta tacctatgaa     240
gagatgcaaa agaaccttca aaataaagca aaggacttga agaaagagaa ggaagacatg     300
aagaagagga tgtcatttag gtgaagggcc atgctggata aggagctggc tgcctctgtg     360
aacatcctac tcaaggcatc ttcactgctg tacatccttt tgaaatccca gagatcttca     420
gtctccctgt ggattaagga gatgtgcagt atttaaagtg gcttcaggaa ggcatggaag     480
aggactgagt gggaaagct ttttgtgcat gctgctggct acctccagcg gctgcctcca     540
gcctccatca gctgcactct ggggaagagg aggctgcctt ctacctccca gcatctctgg     600
atttcatgtt cctgtcagca cagaggagct aaatggcctg tagaggctga aggtctgagg     660

```
ctcctaaagc tggaagaaaa ggctgggcca gtcaggccaa gcaagaacac wrwrywwsty    720
gcctgaagtg ccttccatgg ttaaaggggg cctaaagcag gccacaaagg gccatgaagg    780
aatggttaat atgtaacaga ctgaagggga agaaagccag tgaagatgaa gacttgccca    840
tcttccttga agtcagtaag gcctgcctca ggtgcctagg atgtaattgc tctgctgctt    900
ctcatgggga ggagtggccc tcatgacctt gtttacctgg aagagtgtgg gatgaatgcc    960
tcctcctatg gggactcgca agtgctttag caaaaggata aattgctaat tgtggcattt   1020
cgtggatcag caggattatt tctccttgct aaagaggatt ttgttggtcc tgaattctga   1080
ggaggtggga ctaggaatgg gctccatgag cctgtgtatg actcagggaa tattaggact   1140
ttggcacagc ctcatgggtt gggagtaagt cttggctctt ccctagcctg aatgacagac   1200
atcagatcat tctggtgctt tgtccatgaa gatgtagatt ctgagcccac ccaactaatc   1260
ttttcacttg agcacagaaa cagccccggg aatcggacag acccgtgtct ttcaggtttg   1320
cttcacagag ccccaggggt tgacaatagg tgccttggag actgcctgca tggggatttt   1380
taaaaagctt tctttgttaa aggtttgtaa accactcctc tgagcctgtt ttcattttat   1440
agattattca gggaactgaa ctgcacagag atccagaaag tgggtagtgc aggctgtagt   1500
gctgataact actgtactac ttggatcttt gtgctcccaa ataccaaatg gaagaggatc   1560
tctgagagtc ctttgcaaag atcttgtagg gactttaggc tggggccttc ggaaaattcc   1620
agaggattcc aatggagatt ttgagggact gactcagaag aacaaagaga atgataatgg   1680
tgatgtccct gcttttttaca acagatcatg ttctgatata tatgcaaatc tgtgtaaagt   1740
aaaccctacc taaaatgtac tggggaccca agatggactg cctgtattgc ttccaggata   1800
aagtccaatt tctagctctg gtttttataa ccttgcttca gctcaccttt tccgtcatca   1860
tccctccat ctcctctccc acgctgggaa atggatggct gcactatact gtgtgatgtt   1920
attgctatgt tcatgccatc ccctctgcct ggaatgccct tctgcatgaa tgcctgtgaa   1980
atgttgttgc tcctttgtat ggcctggctt ccgtggttgg caggaatctc ttctttcgtg   2040
gtattcctgt catctttgtg catcacagtc agctttgtat tcctagcttg taagctactt   2100
gaggataggg gcatgtctga atctatttaa tctcttgcac ctgtttggca aattgatgtt   2160
ttaagtattt aaataactaa agctctctct acagtacata ctcacttttg atttatgaat   2220
tggcaaaatt caacttttttt ccttgaatat tcttaaagtg agatgaattc caaggagag   2280
tgttctgtgt gtggccttca ttgagtggtt ttctgttacc agaaagctct tggtggcctt   2340
cctcttccct ggtgtcaagg ttgactgtta taggaaatgg gaggggagag ggccgtttct   2400
gccacgcatt gtcctaggtt cttaacatta tttaatcctt ataatgcaat gttatcctca   2460
ttttacagat gaaacctgag accaaagaac atgtaacaca taaagtacat tgcagagtta   2520
ggatgtgaac ccaactctga ttctaaacct aatgctctca ctctttcatt cagaggttca   2580
gtcagttctt tgtaggctgt agatccagag aagctgccgt agccaacaat aaagttgtta   2640
gtttttaaaa catctatgtg gtaagttggt ctggcactta aaaatgtatt gtttcccagg   2700
cacggtggtt cacacctgta atcccagcat tttgggaggc cgaggcaggc ggatcattag   2760
gtcaaaagat tgagaccatc ctgaccaaca tggtgaaacc ccgtctctac taaaagttac   2820
aaaaattagc tgggtgtggt ggcgcatgcc tctagtccca gctacctggg aggctgaggc   2880
aggagaattg cttgaaccca ggaggcagag gttgcagtga gccaagatca tgctactgca   2940
ctacagcctg gcaacaaagc gagactctgt ctaaaatata tatatatata tatatatata   3000
tatatattgt ttactactca ccacagatct gcaggagttc actgatctct aggatctgcc   3060
```

-continued

```
ttaactccaa cttacatgtt ttggtcacta ttacaaactg tcatcccaga atgatgctgc    3120
agaggctagg gctaggacac agaccagtgt ttcccatgtg ggaattccct cccagtattt    3180
cttaggaaat gtatgttttt tgaatccata atccctagaa aaatcagttg aggaaatgag    3240
aagtattgta attattctgt gaatagtaac acttaccatt atggagacat cactagtttg    3300
aaagaatcca acttcatcaa atattaacgt accgagttga aggctacaan gaactgagac    3360
aggagcatag cagagagaaa cggtcaccat ctcattagcc ctattttttgg ttgttgtgat    3420 gccattacat ctgtatatct ggccatatca gctgctaatg gtgagttctt gcaaacaaaa    3480
tgatttgata aacaacctac catactttat acaaatctta tggtgttccg agaaataaac    3540
tttggnaagc aaaataaaaa aaaaaamaaa aaaaaaaag                           3579
```

<210> SEQ ID NO 10
<211> LENGTH: 79
<212> TYPE: PRT
<213> ORGANISM: Homo sapiens

<400> SEQUENCE: 10

```
Met Asp Gly Cys Thr Ile Leu Cys Asp Val Ile Ala Met Phe Met Pro
 1               5                  10                  15

Ser Pro Leu Pro Gly Met Pro Phe Cys Met Asn Ala Cys Glu Met Leu
            20                  25                  30

Leu Leu Leu Cys Met Ala Trp Leu Pro Trp Leu Ala Gly Ile Ser Ser
        35                  40                  45

Phe Val Val Phe Leu Ser Ser Leu Cys Ile Thr Val Ser Phe Val Phe
    50                  55                  60

Leu Ala Cys Lys Leu Leu Glu Asp Arg Gly Met Ser Glu Ser Ile
65                  70                  75
```

<210> SEQ ID NO 11
<211> LENGTH: 1076
<212> TYPE: DNA
<213> ORGANISM: Homo sapiens
<220> FEATURE:
<221> NAME/KEY: misc_feature
<222> LOCATION: 708, 977, 1003, 1028, 1036
<223> OTHER INFORMATION: n = A,T,C or G

<400> SEQUENCE: 11

```
tcgaccacgc gtccggtgcc catctatcag caggctccgg gctgaagatt gcttctcttc      60
tctcctccaa ggtctagtga cggagcccgc gcgcggcgcc accatgcggc agaaggcggt     120
atcgcttttc ttgtgctacc tgctgctctt cacttgcagt ggggtggagg caggtgagaa     180
tgcgggtaag gatgcaggta agaaaaaagtg ctccggagagc tcggacagcg gctccgggtt     240
ctggaaggcc ctgaccttca tggccgtcgg aggaggactc gcagtcgccg ggctgcccgc     300
gctgggcttc accggcgccg gcatcgcggc caactcggtg gctgcctcgc tgatgagctg     360
gtctgcgatc ctgaatgggg gcggcgtgcc cgccgggggg ctagtggcca cgctgcagag     420
cctcggggct ggtggcagca gcgtcgtcat aggtaatatt ggtgccctga tgggctacgc     480
cacccacaag tatctcgata gtgaggagga tgaggagtag ccagcagctc ccagaacctc     540
ttcttccttc ttggcctaac tcttccagtt aggatctaga actttgcctt ttttttttt      600 tttttttttt ttgagatggg ttctcactat attgtccagg ctagagtgca gtggctattc     660
acagatgcga acatagtaca ctgcagcctc caactcctag cctcaggnga tcctcctgtc     720
tcaacctccc aagtaggatt acaagcatgc gccgacgatg cccagaatcc agaactttgt     780
ctatcactct ccccaacaac ctagatgtga aaacagaata aacttcaccc agaaaacaaa     840
```

```
aaaaaaaaaa aagggcggcc gctagactag tctagagaaa aaacctccca cacctccccc      900
tgaacctgaa acataaaatg aatgcaattg ttgttgttaa cttgtttatt gcagcttata      960
atggttacaa ataaagncaa ttagcatcac aaatttcaca aanaaaggca ttttttttcac    1020 tgcattcnta gttggngggt ttggtccaaa actcatcaaa tggtatcttt atcatg         1076
```

<210> SEQ ID NO 12
<211> LENGTH: 138
<212> TYPE: PRT
<213> ORGANISM: Homo sapiens

<400> SEQUENCE: 12

```
Met Arg Gln Lys Ala Val Ser Leu Phe Leu Cys Tyr Leu Leu Leu Phe
 1               5                  10                  15

Thr Cys Ser Gly Val Glu Ala Gly Glu Asn Ala Gly Lys Asp Ala Gly
            20                  25                  30

Lys Lys Lys Cys Ser Glu Ser Ser Asp Ser Gly Ser Gly Phe Trp Lys
        35                  40                  45

Ala Leu Thr Phe Met Ala Val Gly Gly Gly Leu Ala Val Ala Gly Leu
    50                  55                  60

Pro Ala Leu Gly Phe Thr Gly Ala Gly Ile Ala Ala Asn Ser Val Ala
65                  70                  75                  80

Ala Ser Leu Met Ser Trp Ser Ala Ile Leu Asn Gly Gly Gly Val Pro
                85                  90                  95

Ala Gly Gly Leu Val Ala Thr Leu Gln Ser Leu Gly Ala Gly Gly Ser
            100                 105                 110

Ser Val Val Ile Gly Asn Ile Gly Ala Leu Met Gly Tyr Ala Thr His
        115                 120                 125

Lys Tyr Leu Asp Ser Glu Glu Asp Glu Glu
    130                 135
```

<210> SEQ ID NO 13
<211> LENGTH: 1352
<212> TYPE: DNA
<213> ORGANISM: Homo sapiens
<220> FEATURE:
<221> NAME/KEY: misc_feature
<222> LOCATION: 1139, 1140, 1150, 1155, 1166, 1171, 1181, 1186, 1189,
      1212, 1214, 1252, 1311
<223> OTHER INFORMATION: n = A,T,C or G

<400> SEQUENCE: 13

```
tcaccacgcg tccggaagct ccgggtgtcg cggggggcggg aggaattaag ggagggagag     60
aggcgcgcgg gtgaaaggcg cattgatgca gcctgcggcg gcctcggagc gcggcggagc    120
cagacgctga ccacgttcct ctcctcggtc tcctccgcct ccagctccgc gctgcccggc    180
agccgggagc catgcgaccc cagggccccg ccgcctcccc gcagcggctc cgcggcctcc    240
tgctgctcct gctgctgcag ctgcccgcgc cgtcgagcgc ctctgagatc cccaagggga    300
agcaaaaggc gcagctccgg cagagggagg tggtggacct gtataatgga atgtgcttac    360
aagggccagc aggagtgcct ggtcgagacg ggagccctgg ggccaatggc attccgggta    420
cacctgggat cccaggtcgg gatggattca aggagaaaaa gggggaatgt ctgagggaaa    480
gctttgagga gtcctggaca cccaactaca agcagtgttc atggagttca ttgaattatg    540
gcataaatct tgggaaaatt gcggagtgta catttacaaa gatgcgttca atagtgctc     600 taagagtttt gttcagtggc tcacttcggc taaaatgcag aaatgcatgc tgtcagcgtt    660
ggtatttcac attcaatgga gctgaatgtt caggacctct tcccattgaa gctataattt    720
```

-continued

```
atttggacca aggaagccct gaaatgaatt caacaattaa tattcatcgc acttcttctg     780
tggaaggact ttgtgaagga attggtgctg gattagtgga tgttgctatc tgggttggca     840
cttgttcaga ttacccaaaa ggagatgctt ctactggatg gaattcagtt tctcgcatca     900
ttattgaaga actaccaaaa taaatgcttt aattttcatt tgctacctct tttttatta     960 tgccttggaa tggttcactt aaatgacatt ttaaataagt ttatgtatac atctgaatga    1020
aaagcaaagc taaatatgtt tacagaccaa agtgtgattt ccccctgttt ttaaatctag    1080
cattattcat tttgcttcaa tcaaaagtgg tttcaatatt ttttttagtt ggttagaann    1140
ctttcttcan agtcncattc tctcanccta naatttggaa nattgntgng gtcttttgtt    1200
ttttctctta gnanagcatt tttaaaaaaa tataaaagct accaatcttt gnacaatttg    1260
taaatgttaa gaattttttt tatatctgtt aaataaaaat tatttccacc naaaaaaaaa    1320
aaaaaaaaaa aaaaaaaaa gggcggccgc ta                                   1352
```

<210> SEQ ID NO 14
<211> LENGTH: 243
<212> TYPE: PRT
<213> ORGANISM: Homo sapiens

<400> SEQUENCE: 14

```
Met Arg Pro Gln Gly Pro Ala Ala Ser Pro Gln Arg Leu Arg Gly Leu
 1               5                  10                  15

Leu Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
        35                  40                  45

Asp Leu Tyr Asn Gly Met Cys Leu Gln Gly Pro Ala Gly Val Pro Gly
    50                  55                  60

Arg Asp Gly Ser Pro Gly Ala Asn Gly Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asn Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys
```

<210> SEQ ID NO 15

<211> LENGTH: 2142
<212> TYPE: DNA
<213> ORGANISM: Homo sapiens

<400> SEQUENCE: 15

| | | | | | |
|---|---|---|---|---|---|
| ggagtcgacc | cacgcgtccg | ccccggggga | cccgccgccc | agctcccgag | ggtgcggcag | 60 |
| cctctggcca | ctcagccggg | gccgagaggg | agctgccggg | cggggaggcg | ccgcaggcac | 120 |
| ccggcgggca | gggcggggca | gggcaagacg | gccgcctccg | caagtgccac | ccggcccacc | 180 |
| cgggcctctc | ccttctgccy | srgrcgtcag | cggacsgggc | gctcgcgggc | cggggctgta | 240 |
| tggggctccc | gcgcgggtcg | ttcttctggc | tgctgctcct | gctcacggct | gcctgctcgg | 300 |
| ggctcctctt | tgccctgtac | ttctcggcgg | tgcagcggta | cccggggcca | gcggccggag | 360 |
| ccagggacac | cacatcattt | gaagcattct | ttcaatccaa | ggcatcgaat | tcttggacag | 420 |
| gaaagggcca | ggcctgccga | cacctgcttc | acctggccat | tcagcggcac | ccccacttcc | 480 |
| gtggcctgtt | caatctctcc | attccagtgc | tgctgtgggg | ggacctcttc | accccagcgc | 540 |
| tctgggaccg | cctgagccaa | cacaaagccc | cgtatggctg | gcggggctc | tctcaccaag | 600 |
| tcatcgcctc | cacctgagc | cttctgaacg | gctcagagag | tgccaagctg | tttgccccgc | 660 |
| ccagggacac | ccctccaaag | tgtatccggt | gtgccgtggt | gggcaacgga | ggcattctga | 720 |
| atgggtcccg | ccagggtccc | aacatcgatg | cccatgacta | tgtattcaga | ctcaatggag | 780 |
| ctgtgatcaa | aggcttcgag | cgcgatgtgg | gcaccaagac | ttccttctat | ggtttcactg | 840 |
| tgaacacgat | gaagaactcc | ctcgtctcct | actggaatct | gggcttcacc | tccgtgccac | 900 |
| aaggacagga | cctgcagtat | atcttcatcc | cctcagacat | ccgcgactat | gtgatgctga | 960 |
| gatcggccat | tctgggcgtg | cctgtccctg | agggcctaga | taaaggggac | aggccgcacg | 1020 |
| cctatttgg | accagaagcc | tctgccagta | aattcaagct | gctacatccg | gacttcatca | 1080 |
| gctacctgac | agaaaggttc | ttgaaatcaa | agttgattaa | cacacatttt | ggagacctat | 1140 |
| atatgcctag | taccggggct | ctcatgctgc | tgacagcttt | gcatacctgt | gaccaggtca | 1200 |
| gtgcctatgg | attcatcaca | agcaaactact | ggaaattttc | cgaccactat | ttcgaacgaa | 1260 |
| aaatgaagcc | attgatattt | tatgcaaacc | acgatctgtc | cctggaagct | gccctgtgga | 1320 |
| gggacctgca | caaggccggc | atccttcagc | tgtaccagcg | ctgaccccaa | tgcactgagc | 1380 |
| cctttgcttc | ttcaagagtt | gcggcctgat | cctctcaagt | ggccaaaagc | ttttttaact | 1440 |
| tttcaatctt | caccttccct | tgccaacaga | gggcactggg | gtgaattcaa | gattttcatc | 1500 |
| gaggtctgtt | caatatagga | cacccagct | tgtccttggc | tcatccaaga | actcttctgt | 1560 |
| atctaaaaca | atacatctca | atcttggcca | agggaaaacg | gactgctttg | ctggattggc | 1620 |
| actgagcaac | tttaggaaat | gtcggtggag | tgttcagcaa | gatcagacag | cagtccaggt | 1680 |
| caaaggcaaa | cacacacgct | ccagcccaaa | tcctcctggt | ggcacatcct | accccagatg | 1740 |
| ctaaagtgat | tcaaggactc | caggacacct | cttaagagcc | tttctaagaa | catgataggc | 1800 |
| ttacttctgc | tccataataa | agtgggagaa | aaaagccaga | atataaaact | taaractaga | 1860 |
| taactgcgya | satgatggac | catttttttt | ttttggctgg | gtagagaaat | catataaaac | 1920 |
| gcaggctgtt | tagcatggag | atgactctca | gaacactggr | agggtctggc | acttgatggg | 1980 |
| ggttagttgc | ttggcagcct | gcctgaagtc | ccattagaga | tgtatcaccc | ccttgtcacc | 2040 |
| aacaggatga | tgtccccagg | taataaacct | tcatcctcat | aaaaaaaaaa | aaaaaaaaa | 2100 |
| aaaaaaaaaa | aaaaaaaaaa | aagggcggcc | gctagactag | tc | | 2142 |

<210> SEQ ID NO 16

```
<211> LENGTH: 374
<212> TYPE: PRT
<213> ORGANISM: Homo sapiens

<400> SEQUENCE: 16

Met Gly Leu Pro Arg Gly Ser Phe Phe Trp Leu Leu Leu Leu Leu Thr
 1               5                  10                  15

Ala Ala Cys Ser Gly Leu Leu Phe Ala Leu Tyr Phe Ser Ala Val Gln
            20                  25                  30

Arg Tyr Pro Gly Pro Ala Ala Gly Ala Arg Asp Thr Thr Ser Phe Glu
        35                  40                  45

Ala Phe Phe Gln Ser Lys Ala Ser Asn Ser Trp Thr Gly Lys Gly Gln
    50                  55                  60

Ala Cys Arg His Leu Leu His Leu Ala Ile Gln Arg His Pro His Phe
65                  70                  75                  80

Arg Gly Leu Phe Asn Leu Ser Ile Pro Val Leu Leu Trp Gly Asp Leu
                85                  90                  95

Phe Thr Pro Ala Leu Trp Asp Arg Leu Ser Gln His Lys Ala Pro Tyr
            100                 105                 110

Gly Trp Arg Gly Leu Ser His Gln Val Ile Ala Ser Thr Leu Ser Leu
        115                 120                 125

Leu Asn Gly Ser Glu Ser Ala Lys Leu Phe Ala Pro Pro Arg Asp Thr
130                 135                 140

Pro Pro Lys Cys Ile Arg Cys Ala Val Val Gly Asn Gly Gly Ile Leu
145                 150                 155                 160

Asn Gly Ser Arg Gln Gly Pro Asn Ile Asp Ala His Asp Tyr Val Phe
                165                 170                 175

Arg Leu Asn Gly Ala Val Ile Lys Gly Phe Glu Arg Asp Val Gly Thr
            180                 185                 190

Lys Thr Ser Phe Tyr Gly Phe Thr Val Asn Thr Met Lys Asn Ser Leu
        195                 200                 205

Val Ser Tyr Trp Asn Leu Gly Phe Thr Ser Val Pro Gln Gly Gln Asp
210                 215                 220

Leu Gln Tyr Ile Phe Ile Pro Ser Asp Ile Arg Asp Tyr Val Met Leu
225                 230                 235                 240

Arg Ser Ala Ile Leu Gly Val Pro Val Pro Glu Gly Leu Asp Lys Gly
                245                 250                 255

Asp Arg Pro His Ala Tyr Phe Gly Pro Glu Ala Ser Ala Ser Lys Phe
            260                 265                 270

Lys Leu Leu His Pro Asp Phe Ile Ser Tyr Leu Thr Glu Arg Phe Leu
        275                 280                 285

Lys Ser Lys Leu Ile Asn Thr His Phe Gly Asp Leu Tyr Met Pro Ser
290                 295                 300

Thr Gly Ala Leu Met Leu Leu Thr Ala Leu His Thr Cys Asp Gln Val
305                 310                 315                 320

Ser Ala Tyr Gly Phe Ile Thr Ser Asn Tyr Trp Lys Phe Ser Asp His
                325                 330                 335

Tyr Phe Glu Arg Lys Met Lys Pro Leu Ile Phe Tyr Ala Asn His Asp
            340                 345                 350

Leu Ser Leu Glu Ala Ala Leu Trp Arg Asp Leu His Lys Ala Gly Ile
        355                 360                 365

Leu Gln Leu Tyr Gln Arg
    370

<210> SEQ ID NO 17
```

<211> LENGTH: 1707
<212> TYPE: DNA
<213> ORGANISM: Homo sapiens

<400> SEQUENCE: 17

```
tacttaggga gtcgaccacg cgtccgacta gttctagatc gcgggcaaag atggcggcgg      60
ccaggtgttg gaggcctttg ctacgcggtc cgaggctttc attgcacacc gcggctaatg     120
ccgccgccac ggctacagaa acgacctgcc aagacgtcgc ggcgaccccc gtcgcgcggt     180
acccgccgat tgtggcctcc atgacagccg acagcaaagc tgcacggctg cggcggatcg     240
agcgctggca ggcgacggtg cacgctgcgg agtcggtaga cgagaagctg cgaatcctca     300
ccaagatgca gtttatgaag tacatggttt acccgcagac cttcgcgctg aatgccgacc     360
gctggtacca gtacttcacc aagaccgtgt tcctgtcggg tctgccgccg ccccagcgg      420
agcccgagcc cgagcccgaa cccgaacctg aacctgcgct ggacctcgcg gcgctgcgtg     480
cggtcgcctg cgactgcctg ctgcaggagc acttctacct gcggcgcagg cggcgcgtgc     540
accgttacga ggagagcgag gtcatatctt gcccttcct ggatcagctg gtgtcaaccc      600
tcgtgggcct cctcagccca cacaacccgg ccctggccgc tgccgccctc gattatagat     660
gcccagttca ttttttactgg gtgcgtggtg aagaaattat tcctcgtggt catcgaagag    720
gtcgaattga tgacttgcga taccagatag atgataaacc aaacaaccag attcgaatat     780
ccaagcaact cgcagagttt gtgccattgg attattctgt tcctatagaa atccccacta     840
taaaatgtaa accagacaaa cttccattat tcaaacggca gtatgaaaac cacatatttg     900
ttggctcaaa aactgcagat ccttgctgtt acggtcacac ccagtttcat ctgttacctg     960
acaaattaag aagggaaagg cttttgagac aaaactgtgc tgatcagata gaagttgttt    1020
ttagagctaa tgctattgca agccttttg cttggactgg agcacaagct atgtatcaag    1080
gattctggag tgaagcagat gttactcgac cttttgtctc ccaggctgtg atcacagatg    1140
gaaaatactt ttcctttttc tgctaccagc taaaactttt ggcactgact acacaagctg    1200
atcaaaataa ccctcgtaaa aatatatgtt ggggtacaca agtaagcct ctttatgaaa     1260
caattgagga taatgatgtg aaaggtttta atgatgatgt tctacttcag atagttcact    1320
ttctactgaa tagaccaaaa gaagaaaaat cacagctgtt ggaaaactga aaaagcatat    1380
ttgattgaga actgtgggaa tatttaaatt ttactgaagg aacaataatg atgagatttg    1440
taactgtcaa ctattaaata cattgatttt tgagacaaat aaaaaaaatg tcaacctgtt    1500
attagatctc ttactctgct caaattcatc actgaaagat ttaattttag ttaccttttg    1560
ttgatttaaa ataattgca tttgtatatt gctaactgat aagacaaatt gagttattga     1620
gctattaaat gcacatttta atataaatgc agaaatccca aataaaatgc taacatactg    1680
aattcagtaa ttaaaagaac ccactgc                                        1707
```

<210> SEQ ID NO 18
<211> LENGTH: 439
<212> TYPE: PRT
<213> ORGANISM: Homo sapiens

<400> SEQUENCE: 18

```
Met Ala Ala Ala Arg Cys Trp Arg Pro Leu Leu Arg Gly Pro Arg Leu
  1               5                  10                  15

Ser Leu His Thr Ala Ala Asn Ala Ala Thr Ala Thr Glu Thr Thr
             20                  25                  30

Cys Gln Asp Val Ala Ala Thr Pro Val Ala Arg Tyr Pro Pro Ile Val
         35                  40                  45
```

Ala Ser Met Thr Ala Asp Ser Lys Ala Ala Arg Leu Arg Arg Ile Glu
 50                  55                  60
Arg Trp Gln Ala Thr Val His Ala Ala Glu Ser Val Asp Glu Lys Leu
65                  70                  75                  80
Arg Ile Leu Thr Lys Met Gln Phe Met Lys Tyr Met Val Tyr Pro Gln
                 85                  90                  95
Thr Phe Ala Leu Asn Ala Asp Arg Trp Tyr Gln Tyr Phe Thr Lys Thr
            100                 105                 110
Val Phe Leu Ser Gly Leu Pro Pro Pro Ala Glu Pro Glu Pro Glu
        115                 120                 125
Pro Glu Pro Glu Pro Glu Pro Ala Leu Asp Leu Ala Ala Leu Arg Ala
    130                 135                 140
Val Ala Cys Asp Cys Leu Leu Gln Glu His Phe Tyr Leu Arg Arg Arg
145                 150                 155                 160
Arg Arg Val His Arg Tyr Glu Glu Ser Glu Val Ile Ser Leu Pro Phe
                165                 170                 175
Leu Asp Gln Leu Val Ser Thr Leu Val Gly Leu Leu Ser Pro His Asn
            180                 185                 190
Pro Ala Leu Ala Ala Ala Leu Asp Tyr Arg Cys Pro Val His Phe
        195                 200                 205
Tyr Trp Val Arg Gly Glu Glu Ile Ile Pro Arg Gly His Arg Arg Gly
210                 215                 220
Arg Ile Asp Asp Leu Arg Tyr Gln Ile Asp Lys Pro Asn Asn Gln
225                 230                 235                 240
Ile Arg Ile Ser Lys Gln Leu Ala Glu Phe Val Pro Leu Asp Tyr Ser
                245                 250                 255
Val Pro Ile Glu Ile Pro Thr Ile Lys Cys Lys Pro Asp Lys Leu Pro
            260                 265                 270
Leu Phe Lys Arg Gln Tyr Glu Asn His Ile Phe Val Gly Ser Lys Thr
        275                 280                 285
Ala Asp Pro Cys Cys Tyr Gly His Thr Gln Phe His Leu Leu Pro Asp
    290                 295                 300
Lys Leu Arg Arg Glu Arg Leu Leu Arg Gln Asn Cys Ala Asp Gln Ile
305                 310                 315                 320
Glu Val Val Phe Arg Ala Asn Ala Ile Ala Ser Leu Phe Ala Trp Thr
                325                 330                 335
Gly Ala Gln Ala Met Tyr Gln Gly Phe Trp Ser Glu Ala Asp Val Thr
            340                 345                 350
Arg Pro Phe Val Ser Gln Ala Val Ile Thr Asp Gly Lys Tyr Phe Ser
        355                 360                 365
Phe Phe Cys Tyr Gln Leu Asn Thr Leu Ala Leu Thr Thr Gln Ala Asp
    370                 375                 380
Gln Asn Asn Pro Arg Lys Asn Ile Cys Trp Gly Thr Gln Ser Lys Pro
385                 390                 395                 400
Leu Tyr Glu Thr Ile Glu Asp Asn Asp Val Lys Gly Phe Asn Asp Asp
                405                 410                 415
Val Leu Leu Gln Ile Val His Phe Leu Leu Asn Arg Pro Lys Glu Glu
            420                 425                 430
Lys Ser Gln Leu Leu Glu Asn
        435

<210> SEQ ID NO 19
<211> LENGTH: 2844
<212> TYPE: DNA

<213> ORGANISM: Homo sapiens
<220> FEATURE:
<221> NAME/KEY: misc_feature
<222> LOCATION: 767, 2839, 2842
<223> OTHER INFORMATION: n = A,T,C or G

<400> SEQUENCE: 19

```
cgacccacgc cgtccgggcg gcggcgtccg caggagcccg ggaggcggag gcgggaggcg      60
gcggcggcgc gcggagacgc agcagcggca gcggcagcat gtcggccggc ggagcgtcag     120
tcccgccgcc cccgaacccc gccgtgtcct tcccgccgcc ccgggtcacc ctgcccgccg     180
gccccgacat cctgcggacc tactcgggcg ccttcgtctg cctggagatt ctgttcgggg     240
gtcttgtctg gattttggtt gcctcctcca atgttcctct acctctacta caaggatggg     300
tcatgtttgt gtccgtgaca gcgttttttct tttcgctcct ctttctgggc atgttcctct     360
ctggcatggt ggctcaaatt gatgctaact ggaacttcct ggattttgcc taccattta     420
cagtatttgt cttctatttt ggagccttt tattggaagc agcagccaca tccctgcatg     480
atttgcattg caatacaacc ataaccgggc agccactcct gagtgataac cagtataaca     540
taaacgtagc agcctcaatt tttgccttta tgacgacagc ttgttatggt tgcagtttgg     600
gtctggcttt acgaagatgg cgaccgtaac actccttaga aactggcagt cgtatgttag     660
tttcacttgt ctactttata tgtctgatca atttggatac cattttgtcc agatgcaaaa     720
acattccaaa agtaatgtgt ttagtagaga gagactctaa gctcaangtt ctggtttatt     780
tcatggatgg aatgttaatt ttattatgat attaaagaaa tggccttta ttttacatct     840
ctccccttt tccctttccc cctttatttt cctccttttc tttctgaaag tttccttta     900
tgtccataaa atacaaatat attgttcata aaaaattagt atccctttg tttggttgct     960
gagtcacctg aaccttaatt ttaattggta attacagccc ctaaaaaaaa cacatttcaa    1020
ataggcttcc cactaaactc tatattttag tgtaaaccag gaattggcac acttttttta    1080
gaatgggcca gatggtaaat atttatgctt cacggtccat acagtctctg tcacaactat    1140
tcagttctgc tagtatagcg tgaaagcagc tatacacaat acagaaatga atgagtgtgg    1200
ttatgttcta ataaaactta tttataaaaa caaggggagg ctgggtttag cctgtgggcc    1260
atagtttgtc aaccactggt gtaaaaccct agttatatat gatctgcatt ttcttgaact    1320
gatcattgaa aacttataaa cctaacagaa aagccacata atatttagtg tcattatgca    1380
ataatcacat tgcctttgtg ttaatagtca atacttacc tttggagaat acttacctt    1440
ggaggaatgt ataaaatttc tcaggcagag tcctggatat aggaaaaagt aatttatgaa    1500
gtaaacttca gttgcttaat caaactaatg atagtctaac aactgagcaa gatcctcatc    1560
tgagagtgct aaaatggga tccccagaga ccattaacca atactggaac tggtatctag    1620
ctactgatgt cttactttga gtttatttat gcttcagaat acagttgttt gccctgtgca    1680
taatatacc atatttgtgt gtggatatgt gaagcttttc caaatagagc tctcagaaga    1740
attaagttt tacttctaat tattttgcat tactttgagt taaatttgaa tagagtatta    1800
aatataaagt tgtagattct tatgtgtttt tgtattagcc cagacatctg taatgtttt    1860
gcactggtga cagacaaaat ctgtttttaaa atcatatcca gcacaaaaac tatttctggc    1920
tgaatagcac agaaaagtat tttaacctac ctgtagagat cctcgtcatg gaaggtgcc    1980
aaactgtttt gaatggaagg acaagtaaga gtgaggccac agttcccacc acacgagggc    2040
ttttgtattg ttctacttttt tcagcccttt actttctggc tgaagcatcc ccttggagtg    2100
ccatgtataa gttgggctat tagagttcat ggaacataga acaaccatga atgagtggca    2160
```

```
tgatccgtgc ttaatgatca agtgttactt atctaataat cctctagaaa gaaccctgtt    2220
agatcttggt ttgtgataaa aatataaaga cagaagacat gaggaaaaac aaaaggtttg    2280
aggaaatcag gcatatgact ttatacttaa catcagatct tttctataat atcctactac    2340
tttggttttc ctagctccat accacacacc taaacctgta ttatgaatta catattacaa    2400
agtcataaat gtgccatatg gatatacagt acattctagt tggaatcgtt tactctgcta    2460
gaatttaggt gtgagatttt ttgtttccca ggtatagcag gcttatgttt ggtggcatta    2520
aattggtttc tttaaaatgc tttggtggca cttttgtaaa cagattgctt ctagattgtt    2580
acaaaccaag cctaagacac atctgtgaat acttagattt gtagcttaat cacattctag    2640
acttgtgagt tgaatgacaa agcagttgaa caaaaattat ggcatttaag aatttaacat    2700
gtcttagctg taaaatgag aaagtgttgg ttggttttaa aatctggtaa ctccatgatg    2760
aaagaaattt tattttatac gtgttatgtc tctaataaag tattcatttg ataaaaaaaa    2820
aaaaaaaaaa aaaaaaaang tnhg                                           2844
```

<210> SEQ ID NO 20
<211> LENGTH: 176
<212> TYPE: PRT
<213> ORGANISM: Homo sapiens

<400> SEQUENCE: 20

```
Met Ser Ala Gly Gly Ala Ser Val Pro Pro Pro Asn Pro Ala Val
 1               5                  10                  15

Ser Phe Pro Pro Arg Val Thr Leu Pro Ala Gly Pro Asp Ile Leu
                20                  25                  30

Arg Thr Tyr Ser Gly Ala Phe Val Cys Leu Glu Ile Leu Phe Gly Gly
                35                  40                  45

Leu Val Trp Ile Leu Val Ala Ser Ser Asn Val Pro Leu Pro Leu Leu
        50                  55                  60

Gln Gly Trp Val Met Phe Val Ser Val Thr Ala Phe Phe Phe Ser Leu
65                  70                  75                  80

Leu Phe Leu Gly Met Phe Leu Ser Gly Met Val Ala Gln Ile Asp Ala
                85                  90                  95

Asn Trp Asn Phe Leu Asp Phe Ala Tyr His Phe Thr Val Phe Val Phe
                100                 105                 110

Tyr Phe Gly Ala Phe Leu Leu Glu Ala Ala Ala Thr Ser Leu His Asp
            115                 120                 125

Leu His Cys Asn Thr Thr Ile Thr Gly Gln Pro Leu Leu Ser Asp Asn
        130                 135                 140

Gln Tyr Asn Ile Asn Val Ala Ala Ser Ile Phe Ala Phe Met Thr Thr
145                 150                 155                 160

Ala Cys Tyr Gly Cys Ser Leu Gly Leu Ala Leu Arg Arg Trp Arg Pro
                165                 170                 175
```

<210> SEQ ID NO 21
<211> LENGTH: 12642
<212> TYPE: DNA
<213> ORGANISM: Homo sapiens
<220> FEATURE:
<221> NAME/KEY: misc_feature
<222> LOCATION: 7145, 7158, 7460, 7461, 7462, 7463, 7467, 7717, 7756,
      7795, 7799, 7803, 7818, 7822, 7833, 7842, 7843, 7852, 7860, 7864,
      7871, 7876, 8141, 11251, 11283, 11294, 11301, 11309, 11336,
      11341, 11345, 11352, 11357, 11363, 11373, 11380, 11391
<223> OTHER INFORMATION: n = A,T,C or G
<220> FEATURE:
<221> NAME/KEY: misc_feature
<222> LOCATION: 11399, 11402, 11412, 11424, 11427, 11428, 11435, 11445,

```
             11461, 11472, 11478, 11488, 11490, 11497, 11519, 11527, 11548,
             11551, 12281, 12298, 12394, 12615, 12617, 12618, 12620,
             12621, 12624, 12627, 12628, 12629, 12633, 12634, 12635
<223> OTHER INFORMATION: n = A,T,C or G
<220> FEATURE:
<221> NAME/KEY: misc_feature
<222> LOCATION: 12636, 12637, 12640
<223> OTHER INFORMATION: n = A,T,C or G

<400> SEQUENCE: 21
atggcgagcc tcgccgcgct cgccctcagc ctgctcctga ggctgcagct gccgccactg      60
cccggcgccc gggctcagag cgccccaggt ggctgttcct ttgatgagca ctacagcaac     120
tgtggttata gtgtggctct agggaccaat gggttcacct gggagcagat aacacaacg     180 gagaaaccaa tgctggacca ggcagtgccc acaggatctt tcatgatggt gaacagctct     240
gggagagcct ctggccagaa ggcccacctt ctcctgccaa ccctgaagga gaatgacacc     300
cactgcatcg acttccatta ctacttctcc agccgtgaca ggtccagccc aggggccttg     360
aacgtctacg tgaaggtgaa tggtggcccc caagggaacc ctgtgtggaa tgtgtccggg     420
gtcgtcactg agggctgggt gaaggcagag ctcgccatca gcactttctg ccacatttc     480 tatcaggtga tatttgaatc cgtctcattg aagggtcatc ctggctacat cgccgtggac     540
gaggtccggg tccttgctca tccatgcaga aaagcacctc attttctgcg actccaaaac     600
gtggaggtga atgtggggca gaatgccaca tttcagtgca ttgctggtgg aagtggtct     660 cagcatgaca agctttggct ccagcaatgg aatggcaggg acacggccct gatggtcacc     720
cgtgtggtca ccacaggcg cttctcagcc acagtcagtg tggcagacac tgcccagcgg     780
agcgtcagca gtaccgctg tgtgatccgc tctgatggtg ggtctggtgt gtccaactac     840
gcggagctga tcgtgaaaga gcctcccacg cccattgctc cccagagct gctggctgtg     900 ggggccacat acctgtggat caagccaaat gccaactcca tcatcgggga tggccccatc     960
atcctgaagg aagtggaata tcgcaccacc acaggcacgt gggcagagac ccacatagtc    1020
gactctccca actataagct gtggcatctg accccgatg ttgagtatga atccgagtg    1080 ctcctcacac gaccaggtga gggggtacg ggaccgccag ggctcccct caccaccagg    1140 accaagtgtg cagatccggt acatggccca cagaacgtgg aaatcgtaga catcagagcc    1200
cggcagctga ccctgcagtg ggagccttc ggctacgcgg tgacccgctg ccatagctac    1260
aacctcaccg tgcagtacca gtatgtgttc aaccagcagc agtacgaggc cgaggaggtc    1320
atccagacct cctcccacta caccctgcga ggcctgcgcc ccttcatgac catccggctg    1380
cgactcttgc tgtctaaccc cgagggccga atggagagcg aggagctggt ggtgcagact    1440
gaggaagacg ttccaggagc tgttcctcta gaatccatcc aaggggggcc ctttgaggag    1500
aagatctaca tccagtggaa acctcccaat gagaccaatg gggtcatcac gctctacgag    1560
atcaactaca aggctgtcgg ctcgctggac ccaagtgctg acctctcgag ccagaggggg    1620
aaagtgttca agctccggaa tgaaacccac cacctctttg tgggtctgta cccagggacc    1680
acctattcct tcaccatcaa ggccagcaca gcaaagggct tgggccccc tgtcaccact    1740 cggattgcca ccaaaatttc agctccatcc atgcctgagt cgacacaga caccccattg    1800 aatgagacag acacgaccat cacagtgatg ctgaaacccg ctcagtcccg gggagctcct    1860
gtcagtgttt atcagctggt tgtcaaggag gagcgacttc agaagtcacg gagggcagct    1920
gacattattg agtgcttttc ggtgcccgtg agctatcgga tgcctccag cctcgattct    1980 ctacactact ttgctgctga gttgaagcct gccaacctgc ctgtcaccca gccatttaca    2040
gtgggtgaca ataagacata caatggctac tggaacccttc ctctctctcc cctgaaaagc    2100
```

```
tacagcatct acttccaggc actcagcaaa gccaatggag agaccaaaat caactgtgtt   2160
cgtctggcta caaaagcacc aatgggcagc gcccaggtga ccccggggac tccactctgc   2220
ctcctcacca caggtgcctc cacccagaat tctaacactg tggagccaga gaagcaggtg   2280
gacaacaccg tgaagatggc tggcgtgatc gctggcctcc tcatgttcat catcattctc   2340
ctgggcgtga tgctcaccat caaaaggaga agaaatgctt attcctactc ctattacttg   2400
tcccaaagga agctggccaa gaagcagaag gagacccaga gtggagccca gagggagatg   2460
gggcctgtgg cctctgccga caaacccacc accaagctca cgccagccg caatgatgaa   2520 ggcttctctt ctagttctca ggacgtcaac ggattcacag atggcagccg cggggagctt   2580
tcccagccca ccctcacgat ccagactcat ccctaccgca cctgtgaccc tgtggagatg   2640 agctacccc gggaccagtt ccaactcgcc atccgggtgg ctgacttgct gcagcacatc   2700
acgcagatga agagaggcca gggctacggg ttcaaggagg aatacgaggc cttaccagag   2760
gggcagacag cttcgtggga cacagccaag gaggatgaaa accgcaataa gaatcgatat   2820
gggaacatca tatcctacga ccattcccgg gtgaggctgc tggtgctgga tggagacccg   2880
cactctgact acatcaatgc caactacatt gacggatacc atcgacctcg cactacatt   2940 gcgactcaag gtccgatgca ggagactgta aaggactttt ggagaatgat ctggcaggag   3000
aactccgcca gcatcgtcat ggtcacaaac ctggtggaag tgggcagggt gaaatgtgtg   3060
cgatactggc cagatgacac ggaggtctac ggagacatta aagtcaccct gattgaaaca   3120
gagcccctgg cagaatacgt catacgcacc ttcacagtcc agaagaaagg ctaccatgag   3180
atccgggagc tccgcctctt ccacttcacc agctggcctg accacggcgt tcctgctat    3240 gccactggcc ttctgggctt cgtccgccag gtcaagttcc tcaacccccc ggaagctggg   3300
cccatagtgg tccactgcag tgctggggct gggcggactg gctgcttcat tgccattgac   3360
accatgcttg acatggccga gaatgaaggg gtggtggaca tcttcaactg cgtgcgtgag   3420
ctccgggccc aaaggtcaa cctggtacag acagaggagc aatatgtgtt tgtgcacgat   3480
gccatcctgg aagcgtgcct ctgtggcaac actgccatcc ctgtgtgtga gttccgttct   3540
ctctactaca atatcagcag gctggacccc cagacaaact ccagccaaat caaagatgaa   3600
tttcagaccc tcaacattgt gacaccccgt gtgcggcccg aggactgcag cattgggctc   3660
ctgcccggga accatgataa gaatcgaagt atggacgtgc tgcctctgga ccgctgcctg   3720
cccttcctta tctcagtgga cggagaatcc agcaattaca tcaacgcagc actgatggat   3780
agccacaagc agcctgccgc cttcgtggtc acccagcacc ctctacccaa caccgtggca   3840
gacttctgga ggctggtgtt cgattacaac tgctcctctg tggtgatgct gaatgagatg   3900
gacactgccc agttctgtat gcagtattgg cctgagaaga cctccgggtg ctatgggccc   3960
atccaggtgg agttcgtctc cgcagacatc gacgaggaca tcatccacag aatattccgc   4020
atctgtaaca tggcccggcc acaggatggt tatcgtatag tccagcacct ccagtacatt   4080
ggctggcctg cctaccggga cacgccccc tccaagcgct ctctgctcaa agtggtccga   4140
cgactggaga agtggcagga gcagtatgac gggagggagg acgtactgtc ggtccactgc   4200
ctaaatgggg gaggccgtag tggaaccttc tgtgccatct gcagtgtgtg tgagatgatc   4260
cagcagcaaa acatcattga cgtgttccac atcgtgaaaa cactgcgtaa caacaaatcc   4320
aacatggtgg agaccctgga acagtataaa tttgtatacg aggtggcact ggaatattta   4380
agctcctttt agctcaatgg gatggggaac ctgccggagt ccagaggctg ctgtgaccaa   4440 gcccccttt gtgtgaatgg cagtaactgg gctcaggagc tctgaggtgg caccctgcct   4500
```

-continued

```
gactccaagg agaagactgg tggccctgtg ttccacgggg ggctctgcac cttctgaggg      4560
gtctcctgtt gccgtgggag atgctgctcc aaaaggccca ggcttccttt tcaacctaac      4620
cagccacagc caagggccca agcagaagta cacccacaag caaggccttg gatttctggc      4680
tcccagacca cctgcttttg ttctgagttt gtggatctct tggcaagcca actgtgcagg      4740
tgctggggag tgggaggctc ccctgccctc cttctcctta ggagtggagg agatgtgtgt      4800
tctgctcctc tacgtcatgg aaaagattga ggctcttggg ggtcactgct ctgctgcccc      4860
ctgcaacctc cttcagggc  ctctggcacc agacatttgc agtctggacc agtgtgacct       4920
tacgatgttc cctaggccac aagagaggcc ccccatcctc acacctaacc tgcatggggc      4980
ttcgcccaca accattctgt acccctt ccc cagcctgggc cttgaccgtc cagcattcac      5040
tggccggcca gctgtgtcca cagcagtttt tgataaaggt gttctttgct ttttgtgtg       5100 gtcagtggga gggggtggaa ctgcagggaa cttctctgct cctccttgtc tttgtaaaaa      5160
gggaccacct ccctggggca gggcttgggc tgacctgtag gatgtaaccc ctgtgtttct      5220
ttggtggtag cttctcttgg aagagacaaa caagataaga tttgattatt ttccaaagtg      5280
tatgtgaaaa gaaactttct tttgagggt gtaaaatctt agtctcttat gtcaaaagaa        5340 aggggggcggg ggagtttgag tatgtacctc taagacaaat ctctcgggcc ttttattttt     5400
tcctggcaat gtccttaaaa gctcccaccc tgggacagca tgccactgag caaggagaga      5460
tgggtgagcc tgaagatggt ccctttggtt tctgggcaa  atagagcacc agctttgtgc      5520
ataatttgga tgtccaaatt tgaactcctt cctaaagaaa cccagcagcc accttgaaaa      5580
aggccattgt ggagcccatt atactttgat ttaaaatagg ccaagagaat caggcctgga      5640
gatctagggt cttgtccaaa gtgtgagtga gtcaatgaga gggaaccaac atttgctaag      5700
tctctactgt atgccaggga tcatgcttgg cactttccat aggacatttc acacagtcct      5760
tagaaccccc aggagagagc tactgacttg ttatcatctc catttgatca tctcctccaa      5820
tgaggaaacc cacgcacctt ccttagtaat gaaatcctgg gttccaaagg ggcaggtaat      5880
ggcaatgaga cttctccgtg ctgttttctt catcttctct aagccaagca attattttat      5940
ggagggaaaa taaggccaga aacttctgag cagataactc cacaaatgga aatttagtac      6000
tttcttcctg atgccagttc ttctgggaag cgcagaattt cagatatatt ttagtaacac      6060
attcccagct ccccaggaaa gccagtctca tctaatttct tagtcagtaa aaacaattcc      6120
ctgttccttc aggctatgaa tggaccagcc agggaaactc tcgaccttga tctctagcca      6180
gtgcttaggc ccaatatctg acagcctcag gtgggctggg acctaggaag ctccatcttg      6240
aaggctggtc tagccccaga cagggcatga ggggcagaga attcaagaag gtacagcttt      6300
ggccctcaag agcccactgt atgctgggga aatggaacca tggtgcagta gtgtggagtg      6360
gatgagtgtt ccatgagcct aggagcaaga aagtctcttc ggcctcgggc ttcctggaga      6420
aggggacgtc cattcctgct gggtcttaac aagcataaaa aggaaaaaaa ggaaactcag      6480
gcaaagggat ccatatgtgc aatggcaaag aaatgtgaaa aggcattggg agaagcagtc      6540
tgggggaggc cagcccagtg cgggcacagc acaaacgggg gagcagcaag agatgagcca      6600
gggtccagga gacagatgcc catcgcgagt acagactttg tcctattggc aacaaggagt      6660
ccatggagct ttagagagat gcactcagct tcgtgttggc caagactcct tctgggccaa      6720
tggggctgcc tcttttcctt tcatcagaca ctgtgaaaac attcccttaa gcgtgcactt      6780
tttaatatca catctatttg tctgtctgct cattgttttg ttgctggaac taaatatgca      6840
atggatcatg agactcagat tctatgagaa acccagggtc tctgctttac cacggagcag      6900
```

```
ggtcaccaac ccagatctcc aggcccatga ggatggaaca tgaaaggagc cgacaaaagt   6960
tgcttccatt ggcatgggct ctggagctgt ccagaagtcc agggacacca gacttgatca   7020
aggaagggct gtcactttag aggttcaaaa ggaagtgcct caaagcaaag gcaagcaaag   7080 gaacccacg  atgaacttgc tcttttcctt tgatgagcct ctccccaggt gtatttcagc   7140
agacncccgg ggacccance cccactgggc ctgctggcct ccctcggctc cagcccaatg   7200
ccccagctgg ccttccccag cctgcaagga gcctgtagca tggcaaatct gcctgctgta   7260
tgctattttc ttagatcttg gtacatccag acaggatgag ggtggaggga gagctattta   7320
acacaaatcc taagattttt ttctgctcag gaagggtgaa atagctggc  agatacaaaa   7380 gacagtggct tttatcattt taaatggtag gaatttaagg tgtgacttca gggagaaaca   7440
aacttgcaaa aaaaaaaaan nnntctncag gccatgttgg ggtaacccag caagggccag   7500
tgatgatttc ccccagctca tccccttatt ttccacaac  ccaaccattc tctaaagcag   7560
gacagtgaat aggtcttagg ccagtgcaca caggaagaaa ttgagcctta tggatgggga   7620
tgacttccct aagatcccat gggacaagga tgtggcaagg cttggatgag atggggcacc   7680
agtgcccagg aatttgaaca ttttccttta cccaggnaaa tctccggagc caacaccacc   7740 accccaggg  ggtctnccc  accccacccc atttacaggg tgagctcagc ctgtncatng   7800
agncaggaga aaatattnat tnaatgctct ctngagtctt tnnacaacag gnagctcttn   7860
accntcatag natgtngggc tctgtttggg gaagatgcaa ggaagtaatg agaagcccag   7920
gaaatttctc cacctgtgtt tatggcctaa atagcttcag gatgtatctt agctgcactc   7980
caacattgca tccttctgg  ggtgaagaat ctgggccaac caggggtcct tgggcctcta   8040
gaaggccaca gtaggcctct ctttgtggga atggaaaggg gacagtttgc tttttagtgc   8100
tggccctctc tgtgggtgtg gcctgccaaa ggaaccaaca ngaccctatg cctggggact   8160
cctaacatgt gagcctccat taaattcctt cccagcattc ctaaaggagg gtttgtgatt   8220
gtcaccattt actgatgagg aaactaaggc tcctagggga gaaatcactt gcccacagtt   8280
cccacagcta gtgagtgaat gaaccaggat ttaaaccggt tttttctcac tacagagaca   8340
atatttttcc accattgtat ctcacatttt tcccaggagg ttacccataa cagaagagac   8400
tagagtggaa cagatacgtc agtggataaa gctcaaagca aacaacagta agcttaaaat   8460
tccttcatag tctcatgttt tacgttcaca attcatgcaa aatttgcatt ccactttctg   8520
atttagcctt gttggtttta atatgactct atgaatattt caaaaaaaaa tgtgctctgt   8580
tcctcatgtt gttctgttct gttcaccccg ctatgacgga ccctaggtca gctggtcttc   8640
agcttgaccc tagaattgac tctaggagca gtgaccctgc tgcctcccag agccagttat   8700
aggctcaaga tcaagaccaa ctgaccttct cctaggcagc tcctttggtg tgtgggtgct   8760
ctgacctcac tgttcatgag gggacctcaa ctaaggcatc ttccagttgg gtgctggaag   8820
gaacccatta actcacacta gaatgatgag gatttgctca tctggcgtgg agaaggatga   8880
gcccacaaaa ccctaaaggg aaaagagaag ctggacacag ctgtactcag cagattcctg   8940
aatgctaggc tggaaagtgg tgcctgttgt ccaagtggag tcacatggtt gctaatgtgg   9000
gcaagtctga ggacacactt catgagcagc tggggtctgg aaggctcctc actttaccct   9060
agccacacat aattactggg tgcctacagc acctagcacc ttgaggggg  cactattagg   9120 aaatcgagat tactatggca caattaattc ctgggtaagg catggggttg tggtggacag   9180
agctcagtct ttagtttgaa cgaaaacata catacatgaa aaacatacat gaaaaaagga   9240
ccctcatcaa cattagaagg ggtagatttg gagcacttta ggcaggaaaa caggaacgca   9300
```

```
aggccaggaa actggaaccc agtgaatact cagaaccgag gatgcagatg acttatttag    9360
caaaatggtc acttctgtga catagctgga gaaaggatgg gtaacagctt gccagagcca    9420
cttggaacaa gggcaaatct cagtgtctgg ggcaaaagat gatgcatttc cctctgaccc    9480
atcatgttta ttcatcctcc actccccatt gccacactag ctcttgctgt aagtcctcac    9540
caggatctac atttcctcgt cgctggtggg aacccctttag agtacataga ggtatcagtc    9600
cagtaagact gctctacaca acagaagtga ggcccaggga gtagcagcca ggcccttatc    9660
ctgttacctc tgcaggagtg actgcccaac ccagatccag agacattgaa ggaaatgata    9720
attccttggt acctcactgc cttgggacaa aatgaagaaa gccacccttc cttaggctgc    9780
agcttgccac tcctgggctg ggtaaacagg tcatcagcac caggctcaac caggagtaac    9840
attctggaag acatgggtga gcccaagagg aagcatgaac aggacgctgt tcctaagtca    9900
tgtcaacagg ttgtgctggg ccaggatccc cagggaaaaa aatggtcaac ccaactggag    9960
ggtaggttag aagaaaaaaa acataaacgt ggatagtcat gtcatctcaa atccctgact   10020
tggcttcccc attacttgac agtctgagct ccttcttagc ctgtgaccag cttcaaatca   10080
cagccaagta aaacaaggaa ataggaaaag taaatccaac tagaagagac aagctgagat   10140
tcagatttgt ttactcctcc catgcaaagt ttccctgttg gaggttttcc atgtatacat   10200
gtctagaagt gatagaatgc aaggccttgg ctttgtcttg cagggatctg cctttgaggt   10260
catagactga acagcaggga gagaggttag tggtggagtg tgggggagc tgttctagct    10320 ccagtttctt ctgacacatt tttcaggatc atggatctga tcctccgaag cacagcagag   10380
atatctaagc catatttgtg cacatgagca gactcttcta gttttttagt aaccagggat   10440
gggcttttgc atggcactga ctatagagat gtcttgtaga gatcaagcca gtcttttgca   10500
tcccacctgc ccacctccag aagagatggg aaaaggtcat caagggcat tcaccaactg    10560 aaatccactc atgaatgtta ggtctctaaa aggaggcatc aacactcaca atggtagcct   10620
ccaaacctag catcccacct atctaagagc tcagggtgg tccactgggg cagatacaag    10680
ggaagtgcaa gggctcagga tgaaagaaaa tctattggga agagttttag gggcttgatc   10740
attatggggc ttccttctat atctgagaac tgctctgggt ggtgagatgt ggactctgat   10800
ccttaattgg aatgttcgga gaatgagtgt ctggtggcct tgaagtgttg gacagaaaag   10860
tatcagtata aaagcctgga gctcagggta attaatgtag ttcatggttc cttagtgagc   10920
aggactcttg gatgtggagg agaaagggtc ataggaagta aaccaccaaa attacaaaat   10980
tgagtctctg tacaattact tcagtgcctt tgggcttatg aatacaaatc agtgggcctt   11040
ctctatgatg gtccaacaaa ctctcagtgt ccaccctgtc cctgtatctc ccatggaaga   11100
tgaataatgt caggtgttct ttgggtcaaa ggccccaggg cagtctggag cttagaggg    11160 cagagtggtg tcattccatg taaagttagg cttctgaggg gtcaggcaga atatggtgtc   11220
catatcttcc atagctctgc agattcttgg natgaagtca agcacagttt gctagaccca   11280
ggntcactcc tctngagtat naactaggna cccatgagtg aaacttaata gctgtnaagg   11340
naagnaacct gnctgtnctg ccnagagagg atnaagctgn cccatctcag ncagctgtnc   11400 tnaaagaag gncaggtgtc tctnttnnaa agggnaagag gaagncattg gtggaaatgg    11460
nattttcagg tncacttncc attcccangn atgggtngaa atcttgtgga gctgggatnc   11520
atgtttngaa ctcattcata cctgtagnag ncacgaattc caagtagatt gtgtttggtc   11580
tgtacaggct gaagccccct gctctcccac ccaagtgccc ccactgagca ggccaacatg   11640
ctgttgtggc cacatatact gggctgatcc aggctggtta tcaccaaaca gcaaaccata   11700
```

```
gggaacagct gctttgccat agacccaata cccatgtaga tctctcatga gagcagccat    11760
aactcagacc cactgaccaa cagggccatg agtgacagcc agaaccagtg aaggtccaag    11820
taggacacag agcagggctt ttcttaccat acacattatc tccagaggtt atttctaccc    11880
cactccctat tcaaggcctg ttggagcaca ctgcaaaagc aaaagcacag taactcaatt    11940
tacacatgat tataatcatt tccagtgcac acatttcatc accaggtgga tcctgagcta    12000
gcccatgtaa atccgggtta acccatattg gtaatcatac tcaaaagcac ttttcaccct    12060
acattctact agccaatcaa agacaaagag ttgtggcctc taccattgcc ttggcttctg    12120
gacaccctca caagctatcc caaggttccc ggctcaaccc ccagggrggc cggacatcct    12180
tcacatccca ckgggccata aaatattgc catgagaccc aaagtcctcc cacactcttt    12240
gcagccctcc tcccatgaat ccccaatggc ctgcacttgt nacagtttgg gtgtttgnat    12300
agataaagca cgtatgagaa gagaaaacaa aataaatcaa cttttaaaa aagccagcac    12360 tgtgctgtca atgtttttttt tttcttttca attnctagct cagaaaagca gaaggtaaat    12420
aatgtcaggt caatgaatat cagatatatt ttttgactgt acattacagt gaagtgtaat    12480 cttttttacac ctgcaagtcc atcttattta ttcttgtaaa tgttccctga caatgtttgt    12540
aatatggctg tgttaaaaaa tctatacaat aaagctgtga ccctgagaww matgttttcc    12600
taagataaaa aaaangnnan nstnyknnnc tknnnnngtn hg                      12642
```

<210> SEQ ID NO 22
<211> LENGTH: 1463
<212> TYPE: PRT
<213> ORGANISM: Homo sapiens

<400> SEQUENCE: 22

```
Met Ala Ser Leu Ala Ala Leu Ala Leu Ser Leu Leu Leu Arg Leu Gln
 1               5                  10                  15

Leu Pro Pro Leu Pro Gly Ala Arg Ala Gln Ser Ala Pro Gly Gly Cys
            20                  25                  30

Ser Phe Asp Glu His Tyr Ser Asn Cys Gly Tyr Ser Val Ala Leu Gly
        35                  40                  45

Thr Asn Gly Phe Thr Trp Glu Gln Ile Asn Thr Thr Glu Lys Pro Met
    50                  55                  60

Leu Asp Gln Ala Val Pro Thr Gly Ser Phe Met Met Val Asn Ser Ser
65                  70                  75                  80

Gly Arg Ala Ser Gly Gln Lys Ala His Leu Leu Leu Pro Thr Leu Lys
                85                  90                  95

Glu Asn Asp Thr His Cys Ile Asp Phe His Tyr Tyr Phe Ser Ser Arg
            100                 105                 110

Asp Arg Ser Ser Pro Gly Ala Leu Asn Val Tyr Val Lys Val Asn Gly
        115                 120                 125

Gly Pro Gln Gly Asn Pro Val Trp Asn Val Ser Gly Val Val Thr Glu
    130                 135                 140

Gly Trp Val Lys Ala Glu Leu Ala Ile Ser Thr Phe Trp Pro His Phe
145                 150                 155                 160

Tyr Gln Val Ile Phe Glu Ser Val Ser Leu Lys Gly His Pro Gly Tyr
                165                 170                 175

Ile Ala Val Asp Glu Val Arg Val Leu Ala His Pro Cys Arg Lys Ala
            180                 185                 190

Pro His Phe Leu Arg Leu Gln Asn Val Glu Val Asn Val Gly Gln Asn
        195                 200                 205
```

```
Ala Thr Phe Gln Cys Ile Ala Gly Gly Lys Trp Ser Gln His Asp Lys
    210                 215                 220

Leu Trp Leu Gln Gln Trp Asn Gly Arg Asp Thr Ala Leu Met Val Thr
225                 230                 235                 240

Arg Val Val Asn His Arg Arg Phe Ser Ala Thr Val Ser Val Ala Asp
                245                 250                 255

Thr Ala Gln Arg Ser Val Ser Lys Tyr Arg Cys Val Ile Arg Ser Asp
            260                 265                 270

Gly Gly Ser Gly Val Ser Asn Tyr Ala Glu Leu Ile Val Lys Glu Pro
        275                 280                 285

Pro Thr Pro Ile Ala Pro Pro Glu Leu Leu Ala Val Gly Ala Thr Tyr
    290                 295                 300

Leu Trp Ile Lys Pro Asn Ala Asn Ser Ile Ile Gly Asp Gly Pro Ile
305                 310                 315                 320

Ile Leu Lys Glu Val Glu Tyr Arg Thr Thr Thr Gly Thr Trp Ala Glu
                325                 330                 335

Thr His Ile Val Asp Ser Pro Asn Tyr Lys Leu Trp His Leu Asp Pro
            340                 345                 350

Asp Val Glu Tyr Glu Ile Arg Val Leu Leu Thr Arg Pro Gly Glu Gly
        355                 360                 365

Gly Thr Gly Pro Pro Gly Ala Pro Leu Thr Thr Arg Thr Lys Cys Ala
    370                 375                 380

Asp Pro Val His Gly Pro Gln Asn Val Glu Ile Val Asp Ile Arg Ala
385                 390                 395                 400

Arg Gln Leu Thr Leu Gln Trp Glu Pro Phe Gly Tyr Ala Val Thr Arg
                405                 410                 415

Cys His Ser Tyr Asn Leu Thr Val Gln Tyr Gln Tyr Val Phe Asn Gln
            420                 425                 430

Gln Gln Tyr Glu Ala Glu Glu Val Ile Gln Thr Ser Ser His Tyr Thr
        435                 440                 445

Leu Arg Gly Leu Arg Pro Phe Met Thr Ile Arg Leu Arg Leu Leu Leu
    450                 455                 460

Ser Asn Pro Glu Gly Arg Met Glu Ser Glu Glu Leu Val Val Gln Thr
465                 470                 475                 480

Glu Glu Asp Val Pro Gly Ala Val Pro Leu Glu Ser Ile Gln Gly Gly
                485                 490                 495

Pro Phe Glu Glu Lys Ile Tyr Ile Gln Trp Lys Pro Pro Asn Glu Thr
            500                 505                 510

Asn Gly Val Ile Thr Leu Tyr Glu Ile Asn Tyr Lys Ala Val Gly Ser
        515                 520                 525

Leu Asp Pro Ser Ala Asp Leu Ser Ser Gln Arg Gly Lys Val Phe Lys
    530                 535                 540

Leu Arg Asn Glu Thr His His Leu Phe Val Gly Leu Tyr Pro Gly Thr
545                 550                 555                 560

Thr Tyr Ser Phe Thr Ile Lys Ala Ser Thr Ala Lys Gly Phe Gly Pro
                565                 570                 575

Pro Val Thr Thr Arg Ile Ala Thr Lys Ile Ser Ala Pro Ser Met Pro
            580                 585                 590

Glu Tyr Asp Thr Asp Thr Pro Leu Asn Glu Thr Asp Thr Thr Ile Thr
        595                 600                 605

Val Met Leu Lys Pro Ala Gln Ser Arg Gly Ala Pro Val Ser Val Tyr
    610                 615                 620

Gln Leu Val Val Lys Glu Glu Arg Leu Gln Lys Ser Arg Arg Ala Ala
625                 630                 635                 640
```

-continued

```
Asp Ile Ile Glu Cys Phe Ser Val Pro Val Ser Tyr Arg Asn Ala Ser
                645                 650                 655
Ser Leu Asp Ser Leu His Tyr Phe Ala Ala Glu Leu Lys Pro Ala Asn
            660                 665                 670
Leu Pro Val Thr Gln Pro Phe Thr Val Gly Asp Asn Lys Thr Tyr Asn
            675                 680                 685
Gly Tyr Trp Asn Pro Pro Leu Ser Pro Leu Lys Ser Tyr Ser Ile Tyr
            690                 695                 700
Phe Gln Ala Leu Ser Lys Ala Asn Gly Glu Thr Lys Ile Asn Cys Val
705                 710                 715                 720
Arg Leu Ala Thr Lys Ala Pro Met Gly Ser Ala Gln Val Thr Pro Gly
                725                 730                 735
Thr Pro Leu Cys Leu Leu Thr Gly Ala Ser Thr Gln Asn Ser Asn
                740                 745                 750
Thr Val Glu Pro Glu Lys Gln Val Asp Asn Thr Val Lys Met Ala Gly
            755                 760                 765
Val Ile Ala Gly Leu Leu Met Phe Ile Ile Ile Leu Leu Gly Val Met
770                 775                 780
Leu Thr Ile Lys Arg Arg Asn Ala Tyr Ser Tyr Ser Tyr Tyr Leu
785                 790                 795                 800
Ser Gln Arg Lys Leu Ala Lys Lys Gln Lys Glu Thr Gln Ser Gly Ala
                805                 810                 815
Gln Arg Glu Met Gly Pro Val Ala Ser Ala Asp Lys Pro Thr Thr Lys
            820                 825                 830
Leu Ser Ala Ser Arg Asn Asp Glu Gly Phe Ser Ser Ser Gln Asp
835                 840                 845
Val Asn Gly Phe Thr Asp Gly Ser Arg Gly Glu Leu Ser Gln Pro Thr
            850                 855                 860
Leu Thr Ile Gln Thr His Pro Tyr Arg Thr Cys Asp Pro Val Glu Met
865                 870                 875                 880
Ser Tyr Pro Arg Asp Gln Phe Gln Leu Ala Ile Arg Val Ala Asp Leu
                885                 890                 895
Leu Gln His Ile Thr Gln Met Lys Arg Gly Gln Gly Tyr Gly Phe Lys
            900                 905                 910
Glu Glu Tyr Glu Ala Leu Pro Glu Gly Gln Thr Ala Ser Trp Asp Thr
            915                 920                 925
Ala Lys Glu Asp Glu Asn Arg Asn Lys Asn Arg Tyr Gly Asn Ile Ile
930                 935                 940
Ser Tyr Asp His Ser Arg Val Arg Leu Leu Val Leu Asp Gly Asp Pro
945                 950                 955                 960
His Ser Asp Tyr Ile Asn Ala Asn Tyr Ile Asp Gly Tyr His Arg Pro
                965                 970                 975
Arg His Tyr Ile Ala Thr Gln Gly Pro Met Gln Glu Thr Val Lys Asp
            980                 985                 990
Phe Trp Arg Met Ile Trp Gln Glu Asn Ser Ala Ser Ile Val Met Val
            995                 1000                1005
Thr Asn Leu Val Glu Val Gly Arg Val Lys Cys Val Arg Tyr Trp Pro
        1010                1015                1020
Asp Asp Thr Glu Val Tyr Gly Asp Ile Lys Val Thr Leu Ile Glu Thr
1025                1030                1035                1040
Glu Pro Leu Ala Glu Tyr Val Ile Arg Thr Phe Thr Val Gln Lys Lys
                1045                1050                1055
Gly Tyr His Glu Ile Arg Glu Leu Arg Leu Phe His Phe Thr Ser Trp
```

1060                1065                1070
Pro Asp His Gly Val Pro Cys Tyr Ala Thr Gly Leu Leu Gly Phe Val
            1075                1080                1085
Arg Gln Val Lys Phe Leu Asn Pro Pro Glu Ala Gly Pro Ile Val Val
            1090                1095                1100
His Cys Ser Ala Gly Ala Gly Arg Thr Gly Cys Phe Ile Ala Ile Asp
1105                1110                1115                1120
Thr Met Leu Asp Met Ala Glu Asn Glu Gly Val Val Asp Ile Phe Asn
                1125                1130                1135
Cys Val Arg Glu Leu Arg Ala Gln Arg Val Asn Leu Val Gln Thr Glu
            1140                1145                1150
Glu Gln Tyr Val Phe Val His Asp Ala Ile Leu Glu Ala Cys Leu Cys
            1155                1160                1165
Gly Asn Thr Ala Ile Pro Val Cys Glu Phe Arg Ser Leu Tyr Tyr Asn
            1170                1175                1180
Ile Ser Arg Leu Asp Pro Gln Thr Asn Ser Ser Gln Ile Lys Asp Glu
1185                1190                1195                1200
Phe Gln Thr Leu Asn Ile Val Thr Pro Arg Val Arg Pro Glu Asp Cys
            1205                1210                1215
Ser Ile Gly Leu Leu Pro Arg Asn His Asp Lys Asn Arg Ser Met Asp
            1220                1225                1230
Val Leu Pro Leu Asp Arg Cys Leu Pro Phe Leu Ile Ser Val Asp Gly
            1235                1240                1245
Glu Ser Ser Asn Tyr Ile Asn Ala Ala Leu Met Asp Ser His Lys Gln
            1250                1255                1260
Pro Ala Ala Phe Val Val Thr Gln His Pro Leu Pro Asn Thr Val Ala
1265                1270                1275                1280
Asp Phe Trp Arg Leu Val Phe Asp Tyr Asn Cys Ser Ser Val Val Met
                1285                1290                1295
Leu Asn Glu Met Asp Thr Ala Gln Phe Cys Met Gln Tyr Trp Pro Glu
                1300                1305                1310
Lys Thr Ser Gly Cys Tyr Gly Pro Ile Gln Val Glu Phe Val Ser Ala
            1315                1320                1325
Asp Ile Asp Glu Asp Ile Ile His Arg Ile Phe Arg Ile Cys Asn Met
1330                1335                1340
Ala Arg Pro Gln Asp Gly Tyr Arg Ile Val Gln His Leu Gln Tyr Ile
1345                1350                1355                1360
Gly Trp Pro Ala Tyr Arg Asp Thr Pro Pro Ser Lys Arg Ser Leu Leu
            1365                1370                1375
Lys Val Val Arg Arg Leu Glu Lys Trp Gln Glu Gln Tyr Asp Gly Arg
            1380                1385                1390
Glu Gly Arg Thr Val Val His Cys Leu Asn Gly Gly Gly Arg Ser Gly
            1395                1400                1405
Thr Phe Cys Ala Ile Cys Ser Val Cys Glu Met Ile Gln Gln Gln Asn
            1410                1415                1420
Ile Ile Asp Val Phe His Ile Val Lys Thr Leu Arg Asn Asn Lys Ser
1425                1430                1435                1440
Asn Met Val Glu Thr Leu Glu Gln Tyr Lys Phe Val Tyr Glu Val Ala
                1445                1450                1455
Leu Glu Tyr Leu Ser Ser Phe
            1460

<210> SEQ ID NO 23
<211> LENGTH: 1297

```
<212> TYPE: DNA
<213> ORGANISM: Homo sapiens

<400> SEQUENCE: 23
gtcgacccac gcgtccgtgc tcagcctggt gaaccacaca ggcccgagtt tcacccagtc      60
cccactccac ggtgcagctg cggcttatct ctcagcccag cgagatgcca gccttcctgt     120
cccgggccag cgctctgaca tgcagaaggt gaccctgggc ctgcttgtgt tcctggcagg     180
cttccctgtc ctggacgcca atgacctaga agataaaaac agtcctttct actatgactg     240
gcacagcctc caggttggcg ggctcatctg cgctggggtt ctgtgcgcca tgggcatcat     300
catcgtcatg agtgcaaaat gcaaatgcaa gtttggccag aagtccggtc accatccagg     360
ggagactcca cctctcatca ccccaggctc agcccaaagc tgatgaggac agaccagctg     420
aaattgggtg gaggaccgtt ctctgtcccc aggtcctgtc tctgcacaga aacttgaact     480
ccaggatgga attcttcctc ctctgctggg actcctttgc atggcagggc ctcatctcac     540
ctctcgcaag agggtctctt tgttcaattt tttttaatct aaaatgattg tgcctctgcc     600
caagcagcct ggagacttcc tatgtgtgca ttggggtggg gcttggggca ccatgagaag     660
gttggcgtgc cctggaggct gacacagagg ctggcactga gcctgcttgt tgggaaaagc     720
ccacaggcct gttcccttgt ggcttgggac atggcacagg cccgccctct gcctcctcag     780
ccatgggaac ctcatatgca atttgggatt tactagtagc caaaaggaat gaagagagc     840 tctaaccaga tggaacactg gaacattcca gtggaccctg gaccattcca ggaaaactgg     900
gacataggat cgtcccgcta tgatggaagt gttcagacag tttataatag taagcccctg     960
tgaccctctc acttaccccg agacctcact ttattacaag atctttccaa ataccccaaat    1020 gtccctgcaa gcccgttaaa taattcccta tgctacccctt aataacatac aatgaccaca    1080
tagtgtgaga acttccaaca agcctcaaag tcccttgaga ctccccaata cctaataagg    1140
catgcgaaat gttctcatga actaccccac aacacgccta aaactcaaaa cacccaaaaa    1200
tatctcctcc aatgtcctga acatgaacc caaaaagaga cccacaataa actcgtgact     1260 tgtccccctca aaaaaaaaa aaaaaaaggg cggccgc                              1297

<210> SEQ ID NO 24
<211> LENGTH: 87
<212> TYPE: PRT
<213> ORGANISM: Homo sapiens

<400> SEQUENCE: 24

Met Gln Lys Val Thr Leu Gly Leu Leu Val Phe Leu Ala Gly Phe Pro
 1               5                  10                  15

Val Leu Asp Ala Asn Asp Leu Glu Asp Lys Asn Ser Pro Phe Tyr Tyr
             20                  25                  30

Asp Trp His Ser Leu Gln Val Gly Gly Leu Ile Cys Ala Gly Val Leu
         35                  40                  45

Cys Ala Met Gly Ile Ile Ile Val Met Ser Ala Lys Cys Lys Cys Lys
     50                  55                  60

Phe Gly Gln Lys Ser Gly His His Pro Gly Glu Thr Pro Pro Leu Ile
 65                  70                  75                  80

Thr Pro Gly Ser Ala Gln Ser
             85

<210> SEQ ID NO 25
<211> LENGTH: 1888
<212> TYPE: DNA
<213> ORGANISM: Homo sapiens
```

```
<220> FEATURE:
<221> NAME/KEY: misc_feature
<222> LOCATION: 1814, 1834, 1850
<223> OTHER INFORMATION: n = A,T,C or G

<400> SEQUENCE: 25
aggtacgcgg gggaataatg tgtggcttct gttggattgc ttttctttcc aaaattccta      60
ggcaatgctt ccccgaggtg tgcacctttg tgaggtgttt gtggggttgg gggagcttca     120
ggcgctactc gcgggacgcc gtcacgtgat ccgggacgag gtggagttcg gctttaagga     180
ggcgtctctt cctagcttca tcaatcttta ggatctgagc aggagaaata ccagcggatc     240
ttccccactc tgctcccttc cattcccacc cttccttctt taataagcag gagcgaaaaa     300
gacaaattcc aaagaggatt gttcagttca agggaatgaa gaattcagaa taattttggt     360
aaatggattc caatatgggg aataagaata agctgaacag ttgacctgct ttgaagaaac     420
atactgtcca tttgtctaaa ataatctata acaaccaaac caatcaaaat gaattcaaca     480
ttatttccc aggttgaaaa tcattcagtc cactctaatt tctcagagaa gaatgcccag     540
cttctggctt tgaaaatga tgattgtcat ctgcccttgg ccatgatatt taccttagct     600
cttgcttatg gagctgtgat cattcttggt gtctctggaa acctggcctt gatcataatc     660
atcttgaaac aaaaggagat gagaaatgtt accaacatcc tgattgtgaa cctttccttc     720
tcagacttgc ttgttgccat catgtgtctc cccttttacat ttgtctacac attaatggac     780
cactgggtct tggtgaggc gatgtgtaag ttgaatcctt ttgtgcaatg tgtttcaatc     840
actgtgtcca ttttctctct ggttctcatt gctgtggaac gacatcagct gataatcaac     900
cctcgagggt ggagaccaaa taatagacat gcttatgtag gtattgctgt gatttgggtc     960
cttgctgtgg cttcttcttt gcctttcctg atctaccaag taatgactga tgagccgttc    1020
caaaatgtaa cacttgatgc gtacaaagac aaatacgtgt gctttgatca atttccatcg    1080
gactctcata ggttgtctta taccactctc ctcttggtgc tgcagtattt tggtccactt    1140
tgttttatat ttatttgcta cttcaagata tatatacgcc taaaaggag aaacaacatg    1200
atggacaaga tgagagacaa taagtacagg tccagtgaaa ccaaaagaat caatatcatg    1260
ctgctctcca ttgtggtagc atttgcagtc tgctggctcc ctcttaccat ctttaacact    1320
gtgtttgatt ggaatcatca gatcattgct acctgcaacc acaatctgtt attcctgctc    1380
tgccacctca cagcaatgat atccacttgt gtcaaccca tattttatgg gttcctgaac    1440
aaaaacttcc agagagactt gcagttcttc ttcaacttttt gtgatttccg gtctcgggat    1500
gatgattatg aaacaatagc catgtccacg atgcacacag atgtttccaa aacttctttg    1560
aagcaagcaa gcccagtcgc atttaaaaaa atcaacaaca atgatgataa tgaaaaaatc    1620
tgaaactact tatagcctat ggtcccggat gacatctgtt taaaaacaag cacaacctgc    1680
aacatacttt gattacctgt tctcccaagg amtgggggttg aaatcatttg aaaatgacta    1740
agattttctt gtcttggctt tttactgctt ttgttgtagt tgtcataatt tacatttggg    1800
aacaaaaggg tgtngggctt tkgggatctt tctnggrrat tagkkgttgn accmgacatc    1860
tttgaagtgc ttttgtgaa tttaccag                                         1888

<210> SEQ ID NO 26
<211> LENGTH: 384
<212> TYPE: PRT
<213> ORGANISM: Homo sapiens

<400> SEQUENCE: 26

Met Asn Ser Thr Leu Phe Ser Gln Val Glu Asn His Ser Val His Ser
```

```
                1               5                  10                 15
        Asn Phe Ser Glu Lys Asn Ala Gln Leu Leu Ala Phe Glu Asn Asp Asp
                        20                  25                  30

Cys His Leu Pro Leu Ala Met Ile Phe Thr Leu Ala Leu Ala Tyr Gly
                    35                  40                  45

Ala Val Ile Ile Leu Gly Val Ser Gly Asn Leu Ala Leu Ile Ile Ile
            50                  55                  60

Ile Leu Lys Gln Lys Glu Met Arg Asn Val Thr Asn Ile Leu Ile Val
        65                  70                  75                  80

Asn Leu Ser Phe Ser Asp Leu Leu Val Ala Ile Met Cys Leu Pro Phe
                            85                  90                  95

Thr Phe Val Tyr Thr Leu Met Asp His Trp Val Phe Gly Glu Ala Met
                        100                 105                 110

Cys Lys Leu Asn Pro Phe Val Gln Cys Val Ser Ile Thr Val Ser Ile
                    115                 120                 125

Phe Ser Leu Val Leu Ile Ala Val Glu Arg His Gln Leu Ile Ile Asn
            130                 135                 140

Pro Arg Gly Trp Arg Pro Asn Asn Arg His Ala Tyr Val Gly Ile Ala
        145                 150                 155                 160

Val Ile Trp Val Leu Ala Val Ala Ser Ser Leu Pro Phe Leu Ile Tyr
                            165                 170                 175

Gln Val Met Thr Asp Glu Pro Phe Gln Asn Val Thr Leu Asp Ala Tyr
                        180                 185                 190

Lys Asp Lys Tyr Val Cys Phe Asp Gln Phe Pro Ser Asp Ser His Arg
                    195                 200                 205

Leu Ser Tyr Thr Thr Leu Leu Leu Val Leu Gln Tyr Phe Gly Pro Leu
            210                 215                 220

Cys Phe Ile Phe Ile Cys Tyr Phe Lys Ile Tyr Ile Arg Leu Lys Arg
        225                 230                 235                 240

Arg Asn Asn Met Met Asp Lys Met Arg Asp Asn Lys Tyr Arg Ser Ser
                            245                 250                 255

Glu Thr Lys Arg Ile Asn Ile Met Leu Leu Ser Ile Val Val Ala Phe
                        260                 265                 270

Ala Val Cys Trp Leu Pro Leu Thr Ile Phe Asn Thr Val Phe Asp Trp
                    275                 280                 285

Asn His Gln Ile Ile Ala Thr Cys Asn His Asn Leu Leu Phe Leu Leu
            290                 295                 300

Cys His Leu Thr Ala Met Ile Ser Thr Cys Val Asn Pro Ile Phe Tyr
        305                 310                 315                 320

Gly Phe Leu Asn Lys Asn Phe Gln Arg Asp Leu Gln Phe Phe Phe Asn
                            325                 330                 335

Phe Cys Asp Phe Arg Ser Arg Asp Asp Asp Tyr Glu Thr Ile Ala Met
                        340                 345                 350

Ser Thr Met His Thr Asp Val Ser Lys Thr Ser Leu Lys Gln Ala Ser
                    355                 360                 365

Pro Val Ala Phe Lys Lys Ile Asn Asn Asn Asp Asp Asn Glu Lys Ile
            370                 375                 380

<210> SEQ ID NO 27
<211> LENGTH: 852
<212> TYPE: DNA
<213> ORGANISM: Homo sapiens

<400> SEQUENCE: 27
ctagtcctga cttcacttct gatgaggaag cctctctcct tagccttcag cctttcctcc    60
```

```
caccctgcca taagtaattt gatcctcaag aagttaaacc acacctcatt ggtccctggc      120
taattcacca atttacaaac agcaggaaat agaaacttaa gagaaataca cacttctgag      180
aaactgaaac gacaggggaa aggaggtctc actgagcacc gtcccagcat ccggacacca      240
cagcggccct tcgctccacg cagaaaacca cacttctcaa accttcactc aacacttcct      300
tccccaaagc cagaagatgc acaaggagga acatgaggtg gctgtgctgg gggcaccccc      360
cagcaccatc cttccaaggt ccaccgtgat caacatccac agcgagacct ccgtgcccga      420
ccatgtcgtc tggtccctgt tcaacaccct cttcttgaac tggtgctgtc tgggcttcat      480
agcattcgcc tactccgtga agtctaggga caggaagatg gttggcgacg tgaccggggc      540
ccaggcctat gcctccaccg ccaagtgcct gaacatctgg gccctgattc tgggcatcct      600
catgaccatt ggattcatcc tgttactggt attcggctct gtgacagtct accatattat      660
gttacagata atacaggaaa aacggggtta ctagtagccg cccatagcct gcaacctttg      720
cactccactg tgcaatgctg gccctgcacc tggggctgtt gcccctgccc ccttggtcct      780
gcccctagat acagcagttt atacccacac acctgtctac agtgtcattc aataaagtgc      840
acgtgcttgt ga                                                         852
```

<210> SEQ ID NO 28
<211> LENGTH: 125
<212> TYPE: PRT
<213> ORGANISM: Homo sapiens

<400> SEQUENCE: 28

```
Met His Lys Glu Glu His Glu Val Ala Val Leu Gly Ala Pro Pro Ser
 1               5                  10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
        35                  40                  45

Trp Cys Cys Leu Gly Phe Ile Ala Phe Ala Tyr Ser Val Lys Ser Arg
    50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Leu Val Phe Gly Ser Val Thr Val Tyr
            100                 105                 110

His Ile Met Leu Gln Ile Ile Gln Glu Lys Arg Gly Tyr
        115                 120                 125
```

<210> SEQ ID NO 29
<211> LENGTH: 1106
<212> TYPE: DNA
<213> ORGANISM: Homo sapiens

<400> SEQUENCE: 29

```
cagagctgct gtcatggcgg ccgctctgtg gggcttcttt cccgtcctgc tgctgctgct       60
gctatcgggg gatgtccaga gctcggaggt gcccggggct gctgctgagg gatcgggagg      120
gagtggggtc ggcataggag atcgcttcaa gattgagggg cgtgcagttg ttccaggggt      180
gaagcctcag gactggatct cggcggcccg agtgctggta gacggagaag agcacgtcgg      240
tttccttaag acagatggga gttttgtggt tcatgatata ccttctggat cttatgtagt      300
ggaagttgta tctccagctt acagatttga tcccgttcga gtggatatca cttcgaaagg      360
```

```
aaaaatgaga gcaagatatg tgaattacat caaaacatca gaggttgtca gactgcccta    420
tcctctccaa atgaaatctt caggtccacc ttcttacttt attaaaaggg aatcgtgggg    480
ctggacagac tttctaatga acccaatggt tatgatgatg gttcttcctt tattgatatt    540
tgtgcttctg cctaaagtgg tcaacacaag tgatcctgac atgagacggg aaatggagca    600
gtcaatgaat atgctgaatt ccaaccatga gttgcctgat gtttctgagt tcatgacaag    660
actcttctct tcaaaatcat ctggcaaatc tagcagcggc agcagtaaaa caggcaaaag    720
tggggctggc aaaaggaggt agtcaggccg tccagagctg gcatttgcac aaacacggca    780
acactgggtg gcatccaagt cttggaaaac cgtgtgaagc aactactata aacttgagtc    840
atcccgacgt tgatctctta caactgtgta tgttaacttt ttagcacatg ttttgtactt    900
ggtacacgag aaaacccagc tttcatcttt tgtctgtatg aggtcaatat tgatgtcact    960
gaattaatta cagtgtccta tagaaaatgc cattaataaa ttatatgaac tactatacat   1020
tatgtatatt aattaaaaca tcttaatcca gaaaaaaaaa aaaaaaaaaa aaaaaaaaa    1080 armaaamgcg ggcgcggggg cgasky                                        1106

<210> SEQ ID NO 30
<211> LENGTH: 242
<212> TYPE: PRT
<213> ORGANISM: Homo sapiens

<400> SEQUENCE: 30

Met Ala Ala Ala Leu Trp Gly Phe Phe Pro Val Leu Leu Leu Leu Leu
 1               5                  10                  15

Leu Ser Gly Asp Val Gln Ser Ser Glu Val Pro Gly Ala Ala Ala Glu
                20                  25                  30

Gly Ser Gly Ser Gly Val Gly Ile Gly Asp Arg Phe Lys Ile Glu
            35                  40                  45

Gly Arg Ala Val Val Pro Gly Val Lys Pro Gln Asp Trp Ile Ser Ala
        50                  55                  60

Ala Arg Val Leu Val Asp Gly Glu Glu His Val Gly Phe Leu Lys Thr
65                  70                  75                  80

Asp Gly Ser Phe Val Val His Asp Ile Pro Ser Gly Ser Tyr Val Val
                85                  90                  95

Glu Val Val Ser Pro Ala Tyr Arg Phe Asp Pro Val Arg Val Asp Ile
               100                 105                 110

Thr Ser Lys Gly Lys Met Arg Ala Arg Tyr Val Asn Tyr Ile Lys Thr
           115                 120                 125

Ser Glu Val Val Arg Leu Pro Tyr Pro Leu Gln Met Lys Ser Ser Gly
       130                 135                 140

Pro Pro Ser Tyr Phe Ile Lys Arg Glu Ser Trp Gly Trp Thr Asp Phe
145                 150                 155                 160

Leu Met Asn Pro Met Val Met Met Val Leu Pro Leu Leu Ile Phe
               165                 170                 175

Val Leu Leu Pro Lys Val Val Asn Thr Ser Asp Pro Asp Met Arg Arg
           180                 185                 190

Glu Met Glu Gln Ser Met Asn Met Leu Asn Ser Asn His Glu Leu Pro
       195                 200                 205

Asp Val Ser Glu Phe Met Thr Arg Leu Phe Ser Ser Lys Ser Ser Gly
   210                 215                 220

Lys Ser Ser Ser Gly Ser Ser Lys Thr Gly Lys Ser Gly Ala Gly Lys
225                 230                 235                 240
```

Arg Arg

<210> SEQ ID NO 31
<211> LENGTH: 2795
<212> TYPE: DNA
<213> ORGANISM: Homo sapiens

<400> SEQUENCE: 31

| | | | | | |
|---|---|---|---|---|---|
| ggagctgaat | accctcccag | gcacacacag | gtgggacaca | aataagggtt | ttggaaccac | 60 |
| tattttctca | tcacgacagc | aacttaaaat | gcctgggaag | atggtcgtga | tccttggagc | 120 |
| ctcaaatata | ctttggataa | tgtttgcagc | ttctcaagct | tttaaaatcg | agaccacccc | 180 |
| agaatctaga | tatcttgctc | agattggtga | ctccgtctca | ttgacttgca | gcaccacagg | 240 |
| ctgtgagtcc | ccattttct | cttggagaac | ccagatagat | agtccactga | atgggaaggt | 300 |
| gacgaatgag | gggaccacat | ctacgctgac | aatgaatcct | gttagttttg | ggaacgaaca | 360 |
| ctcttacctg | tgcacagcaa | cttgtgaatc | taggaaattg | gaaaaaggaa | tccaggtgga | 420 |
| gatctactct | tttcctaagg | atccagagat | tcatttgagt | ggccctctgg | aggctgggaa | 480 |
| gccgatcaca | gtcaagtgtt | cagttgctga | tgtataccca | tttgacaggc | tggagataga | 540 |
| cttactgaaa | ggagatcatc | tcatgaagag | tcaggaattt | ctggaggatg | cagacaggaa | 600 |
| gtccctggaa | accaagagtt | tggaagtaac | ctttactcct | gtcattgagg | atattggaaa | 660 |
| agttcttgtt | tgccgagcta | aattacacat | tgatgaaatg | gattctgtgc | ccacagtaag | 720 |
| gcaggctgta | aaagaattgc | aagtctacat | atcacccaag | aatacagtta | tttctgtgaa | 780 |
| tccatccaca | aagctgcaag | aaggtggctc | tgtgaccatg | acctgttcca | gcgagggtct | 840 |
| accagctcca | gagattttct | ggagtaagaa | attagataat | gggaatctac | agcacctttc | 900 |
| tggaaatgca | actctcacct | taattgctat | gaggatggaa | gattctggaa | tttatgtgtg | 960 |
| tgaaggagtt | aatttgattg | ggaaaaacag | aaaagaggtg | gaattaattg | ttcaagcatt | 1020 |
| ccctagagat | ccagaaatcg | agatgagtgg | tggcctcgtg | aatgggagct | ctgtcactgt | 1080 |
| aagctgcaag | gttcctagcg | tgtacccct | tgaccggctg | gagattgaat | acttaaggg | 1140 |
| ggagactatt | ctgagaatta | tagagttttt | ggaggatacg | gatatgaaat | ctctagaaa | 1200 |
| caaaagtttg | gaaatgacct | tcatccctac | cattgaagat | actggaaaag | ctcttgtttg | 1260 |
| tcaggctaag | ttacatattg | atgacatgga | attcgaaccc | aaacaaaggc | agagtacgca | 1320 |
| aacactttat | gtcaatgttg | cccccagaga | tacaaccgtc | ttggtcagcc | cttcctccat | 1380 |
| cctggaggaa | gcagttctg | tgaatatgac | atgcttgagc | cagggctttc | ctgctccgaa | 1440 |
| aatcctgtgg | agcaggcagc | tccctaacgg | ggagctacag | cctctttctg | agaatgcaac | 1500 |
| tctcacctta | atttctacaa | aaatggaaga | ttctggggtt | tatttatgtg | aaggaattaa | 1560 |
| ccaggctgga | agaagcagaa | aggaagtgga | attaattatc | caagttactc | caaaagacat | 1620 |
| aaaacttaca | gcttttcctt | ctgagagtgt | caaagaagga | gacactgtca | tcatctcttg | 1680 |
| tacatgtgga | aatgttccag | aaacatggat | aatcctgaag | aaaaaagcgg | agacaggaga | 1740 |
| cacagtacta | aaatctatag | atggcgccta | taccatccga | aagcccagt | tgaaggatgc | 1800 |
| gggagtatat | gaatgtgaat | ctaaaaacaa | agttggctca | caattaagaa | gtttaacact | 1860 |
| tgatgttcaa | ggaagagaaa | acaacaaaga | ctatttttct | cctgagcttc | tcgtgctcta | 1920 |
| ttttgcatcc | tccttaataa | tacctgccat | tggaatgata | atttactttg | caagaaaagc | 1980 |
| caacatgaag | gggtcatata | gtcttgtaga | agcacagaaa | tcaaagtgt | agctaatgct | 2040 |
| tgatatgttc | aactggagac | actatttatc | tgtgcaaatc | cttgatactg | ctcatcattc | 2100 |

```
cttgagaaaa acaatgagct gagaggcaga cttccctgaa tgtattgaac ytggaaagaa    2160
atgcccatct atgtcccttg ctgtgagcaa gaagtcaaag taaaacttgc tgcctgaaga    2220
acagtaactg ccatcaagat gagagaactg gaggagttcc ttgatctgta tatacaataa    2280
cataatttgt acatatgtaa aataaaatta tgccatagca agattgctta aaatagcaac    2340
actctatatt tagawtgtta aaawaamyag tgttgcytgg actattataa tttaatgcat    2400
gttaggaaaa ttycacatta awatttgckg acagctgacc yttgtcatct ttctyctatt    2460
ttatycccTT ycacaaaatt ttatycctat atagtttatt gacaataatt tcaggttttg    2520
taaagatgcc gggttttata tttttataga caaataataa gcaaagggag cactgggttg    2580
actttcaggt actaaatacc tcaacctatg gtataatggt tgactgggtt tctctgtata    2640
gtactggcat ggtacggaga tgtttcacga agtttgttca tcagactcct gtgcaacttt    2700
cccaatgtgg cctaaaaatg caacttcttt ttattttctt ttgtaaatgt ttaggttttt    2760
ttgtatagta aagtgataat ttctggaaww aaaaa                               2795

<210> SEQ ID NO 32
<211> LENGTH: 647
<212> TYPE: PRT
<213> ORGANISM: Homo sapiens

<400> SEQUENCE: 32

Met Pro Gly Lys Met Val Val Ile Leu Gly Ala Ser Asn Ile Leu Trp
  1               5                  10                  15

Ile Met Phe Ala Ala Ser Gln Ala Phe Lys Ile Glu Thr Thr Pro Glu
             20                  25                  30

Ser Arg Tyr Leu Ala Gln Ile Gly Asp Ser Val Ser Leu Thr Cys Ser
         35                  40                  45

Thr Thr Gly Cys Glu Ser Pro Phe Phe Ser Trp Arg Thr Gln Ile Asp
     50                  55                  60

Ser Pro Leu Asn Gly Lys Val Thr Asn Glu Gly Thr Thr Ser Thr Leu
 65                  70                  75                  80

Thr Met Asn Pro Val Ser Phe Gly Asn Glu His Ser Tyr Leu Cys Thr
                 85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255
```

```
Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Ala Phe Pro Arg Asp Pro Glu Ile Glu Met Ser
305                 310                 315                 320

Gly Gly Leu Val Asn Gly Ser Ser Val Thr Val Ser Cys Lys Val Pro
                325                 330                 335

Ser Val Tyr Pro Leu Asp Arg Leu Glu Ile Glu Leu Leu Lys Gly Glu
            340                 345                 350

Thr Ile Leu Glu Asn Ile Glu Phe Leu Glu Asp Thr Asp Met Lys Ser
        355                 360                 365

Leu Glu Asn Lys Ser Leu Glu Met Thr Phe Ile Pro Thr Ile Glu Asp
    370                 375                 380

Thr Gly Lys Ala Leu Val Cys Gln Ala Lys Leu His Ile Asp Asp Met
385                 390                 395                 400

Glu Phe Glu Pro Lys Gln Arg Gln Ser Thr Gln Thr Leu Tyr Val Asn
                405                 410                 415

Val Ala Pro Arg Asp Thr Thr Val Leu Val Ser Pro Ser Ser Ile Leu
            420                 425                 430

Glu Glu Gly Ser Ser Val Asn Met Thr Cys Leu Ser Gln Gly Phe Pro
        435                 440                 445

Ala Pro Lys Ile Leu Trp Ser Arg Gln Leu Pro Asn Gly Glu Leu Gln
    450                 455                 460

Pro Leu Ser Glu Asn Ala Thr Leu Thr Leu Ile Ser Thr Lys Met Glu
465                 470                 475                 480

Asp Ser Gly Val Tyr Leu Cys Glu Gly Ile Asn Gln Ala Gly Arg Ser
                485                 490                 495

Arg Lys Glu Val Glu Leu Ile Ile Gln Val Thr Pro Lys Asp Ile Lys
            500                 505                 510

Leu Thr Ala Phe Pro Ser Glu Ser Val Lys Glu Gly Asp Thr Val Ile
        515                 520                 525

Ile Ser Cys Thr Cys Gly Asn Val Pro Glu Thr Trp Ile Ile Leu Lys
    530                 535                 540

Lys Lys Ala Glu Thr Gly Asp Thr Val Leu Lys Ser Ile Asp Gly Ala
545                 550                 555                 560

Tyr Thr Ile Arg Lys Ala Gln Leu Lys Asp Ala Gly Val Tyr Glu Cys
                565                 570                 575

Glu Ser Lys Asn Lys Val Gly Ser Gln Leu Arg Ser Leu Thr Leu Asp
            580                 585                 590

Val Gln Gly Arg Glu Asn Asn Lys Asp Tyr Phe Ser Pro Glu Leu Leu
        595                 600                 605

Val Leu Tyr Phe Ala Ser Ser Leu Ile Ile Pro Ala Ile Gly Met Ile
    610                 615                 620

Ile Tyr Phe Ala Arg Lys Ala Asn Met Lys Gly Ser Tyr Ser Leu Val
625                 630                 635                 640

Glu Ala Gln Lys Ser Lys Val
                645

<210> SEQ ID NO 33
<211> LENGTH: 1375
<212> TYPE: DNA
<213> ORGANISM: Homo sapiens
```

```
<220> FEATURE:
<221> NAME/KEY: misc_feature
<222> LOCATION: 1327, 1328, 1329, 1330, 1331, 1332, 1333, 1334, 1335,
      1336, 1337, 1338, 1339, 1340, 1341, 1342, 1343, 1344, 1345, 1346,
      1347, 1348, 1349, 1350, 1351, 1352, 1353, 1354, 1355, 1356,
      1357, 1358, 1359, 1360, 1361, 1362, 1363, 1364, 1365
<223> OTHER INFORMATION: n = A,T,C or G
<220> FEATURE:
<221> NAME/KEY: misc_feature
<222> LOCATION: 1366, 1367, 1368, 1369, 1370, 1371, 1372
<223> OTHER INFORMATION: n = A,T,C or G

<400> SEQUENCE: 33
gagtcgaccc acgcgtccgc ccacgcgtcc gagcggtctg acagcgcgt ggccggcgcc      60
gctgtgggga cagcatgagc ggcggttgga tggcgcaggt tggagcgtgg cgaacagggg   120
ctctgggcct ggcgctgctg ctgctgctcg gcctcggact aggcctggag ccgccgcga    180
gcccgctttc caccccgacc tctgcccagg ccgcaggccc cagctcaggc tcgtgcccac    240
ccaccaagtt ccagtgccgc accagtggct tatgcgtgcc cctcacctgg cgctgcgaca    300
gggacttgga ctgcagcgat ggcagcgatg aggaggagtg caggattgag ccatgtaccc    360
agaaagggca atgcccaccg ccccctggcc tcccctgccc ctgcaccggc gtcagtgact    420
gctctggggg aactgacaag aaactgcgca actgcagccg cctggcctgc ctagcaggcg    480
agctccgttg cacgctgagc gatgactgca ttccactcac gtggcgctgc gacggccacc    540
cagactgtcc cgactccagc gacgagctcg gctgtggaac caatgagatc ctcccggaag    600
gggatgccac aaccatgggg cccctgtga cctggagag tgtcacctct ctcaggaatg     660
ccacaaccat ggggccccct gtgaccctgg agagtgtccc ctctgtcggg aatgccacat    720
cctcctctgc cggagaccag tctggaagcc caactgccta tgggttatt gcagctgctg    780
cggtgctcag tgcaagcctg gtcaccgcca ccctcctcct tttgtcctgg ctccgagccc    840
aggagcgcct ccgcccactg gggttactgg tggccatgaa ggagtccctg ctgctgtcag    900
aacagaagac ctcgctgccc tgaggacaag cacttgccac caccgtcact cagccctggg    960
cgtagccgga caggaggaga gcagtgatgc ggatgggtac ccgggcacac cagccctcag   1020
agacctgagc tcttctggcc acgtggaacc tcgaacccga gctcctgcag gaagtggccc   1080
tggagattga gggtccctgg acactcccta tggagatccg gggagctagg atggggaacc   1140
tgccacagcc agaactgagg ggctggcccc aggcagctcc caggggggtag aacgccctg   1200
tgcttaagac actcctgctg ccccgtctga gggtggcgat taaagttgct tcacatcctc   1260
aaaaaaaaaa aaaaaaaaaa aaaaaaaaa aaaaaaaaa aaaaaaargg gcggccgct     1320
agactannnn nnnnnnnnnn nnnnnnnnnn nnnnnnnnnn nnnnnnnnnn nngaa          1375

<210> SEQ ID NO 34
<211> LENGTH: 282
<212> TYPE: PRT
<213> ORGANISM: Homo sapiens

<400> SEQUENCE: 34

Met Ser Gly Gly Trp Met Ala Gln Val Gly Ala Trp Arg Thr Gly Ala
 1               5                  10                  15
Leu Gly Leu Ala Leu Leu Leu Leu Gly Leu Gly Leu Gly Leu Glu
            20                  25                  30
Ala Ala Ala Ser Pro Leu Ser Thr Pro Thr Ser Ala Gln Ala Ala Gly
        35                  40                  45
Pro Ser Gly Ser Cys Pro Pro Thr Lys Phe Gln Cys Arg Thr Ser
    50                  55                  60
```

```
Gly Leu Cys Val Pro Leu Thr Trp Arg Cys Asp Arg Asp Leu Asp Cys
 65                  70                  75                  80

Ser Asp Gly Ser Asp Glu Glu Glu Cys Arg Ile Glu Pro Cys Thr Gln
                 85                  90                  95

Lys Gly Gln Cys Pro Pro Pro Gly Leu Pro Cys Pro Cys Thr Gly
            100                 105                 110

Val Ser Asp Cys Ser Gly Gly Thr Asp Lys Lys Leu Arg Asn Cys Ser
            115                 120                 125

Arg Leu Ala Cys Leu Ala Gly Glu Leu Arg Cys Thr Leu Ser Asp Asp
        130                 135                 140

Cys Ile Pro Leu Thr Trp Arg Cys Asp Gly His Pro Cys Pro Asp
145                 150                 155                 160

Ser Ser Asp Glu Leu Gly Cys Gly Thr Asn Glu Ile Leu Pro Glu Gly
                165                 170                 175

Asp Ala Thr Thr Met Gly Pro Pro Val Thr Leu Glu Ser Val Thr Ser
            180                 185                 190

Leu Arg Asn Ala Thr Thr Met Gly Pro Pro Val Thr Leu Glu Ser Val
        195                 200                 205

Pro Ser Val Gly Asn Ala Thr Ser Ser Ser Ala Gly Asp Gln Ser Gly
210                 215                 220

Ser Pro Thr Ala Tyr Gly Val Ile Ala Ala Ala Val Leu Ser Ala
225                 230                 235                 240

Ser Leu Val Thr Ala Thr Leu Leu Leu Ser Trp Leu Arg Ala Gln
                245                 250                 255

Glu Arg Leu Arg Pro Leu Gly Leu Leu Val Ala Met Lys Glu Ser Leu
            260                 265                 270

Leu Leu Ser Glu Gln Lys Thr Ser Leu Pro
        275                 280

<210> SEQ ID NO 35
<211> LENGTH: 1798
<212> TYPE: DNA
<213> ORGANISM: Homo sapiens
<220> FEATURE:
<221> NAME/KEY: misc_feature
<222> LOCATION: 6, 7
<223> OTHER INFORMATION: n = A,T,C or G

<400> SEQUENCE: 35 ttcganngge cgcccgggca ggtacctcaa attttaggg gagggtgggt tagggactga      60
tactcagatt gtggataata attgaattgg tttttaaagg caacatagca ttctacagca    120
gggttaatct attatcaaga acagtcaccc tggttaataa caagttttac tgatcagttg    180
ctggttggtt ggttggttgg catgtgggtg tgtgggtgta taggtgtgtg tgggtgtgtg    240
tgtgtatttt tccccatgag tccttttttt aatcctgtgg cttttttcact tacaactagc    300 ctaaccctgt aattttccta catccaagaa acaatcaca aagtagtggt ttaaatactt     360 tgttgtatttt ggctaatttt gctgtcttaa tgcagcctat taagagttgg gttaaaaatc    420
agtaatcagt actttattac atcactgaac taaaatatgg agacatcctc attgaaaatg    480
gagggcactc tatcagtcta taactatcaa cgtagtgcaa cagggtgttt tgatacctttt    540 gttttcacct cttgacataa tgctatttaa aggcttgaat ttttcccttt atataatttt    600 caccttact ttcaaagtgt tttgttgtag ttggctattg cagagagtgc attgtcctat     660
cattcctaaa cctggtctgc tttctacatt catggtatgg aaaccatgtg attctttgta    720
cagtttatcc tgatgttgct tgtaatgcag tagaggctat ttcgccttcg cttttctttc    780
```

-continued

```
tcgaccttttt tgtaaaccct ataattatga agcgattgct tgagaaaata acatataaac    840
atagaataga atagactgac caagatggtt cacagtttct ttttttaact aggttattta    900
taatgtattt ctgaaccact tggcagacaa attcacaaca cttaatgttc atattttgag    960
taaaggaagc taaaaccatg tttgctttct ggtactacat gcattagcga aaggttaagt   1020
aagttttgtt ctccactgaa gtaatactta acatctcaga aaaaattttg catgttctgt   1080
agttttgtat taaatcagtc atttcatatg cactatatca agtacaaaca ggtagtttac   1140
ctgtttatag tagtgtacta acaaagtctc ccttgcagct tcagactgtt atctataggc   1200
ttatcgttca aatacagcac ttgaatatcc caagtagttc ttctacgcat agctcacctt   1260
tctaaaccca gttaagcatg aagagaggt agtaggtagg tgcagtgtgt ggaagctgca    1320
aacaagtagg cctttttattc attgatatct tttcccaagt actggatttt aaatctgwat  1380
gtatctgttt gatttttttt tctaatattt cagttgagct gctgttttct tccatgcaat   1440
attgtatact caattgtgta tagaagaagc tggtgagagt gccctcctac ataaataagc   1500
aattgcagtg ttttgcatgc aaaatataaa aaatttaaat tgtcctgatt ctattttgta   1560
aatggagaaa caatcatatc tttctaagcg gtaatggagg aagactagtg ctttgtgcat   1620
tttgatatat ttgagttcat ttttttccaca atgtcatact tttgacgcag ttgggtttct  1680
catargtatc ctagttcatg tacatccgaa tgctaaataa tactgtgttt taagttttgt   1740
gttgcaagaa caaatggaat aaacttgaat tgtgctacaa aaaaaaaaaa aaaaaaa      1798
```

<210> SEQ ID NO 36
<211> LENGTH: 57
<212> TYPE: PRT
<213> ORGANISM: Homo sapiens

<400> SEQUENCE: 36

```
Met Leu Phe Lys Gly Leu Asn Phe Ser Leu Tyr Ile Ile Phe Thr Phe
 1               5                  10                  15

Thr Phe Lys Val Phe Cys Cys Ser Trp Leu Leu Gln Arg Val His Cys
            20                  25                  30

Pro Ile Ile Pro Lys Pro Gly Leu Leu Ser Thr Phe Met Val Trp Lys
        35                  40                  45

Pro Cys Asp Ser Leu Tyr Ser Leu Ser
    50                  55
```

<210> SEQ ID NO 37
<211> LENGTH: 3113
<212> TYPE: DNA
<213> ORGANISM: Homo sapiens
<220> FEATURE:
<221> NAME/KEY: misc_feature
<222> LOCATION: 68, 92, 94, 106, 145
<223> OTHER INFORMATION: n = A,T,C or G

<400> SEQUENCE: 37

```
gacccacgms yccgcgtcgt ccgcgcgtcg ccggaagggg aagtttcgcc tcagaaggct     60
gcctcgcntg gtccgaattc ggtggcgcca cngntccgcc cgtctnccgc cttctgcatc   120
gcggcttcgg cggcttccac ctagnacacc taacagtcgc ggagccggcc gcgtcgtgag   180
ggggtcggca cggggagtcg ggcggtcttg tgcatcttgg ctacctgtgg gtcgaagatg   240
tcggacatcg gagactggtt caggagcatc ccggcgatca cgcgctattg gttcgccgcc   300
accgtcgccg tgcccttggt cggcaaactc ggcctcatca gcccggccta cctcttcctc   360 tggccccgaag ccttccttta tcgctttcag atttggaggc caatcactgc caccttttat   420
```

```
ttccctgtgg gtccaggaac tggatttctt tatttggtca atttatattt cttatatcag    480
tattctacgc gacttgaaac aggagctttt gatgggaggc cagcagacta tttattcatg    540
ctcctcttta actggatttg catcgtgatt actggcttag caatggatat gcagttgctg    600
atgattcctc tgatcatgtc agtacttat gtctgggccc agctgaacag agacatgatt    660
gtatcatttt ggtttggaac acgatttaag gcctgctatt taccctgggt tatccttgga    720
ttcaactata tcatcggagg ctcggtaatc aatgagctta ttggaaatct ggttggacat    780
ctttattttt tcctaatgtt cagataccca atggacttgg gaggaagaaa ttttctatcc    840
acacctcagt ttttgtaccg ctggctgccc agtaggagag gaggagtatc aggatttggt    900
gtgccccctg ctagcatgag gcgagctgct gatcagaatg gcggaggcgg gagacacaac    960
tggggccagg gctttcgact tggagaccag tgaaggggcg gcctcgggca gccgctcctc   1020
tcaagccaca tttcctccca gtgctgggtg cgcttaacaa ctgcgttctg ctaacactg    1080 ttggacctga cccacactga atgtagtctt tcagtacgag acaaagtttc ttaaatcccg   1140
aagaaaaata taagtgttcc acaagtttca cgattctcat tcaagtcctt actgctgtga   1200
agaacaaata ccaactgtgc aaattgcaaa actgactaca ttttttggtg tcttctcttc   1260 tccccttcc gtctgaataa tgggttttag cgggtcctag tctgctggca ttgagctggg   1320
gctgggtcac caaacccttc ccaaaaggac ccttatctct ttcttgcaca catgcctctc   1380
tcccactttt cccaaccccc acatttgcaa ctagaagagg ttgcccataa aattgctctg   1440
cccttgacag gttctgttat ttattgactt ttgccaaggc ttggtcacaa caatcatatt   1500
cacgtaattt tcccccttg gtggcagaac tgtagcaata gggggagaag acaagcagcg   1560
gatgaagcgt tttctcagct tttgaaattg cttcgacctg acatccgttg taaccgtttg   1620
ccacttcttc agatatttt ataaaaagt accactgagt cagtgagggc cacagattgg    1680
tattaatgag atacgagggt tgttgctggg tgtttgtttc ctgagctaag tgatcaagac   1740
tgtagtggag ttgcagctaa catgggttag gtttaaacca tggggatgc aaccccttg    1800 cgtttcatat gtaggcctac tggctttgtg tagctggagt agttgggttg ctttgtgtta   1860
ggaggatcca gatcatgttg gctacaggga gatgctctct ttgagaggct cctgggcatt   1920
gattccattt caatctcatt ctggatatgt gttcattgag taaaggagga gagaccctca   1980
tacgctattt aaatgtcact tttttgccta tcccccgttt tttggtcatg tttcaattaa   2040
ttgtgaggaa ggcgcagctc ctctctgcac gtagatcatt ttttaaagct aatgtaagca   2100
catctaaggg aataacatga tttaaggttg aaatggcttt agaatcattt gggtttgagg   2160
gtgtgttatt ttgagtcatg aatgtacaag ctctgtgaat cagaccagct taaataccca   2220 caccttttt tcgtaggtgg gcttttccta tcagagcttg gctcataacc aaataaagtt   2280
ttttgaaggc catggctttt cacacagtta ttttatttta tgacgttatc tgaaagcaga   2340
ctgttaggag cagtattgag tggctgtcac actttgaggc aactaaaaag gcttcaaacg   2400
ttttgatcag tttcttttca ggaaacattg tgctctaaca gtatgactat tctttccccc   2460
actcttaaac agtgtgatgt gtgttatcct aggaaatgag agttggcaaa caacttctca   2520
ttttgaatag agtttgtgtg tacctctcca tatttaattt atatgataaa ataggtgggg   2580
agagtctgaa ccttaactgt catgtttttgt tgttcatctg tggccacaat aaagtttact   2640
tgtaaaattt tagaggccat tactccaatt atgttgcacg tacactcatt gtacaggcgt   2700
ggagactcat tgtatgtata agaatattct gacagtgagt gacccggagt ctctggtgta   2760
ccctcttacc agtcagctgc ctgcgagcag tcatttttc ctaaaggttt acaagtattt   2820
```

```
agaactcttc agttcagggc aaaatgttca tgaagttatt cctcttaaac atggttagga    2880
agctgatgac gttattgatt ttgtctggat tatgtttctg gaataatttt accaaaacaa    2940
gctatttgag ttttgacttg acaaggcaaa acatgacagt ggattctctt tacaaatgga    3000
aaaaaaaaat ccttattttg tataaaggac ttcccttttt gtaaactaat ccttttatt     3060 ggtaaaaatt gtaaattaaa atgtgcaact tgaaaaaaaa aaaaaaaaa aaa            3113
```

<210> SEQ ID NO 38
<211> LENGTH: 251
<212> TYPE: PRT
<213> ORGANISM: Homo sapiens

<400> SEQUENCE: 38

```
Met Ser Asp Ile Gly Asp Trp Phe Arg Ser Ile Pro Ala Ile Thr Arg
 1               5                   10                  15

Tyr Trp Phe Ala Ala Thr Val Ala Val Pro Leu Val Gly Lys Leu Gly
                20                  25                  30

Leu Ile Ser Pro Ala Tyr Leu Phe Leu Trp Pro Glu Ala Phe Leu Tyr
            35                  40                  45

Arg Phe Gln Ile Trp Arg Pro Ile Thr Ala Thr Phe Tyr Phe Pro Val
 50                  55                  60

Gly Pro Gly Thr Gly Phe Leu Tyr Leu Val Asn Leu Tyr Phe Leu Tyr
 65                  70                  75                  80

Gln Tyr Ser Thr Arg Leu Glu Thr Gly Ala Phe Asp Gly Arg Pro Ala
                85                  90                  95

Asp Tyr Leu Phe Met Leu Leu Phe Asn Trp Ile Cys Ile Val Ile Thr
            100                 105                 110

Gly Leu Ala Met Asp Met Gln Leu Leu Met Ile Pro Leu Ile Met Ser
            115                 120                 125

Val Leu Tyr Val Trp Ala Gln Leu Asn Arg Asp Met Ile Val Ser Phe
130                 135                 140

Trp Phe Gly Thr Arg Phe Lys Ala Cys Tyr Leu Pro Trp Val Ile Leu
145                 150                 155                 160

Gly Phe Asn Tyr Ile Ile Gly Gly Ser Val Ile Asn Glu Leu Ile Gly
                165                 170                 175

Asn Leu Val Gly His Leu Tyr Phe Phe Leu Met Phe Arg Tyr Pro Met
            180                 185                 190

Asp Leu Gly Gly Arg Asn Phe Leu Ser Thr Pro Gln Phe Leu Tyr Arg
            195                 200                 205

Trp Leu Pro Ser Arg Arg Gly Gly Val Ser Gly Phe Gly Val Pro Pro
210                 215                 220

Ala Ser Met Arg Arg Ala Ala Asp Gln Asn Gly Gly Gly Arg His
225                 230                 235                 240

Asn Trp Gly Gln Gly Phe Arg Leu Gly Asp Gln
                245                 250
```

<210> SEQ ID NO 39
<211> LENGTH: 3599
<212> TYPE: DNA
<213> ORGANISM: Homo sapiens
<220> FEATURE:
<221> NAME/KEY: misc_feature
<222> LOCATION: 3390, 3420
<223> OTHER INFORMATION: n = A,T,C or G

<400> SEQUENCE: 39

```
cagtttggga ccaaagccaa agataaccag gttcatatta attacacgga ataggcaaga    60
```

```
aagcatgagc cctgaggagg aaggaaaggg actgtcccag gtgtacttac ctcaaagatg    120
aagaaatatc aaagacagga aaccctaggt tcttgccctt cagtcgctat ctccttgccc    180
attagtaaaa tgcggccgat gaatgtcctc acttctgtcc atctgggcag gaggtgggaa    240
gggtgacgtg caaatggatg ggaggaaccc ttttttcggc agcacccacc acacccagcc    300
tagtgccacg caccgcaagc gctccataaa cgcacacagc gtcgcswcya csmgkmyscc    360
gggcggcctt cgcgggattt ctcctggcgt cggctttcag actcccgagg gtgggataaa    420
tcgagagggt ggcatccttt ggcttttctt ctcccaggca gctctgaacc atgtttatgc    480
aacgtttaat gggctctaat aaaacggcta ataattttga tccgcggaag caccgactcg    540
ctcgctaagc cgagtctgcg agggtgaagc tgcaactcca acgccggaaa gcgcggctac    600
cgaaaagcgc atgcgccacg gggtggcacg aagctagagt aagctgagga ggtgggcgga    660
aaccatggca accatgggtg atgacgacat ggggagcgtc tctagcgctg gattatgacg    720
ctggattatg acgcatgcag tgggcgcccg ctctgcggtt cgcttgactg acggcgcagc    780
ctccgggcct agccacagca gcaacggcag aggccagcgg gcgaggtcaa gatggtggct    840
ccgcgggcgg gggaggcagt ggaggggagga ggagtcagac cttagccagc cggaaacacc    900
gaaacccaga gacctcctgg ggagccgtcg ccgccgccgc cctctcggcc atcgctgcct    960
ccgccgcctg ctccacctcg agggacgcga gcgggcggcg gggctggccg tgagagagac   1020
aggagaggaa ggagggcagg ggcggagttg cccgccttag cccccgcccc cggccgcggc   1080
cccgggccct gccccgcgcg gccctgcccg gcccaccgag ccctggtgtg gcagcggctc   1140
atggcggccg tggggccccc gcagcagcag gtgcggatgg cccatcagca ggtctgggcg   1200
gcgctcgaag tggcgctccg ggtgccctgc ctttacatca tcgacgccat cttcaactcc   1260
tacccggatt ccagccaaag ccggttctgc atcgtgctcc agatcttcct ccggctcttt   1320
ggtgtatttg catccagtat tgttctgatc ttgtcacaac gatcactttt caagttttac   1380
acgtacagct cagcctttct gttagctgca acttcagtgt tggtgaatta ttatgcttct   1440
ttgcacattg acttctatgg tgcctacaac acgtcagctt ttggaattga gctgcttcct   1500
cgaaaaggtc cctcgctgtg gatggcactt atcgttctac agctaacatt tggaattgga   1560
tacgttacac tactccagat tcattccatc tattcacaat taattatttt ggatctcttg   1620
gttcctgtaa taggcttaat cacagagcta ccattacaca tcagagagac tttactgttt   1680
acttcttcct tgattctcac attaaataca gtgtttgtcc tggcagtgaa actgaagtgg   1740
ttttattatt ccacacgata tgtttatctt ttggtgaggc acatgtatcg aatttatgga   1800
ttacagttat tgatggagga cacatggaag aggattcgtt tcccagacat actacgagtc   1860
ttttggctaa caagagttac agctcaggct acagtgttaa tgtacatctt aaggatggca   1920
aatgaaactg attccttctt tatttcttgg gatgattttt gggacctcat tgcaatctt    1980 ataattagtg ggtgcgattc tacactaact gtactgggca tgagtgctgt aatttcctca   2040
gtagcccatt atttggggct tggaatattg gcctttattg gatcaactga ggaagatgac   2100
aggcgtcttg gctttgttgc acctgttta ttttttattt tggctcttca gactgggtta    2160
agtgggctaa gaccagaaga gagacttatt cgcttaagta gaaacatgtg ccttttatta   2220
actgcagtcc tgcattttat ccatggaatg acagaccctg tattaatgtc tctcagtgcc   2280
tctcatgtgt catcttttcg tagacatttt cctgtgctgt ttgtctctgc ttgcctgttt   2340
attcttcctg tcttactcag ttatgttctt tggcatcact atgcactaaa tacatggttg   2400
tttgcagtta cagcattttg tgtggaactg tgcttaaaag taattgtttc tctcactgtt   2460
```

-continued

```
tatacgttat tcatgattga tggctactat aatgtcctct gggaaaagct tgacgattat    2520
gtctactacg ttcgttcaac aggcagtatt attgaattta tatttggagt tgtaatgttt    2580
ggaaatgggg cttacactat gatgtttgag tcgggaagta aaattcgggc ttttatgatg    2640
tgcctacatg catattttaa catctactta caagccaaaa atggctggaa gacatttatg    2700
aatcgtagga ctgctgtgaa gaaaattaat tcacttcctg aaataaaagg gagccgctta    2760
caagaaataa atgatgtatg tgcaatctgc tatcatgagt ttacaacatc tgctcgtatt    2820
acaccgtgta atcattattt ccatgcactt tgccttcgga atggctgta cattcaagat    2880 acttgtccaa tgtgccatca gaaagtatac atcgaagatg atatcaagga taattcaaat    2940
gtatctaaca acaatggatt tattccaccc aatgaaactc cagaggaagc tgtaagagaa    3000
gctgctgctg aatctgacag ggaattgaac gaagatgaca gtacagattg tgatgatgat    3060
gttcaaagag aaagaaatgg agtgattcag cacacaggcg cagcagctga agaatttaat    3120
gatgatactg actgatgaaa atagcattta ttaatgattg aggtatttgt ttaaaattca    3180
gttcatccaa aatggagtaa tatccttcac cttcagtgtg taaccaagca caaaaacagt    3240
atcaatgttg aatctgtgaa tggttttccg tttactgtga tgtgctactg taaatatacc    3300
tctttaatta cttctggtct ctttggtgac ctgtttaaat ttgtgtacat tattgtacat    3360
agaataaaat gttttcacat ttttatgacn aaaawwwraa caaatagctt tttaatagan    3420
tgtaatgatc atatggtgcg tcacctgtgc caaatattct tcaatgaaat tatataatgt    3480
aactttggac ctcagttttt ctttagaaat gggtgggaga atgaaaatgc aaatcaggaa    3540
accacattaa agtcaaggaa ataaaataat ttgaccagag gataaaggac atgagagag    3599
```

<210> SEQ ID NO 40
<211> LENGTH: 664
<212> TYPE: PRT
<213> ORGANISM: Homo sapiens

<400> SEQUENCE: 40

```
Met Ala Ala Val Gly Pro Pro Gln Gln Gln Val Arg Met Ala His Gln
  1               5                  10                  15

Gln Val Trp Ala Ala Leu Glu Val Ala Leu Arg Val Pro Cys Leu Tyr
             20                  25                  30

Ile Ile Asp Ala Ile Phe Asn Ser Tyr Pro Asp Ser Ser Gln Ser Arg
         35                  40                  45

Phe Cys Ile Val Leu Gln Ile Phe Leu Arg Leu Phe Gly Val Phe Ala
     50                  55                  60

Ser Ser Ile Val Leu Ile Leu Ser Gln Arg Ser Leu Phe Lys Phe Tyr
 65                  70                  75                  80

Thr Tyr Ser Ser Ala Phe Leu Leu Ala Ala Thr Ser Val Leu Val Asn
                 85                  90                  95

Tyr Tyr Ala Ser Leu His Ile Asp Phe Tyr Gly Ala Tyr Asn Thr Ser
            100                 105                 110

Ala Phe Gly Ile Glu Leu Leu Pro Arg Lys Gly Pro Ser Leu Trp Met
        115                 120                 125

Ala Leu Ile Val Leu Gln Leu Thr Phe Gly Ile Gly Tyr Val Thr Leu
    130                 135                 140

Leu Gln Ile His Ser Ile Tyr Ser Gln Leu Ile Ile Leu Asp Leu Leu
145                 150                 155                 160

Val Pro Val Ile Gly Leu Ile Thr Glu Leu Pro Leu His Ile Arg Glu
                165                 170                 175

Thr Leu Leu Phe Thr Ser Ser Leu Ile Leu Thr Leu Asn Thr Val Phe
```

-continued

```
                180                 185                 190
Val Leu Ala Val Lys Leu Lys Trp Phe Tyr Tyr Ser Thr Arg Tyr Val
            195                 200                 205

Tyr Leu Leu Val Arg His Met Tyr Arg Ile Tyr Gly Leu Gln Leu Leu
            210                 215                 220

Met Glu Asp Thr Trp Lys Arg Ile Arg Phe Pro Asp Ile Leu Arg Val
225                 230                 235                 240

Phe Trp Leu Thr Arg Val Thr Ala Gln Ala Thr Val Leu Met Tyr Ile
            245                 250                 255

Leu Arg Met Ala Asn Glu Thr Asp Ser Phe Phe Ile Ser Trp Asp Asp
            260                 265                 270

Phe Trp Asp Leu Ile Cys Asn Leu Ile Ile Ser Gly Cys Asp Ser Thr
            275                 280                 285

Leu Thr Val Leu Gly Met Ser Ala Val Ile Ser Ser Val Ala His Tyr
            290                 295                 300

Leu Gly Leu Gly Ile Leu Ala Phe Ile Gly Ser Thr Glu Glu Asp Asp
305                 310                 315                 320

Arg Arg Leu Gly Phe Val Ala Pro Val Leu Phe Phe Ile Leu Ala Leu
            325                 330                 335

Gln Thr Gly Leu Ser Gly Leu Arg Pro Glu Glu Arg Leu Ile Arg Leu
            340                 345                 350

Ser Arg Asn Met Cys Leu Leu Leu Thr Ala Val Leu His Phe Ile His
            355                 360                 365

Gly Met Thr Asp Pro Val Leu Met Ser Leu Ser Ala Ser His Val Ser
            370                 375                 380

Ser Phe Arg Arg His Phe Pro Val Leu Phe Val Ser Ala Cys Leu Phe
385                 390                 395                 400

Ile Leu Pro Val Leu Leu Ser Tyr Val Leu Trp His His Tyr Ala Leu
            405                 410                 415

Asn Thr Trp Leu Phe Ala Val Thr Ala Phe Cys Val Glu Leu Cys Leu
            420                 425                 430

Lys Val Ile Val Ser Leu Thr Val Tyr Thr Leu Phe Met Ile Asp Gly
            435                 440                 445

Tyr Tyr Asn Val Leu Trp Glu Lys Leu Asp Asp Tyr Val Tyr Tyr Val
            450                 455                 460

Arg Ser Thr Gly Ser Ile Ile Glu Phe Ile Phe Gly Val Val Met Phe
465                 470                 475                 480

Gly Asn Gly Ala Tyr Thr Met Met Phe Glu Ser Gly Ser Lys Ile Arg
            485                 490                 495

Ala Phe Met Met Cys Leu His Ala Tyr Phe Asn Ile Tyr Leu Gln Ala
            500                 505                 510

Lys Asn Gly Trp Lys Thr Phe Met Asn Arg Arg Thr Ala Val Lys Lys
            515                 520                 525

Ile Asn Ser Leu Pro Glu Ile Lys Gly Ser Arg Leu Gln Glu Ile Asn
            530                 535                 540

Asp Val Cys Ala Ile Cys Tyr His Glu Phe Thr Thr Ser Ala Arg Ile
545                 550                 555                 560

Thr Pro Cys Asn His Tyr Phe His Ala Leu Cys Leu Arg Lys Trp Leu
            565                 570                 575

Tyr Ile Gln Asp Thr Cys Pro Met Cys His Gln Lys Val Tyr Ile Glu
            580                 585                 590

Asp Asp Ile Lys Asp Asn Ser Asn Val Ser Asn Asn Gly Phe Ile
            595                 600                 605
```

```
Pro Pro Asn Glu Thr Pro Glu Glu Ala Val Arg Glu Ala Ala Ala Glu
    610                 615                 620

Ser Asp Arg Glu Leu Asn Glu Asp Asp Ser Thr Asp Cys Asp Asp Asp
625                 630                 635                 640

Val Gln Arg Glu Arg Asn Gly Val Ile Gln His Thr Gly Ala Ala Ala
                645                 650                 655

Glu Glu Phe Asn Asp Asp Thr Asp
            660
```

<210> SEQ ID NO 41
<211> LENGTH: 2080
<212> TYPE: DNA
<213> ORGANISM: Homo sapiens
<220> FEATURE:
<221> NAME/KEY: misc_feature
<222> LOCATION: 34, 85, 95
<223> OTHER INFORMATION: n = A,T,C or G

<400> SEQUENCE: 41

```
cgaccccgcs tccrcmgssr rkkgcgtccg cggnggcgcg gggagagtag ggtgctgtgg      60
tctgagctag agggtgaagc tggcnggagc agganggatg ggcgagcagt ctgaatgcca     120
gaatggataa ccgttttgct acagcatttg taattgcttg tgtgcttagc ctcatttcca     180
ccatctacat ggcagcctcc attggcacag acttctggta tgaatatcga agtccagttc     240
aagaaaattc cagtgatttg aataaaagca tctgggatga attcattagt gatgaggcag     300
atgaaaagac ttataatgat gcacttttc gatacaatgg cacagtggga ttgtggagac     360
ggtgtatcac catacccaaa acatgcatt ggtatagccc accagaaagg acagagtcat     420
ttgatgtggt cacaaaatgt gtgagtttca cactaactga gcagttcatg gagaaatttg     480
ttgatcccgg aaaccacaat agcgggattg atctccttag gacctatctt tggcgttgcc     540
agttcctttt acctttgtg agtttaggtt tgatgtgctt tggggctttg atcggacttt     600
gtgcttgcat ttgccgaagc ttatatccca ccattgccac gggcattctc catctccttg     660
caggtctgtg tacactgggc tcagtaagtt gttatgttgc tggaattgaa ctactccacc     720
agaaactaga gctccctgac aatgtatccg gtgaatttgg atggtccttc tgcctggctt     780
gtgtctctgc tcccttacag ttcatggctt ctgctctctt catctgggct gctcacacca     840
accggaaaga gtacaccta tgaaggcat atcgtgtggc atgagcaaga aactgcctgc     900
tttacaattg ccatttttat ttttttaaaa taatactgat attttcccca cctctcaatt     960
gttttaatt tttattgtg gatataccat tttattatga aaatctattt tatttataca    1020
cattcaccac taaatacaca cttaatacca ctaaaattta tgtggtttac tttaagcgat    1080
gccatctttc aaataaacta atctaggtct agacagaaag aaatggatag agacttgaca    1140
caaatttatg aaagaaaatt gggagtagga atgtgaccga aaacaagttg tgctaatgtc    1200
tgttagactt tcagtaaaaa ctaaagtaac tgtatctgtt caactaaaaa ctctatatta    1260
gtttctttgg gaaacctctc atcgtcaaaa ctttatgttc actttgctgt tgtagatagc    1320
cagtcaacca gcagtattag tgctgttttc aaagatttaa gctctataaa attgggaaat    1380
tatctaagat cattttccct aagcattgac acatagcttc atctgaggtg agatatggca    1440
gctgtttgta tctgcactgt gtctgtctac aaaaagtgaa aaatacagtg tttacttgaa    1500
attttaactt tgtaactgca agaattccag ttcagccggg cgaggattag tattattttt    1560
aactctccgt aagattttca gtaccaccaa attgttttgg attttttttc tttcctcttc    1620
acataccagg gttattaaaa gtgtgctttc ttttacatt atattacagt tacaaggtaa    1680
```

-continued

```
aattcctcaa ctgctatttα tttattccag cccagtacta taagaacgt ttcaccataa      1740 tgaccctcca gagctgggaa acctaccaca agatctaaag ttctggctgt ccattaacct      1800
ccaactatgg tctttatttc ttgtggtaat atgatgtgcc tttccttgcc taaatccctt      1860
cctggtgtgt atcaacatta tttaatgtct tctaattcag tcattttttt ataagtatgt      1920
ctataaacat tgaactttaa aaaacttatt tatttattcc actactgtag caattgacag      1980
attaaaaaaa tgtaacttca taatttctta ccataacctc aatgtctttt ttaaaaaata      2040
aaattaaaaa tgaaaagaga aaaaaaaaaa aaaaaaaaac                            2080
```

<210> SEQ ID NO 42
<211> LENGTH: 253
<212> TYPE: PRT
<213> ORGANISM: Homo sapiens

<400> SEQUENCE: 42

```
Met Asp Asn Arg Phe Ala Thr Ala Phe Val Ile Ala Cys Val Leu Ser
  1               5                  10                  15

Leu Ile Ser Thr Ile Tyr Met Ala Ala Ser Ile Gly Thr Asp Phe Trp
             20                  25                  30

Tyr Glu Tyr Arg Ser Pro Val Gln Glu Asn Ser Ser Asp Leu Asn Lys
         35                  40                  45

Ser Ile Trp Asp Glu Phe Ile Ser Asp Glu Ala Asp Glu Lys Thr Tyr
     50                  55                  60

Asn Asp Ala Leu Phe Arg Tyr Asn Gly Thr Val Gly Leu Trp Arg Arg
 65                  70                  75                  80

Cys Ile Thr Ile Pro Lys Asn Met His Trp Tyr Ser Pro Pro Glu Arg
                 85                  90                  95

Thr Glu Ser Phe Asp Val Val Thr Lys Cys Val Ser Phe Thr Leu Thr
            100                 105                 110

Glu Gln Phe Met Glu Lys Phe Val Asp Pro Gly Asn His Asn Ser Gly
        115                 120                 125

Ile Asp Leu Leu Arg Thr Tyr Leu Trp Arg Cys Gln Phe Leu Leu Pro
    130                 135                 140

Phe Val Ser Leu Gly Leu Met Cys Phe Gly Ala Leu Ile Gly Leu Cys
145                 150                 155                 160

Ala Cys Ile Cys Arg Ser Leu Tyr Pro Thr Ile Ala Thr Gly Ile Leu
                165                 170                 175

His Leu Leu Ala Gly Leu Cys Thr Leu Gly Ser Val Ser Cys Tyr Val
            180                 185                 190

Ala Gly Ile Glu Leu Leu His Gln Lys Leu Glu Leu Pro Asp Asn Val
        195                 200                 205

Ser Gly Glu Phe Gly Trp Ser Phe Cys Leu Ala Cys Val Ser Ala Pro
    210                 215                 220

Leu Gln Phe Met Ala Ser Ala Leu Phe Ile Trp Ala Ala His Thr Asn
225                 230                 235                 240

Arg Lys Glu Tyr Thr Leu Met Lys Ala Tyr Arg Val Ala
                245                 250
```

<210> SEQ ID NO 43
<211> LENGTH: 2015
<212> TYPE: DNA
<213> ORGANISM: Homo sapiens

<400> SEQUENCE: 43

```
cttcacccgt ccgtgataag gagatttaag aagtctgagg gtggtgttaa gtttctcaga        60
```

| | |
|---|---|
| acagacgcat atttgcggat gcaattgcag aacaggaaac agaaccaggg agaattttag | 120 |
| gtaccccaa atctcattgg ccctccgcac aagccaagcc acagccactc ctgccacaca | 180 |
| atcggatcgc tttcagcact cgcagccgtg acagctccc tcgccgcgcg gtcctttcct | 240 |
| ctgcagtgag ctgatttgct ctgccagcag ctgtcggtgc cgcgctcgac accgagtcct | 300 |
| agctagcgct cacagaatac gcgctccctc cctccccctt ctctgtcccc cgcctctcgc | 360 |
| tcaccccggc ccactccagc ggcgactttg agggattccc tctctggcgg cctctgcagc | 420 |
| agcacagccg gcctcattcg gggcactgcg agtatggatc tccaaggaag aggggtcccc | 480 |
| agcatcgaca gacttcgagt tctcctgatg ttgttccata caatggctca aatcatggca | 540 |
| gaacaagaag tggaaaatct ctcaggcctt tccactaacc ctgaaaaaga tatatttgtg | 600 |
| gtgcgggaaa atgggacgac gtgtctcatg gcagagtttg cagccaaatt tattgtacct | 660 |
| tatgatgtgt gggccagcaa ctacgtagat ctgatcacag aacaggccga tatcgcattg | 720 |
| acccggggag ctgaggtgaa gggccgctgt ggccacagcg agtcggagct gcaagtgttc | 780 |
| tgggtggatc gcgcatatgc actcaaaatg ctctttgtaa aggaaagcca caacatgtcc | 840 |
| aagggacctg aggcgacttg gaggctgagc aaagtgcagt ttgtctacga ctcctcggag | 900 |
| aaaacccact tcaaagacgc agtcagtgct gggaagcaca cagccaactc gcaccacctc | 960 |
| tctgccttgg tcaccccgc tgggaagtcc tatgagtgtc aagctcaaca aaccatttca | 1020 |
| ctggcctcta gtgatccgca aagacggtc accatgatcc tgtctgcggt ccacatccaa | 1080 |
| ccttttgaca ttatctcaga ttttgtcttc agtgaagagc ataaatgccc agtggatgag | 1140 |
| cgggagcaac tggaagaaac cttgcccctg attttggggc tcatcttggg cctcgtcatc | 1200 |
| atggtaacac tcgcgattta ccacgtccac cacaaaatga ctgccaacca ggtgcagatc | 1260 |
| cctcgggaca gatcccagta taagcacatg ggctagaggc cgttaggcag gcaccccta | 1320 |
| ttcctgctcc cccaactgga tcaggtagaa caacaaaagc acttttccat cttgtacacg | 1380 |
| agatacacca acatagctac aatcaaacag gcctgggtat ctgaggcttg cttggcttgt | 1440 |
| gtccatgctt aaacccacgg aaggggggaga ctctttcgga tttgtagggt gaaatggcaa | 1500 |
| ttattctctc catgctgggg aggaggggag gagggtctca gacagctttc gtgctcatgg | 1560 |
| tggcttggct ttgactctcc aaagagcaat aaatgccact tggagctgta tctggcccca | 1620 |
| aagtttaggt attgaaaaca tgcttctttg aggaggaaac ccctttaggt tcagaagaat | 1680 |
| atggggtgct ttgctcccctt ggacacagct ggcttatcct atacagttgt caatgcacac | 1740 |
| agaatacaac ctcatgctcc ctgcagcaag acccctgaaa gtgattcatg cttctggctg | 1800 |
| gcattctgca tgtttagtga ttgtcttggg aatgtttcac tgctacccgc atccagcgac | 1860 |
| tgcagcacca gaaacgact aatgtaacta tgcagagttg tttggacttc ttcctgtgcc | 1920 |
| aggtccaagt cggggggacct gaagaatcaa tctgtgtgag tctgttttc aaaatgaaat | 1980 |
| aaaacacact attctctggc aaaaaaaaaa aaaaa | 2015 |

<210> SEQ ID NO 44
<211> LENGTH: 280
<212> TYPE: PRT
<213> ORGANISM: Homo sapiens

<400> SEQUENCE: 44

Met Asp Leu Gln Gly Arg Gly Val Pro Ser Ile Asp Arg Leu Arg Val
1               5                   10                  15

Leu Leu Met Leu Phe His Thr Met Ala Gln Ile Met Ala Glu Gln Glu
            20                  25                  30

-continued

```
Val Glu Asn Leu Ser Gly Leu Ser Thr Asn Pro Glu Lys Asp Ile Phe
             35                  40                  45
Val Val Arg Glu Asn Gly Thr Thr Cys Leu Met Ala Glu Phe Ala Ala
     50                  55                  60
Lys Phe Ile Val Pro Tyr Asp Val Trp Ala Ser Asn Tyr Val Asp Leu
65                  70                  75                  80
Ile Thr Glu Gln Ala Asp Ile Ala Leu Thr Arg Gly Ala Glu Val Lys
                 85                  90                  95
Gly Arg Cys Gly His Ser Glu Ser Glu Leu Gln Val Phe Trp Val Asp
            100                 105                 110
Arg Ala Tyr Ala Leu Lys Met Leu Phe Val Lys Glu Ser His Asn Met
        115                 120                 125
Ser Lys Gly Pro Glu Ala Thr Trp Arg Leu Ser Lys Val Gln Phe Val
    130                 135                 140
Tyr Asp Ser Ser Glu Lys Thr His Phe Lys Asp Ala Val Ser Ala Gly
145                 150                 155                 160
Lys His Thr Ala Asn Ser His His Leu Ser Ala Leu Val Thr Pro Ala
                165                 170                 175
Gly Lys Ser Tyr Glu Cys Gln Ala Gln Gln Thr Ile Ser Leu Ala Ser
            180                 185                 190
Ser Asp Pro Gln Lys Thr Val Thr Met Ile Leu Ser Ala Val His Ile
        195                 200                 205
Gln Pro Phe Asp Ile Ile Ser Asp Phe Val Phe Ser Glu Glu His Lys
    210                 215                 220
Cys Pro Val Asp Glu Arg Glu Gln Leu Glu Glu Thr Leu Pro Leu Ile
225                 230                 235                 240
Leu Gly Leu Ile Leu Gly Leu Val Ile Met Val Thr Leu Ala Ile Tyr
                245                 250                 255
His Val His His Lys Met Thr Ala Asn Gln Val Gln Ile Pro Arg Asp
                260                 265                 270
Arg Ser Gln Tyr Lys His Met Gly
            275                 280
```

```
<210> SEQ ID NO 45
<211> LENGTH: 2937
<212> TYPE: DNA
<213> ORGANISM: Homo sapiens

<400> SEQUENCE: 45
```

| | | |
|---|---|---:|
| ttagggagtc gacccacgcg tccgcggacg cgtgggcgga cgcgtgggtt cggggactaa | | 60 |
| ctgcaacgga gagactcaag atgattccct ttttacccat gttttctcta ctattgctgc | | 120 |
| ttattgttaa ccctataaac gccaacaatc attatgacaa gatcttggct catagtcgta | | 180 |
| tcaggggtcg ggaccaaggc ccaaatgtct gtgcccttca acagattttg gcaccaaaa | | 240 |
| agaaatactt cagcacttgt aagaactggt ataaaaagtc catctgtgga cagaaaacga | | 300 |
| ctgtgttata tgaatgttgc cctggttata tgagaatgga aggaatgaaa ggctgcccag | | 360 |
| cagttttgcc cattgaccat gtttatggca ctctgggcat cgtgggagcc accacaacgc | | 420 |
| agcgctattc tgacgcctca aaactgaggg aggagatcga gggaagggga tccttcactt | | 480 |
| actttgcacc gagtaatgag gcttgggaca cttggattc tgatatccgt agaggttttgg | | 540 |
| agagcaacgt gaatgttgaa ttactgaatg ctttacatag tcacatgatt aataagagaa | | 600 |
| tgttgaccaa ggacttaaaa aatggcatga ttattcctttc aatgtataac aatttggggc | | 660 |
| ttttcattaa ccattatcct aatggggttg tcactgttaa ttgtgctcga atcatccatg | | 720 |

-continued

| | | | |
|---|---|---|---|
| ggaaccagat tgcaacaaat ggtgttgtcc atgtcattga ccgtgtgctt acacaaattg | 780 |
| gtacctcaat tcaagacttc attgaagcag aagatgacct ttcatctttt agagcagctg | 840 |
| ccatcacatc ggacatattg gaggcccttg aagagacgg tcacttcaca ctctttgctc | 900 |
| ccaccaatga ggcttttgag aaacttccac gaggtgtcct agaaaggatc atgggagaca | 960 |
| aagtggcttc cgaagctctt atgaagtacc acatcttaaa tactctccag tgttctgagt | 1020 |
| ctattatggg aggagcagtc tttgagacgc tggaaggaaa tacaattgag ataggatgtg | 1080 |
| acggtgacag tataacagta aatggaatca aatggtgaa caaaaaggat attgtgacaa | 1140 |
| ataatggtgt gatccatttg attgatcagg tcctaattcc tgattctgcc aaacaagtta | 1200 |
| ttgagctggc tggaaaacag caaccacct tcacggatct tgtggcccaa ttaggcttgg | 1260 |
| catctgctct gaggccagat ggagaataca ctttgctggc acctgtgaat aatgcatttt | 1320 |
| ctgatgatac tctcagcatg gatcagcgcc tccttaaatt aattctgcag aatcacatat | 1380 |
| tgaaagtaaa agttggcctt aatgagcttt acaacgggca aatactggaa accatcggag | 1440 |
| gcaaacagct cagagtcttc gtatatcgta cagctgtctg cattgaaaat tcatgcatgg | 1500 |
| agaaagggag taagcaaggg agaaacggtg cgattcacat attccgcgag atcatcaagc | 1560 |
| cagcagagaa atccctccat gaaaagttaa aacaagataa gcgctttagc accttcctca | 1620 |
| gcctacttga agctgcagac ttgaaagagc tcctgacaca acctggagac tggacattat | 1680 |
| ttgtgccaac caatgatgct tttaagggaa tgactagtga agaaaagaa attctgatac | 1740 |
| gggacaaaaa tgctcttcaa aacatcattc tttatcacct gacaccagga gttttcattg | 1800 |
| gaaaaggatt tgaacctggt gttactaaca ttttaaagac cacacaagga agcaaaatct | 1860 |
| ttctgaaaga agtaaatgat acacttctgg tgaatgaatt gaaatcaaaa gaatctgaca | 1920 |
| tcatgacaac aaatggtgta attcatgttg tagataaact cctctatcca gcagacacac | 1980 |
| ctgttggaaa tgatcaactg ctggaaatac ttaataaatt aatcaaatac atccaaatta | 2040 |
| agtttgttcg tggagaaaca gaagaaactc tgaagaaatt gttacaagaa gacacacccg | 2100 |
| tgaggaagtt gcaagccaac aaaaaagttc aaggatctag aagacgatta agggaaggtc | 2160 |
| gttctcagtg aaaatccaaa aaccagaaaa aaatgtttat acaaccctaa gtcaataacc | 2220 |
| tgaccttaga aaattgtgag agccaagttg acttcaggaa ctgaaacatc agcacaaaga | 2280 |
| agcaatcatc aaataattct gaacacaaat ttaatatttt tttttctgaa tgagaaacat | 2340 |
| gagggaaatt gtggagttag cctcctgtgg taaaggaatt gaagaaaata taacaccta | 2400 |
| cacccttttt catcttgaca ttaaaagttc tggctaactt tggaatccat tagagaaaaa | 2460 |
| tccttgtcac cagattcatt acaattcaaa tcgaagagtt gtgaactgtt atcccattga | 2520 |
| aaagaccgag cctgtatgt atgttatgga tacataaaat gcacgcaagc cattatctct | 2580 |
| ccatgggaag ctaagttata aaataggtg cttggtgtac aaaacttttt atatcaaaag | 2640 |
| gctttgcaca tttctatatg agtgggttta ctggtaaatt atgttatttt ttacaactaa | 2700 |
| ttttgtactc tcagaatgtc atatgcttct tgcaatgcat attttttaat ctcaaacgtt | 2760 |
| tcaataaaac catttttcag atataaagag aattacttca aattgagtaa ttcagaaaaa | 2820 |
| ctcaagattt aagttaaaaa gtggtttgga cttgggaaca ggactttata cctctttac | 2880 |
| tgtaacaagt actcattaaa ggaaattgaa tgaaaaaaa aaaaaagggg cggccgc | 2937 |

<210> SEQ ID NO 46
<211> LENGTH: 696
<212> TYPE: PRT
<213> ORGANISM: Homo sapiens

```
<400> SEQUENCE: 46

Met Ile Pro Phe Leu Pro Met Phe Ser Leu Leu Leu Leu Ile Val
 1               5                  10                  15

Asn Pro Ile Asn Ala Asn Asn His Tyr Asp Lys Ile Leu Ala His Ser
                 20                  25                  30

Arg Ile Arg Gly Arg Asp Gln Gly Pro Asn Val Cys Ala Leu Gln Gln
             35                  40                  45

Ile Leu Gly Thr Lys Lys Tyr Phe Ser Thr Cys Lys Asn Trp Tyr
 50                  55                  60

Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415
```

```
Thr Leu Ser Met Asp Gln Arg Leu Leu Lys Leu Ile Leu Gln Asn His
            420                 425                 430
Ile Leu Lys Val Lys Val Gly Leu Asn Glu Leu Tyr Asn Gly Gln Ile
            435                 440                 445
Leu Glu Thr Ile Gly Gly Lys Gln Leu Arg Val Phe Val Tyr Arg Thr
450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Leu Thr Gln Pro
            515                 520                 525
Gly Asp Trp Thr Leu Phe Val Pro Thr Asn Asp Ala Phe Lys Gly Met
530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
            595                 600                 605
Ser Lys Glu Ser Asp Ile Met Thr Thr Asn Gly Val Ile His Val Val
            610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Glu Thr Glu Thr Leu Lys Lys Leu Leu Gln Glu Asp Thr
            660                 665                 670
Pro Val Arg Lys Leu Gln Ala Asn Lys Lys Val Gln Gly Ser Arg Arg
            675                 680                 685
Arg Leu Arg Glu Gly Arg Ser Gln
690                 695

<210> SEQ ID NO 47
<211> LENGTH: 3417
<212> TYPE: DNA
<213> ORGANISM: Homo sapiens

<400> SEQUENCE: 47
gccccgcgtc cgcgcctccg ggctccttcg gccccgccat gggctgctgc agctccgcct      60
cctccgccgc gcagagctcc aaacgagaat ggaagccgct ggaggaccgt agctgcacag     120
acataccatg gctgctgctc ttcatcctct tctgcattgg gatgggattt atttgtggct     180
tttcaatagc aacaggtgca gcagcaagac tagtgtcagg atacgacagc tatgaaaata     240
tctgtgggca gaaaaataca aagttggaag caataccaaa cagtggcatg gaccacaccc     300
agcggaagta tgtattcttt ttggatccat gcaacctgga cttgataaac cggaagatta     360
agtctgtagc actgtgtgta gcagcgtgtc aaggcaaga actgaaaact ctgagtgatg     420
ttcagaagtt tgcagagata aatggttcag ccctatgtag ctacaaccta aagccttctg     480
aatacactac atctccaaaa tcttctgttc tctgccccaa actaccagtt ccagcgagtg     540
```

```
cacctattcc attcttccat cgctgtgctc ctgtgaacat ttcctgctat gccaagtttg    600
cagaggccct gatcaccttt gtcagtgaca atagtgtctt acacaggctg attagtggag    660
taatgaccag caaagaaatt atattgggac tttgcttgtt atcactagtt ctatccatga    720
ttttgatggt gataatcagg tatatatcaa gagtacttgt gtggatctta acgattctgg    780
tcatactcgg ttcacttgga ggcacaggtg tactatggtg gctgtatgca agcaaagaa    840 ggtctcccaa agaaactgtt actcctgagc agcttcagat agctgaagac aatcttcggg    900
ccctcctcat ttatgccatt tcagctacag tgttcacagt gatcttattc ctgataatgt    960
tggttatgcg caaacgtgtt gctcttacca tcgccttgtt ccacgtagct ggcaaggtct   1020
tcattcactt gccactgcta gtcttccaac ccttctggac tttctttgct cttgtcttgt   1080
tttgggtgta ctggatcatg acacttcttt tccttggcac taccggcagt cctgttcaga   1140
atgagcaagg ctttgtggag ttcaaaattt ctgggcctct gcagtacatg tggtggtacc   1200
atgtggtggg cctgatttgg atcagtgaat ttattctagc atgtcagcag atgacagtgg   1260
caggagctgt ggtaacatac tattttacta gggataaaag gaatttgcca tttacaccta   1320
ttttggcatc agtaaatcgc cttattcgtt accacctagg tacggtggca aaaggatctt   1380
tcattatcac attagtcaaa attccgcgaa tgatccttat gtatattcac agtcagctca   1440
aaggaaagga aaatgcttgt gcacgatgtg tgctgaaatc ttgcatttgt tgcctttggt   1500
gtcttgaaaa gtgcctaaat tatttaaatc agaatgcata cacagccaca gctatcaaca   1560
gcaccaactt ctgcacctca gcaaaggatg cctttgtcat tctggtggag aatgctttgc   1620
gagtggctac catcaacaca gtaggagatt ttatgttatt ccttggcaag gtgctgatag   1680
tctgcagcac aggtttagct gggattatgc tgctcaacta ccagcaggac tacacagtat   1740
gggtgctgcc tctgatcatc gtctgcctct ttgctttcct agtcgctcat tgcttcctgt   1800
ctatttatga atggtagtg gatgtattat tcttgtgttt tgccattgat acaaaataca   1860
atgatgggag ccctggcaga gaattctata tggataaagt gctgatggag tttgtggaaa   1920
acagtaggaa agcaatgaaa gaagctggta agggaggcgt cgctgattcc agagagctaa   1980
agccgatggc ttcgggagca agttctgctt gaacctagcc gacggttatg gaaacccatt   2040
gacattccaa aacaatatat acacataact atgtatttgt gtgtgtgggt gtgtgtatat   2100
atgtatatgt atgtgtgtat atatgtatat gtatatacac acacacacat aaatcagcca   2160
aaatcagaga aaaggaacag ggatttaata cctttttat gcttattttt gtcaaacatg    2220
tactcctttc atacgggtgg cttttacaag gcaacttccg tcatttaatg ttttcaactg   2280
taattgtctt aatggaaatg ttaaaattca tatctgatta acatttttaa taacttagag   2340
gagattttaa ctttatttaa aaataggtaa aattattgta cctaattatg tctaaagttt   2400
attcaggggt aatttccctg atgtctgtat aaaatcaaga tcttatttta ctgatgcata   2460
agtcctagtg ggtcaagact aggcatatgc tttcagataa ataaggaatt actccaatca   2520
gttttcccca atcaaagaag ccatgtcatt ttacttttag aaacatacaa ttgggcccaa   2580
tatgggaatt tcataatag ttcatacatt tgtcagccaa cattaaaagg taaccaactc    2640
ctcaggtatt tgtagtttac cctaacgctt cttttaaaga agtaggtaa aaaagaaaa     2700 gggtagataa tctttcgtat gcaaactttt cccttatatt ttgtctttct ttccttttg    2760 actttagtag catcctccac acatttgtgt gcctgatttg aaaggaagct ggggcaccca   2820
gcgagtttag cctttaagtt tctgtgtatt gatttgcaga ttaagtaatg ctgagaggaa   2880
taaagaaggg acagaaacat ggaacataaa gcattgaaaa ttccggtgct tgggcttcgg   2940
```

```
cttcagagta acgtcagtgg cttagggtta aacggccatt ttattcaaat gcttgctata    3000
caatctgaaa acacactggc aggtgctcct ctccttggca attcattgag tatccagagt    3060
tctacgatgt ttaactgaag aattggctaa tgttttgatc ctccagtgtg actgttgttt    3120
ttgtttgggg gtgggtttgg ggttttttgc ttttttattc ctgaagctta ccagatatga    3180
atggctaata ctccattgtt ctgcttgttg taatggtgaa tgctttaaga aaaaaagtg     3240 taatttgcta agaataattc atgatctgtt tatgcgataa ctccttttg ttacaatttt     3300 tttaaaaaaa gctattttg ttaatgtaaa gtaaatattt cagagcaaat tttttaaact     3360
tattgcacta aatacaggct ctgtacaaaa aaaaaaaaa agggcggccg ctagact        3417
```

<210> SEQ ID NO 48
<211> LENGTH: 657
<212> TYPE: PRT
<213> ORGANISM: Homo sapiens

<400> SEQUENCE: 48

```
Met Gly Cys Cys Ser Ser Ala Ser Ser Ala Gln Ser Ser Lys Arg
 1               5                  10                  15

Glu Trp Lys Pro Leu Glu Asp Arg Ser Cys Thr Asp Ile Pro Trp Leu
                20                  25                  30

Leu Leu Phe Ile Leu Phe Cys Ile Gly Met Gly Phe Ile Cys Gly Phe
            35                  40                  45

Ser Ile Ala Thr Gly Ala Ala Ala Arg Leu Val Ser Gly Tyr Asp Ser
        50                  55                  60

Tyr Gly Asn Ile Cys Gly Gln Lys Asn Thr Lys Leu Glu Ala Ile Pro
65                  70                  75                  80

Asn Ser Gly Met Asp His Thr Gln Arg Lys Tyr Val Phe Phe Leu Asp
                85                  90                  95

Pro Cys Asn Leu Asp Leu Ile Asn Arg Lys Ile Lys Ser Val Ala Leu
            100                 105                 110

Cys Val Ala Ala Cys Pro Arg Gln Glu Leu Lys Thr Leu Ser Asp Val
        115                 120                 125

Gln Lys Phe Ala Glu Ile Asn Gly Ser Ala Leu Cys Ser Tyr Asn Leu
    130                 135                 140

Lys Pro Ser Glu Tyr Thr Thr Ser Pro Lys Ser Ser Val Leu Cys Pro
145                 150                 155                 160

Lys Leu Pro Val Pro Ala Ser Ala Pro Ile Pro Phe Phe His Arg Cys
                165                 170                 175

Ala Pro Val Asn Ile Ser Cys Tyr Ala Lys Phe Ala Glu Ala Leu Ile
            180                 185                 190

Thr Phe Val Ser Asp Asn Ser Val Leu His Arg Leu Ile Ser Gly Val
        195                 200                 205

Met Thr Ser Lys Glu Ile Ile Leu Gly Leu Cys Leu Leu Ser Leu Val
    210                 215                 220

Leu Ser Met Ile Leu Met Val Ile Arg Tyr Ile Ser Arg Val Leu
225                 230                 235                 240

Val Trp Ile Leu Thr Ile Leu Val Ile Leu Gly Ser Leu Gly Gly Thr
                245                 250                 255

Gly Val Leu Trp Trp Leu Tyr Ala Lys Gln Arg Arg Ser Pro Lys Glu
            260                 265                 270

Thr Val Thr Pro Glu Gln Leu Gln Ile Ala Glu Asp Asn Leu Arg Ala
        275                 280                 285

Leu Leu Ile Tyr Ala Ile Ser Ala Thr Val Phe Thr Val Ile Leu Phe
    290                 295                 300
```

Leu Ile Met Leu Val Met Arg Lys Arg Val Ala Leu Thr Ile Ala Leu
305                 310                 315                 320

Phe His Val Ala Gly Lys Val Phe Ile His Leu Pro Leu Leu Val Phe
                325                 330                 335

Gln Pro Phe Trp Thr Phe Phe Ala Leu Val Leu Phe Trp Val Tyr Trp
                340                 345                 350

Ile Met Thr Leu Leu Phe Leu Gly Thr Thr Gly Ser Pro Val Gln Asn
                355                 360                 365

Glu Gln Gly Phe Val Glu Phe Lys Ile Ser Gly Pro Leu Gln Tyr Met
370                 375                 380

Trp Trp Tyr His Val Gly Leu Ile Trp Ile Ser Glu Phe Ile Leu
385                 390                 395                 400

Ala Cys Gln Gln Met Thr Val Ala Gly Ala Val Val Thr Tyr Tyr Phe
                405                 410                 415

Thr Arg Asp Lys Arg Asn Leu Pro Phe Thr Pro Ile Leu Ala Ser Val
                420                 425                 430

Asn Arg Leu Ile Arg Tyr His Leu Gly Thr Val Ala Lys Gly Ser Phe
            435                 440                 445

Ile Ile Thr Leu Val Lys Ile Pro Arg Met Ile Leu Met Tyr Ile His
450                 455                 460

Ser Gln Leu Lys Gly Lys Glu Asn Ala Cys Ala Arg Cys Val Leu Lys
465                 470                 475                 480

Ser Cys Ile Cys Cys Leu Trp Cys Leu Glu Lys Cys Leu Asn Tyr Leu
                485                 490                 495

Asn Gln Asn Ala Tyr Thr Ala Thr Ala Ile Asn Ser Thr Asn Phe Cys
                500                 505                 510

Thr Ser Ala Lys Asp Ala Phe Val Ile Leu Val Glu Asn Ala Leu Arg
            515                 520                 525

Val Ala Thr Ile Asn Thr Val Gly Asp Phe Met Leu Phe Leu Gly Lys
530                 535                 540

Val Leu Ile Val Cys Ser Thr Gly Leu Ala Gly Ile Met Leu Leu Asn
545                 550                 555                 560

Tyr Gln Gln Asp Tyr Thr Val Trp Val Leu Pro Leu Ile Ile Val Cys
                565                 570                 575

Leu Phe Ala Phe Leu Val Ala His Cys Phe Leu Ser Ile Tyr Glu Met
                580                 585                 590

Val Val Asp Val Leu Phe Leu Cys Phe Ala Ile Asp Thr Lys Tyr Asn
            595                 600                 605

Asp Gly Ser Pro Gly Arg Glu Phe Tyr Met Asp Lys Val Leu Met Glu
610                 615                 620

Phe Val Glu Asn Ser Arg Lys Ala Met Lys Glu Ala Gly Lys Gly Gly
625                 630                 635                 640

Val Ala Asp Ser Arg Glu Leu Lys Pro Met Ala Ser Gly Ala Ser Ser
                645                 650                 655

Ala

<210> SEQ ID NO 49
<211> LENGTH: 3758
<212> TYPE: DNA
<213> ORGANISM: Homo sapiens

<400> SEQUENCE: 49
cctcgcgtcc gcgcacaccg gggtggcagc gccgcagcgg gcagggcgcc cgcactccgc        60
cgcctctgcc cgcaaccgct gagccatcca tggggtcgc gggccgcaac cgtcccgggg       120

```
cggcctgggc ggtgctgctg ctgctgctgc cgccactgct gctgctggcg ggggccgtcc    180
cgccgggtcg gggccgtgcc gcggggccgc aggaggatgt agatgagtgt ccgcaagggc    240
tagatgactg ccatgccgac gccctgtgtc agaacacacc cacctcctac aagtgctcct    300
gcaagcctgg ctaccaaggg gaaggcaggc agtgtgagga catcgatgaa tgtggaaatg    360
agctcaatgg aggctgtgtc catgactgtt gaatattcc aggcaattat cgttgcactt    420
gttttgatgg cttcatgttg gctcatgacg gtcataattg tcttgatgtg gacgagtgcc    480
tggagaacaa tggcggctgc cagcatacct gtgtcaacgt catggggagc tatgagtgct    540
gctgcaagga ggggtttttc ctgagtgaca atcagcacac ctgcattcac cgctcggaag    600
agggcctgag ctgcatgaat aaggatcacg ctgtagtca catctgcaag gaggccccaa    660
ggggcagcgt cgcctgtgag tgcaggcctg gttttgagct ggccaagaac cagagagact    720
gcatcttgac ctgtaaccat gggaacggtg ggtgccagca ctcctgtgac gatacagccg    780
atggcccaga gtgcagctgc catccacagt acaagatgca cacagatggg aggagctgcc    840
ttgagcgaga ggacactgtc ctggaggtga cagagagcaa caccacatca gtggtggatg    900
gggataaacg ggtgaaacgg cggctgctca tggaaacgtg tgctgtcaac aatggaggct    960
gtgaccgcac ctgtaaggat acttcgacag gtgtccactg cagttgtcct gttggattca   1020
ctctccagtt ggatgggaag acatgtaaag atattgatga gtgccagacc cgcaatggag   1080
gttgtgatca tttctgcaaa aacatcgtgg gcagttttga ctgcggctgc aagaaggat   1140 ttaaattatt aacagatgag aagtcttgcc aagatgtgga tgagtgctct ttggatagga   1200
cctgtgacca cagctgcatc aaccaccctg gcacatttgc ttgtgcttgc aaccgagggt   1260
acacactgta tggcttcacc cactgtggag acaccaatga gtgcagcatc aacaacggag   1320
gctgtcagca ggtctgtgtg aacacagtgg gcagctatga atgccagtgc cacctgggt   1380 acaagctcca ctggaataaa aaagactgtg tggaagtgaa ggggctcctg cccacaagtg   1440
tgtcaccccg tgtgtccctg cactgcggta agagtggtgg aggagacggg tgcttcctca   1500
gatgtcactc tggcattcac ctctcttcag atgtcaccac catcaggaca agtgtaacct   1560
ttaagctaaa tgaaggcaag tgtagtttga aaaatgctga gctgtttccc gagggtctgc   1620
gaccagcact accagagaag cacagctcag taaaagagag cttccgctac gtaaaccta   1680 catgcagctc tggcaagcaa gtcccaggag cccctggccg accaagcacc cctaaggaaa   1740
tgtttatcac tgttgagttt gagcttgaaa ctaaccaaaa ggaggtgaca gcttcttgtg   1800
acctgagctg catcgtaaag cgaaccgaga agcggctccg taaagccatc cgcacgctca   1860
gaaaggccgt ccacagggag cagtttcacc tccagctctc aggcatgaac ctcgacgtgg   1920
ctaaaaagcc tcccagaaca tctgaacgcc aggcagagtc ctgtggagtg ggccagggtc   1980
atgcagaaaa ccaatgtgtc agttgcaggg ctgggaccta ttatgatgga gcacgagaac   2040
gctgcatttt atgtccaaat ggaaccttcc aaaatgagga aggacaaatg acttgtgaac   2100
catgcccaag accaggaaat tctggggccc tgaagacccc agaagcttgg aatatgtctg   2160
aatgtggagg tctgtgtcaa cctggtgaat attctgcaga tggctttgca ccttgccagc   2220
tctgtgccct gggcacgttc agcctgaag ctggtcgaac ttcctgcttc ccctgtggag   2280
gaggccttgc caccaaacat cagggagcta cttcctttca ggactgtgaa accagagttc   2340
aatgttcacc tggacatttc tacaacacca ccactcaccg atgtattcgt tgcccagtgg   2400
gaacatacca gcctgaattt ggaaaaaata attgtgtttc ttgcccagga aatactacga   2460
ctgactttga tggctccaca aacataaccc agtgtaaaaa cagaagatgt ggaggggagc   2520
```

```
tgggagattt cactgggtac attgaatccc caaactaccc aggcaattac ccagccaaca    2580
ccgagtgtac gtggaccatc aacccacccc ccaagcgccg catcctgatc gtggtccctg    2640
agatcttcct gcccatagag gacgactgtg gggactatct ggtgatgcgg aaaacctctt    2700
catccaattc tgtgacaaca tatgaaacct gccagaccta cgaacgcccc atcgccttca    2760
cctccaggtc aaagaagctg tggattcagt tcaagtccaa tgaagggaac agcgctagag    2820
ggttccaggt cccatacgtg acatatgatg aggactacca ggaactcatt gaagacatag    2880
ttcgagatgg caggctctat gcatctgaga accatcagga aatacttaag gataagaaac    2940
ttatcaaggc tctgtttgat gtcctggccc atccccagaa ctatttcaag tacacagccc    3000
aggagtcccg agagatgttt ccaagatcgt tcatccgatt gctacgttcc aaagtgtcca    3060 ggttttgag accttacaaa tgactcagcc cacgtgccac tcaatacaaa tgttctgcta    3120
tagggttggt gggacagagc tgtcttcctt ctgcatgtca gcacagtcgg tattgctgc    3180 ctcccgtatc agtgactcat tagagttcaa ttttttataga taatacagat attttggtaa    3240
attgaacttg gtttttcttt cccagcatcg tggatgtaga ctgagaatgg ctttgagtgg    3300
catcagcttc tcactgctgt gggcggatgt cttggataga tcacgggctg ctgagctgg    3360 actttggtca gcctaggtga gactcacctg tccttctggg gtcttactcc tcctcaagga    3420
gtctgtagtg gaaaggaggc cacagaataa gctgcttatt ctgaaacttc agcttcctct    3480
agcccggccc tctctaaggg agccctctgc actcgtgtgc aggctctgac caggcagaac    3540
aggcaagagg ggagggaagg agaccctgc aggctccctc cacccacctt gagacctggg    3600
aggactcagt ttctccacag ccttctccag cctgtgtgat acaagtttga tcccaggaac    3660
ttgagttcta agcagtgctc gtgaaaaaaa aaagcagaaa gaattagaaa taaataaaaa    3720
ctaagcactt ctggagacac ctataggagt cgtattac                            3758
```

<210> SEQ ID NO 50
<211> LENGTH: 997
<212> TYPE: PRT
<213> ORGANISM: Homo sapiens

<400> SEQUENCE: 50

```
Met Gly Val Ala Gly Arg Asn Arg Pro Gly Ala Ala Trp Ala Val Leu
 1               5                   10                  15

Leu Leu Leu Leu Pro Pro Leu Leu Leu Ala Gly Ala Val Pro Pro
             20                  25                  30

Gly Arg Gly Arg Ala Ala Gly Pro Gln Glu Asp Val Asp Glu Cys Pro
         35                  40                  45

Gln Gly Leu Asp Asp Cys His Ala Asp Ala Leu Cys Gln Asn Thr Pro
     50                  55                  60

Thr Ser Tyr Lys Cys Ser Cys Lys Pro Gly Tyr Gln Gly Glu Gly Arg
 65                  70                  75                  80

Gln Cys Glu Asp Ile Asp Glu Cys Gly Asn Glu Leu Asn Gly Gly Cys
                 85                  90                  95

Val His Asp Cys Leu Asn Ile Pro Gly Asn Tyr Arg Cys Thr Cys Phe
            100                 105                 110

Asp Gly Phe Met Leu Ala His Asp Gly His Asn Cys Leu Asp Val Asp
        115                 120                 125

Glu Cys Leu Glu Asn Asn Gly Gly Cys Gln His Thr Cys Val Asn Val
    130                 135                 140

Met Gly Ser Tyr Glu Cys Cys Cys Lys Glu Gly Phe Phe Leu Ser Asp
145                 150                 155                 160
```

```
Asn Gln His Thr Cys Ile His Arg Ser Glu Glu Gly Leu Ser Cys Met
                165                 170                 175
Asn Lys Asp His Gly Cys Ser His Ile Cys Lys Glu Ala Pro Arg Gly
                180                 185                 190
Ser Val Ala Cys Glu Cys Arg Pro Gly Phe Glu Leu Ala Lys Asn Gln
                195                 200                 205
Arg Asp Cys Ile Leu Thr Cys Asn His Gly Asn Gly Gly Cys Gln His
                210                 215                 220
Ser Cys Asp Asp Thr Ala Asp Gly Pro Glu Cys Ser Cys His Pro Gln
225                 230                 235                 240
Tyr Lys Met His Thr Asp Gly Arg Ser Cys Leu Glu Arg Glu Asp Thr
                245                 250                 255
Val Leu Glu Val Thr Glu Ser Asn Thr Thr Ser Val Val Asp Gly Asp
                260                 265                 270
Lys Arg Val Lys Arg Arg Leu Leu Met Glu Thr Cys Ala Val Asn Asn
                275                 280                 285
Gly Gly Cys Asp Arg Thr Cys Lys Asp Thr Ser Thr Gly Val His Cys
                290                 295                 300
Ser Cys Pro Val Gly Phe Thr Leu Gln Leu Asp Gly Lys Thr Cys Lys
305                 310                 315                 320
Asp Ile Asp Glu Cys Gln Thr Arg Asn Gly Gly Cys Asp His Phe Cys
                325                 330                 335
Lys Asn Ile Val Gly Ser Phe Asp Cys Gly Cys Lys Lys Gly Phe Lys
                340                 345                 350
Leu Leu Thr Asp Glu Lys Ser Cys Gln Asp Val Asp Glu Cys Ser Leu
                355                 360                 365
Asp Arg Thr Cys Asp His Ser Cys Ile Asn His Pro Gly Thr Phe Ala
                370                 375                 380
Cys Ala Cys Asn Arg Gly Tyr Thr Leu Tyr Gly Phe Thr His Cys Gly
385                 390                 395                 400
Asp Thr Asn Glu Cys Ser Ile Asn Asn Gly Gly Cys Gln Gln Val Cys
                405                 410                 415
Val Asn Thr Val Gly Ser Tyr Glu Cys Gln Cys His Pro Gly Tyr Lys
                420                 425                 430
Leu His Trp Asn Lys Lys Asp Cys Val Glu Val Lys Gly Leu Leu Pro
                435                 440                 445
Thr Ser Val Ser Pro Arg Val Ser Leu His Cys Gly Lys Ser Gly Gly
                450                 455                 460
Gly Asp Gly Cys Phe Leu Arg Cys His Ser Gly Ile His Leu Ser Ser
465                 470                 475                 480
Asp Val Thr Thr Ile Arg Thr Ser Val Thr Phe Lys Leu Asn Glu Gly
                485                 490                 495
Lys Cys Ser Leu Lys Asn Ala Glu Leu Phe Pro Glu Gly Leu Arg Pro
                500                 505                 510
Ala Leu Pro Glu Lys His Ser Ser Val Lys Glu Ser Phe Arg Tyr Val
                515                 520                 525
Asn Leu Thr Cys Ser Ser Gly Lys Gln Val Pro Gly Ala Pro Gly Arg
                530                 535                 540
Pro Ser Thr Pro Lys Glu Met Phe Ile Thr Val Glu Phe Glu Leu Glu
545                 550                 555                 560
Thr Asn Gln Lys Glu Val Thr Ala Ser Cys Asp Leu Ser Cys Ile Val
                565                 570                 575
Lys Arg Thr Glu Lys Arg Leu Arg Lys Ala Ile Arg Thr Leu Arg Lys
```

```
                580                 585                 590
Ala Val His Arg Glu Gln Phe His Leu Gln Leu Ser Gly Met Asn Leu
        595                 600                 605

Asp Val Ala Lys Lys Pro Pro Arg Thr Ser Glu Arg Gln Ala Glu Ser
        610                 615                 620

Cys Gly Val Gly Gln Gly His Ala Glu Asn Gln Cys Val Ser Cys Arg
625                 630                 635                 640

Ala Gly Thr Tyr Tyr Asp Gly Ala Arg Glu Arg Cys Ile Leu Cys Pro
                645                 650                 655

Asn Gly Thr Phe Gln Asn Glu Glu Gly Gln Met Thr Cys Glu Pro Cys
                660                 665                 670

Pro Arg Pro Gly Asn Ser Gly Ala Leu Lys Thr Pro Glu Ala Trp Asn
            675                 680                 685

Met Ser Glu Cys Gly Gly Leu Cys Gln Pro Gly Glu Tyr Ser Ala Asp
        690                 695                 700

Gly Phe Ala Pro Cys Gln Leu Cys Ala Leu Gly Thr Phe Gln Pro Glu
705                 710                 715                 720

Ala Gly Arg Thr Ser Cys Phe Pro Cys Gly Gly Gly Leu Ala Thr Lys
                725                 730                 735

His Gln Gly Ala Thr Ser Phe Gln Asp Cys Glu Thr Arg Val Gln Cys
            740                 745                 750

Ser Pro Gly His Phe Tyr Asn Thr Thr Thr His Arg Cys Ile Arg Cys
        755                 760                 765

Pro Val Gly Thr Tyr Gln Pro Glu Phe Gly Lys Asn Asn Cys Val Ser
        770                 775                 780

Cys Pro Gly Asn Thr Thr Thr Asp Phe Asp Gly Ser Thr Asn Ile Thr
785                 790                 795                 800

Gln Cys Lys Asn Arg Arg Cys Gly Gly Glu Leu Gly Asp Phe Thr Gly
                805                 810                 815

Tyr Ile Glu Ser Pro Asn Tyr Pro Gly Asn Tyr Pro Ala Asn Thr Glu
            820                 825                 830

Cys Thr Trp Thr Ile Asn Pro Pro Lys Arg Arg Ile Leu Ile Val
        835                 840                 845

Val Pro Glu Ile Phe Leu Pro Ile Glu Asp Asp Cys Gly Asp Tyr Leu
        850                 855                 860

Val Met Arg Lys Thr Ser Ser Asn Ser Val Thr Thr Tyr Glu Thr
865                 870                 875                 880

Cys Gln Thr Tyr Glu Arg Pro Ile Ala Phe Thr Ser Arg Ser Lys Lys
                885                 890                 895

Leu Trp Ile Gln Phe Lys Ser Asn Glu Gly Asn Ser Ala Arg Gly Phe
                900                 905                 910

Gln Val Pro Tyr Val Thr Tyr Asp Glu Asp Tyr Gln Glu Leu Ile Glu
            915                 920                 925

Asp Ile Val Arg Asp Gly Arg Leu Tyr Ala Ser Glu Asn His Gln Glu
        930                 935                 940

Ile Leu Lys Asp Lys Lys Leu Ile Lys Ala Leu Phe Asp Val Leu Ala
945                 950                 955                 960

His Pro Gln Asn Tyr Phe Lys Tyr Thr Ala Gln Glu Ser Arg Glu Met
                965                 970                 975

Phe Pro Arg Ser Phe Ile Arg Leu Leu Arg Ser Lys Val Ser Arg Phe
            980                 985                 990

Leu Arg Pro Tyr Lys
        995
```

<210> SEQ ID NO 51
<211> LENGTH: 3586
<212> TYPE: DNA
<213> ORGANISM: Homo sapiens

<400> SEQUENCE: 51

```
ccgcggcgct gcgcgcggcg gtaattagtg attgtcttcc agcttcgcga aggctagggg      60
cgcggctgcc gggtggctgc gcggcgctgc ccccggaccg aggggcagcc aatccaatga     120
aaccaccgcg tgttcgcgcc tggtagagat ttctcgaaga caccagtggg cccgttccga     180
gccctctgga ccgcccgtgt ggaaccaaac ctgcgcgcgt ggccgggccg tgggacaacg     240
aggccgcgga gacgaaggcg caatggcgag gaagttatct gtaatcttga tcctgacctt     300
tgccctctct gtcacaaatc cccttcatga actaaaagca gctgctttcc cccagaccac     360
tgagaaaatt agtccgaatt gggaatctgg cattaatgtt gacttggcaa tttccacacg     420
gcaatatcat ctacaacagc ttttctaccg ctatggagaa aataattctt tgtcagttga     480
agggttcaga aaattacttc aaaatatagg catagataag attaaaagaa tccatataca     540
ccatgaccac gaccatcact cagaccacga gcatcactca gaccatgagc gtcactcaga     600
ccatgagcat cactcagacc acgagcatca ctctgaccat gatcatcact cttctggtaa     660
aaataagcga aaagctcttt gcccagacca tgactcagat agttcaggta agatcctag     720
aaacagccag gggaaaggag ctcaccgacc agaacatgcc agtggtagaa ggaatgtcaa     780
ggacagtgtt agtgctagtg aagtgacctc aactgtgtac aacactgtct ctgaaggaac     840
tcactttcta gagacaatag agactccaag acctggaaaa ctcttcccca agatgtaag     900
cagctccact ccacccagtg tcacatcaaa gagccgggtg agccggctgg ctggtaggaa     960
aacaaatgaa tctgtgagtg agccccgaaa aggctttatg tattccagaa acacaaatga    1020
aaatcctcag gagtgtttca atgcatcaaa gctactgaca tctcatggca tgggcatcca    1080
ggttccgctg aatgcaacag agttcaacta tctctgtcca gccatcatca accaaattga    1140
tgctagatct tgtctgattc atacaagtga aaagaaggct gaaatccctc aaagaccta    1200
ttcattacaa atagcctggg ttggtggttt tatagccatt tccatcatca gtttcctgtc    1260
tctgctgggg gttatcttag tgcctctcat gaatcgggtg ttttttcaaat ttctcctgag    1320
tttccttgtg gcactggccg ttgggacttt gagtggtgat gcttttttac accttcttcc    1380
acattctcat gcaagtcacc accatagtca tagccatgaa gaaccagcaa tggaaatgaa    1440
aagaggacca cttttcagtc atctgtcttc tcaaaacata gaagaaagtg cctatttga    1500
ttccacgtgg aagggtctaa cagctctagg aggcctgtat ttcatgtttc ttgttgaaca    1560
tgtcctcaca ttgatcaaac aatttaaaga taagaagaaa aagaatcaga agaaacctga    1620
aaatgatgat gatgtggaga ttaagaagca gttgtccaag tatgaatctc aactttcaac    1680
aaatgaggag aaagtagata cagatgatcg aactgaaggc tatttacgag cagactcaca    1740
agagccctcc cactttgatt ctcagcagcc tgcagtcttg gaagaagaag aggtcatgat    1800
agctcatgct catccacagg aagtctacaa tgaatatgta cccagagggt gcaagaataa    1860
atgccattca catttccacg atacactcgg ccagtcagac gatctcattc accaccatca    1920
tgactaccat catattctcc atcatccaca ccaccaaaac caccatcctc acagtcacag    1980
ccagcgctac tctcgggagg agctgaaaga tgccggcgtc gccactttgg cctggatggt    2040
gataatgggt gatggcctgc acaatttcag cgatggccta gcaattggtg ctgcttttac    2100
tgaaggctta tcaagtggtt taagtacttc tgttgctgtg ttctgtcatg agttgcctca    2160
```

-continued

```
tgaattaggt gactttgctg ttctactaaa ggctggcatg accgttaagc aggctgtcct    2220
ttataatgca ttgtcagcca tgctggcgta tcttggaatg caacaggaa ttttcattgg     2280 tcattatgct gaaatgttt ctatgtggat atttgcactt actgctggct tattcatgta    2340
tgttgctctg gttgatatgg tacctgaaat gctgcacaat gatgctagtg accatggatg   2400
tagccgctgg gggtatttct ttttacagaa tgctgggatg cttttgggtt ttggaattat   2460
gttacttatt ccatatttga acataaaatc gtgttcgtat aaatttctag ttaaggttta   2520
aatgctagag tagcttaaaa agttgtcata gtttcagtag gtcatagga gatgagtttg    2580 tatgctgtac tatgcagcgt ttaaagttag tgggttttgt gattttttgta ttgaatattg  2640 ctgtctgtta caaagtcagt taaaggtacg ttttaatatt taagttattc tatcttggag   2700
ataaaatctg tatgtgcaat tcaccggtat taccagttta ttatgtaaac aagagatttg   2760
gcatgacatg ttctgtatgt ttcagggaaa aatgtcttta atgcttttc aagaactaac    2820 acagttattc ctatactgga ttttaggtct ctgaagaact gctggtgttt aggaataaga   2880
atgtgcatga agcctaaaat accaagaaag cttatactga atttaagcaa agaaataaag   2940
gagaaaagag aagaatctga gaattgggga ggcatagatt cttataaaaa tcacaaaatt   3000
tgttgtaaat tagaggggag aaatttagaa ttaagtataa aaaggcagaa ttagtataga   3060
gtacattcat taaacatttt tgtcaggatt atttcccgta aaaacgtagt gagcactctc   3120
atatactaat tagtgtacat ttaactttgt ataatacaga aatctaaata tatttaatga   3180
attcaagcaa tatacacttg accaagaaat tggaatttca aaatgttcgt gcgggttata   3240
taccagatga gtacagtgag tagtttatgt atcaccagac tgggttattg ccaagttata   3300
tatcaccaaa agctgtatga ctggatgttc tggttacctg gtttacaaaa ttatcagagt   3360
agtaaaactt tgatatatat gaggatatta aaactacact aagtatcatt tgattcgatt   3420
cagaaagtac tttgatatct ctcagtgctt cagtgctatc attgtgagca attgtcttta   3480
tatacggtac tgtagccata ctaggcctgt ctgtggcatt ctctagatgt ttcttttta    3540 cacaataaat tccttatatc agcttgaaaa aaaaaaaaa aaaaaa                   3586
```

<210> SEQ ID NO 52
<211> LENGTH: 752
<212> TYPE: PRT
<213> ORGANISM: Homo sapiens

<400> SEQUENCE: 52

```
Met Ala Arg Lys Leu Ser Val Ile Leu Ile Leu Thr Phe Ala Leu Ser
 1               5                  10                  15

Val Thr Asn Pro Leu His Glu Leu Lys Ala Ala Ala Phe Pro Gln Thr
            20                  25                  30

Thr Glu Lys Ile Ser Pro Asn Trp Glu Ser Gly Ile Asn Val Asp Leu
        35                  40                  45

Ala Ile Ser Thr Arg Gln Tyr His Leu Gln Gln Leu Phe Tyr Arg Tyr
    50                  55                  60

Gly Glu Asn Asn Ser Leu Ser Val Glu Gly Phe Arg Lys Leu Leu Gln
65                  70                  75                  80

Asn Ile Gly Ile Asp Lys Ile Lys Arg Ile His Ile His His Asp His
                85                  90                  95

Asp His His Ser Asp His Glu His Ser Asp His Glu Arg His Ser
            100                 105                 110

Asp His Glu His His Ser Asp His Glu His Ser Asp His Asp His
        115                 120                 125
```

```
His Ser Ser Gly Lys Asn Lys Arg Lys Ala Leu Cys Pro Asp His Asp
    130                 135                 140

Ser Asp Ser Ser Gly Lys Asp Pro Arg Asn Ser Gln Gly Lys Gly Ala
145                 150                 155                 160

His Arg Pro Glu His Ala Ser Gly Arg Arg Asn Val Lys Asp Ser Val
                165                 170                 175

Ser Ala Ser Glu Val Thr Ser Thr Val Tyr Asn Thr Val Ser Glu Gly
            180                 185                 190

Thr His Phe Leu Glu Thr Ile Glu Thr Pro Arg Pro Gly Lys Leu Phe
        195                 200                 205

Pro Lys Asp Val Ser Ser Thr Pro Ser Val Thr Ser Lys Ser
    210                 215                 220

Arg Val Ser Arg Leu Ala Gly Arg Lys Thr Asn Glu Ser Val Ser Glu
225                 230                 235                 240

Pro Arg Lys Gly Phe Met Tyr Ser Arg Asn Thr Asn Glu Asn Pro Gln
                245                 250                 255

Glu Cys Phe Asn Ala Ser Lys Leu Leu Thr Ser His Gly Met Gly Ile
            260                 265                 270

Gln Val Pro Leu Asn Ala Thr Glu Phe Asn Tyr Leu Cys Pro Ala Ile
        275                 280                 285

Ile Asn Gln Ile Asp Ala Arg Ser Cys Leu Ile His Thr Ser Glu Lys
    290                 295                 300

Lys Ala Glu Ile Pro Pro Lys Thr Tyr Ser Leu Gln Ile Ala Trp Val
305                 310                 315                 320

Gly Gly Phe Ile Ala Ile Ser Ile Ile Ser Phe Leu Ser Leu Leu Gly
                325                 330                 335

Val Ile Leu Val Pro Leu Met Asn Arg Val Phe Phe Lys Phe Leu Leu
            340                 345                 350

Ser Phe Leu Val Ala Leu Ala Val Gly Thr Leu Ser Gly Asp Ala Phe
        355                 360                 365

Leu His Leu Leu Pro His Ser His Ala Ser His His Ser His Ser
    370                 375                 380

His Glu Glu Pro Ala Met Glu Met Lys Arg Gly Pro Leu Phe Ser His
385                 390                 395                 400

Leu Ser Ser Gln Asn Ile Glu Glu Ser Ala Tyr Phe Asp Ser Thr Trp
                405                 410                 415

Lys Gly Leu Thr Ala Leu Gly Gly Leu Tyr Phe Met Phe Leu Val Glu
            420                 425                 430

His Val Leu Thr Leu Ile Lys Gln Phe Lys Asp Lys Lys Lys Asn
        435                 440                 445

Gln Lys Lys Pro Glu Asn Asp Asp Val Glu Ile Lys Lys Gln Leu
450                 455                 460

Ser Lys Tyr Glu Ser Gln Leu Ser Thr Asn Glu Glu Lys Val Asp Thr
465                 470                 475                 480

Asp Asp Arg Thr Glu Gly Tyr Leu Arg Ala Asp Ser Gln Glu Pro Ser
                485                 490                 495

His Phe Asp Ser Gln Gln Pro Ala Val Leu Glu Glu Glu Val Met
            500                 505                 510

Ile Ala His Ala His Pro Gln Glu Val Tyr Asn Glu Tyr Val Pro Arg
        515                 520                 525

Gly Cys Lys Asn Lys Cys His Ser His Phe His Asp Thr Leu Gly Gln
530                 535                 540

Ser Asp Asp Leu Ile His His His His Asp Tyr His His Ile Leu His
545                 550                 555                 560
```

```
His His His His Gln Asn His His Pro His Ser His Ser Gln Arg Tyr
                565                 570                 575

Ser Arg Glu Glu Leu Lys Asp Ala Gly Val Ala Thr Leu Ala Trp Met
            580                 585                 590

Val Ile Met Gly Asp Gly Leu His Asn Phe Ser Asp Gly Leu Ala Ile
            595                 600                 605

Gly Ala Ala Phe Thr Glu Gly Leu Ser Ser Gly Leu Ser Thr Ser Val
            610                 615                 620

Ala Val Phe Cys His Glu Leu Pro His Glu Leu Gly Asp Phe Ala Val
625                 630                 635                 640

Leu Leu Lys Ala Gly Met Thr Val Lys Gln Ala Val Leu Tyr Asn Ala
                645                 650                 655

Leu Ser Ala Met Leu Ala Tyr Leu Gly Met Ala Thr Gly Ile Phe Ile
                660                 665                 670

Gly His Tyr Ala Glu Asn Val Ser Met Trp Ile Phe Ala Leu Thr Ala
                675                 680                 685

Gly Leu Phe Met Tyr Val Ala Leu Val Asp Met Val Pro Glu Met Leu
            690                 695                 700

His Asn Asp Ala Ser Asp His Gly Cys Ser Arg Trp Gly Tyr Phe Phe
705                 710                 715                 720

Leu Gln Asn Ala Gly Met Leu Leu Gly Phe Gly Ile Met Leu Leu Ile
                725                 730                 735

Pro Tyr Leu Asn Ile Lys Ser Cys Ser Tyr Lys Phe Leu Val Lys Val
                740                 745                 750

<210> SEQ ID NO 53
<211> LENGTH: 9646
<212> TYPE: DNA
<213> ORGANISM: Homo sapiens
<220> FEATURE:
<221> NAME/KEY: misc_feature
<222> LOCATION: 9026, 9030
<223> OTHER INFORMATION: n = A,T,C or G

<400> SEQUENCE: 53
atgcccaagc gcgcgcactg gggggccctc tccgtggtgc tgatcctgct ttggggccat      60
ccgcgagtgg cgctggcctg cccgcatcct tgtgcctgct acgtcccag cgaggtccac      120 tgcacgttcc gatccctggc ttccgtgccc gctggcattg ctagacacgt ggaaagaatc     180
aatttggggt ttaatagcat acaggccctg tcagaaacct catttgcagg actgaccaag     240
ttggagctac ttatgattca cggcaatgag atcccaagca tccccgatgg agctttaaga     300
gacctcagct ctcttcaggt tttcaagttc agctacaaca agctgagagt gatcacagga     360
cagaccctcc agggtctctc taacttaatg aggctgcaca ttgaccacaa caagatcgag     420
tttatccacc ctcaagcttt caacggctta acgtctctga ggctactcca tttggaagga     480
aatctcctcc accagctgca ccccagcacc ttctccacgt tcacattttt ggattatttc     540
agactctcca ccataaggca cctctactta gcagagaaca tggttagaac tcttcctgcc     600
agcatgcttc ggaacatgcc gcttctggag aatctttact gcagggaaa tccgtggacc      660 tgcgattgtg agatgagatg gttttttgaa tgggatgcaa atccagagg aattctgaag     720 tgtaaaaagg acaaagctta tgaaggcggt cagttgtgtg caatgtgctt cagtccaaag     780
aagttgtaca acatgagat acacaagctg aaggacatga cttgtctgaa gccttcaata     840
gagtcccctc tgagacagaa caggagcagg agtattgagg aggagcaaga acaggaagag     900
gatggtggca gccagctcat cctggagaaa ttccaactgc cccagtggag catctctttg     960
```

```
aatatgaccg acgagcacgg gaacatggtg aacttggtct gtgacatcaa gaaaccaatg    1020
gatgtgtaca agattcactt gaaccaaacg gatcctccag atattgacat aaatgcaaca    1080
gttgccttgg actttgagtg tccaatgacc cgagaaaact atgaaaagct atggaaattg    1140
atagcatact acagtgaagt tcccgtgaag ctacacagag agctcatgct cagcaaagac    1200
cccagagtca gctaccagta caggcaggat gctgatgagg aagctcttta ctacacaggt    1260
gtgagagccc agattcttgc agaaccagaa tgggtcatgc agccatccat agatatccag    1320
ctgaaccgac gtcagagtac ggccaagaag gtgctacttt cctactacac ccagtattct    1380
caaacaatat ccaccaaaga tacaaggcag gctcggggca gaagctgggt aatgattgag    1440
cctagtggag ctgtgcaaag agatcagact gtcctggaag ggggtccatg ccagttgagc    1500
tgcaacgtga aagcttctga gagtccatct atcttctggg tgcttccaga tggctccatc    1560
ctgaaagcgc ccatggatga cccagacagc aagttctcca ttctcagcag tggctggctg    1620
aggatcaagt ccatggagcc atctgactca ggcttgtacc agtgcattgc tcaagtgagg    1680
gatgaaatgg accgcatggt atatagggta cttgtgcagt ctccctccac tcagccagcc    1740
gagaaagaca cagtgacaat tggcaagaac ccaggggagt cggtgacatt gccttgcaat    1800
gctttagcaa tacccgaagc ccaccttagc tggattcttc caaacagaag gataattaat    1860
gatttggcta acacatcaca tgtatacatg ttgccaaatg gaactctttc catcccaaag    1920
gtccaagtca gtgatagtgg ttactacaga tgtgtggctg tcaaccagca aggggcagac    1980
cattttacgg tgggaatcac agtgaccaag aaagggtctg gcttgccatc caaaagaggc    2040
agacgcccag gtgcaaaggc tctttccaga gtcagagaag acatcgtgga ggatgaaggg    2100
ggctcgggca tgggagatga agagaacact tcaaggagac ttctgcatcc aaaggaccaa    2160
gaggtgttcc tcaaaacaaa ggatgatgcc atcaatggag acaagaaagc caagaagggg    2220
agaagaaagc tgaaactctg gaagcattcg gaaaaagaac cagagaccaa tgttgcagaa    2280
ggtcgcagag tgtttgaatc tagacgaagg ataaacatgg caaacaaaca gattaatccg    2340
gagcgctggg ctgatatttt agccaaagtc cgtgggaaaa atctccctaa gggcacagaa    2400 gtaccccgt tgattaaaac cacaagtcct ccatccttga gcctagaagt cacaccacct    2460
tttcctgctg tttctccccc ctcagcatct cctgtgcaga cagtaaccag tgctgaagaa    2520
tcctcagcag atgtacctct acttggtgaa gaagagcacg ttttgggtac catttcctca    2580
gccagcatgg ggctagaaca caaccacaat ggagttattc ttgttgaacc tgaagtaaca    2640
agcacacctc tggaggaagt tgttgatgac ctttctgaga agactgagga gataacttcc    2700
actgaaggag acctgaaggg gacagcagcc cctacactta tatctgagcc ttatgaacca    2760
tctcctactc tgcacacatt agacacagtc tatgaaaagc ccacccatga agagacggca    2820
acagagggtt ggtctgcagc agatgttgga tcgtcaccag agcccacatc cagtgagtat    2880
gagcctccat tggatgctgt ctccttggct gagtctgagc ccatgcaata ctttgaccca    2940
gatttggaga ctaagtcaca accagatgag gataagatga agaagacac ctttgcacac    3000 cttactccaa cccccaccat ctgggttaat gactccagta catcacagtt atttgaggat    3060
tctactatag gggaaccagg tgtcccaggc caatcacatc tacaaggact gacagacaac    3120
atccaccttg tgaaaagtag tctaagcact caagacacct tactgattaa aagggtatg    3180 aaagagatgt ctcagacact acagggagga aatatgctag agggagaccc cacacactcc    3240
agaagttctg agagtgaggg ccaagagagc aaatccatca ctttgcctga ctccacactg    3300
ggtataatga gcagtatgtc tccagttaag aagcctgcgg aaaccacagt tggtacccte    3360
```

```
ctagacaaag acaccacaac agtaacaaca acaccaaggc aaaaagttgc tccgtcatcc    3420
accatgagca ctcacccttc tcgaaggaga cccaacggga gaaggagatt acgcccccaac   3480 aaattccgcc accggcacaa gcaaacccca cccacaactt ttgccccatc agagactttt    3540
tctactcaac caactcaagc acctgacatt aagatttcaa gtcaagtgga gagttctctg    3600
gttcctacag cttgggtgga taacacagtt aatacccccca aacagttgga aatggagaag   3660
aatgcagaac ccacatccaa gggaacacca cggagaaaac acgggaagag gccaaacaaa    3720
catcgatata ccccttctac agtgagctca agagcgtccg gatccaagcc cagcccttct    3780
ccagaaaata aacatagaaa cattgttact cccagttcag aaactatact tttgcctaga    3840
actgtttctc tgaaaactga gggcccttat gattccttag attacatgac aaccaccaga    3900
aaaatatatt catcttaccc taaagtccaa gagacacttc cagtcacata taaacccaca    3960
tcagatggaa aagaaattaa ggatgatgtt gccacaaatg ttgacaaaca taaaagtgac    4020
attttagtca ctggtgaatc aattactaat gccataccaa cttctcgctc cttggtctcc    4080
actatgggag aatttaagga agaatcctct cctgtaggct ttccaggaac tccaacctgg    4140
aatccctcaa ggacggccca gcctggggagg ctacagacag acatacctgt taccacttct    4200
ggggaaaatc ttacagaccc tccccttctt aaagagcttg aggatgtgga tttcacttcc    4260 gagttttttgt cctctttgac agtctccaca ccatttcacc aggaagaagc tggttcttcc    4320
acaactctct caagcataaa agtggaggtg gcttcaagtc aggcagaaac caccacccett   4380 gatcaagatc atcttgaaac cactgtggct attctccttt ctgaaactag accacagaat    4440
cacaccccta ctgctgcccg gatgaaggag ccagcatcct cgtccccatc cacaattctc    4500
atgtctttgg gacaaaccac caccactaag ccagcacttc ccagtccaag aatatctcaa    4560
gcatctagag attccaagga aaatgttttc ttgaattatg tggggaatcc agaaacagaa    4620 gcaacccccag tcaacaatga aggaacacag catatgtcag ggccaaatga attatcaaca    4680
ccctcttccg accgggatgc atttaacttg tctacaaagc tggaattgga aaagcaagta    4740
tttggtagta ggagtctacc acgtggccca gatagccaac gccaggatgg aagagttcat    4800
gcttctcatc aactaaccag agtccctgcc aaacccatcc taccaacagc aacagtgagg    4860
ctacctgaaa tgtccacaca aagcgcttcc agatactttg taacttccca gtcacctcgt    4920
cactggacca acaaaccgga aataactaca tatccttctg gggcttttgcc agagaacaaa    4980 cagtttacaa ctccaagatt atcaagtaca acaattcctc tcccattgca catgtccaaa    5040
cccagcattc ctagtaagtt tactgaccga agaactgacc aattcaatgg ttactccaaa    5100
gtgtttggaa ataacaacat ccctgaggca agaaacccag ttggaaagcc tcccagtcca    5160
agaattcctc attattccaa tggaagactc cctttctttaa ccaacaagac tctttctttt    5220
ccacagttgg gagtcacccg gagaccccag atacccactt ctcctgcccc agtaatgaga    5280
gagagaaaag ttattccagg ttcctacaac aggatacatt cccatagcac cttccatctg    5340
gactttggcc ctccggcacc tccgttgttg cacactccgc agaccacggg atcccctca    5400 actaacttac agaatatccc tatggtctct tccacccaga gttctatctc ctttataaca    5460
tcttctgtcc agtcctcagg aagcttccac cagagcagct caaagttctt gcaggagga    5520 cctcctgcat ccaaattctg gtctcttggg gaaaagccccc aaatcctcac caagtcccca    5580
cagactgtgt ccgtcaccgc tgagacagac actgtgttcc cctgtgaggc aacaggaaaa    5640
ccaaagcctt tcgttacttg gacaaaggtt tccacaggag ctcttatgac tccgaatacc    5700
aggatacaac ggtttgaggt tctcaagaac ggtaccttag tgatacggaa ggttcaagta    5760
```

```
caagatcgag gccagtatat gtgcaccgcc agcaacctgc acggcctgga caggatggtg    5820
gtcttgcttt cggtcaccgt gcagcaacct caaatcctag cctcccacta ccaggacgtc    5880
actgtctacc tgggagacac cattgcaatg gagtgtctgg ccaaagggac cccagccccc    5940
caaatttcct ggatcttccc tgacaggagg gtgtggcaaa ctgtgtcccc cgtggagagc    6000
cgcatcaccc tgcacgaaaa ccggacccct tccatcaagg aggcgtcctt ctcagacaga    6060
ggcgtctata agtgcgtggc cagcaatgca gccggggcgg acagcctggc catccgcctg    6120
cacgtggcgg cactgccccc cgttatccac caggagaagc tggagaacat ctcgctgccc    6180
ccggggctca gcattcacat tcactgcact gccaaggctg cgcccctgcc cagcgtgcgc    6240
tgggtgctcg ggacggtac ccagatccgc ccctcgcagt tcctccacgg gaacttgttt    6300
gttttcccca acgggacgct ctacatccgc aacctcgcgc caaggacag cgggcgctat    6360
gagtgcgtgg ccgccaacct ggtaggctcc gcgcgcagga cggtgcagct gaacgtgcag    6420
cgtgcagcag ccaacgcgcg catcacgggc acctccccgc ggaggacgga cgtcaggtac    6480
ggaggaaccc tcaagctgga ctgcagcgcc tcggggacc cctggccgcg catcctctgg    6540
aggctgccgt ccaagaggat gatcgacgcg ctcttcagtt ttgatagcag aatcaaggtg    6600
tttgccaatg ggaccctggt ggtgaaatca gtgacggaca agatgccgg agattacctg    6660
tgcgtagctc gaaataaggt tggtgatgac tacgtggtgc tcaaagtgga tgtggtgatg    6720
aaaccggcca agattgaaca caaggaggag aacgaccaca agtcttcta cgggggtgac    6780
ctgaaagtgg actgtgtggc caccgggctt cccaatcccg agatctcctg gagcctccca    6840
gacgggagtc tggtgaactc cttcatgcag tcggatgaca gcggtggacg caccaagcgc    6900
tatgtcgtct tcaacaatgg gacactctac tttaacgaag tggggatgag ggaggaagga    6960
gactacacct gctttgctga aaatcaggtc gggaaggacg agatgagagt cagagtcaag    7020
gtggtgacag cgcccgccac catccggaac aagacttact ggcggttca ggtgccctat    7080
ggagacgtgg tcactgtagc ctgtgaggcc aaaggagaac ccatgcccaa ggtgacttgg    7140
ttgtccccaa ccaacaaggt gatccccacc tcctctgaga agtatcagat ataccaagat    7200
ggcactctcc ttattcagaa agcccagcgt tctgacagcg gcaactacac ctgcttggtc    7260
aggaacagcg cgggagagga taggaagacg gtgtggattc acgtcaacgt ccagccaccc    7320
aagatcaacg gtaaccccaa ccccatcacc accgtgcggg agatagcagc cggggcagt    7380
cggaaactga ttgactgcaa agctgaaggc atcccccacc cgagggtgtt atgggctttt    7440
cccgagggtg tggttctgcc agctccatac tatggaaacc ggatcactgt ccatggcaac    7500
ggttccctgg acatcaggag tttgaggaag agcgactccg tccagctggt atgcatggca    7560
cgcaacgagg aggggaggc gaggttgatc gtgcagctca ctgtcctgga gcccatggag    7620
aaacccatct tccacgaccc gatcagcgag aagatcacgg ccatggcggg ccacaccatc    7680
agcctcaact gctctgccgc ggggacccccg acacccagcc tggtgtgggt ccttcccaat    7740
ggcaccgatc tgcagagtgg acagcagctg cagcgcttct accacaaggc tgacggcatg    7800
ctacacatta gcggtctctc ctcggtggac gcyggggcct accgctgcgt ggcccgcaat    7860
gccgctggcc acacggagag gctggtctcc ctgaaggtgg gactgaagcc agaagcaaac    7920
aagcagtatc ataacctggt cagcatcatc aatggtgaga ccctgaagct cccctgcacc    7980
cctcccgggg ctgggcaggg acgtttctcc tggacgctcc ccaatggcat gcatctggag    8040
ggcccccaaa ccctgggacg cgtttctctt ctggacaatg gcaccctcac ggttcgtgag    8100
gcctcggtgt ttgacagggg tacctatgta tgcaggatgg agacggagta cggcccttcg    8160
```

```
gtcaccagca tccccgtgat tgtgatcgcc tatcctcccc ggatcaccag cgagcccacc    8220
ccggtcatct acacccggcc cgggaacacc gtgaaactga actgcatggc tatggggatt    8280
cccaaagctg acatcacgtg ggagttaccg gataagtcgc atctgaaggc aggggttcag    8340
gctcgtctgt atggaaacag atttcttcac ccccagggat cactgaccat ccagcatgcc    8400
acacagagag atgccggctt ctacaagtgc atggcaaaaa acattctcgg cagtgactcc    8460
aaaacaactt acatccacgt cttctgaaat gtggattcca gaatgattgc ttaggaactg    8520
acaacaaagc ggggtttgta agggaagcca ggttggggaa taggagctct taaataatgt    8580
gtcacagtgc atggtggcct ctggtgggtt tcaagttgag gttgatcttg atctacaatt    8640
gttgggaaaa ggaagcaatg cagacacgag aaggagggct cagccttgct gagacacttt    8700
cttttgtgtt tacatcatgc cagggcttc attcagggtg tctgtgctct gactgcaatt    8760 tttcttttt tgcaaatgcc actcgactgc cttcataagc gtccatagga tatctgagga    8820
acattcatca aaaataagcc atagacatga acaacacctc actaccccat tgaagacgca    8880
tcacctagtt aacctgctgc agttttaca tgatagactt tgttccagat tgacaagtca    8940
tctttcagtt atttcctctg tcacttcaaa actccagctt gcccaataag gatttagaac    9000
cagagtgact gatatatata tatatntttn aattcagagt tacatacata cagctaccat    9060
tttatatgaa aaagaaaaa catttcttcc tggaactcac tttttatata atgttttata    9120
tatatatttt tkccttttcaa atcagacgat gagactagaa ggagaaatac tttctgtctt    9180
attaaaatta ataaattatt ggtctttaca agacttggat acattacagc agacatggaa    9240
aatataattt taaaaatt ctctccaacc tccttcaaat tcagtcacca ctgttatatt    9300
accttctcca ggaaccctcc agtggggaag gctgcgatat tagatttcct tgtatgcaaa    9360 gttttttgttg aaagctgtgc tcagaggagg tgagaggaga ggaaggagaa aactgcatca    9420
taactttaca gaattgaatc tagagtcttc cccgaaaagc ccagaaactt ctctgcagta    9480
tctggcttgt ccatctggtc taaggtggct gcttcttccc cagccatgag tcagtttgtg    9540
cccatgaata atacacgacc tgttatttcc atgactgctt tactgtattt ttaaggtcaa    9600
tatactgtac atttgataat aaaataatat tctcccaaaa aaaaaa              9646
```

<210> SEQ ID NO 54
<211> LENGTH: 2828
<212> TYPE: PRT
<213> ORGANISM: Homo sapiens

<400> SEQUENCE: 54

```
Met Pro Lys Arg Ala His Trp Gly Ala Leu Ser Val Val Leu Ile Leu
  1               5                  10                  15

Leu Trp Gly His Pro Arg Val Ala Leu Ala Cys Pro His Pro Cys Ala
                 20                  25                  30

Cys Tyr Val Pro Ser Glu Val His Cys Thr Phe Arg Ser Leu Ala Ser
             35                  40                  45

Val Pro Ala Gly Ile Ala Arg His Val Glu Arg Ile Asn Leu Gly Phe
         50                  55                  60

Asn Ser Ile Gln Ala Leu Ser Glu Thr Ser Phe Ala Gly Leu Thr Lys
 65                  70                  75                  80

Leu Glu Leu Leu Met Ile His Gly Asn Glu Ile Pro Ser Ile Pro Asp
                 85                  90                  95

Gly Ala Leu Arg Asp Leu Ser Ser Leu Gln Val Phe Lys Phe Ser Tyr
            100                 105                 110
```

```
Asn Lys Leu Arg Val Ile Thr Gly Gln Thr Leu Gln Gly Leu Ser Asn
            115                 120                 125
Leu Met Arg Leu His Ile Asp His Asn Lys Ile Glu Phe Ile His Pro
        130                 135                 140
Gln Ala Phe Asn Gly Leu Thr Ser Leu Arg Leu Leu His Leu Glu Gly
145                 150                 155                 160
Asn Leu Leu His Gln Leu His Pro Ser Thr Phe Ser Thr Phe Thr Phe
                165                 170                 175
Leu Asp Tyr Phe Arg Leu Ser Thr Ile Arg His Leu Tyr Leu Ala Glu
                180                 185                 190
Asn Met Val Arg Thr Leu Pro Ala Ser Met Leu Arg Asn Met Pro Leu
            195                 200                 205
Leu Glu Asn Leu Tyr Leu Gln Gly Asn Pro Trp Thr Cys Asp Cys Glu
210                 215                 220
Met Arg Trp Phe Leu Glu Trp Asp Ala Lys Ser Arg Gly Ile Leu Lys
225                 230                 235                 240
Cys Lys Lys Asp Lys Ala Tyr Glu Gly Gly Gln Leu Cys Ala Met Cys
                245                 250                 255
Phe Ser Pro Lys Lys Leu Tyr Lys His Glu Ile His Lys Leu Lys Asp
                260                 265                 270
Met Thr Cys Leu Lys Pro Ser Ile Glu Ser Pro Leu Arg Gln Asn Arg
            275                 280                 285
Ser Arg Ser Ile Glu Glu Gln Glu Gln Glu Asp Gly Gly Ser
290                 295                 300
Gln Leu Ile Leu Glu Lys Phe Gln Leu Pro Gln Trp Ser Ile Ser Leu
305                 310                 315                 320
Asn Met Thr Asp Glu His Gly Asn Met Val Asn Leu Val Cys Asp Ile
                325                 330                 335
Lys Lys Pro Met Asp Val Tyr Lys Ile His Leu Asn Gln Thr Asp Pro
            340                 345                 350
Pro Asp Ile Asp Ile Asn Ala Thr Val Ala Leu Asp Phe Glu Cys Pro
            355                 360                 365
Met Thr Arg Glu Asn Tyr Glu Lys Leu Trp Lys Leu Ile Ala Tyr Tyr
        370                 375                 380
Ser Glu Val Pro Val Lys Leu His Arg Glu Leu Met Leu Ser Lys Asp
385                 390                 395                 400
Pro Arg Val Ser Tyr Gln Tyr Arg Gln Asp Ala Asp Glu Glu Ala Leu
                405                 410                 415
Tyr Tyr Thr Gly Val Arg Ala Gln Ile Leu Ala Glu Pro Glu Trp Val
                420                 425                 430
Met Gln Pro Ser Ile Asp Ile Gln Leu Asn Arg Arg Gln Ser Thr Ala
        435                 440                 445
Lys Lys Val Leu Leu Ser Tyr Tyr Thr Gln Tyr Ser Gln Thr Ile Ser
            450                 455                 460
Thr Lys Asp Thr Arg Gln Ala Arg Gly Arg Ser Trp Val Met Ile Glu
465                 470                 475                 480
Pro Ser Gly Ala Val Gln Arg Asp Gln Thr Val Leu Glu Gly Gly Pro
                485                 490                 495
Cys Gln Leu Ser Cys Asn Val Lys Ala Ser Glu Ser Pro Ser Ile Phe
                500                 505                 510
Trp Val Leu Pro Asp Gly Ser Ile Leu Lys Ala Pro Met Asp Asp Pro
            515                 520                 525
Asp Ser Lys Phe Ser Ile Leu Ser Ser Gly Trp Leu Arg Ile Lys Ser
            530                 535                 540
```

```
Met Glu Pro Ser Asp Ser Gly Leu Tyr Gln Cys Ile Ala Gln Val Arg
545                 550                 555                 560

Asp Glu Met Asp Arg Met Val Tyr Arg Val Leu Val Gln Ser Pro Ser
            565                 570                 575

Thr Gln Pro Ala Glu Lys Asp Thr Val Thr Ile Gly Lys Asn Pro Gly
                580                 585                 590

Glu Ser Val Thr Leu Pro Cys Asn Ala Leu Ala Ile Pro Glu Ala His
            595                 600                 605

Leu Ser Trp Ile Leu Pro Asn Arg Arg Ile Ile Asn Asp Leu Ala Asn
        610                 615                 620

Thr Ser His Val Tyr Met Leu Pro Asn Gly Thr Leu Ser Ile Pro Lys
625                 630                 635                 640

Val Gln Val Ser Asp Ser Gly Tyr Tyr Arg Cys Val Ala Val Asn Gln
                645                 650                 655

Gln Gly Ala Asp His Phe Thr Val Gly Ile Thr Val Thr Lys Lys Gly
            660                 665                 670

Ser Gly Leu Pro Ser Lys Arg Gly Arg Pro Gly Ala Lys Ala Leu
        675                 680                 685

Ser Arg Val Arg Glu Asp Ile Val Glu Asp Glu Gly Ser Gly Met
690                 695                 700

Gly Asp Glu Glu Asn Thr Ser Arg Arg Leu Leu His Pro Lys Asp Gln
705                 710                 715                 720

Glu Val Phe Leu Lys Thr Lys Asp Asp Ala Ile Asn Gly Asp Lys Lys
                725                 730                 735

Ala Lys Lys Gly Arg Arg Lys Leu Lys Leu Trp Lys His Ser Glu Lys
                740                 745                 750

Glu Pro Glu Thr Asn Val Ala Glu Gly Arg Arg Val Phe Glu Ser Arg
            755                 760                 765

Arg Arg Ile Asn Met Ala Asn Lys Gln Ile Asn Pro Glu Arg Trp Ala
        770                 775                 780

Asp Ile Leu Ala Lys Val Arg Gly Lys Asn Leu Pro Lys Gly Thr Glu
785                 790                 795                 800

Val Pro Pro Leu Ile Lys Thr Thr Ser Pro Pro Ser Leu Ser Leu Glu
                805                 810                 815

Val Thr Pro Pro Phe Pro Ala Val Ser Pro Pro Ser Ala Ser Pro Val
            820                 825                 830

Gln Thr Val Thr Ser Ala Glu Glu Ser Ala Asp Val Pro Leu Leu
        835                 840                 845

Gly Glu Glu Glu His Val Leu Gly Thr Ile Ser Ser Ala Ser Met Gly
850                 855                 860

Leu Glu His Asn His Asn Gly Val Ile Leu Val Glu Pro Glu Val Thr
865                 870                 875                 880

Ser Thr Pro Leu Glu Glu Val Val Asp Asp Leu Ser Glu Lys Thr Glu
                885                 890                 895

Glu Ile Thr Ser Thr Glu Gly Asp Leu Lys Gly Thr Ala Ala Pro Thr
            900                 905                 910

Leu Ile Ser Glu Pro Tyr Glu Pro Ser Pro Thr Leu His Thr Leu Asp
        915                 920                 925

Thr Val Tyr Glu Lys Pro Thr His Glu Glu Thr Ala Thr Glu Gly Trp
930                 935                 940

Ser Ala Ala Asp Val Gly Ser Ser Pro Glu Pro Thr Ser Ser Glu Tyr
945                 950                 955                 960

Glu Pro Pro Leu Asp Ala Val Ser Leu Ala Glu Ser Glu Pro Met Gln
```

-continued

```
                965                 970                 975
Tyr Phe Asp Pro Asp Leu Glu Thr Lys Ser Gln Pro Asp Glu Asp Lys
            980                 985                 990

Met Lys Glu Asp Thr Phe Ala His Leu Thr Pro Thr Pro Thr Ile Trp
            995                1000                1005

Val Asn Asp Ser Ser Thr Ser Gln Leu Phe Glu Asp Ser Thr Ile Gly
           1010                1015                1020

Glu Pro Gly Val Pro Gly Gln Ser His Leu Gln Gly Leu Thr Asp Asn
       1025                1030                1035                1040

Ile His Leu Val Lys Ser Ser Leu Ser Thr Gln Asp Thr Leu Leu Ile
                1045                1050                1055

Lys Lys Gly Met Lys Glu Met Ser Gln Thr Leu Gln Gly Gly Asn Met
                1060                1065                1070

Leu Glu Gly Asp Pro Thr His Ser Arg Ser Ser Glu Ser Glu Gly Gln
            1075                1080                1085

Glu Ser Lys Ser Ile Thr Leu Pro Asp Ser Thr Leu Gly Ile Met Ser
            1090                1095                1100

Ser Met Ser Pro Val Lys Lys Pro Ala Glu Thr Thr Val Gly Thr Leu
1105                1110                1115                1120

Leu Asp Lys Asp Thr Thr Thr Val Thr Thr Thr Pro Arg Gln Lys Val
                1125                1130                1135

Ala Pro Ser Ser Thr Met Ser Thr His Pro Ser Arg Arg Pro Asn
                1140                1145                1150

Gly Arg Arg Arg Leu Arg Pro Asn Lys Phe Arg His Arg His Lys Gln
                1155                1160                1165

Thr Pro Pro Thr Thr Phe Ala Pro Ser Glu Thr Phe Ser Thr Gln Pro
            1170                1175                1180

Thr Gln Ala Pro Asp Ile Lys Ile Ser Ser Gln Val Glu Ser Ser Leu
1185                1190                1195                1200

Val Pro Thr Ala Trp Val Asp Asn Thr Val Asn Thr Pro Lys Gln Leu
                1205                1210                1215

Glu Met Glu Lys Asn Ala Glu Pro Thr Ser Lys Gly Thr Pro Arg Arg
            1220                1225                1230

Lys His Gly Lys Arg Pro Asn Lys His Arg Tyr Thr Pro Ser Thr Val
            1235                1240                1245

Ser Ser Arg Ala Ser Gly Ser Lys Pro Ser Pro Ser Pro Glu Asn Lys
            1250                1255                1260

His Arg Asn Ile Val Thr Pro Ser Ser Glu Thr Ile Leu Leu Pro Arg
1265                1270                1275                1280

Thr Val Ser Leu Lys Thr Glu Gly Pro Tyr Asp Ser Leu Asp Tyr Met
                1285                1290                1295

Thr Thr Thr Arg Lys Ile Tyr Ser Ser Tyr Pro Lys Val Gln Glu Thr
                1300                1305                1310

Leu Pro Val Thr Tyr Lys Pro Thr Ser Asp Gly Lys Glu Ile Lys Asp
            1315                1320                1325

Asp Val Ala Thr Asn Val Asp Lys His Lys Ser Asp Ile Leu Val Thr
            1330                1335                1340

Gly Glu Ser Ile Thr Asn Ala Ile Pro Thr Ser Arg Ser Leu Val Ser
1345                1350                1355                1360

Thr Met Gly Glu Phe Lys Glu Glu Ser Ser Pro Val Gly Phe Pro Gly
                1365                1370                1375

Thr Pro Thr Trp Asn Pro Ser Arg Thr Ala Gln Pro Gly Arg Leu Gln
            1380                1385                1390
```

```
Thr Asp Ile Pro Val Thr Thr Ser Gly Glu Asn Leu Thr Asp Pro Pro
        1395                1400                1405

Leu Leu Lys Glu Leu Glu Asp Val Asp Phe Thr Ser Glu Phe Leu Ser
    1410                1415                1420

Ser Leu Thr Val Ser Thr Pro Phe His Gln Glu Glu Ala Gly Ser Ser
1425                1430                1435                1440

Thr Thr Leu Ser Ser Ile Lys Val Glu Val Ala Ser Ser Gln Ala Glu
            1445                1450                1455

Thr Thr Thr Leu Asp Gln Asp His Leu Glu Thr Thr Val Ala Ile Leu
                1460                1465                1470

Leu Ser Glu Thr Arg Pro Gln Asn His Thr Pro Thr Ala Ala Arg Met
    1475                1480                1485

Lys Glu Pro Ala Ser Ser Pro Ser Thr Ile Leu Met Ser Leu Gly
    1490                1495                1500

Gln Thr Thr Thr Lys Pro Ala Leu Pro Ser Pro Arg Ile Ser Gln
1505                1510                1515                1520

Ala Ser Arg Asp Ser Lys Glu Asn Val Phe Leu Asn Tyr Val Gly Asn
                1525                1530                1535

Pro Glu Thr Glu Ala Thr Pro Val Asn Asn Glu Gly Thr Gln His Met
        1540                1545                1550

Ser Gly Pro Asn Glu Leu Ser Thr Pro Ser Ser Asp Arg Asp Ala Phe
    1555                1560                1565

Asn Leu Ser Thr Lys Leu Glu Leu Glu Lys Gln Val Phe Gly Ser Arg
    1570                1575                1580

Ser Leu Pro Arg Gly Pro Asp Ser Gln Arg Gln Asp Gly Arg Val His
1585                1590                1595                1600

Ala Ser His Gln Leu Thr Arg Val Pro Ala Lys Pro Ile Leu Pro Thr
                1605                1610                1615

Ala Thr Val Arg Leu Pro Glu Met Ser Thr Gln Ser Ala Ser Arg Tyr
                1620                1625                1630

Phe Val Thr Ser Gln Ser Pro Arg His Trp Thr Asn Lys Pro Glu Ile
            1635                1640                1645

Thr Thr Tyr Pro Ser Gly Ala Leu Pro Glu Asn Lys Gln Phe Thr Thr
    1650                1655                1660

Pro Arg Leu Ser Ser Thr Thr Ile Pro Leu Pro Leu His Met Ser Lys
1665                1670                1675                1680

Pro Ser Ile Pro Ser Lys Phe Thr Asp Arg Arg Thr Asp Gln Phe Asn
            1685                1690                1695

Gly Tyr Ser Lys Val Phe Gly Asn Asn Asn Ile Pro Glu Ala Arg Asn
                1700                1705                1710

Pro Val Gly Lys Pro Pro Ser Pro Arg Ile Pro His Tyr Ser Asn Gly
            1715                1720                1725

Arg Leu Pro Phe Phe Thr Asn Lys Thr Leu Ser Phe Pro Gln Leu Gly
    1730                1735                1740

Val Thr Arg Arg Pro Gln Ile Pro Thr Ser Pro Ala Pro Val Met Arg
1745                1750                1755                1760

Glu Arg Lys Val Ile Pro Gly Ser Tyr Asn Arg Ile His Ser His Ser
                1765                1770                1775

Thr Phe His Leu Asp Phe Gly Pro Pro Ala Pro Pro Leu Leu His Thr
            1780                1785                1790

Pro Gln Thr Thr Gly Ser Pro Ser Thr Asn Leu Gln Asn Ile Pro Met
        1795                1800                1805

Val Ser Ser Thr Gln Ser Ser Ile Ser Phe Ile Thr Ser Ser Val Gln
    1810                1815                1820
```

```
Ser Ser Gly Ser Phe His Gln Ser Ser Lys Phe Ala Gly Gly
1825                1830                1835                1840

Pro Pro Ala Ser Lys Phe Trp Ser Leu Gly Glu Lys Pro Gln Ile Leu
            1845                1850                1855

Thr Lys Ser Pro Gln Thr Val Ser Val Thr Ala Glu Thr Asp Thr Val
        1860                1865                1870

Phe Pro Cys Glu Ala Thr Gly Lys Pro Lys Pro Phe Val Thr Trp Thr
            1875                1880                1885

Lys Val Ser Thr Gly Ala Leu Met Thr Pro Asn Thr Arg Ile Gln Arg
        1890                1895                1900

Phe Glu Val Leu Lys Asn Gly Thr Leu Val Ile Arg Lys Val Gln Val
1905                1910                1915                1920

Gln Asp Arg Gly Gln Tyr Met Cys Thr Ala Ser Asn Leu His Gly Leu
                1925                1930                1935

Asp Arg Met Val Val Leu Leu Ser Val Thr Val Gln Gln Pro Gln Ile
            1940                1945                1950

Leu Ala Ser His Tyr Gln Asp Val Thr Val Tyr Leu Gly Asp Thr Ile
        1955                1960                1965

Ala Met Glu Cys Leu Ala Lys Gly Thr Pro Ala Pro Gln Ile Ser Trp
    1970                1975                1980

Ile Phe Pro Asp Arg Arg Val Trp Gln Thr Val Ser Pro Val Glu Ser
1985                1990                1995                2000

Arg Ile Thr Leu His Glu Asn Arg Thr Leu Ser Ile Lys Glu Ala Ser
                2005                2010                2015

Phe Ser Asp Arg Gly Val Tyr Lys Cys Val Ala Ser Asn Ala Ala Gly
            2020                2025                2030

Ala Asp Ser Leu Ala Ile Arg Leu His Val Ala Ala Leu Pro Pro Val
        2035                2040                2045

Ile His Gln Glu Lys Leu Glu Asn Ile Ser Leu Pro Pro Gly Leu Ser
    2050                2055                2060

Ile His Ile His Cys Thr Ala Lys Ala Ala Pro Leu Pro Ser Val Arg
2065                2070                2075                2080

Trp Val Leu Gly Asp Gly Thr Gln Ile Arg Pro Ser Gln Phe Leu His
                2085                2090                2095

Gly Asn Leu Phe Val Phe Pro Asn Gly Thr Leu Tyr Ile Arg Asn Leu
            2100                2105                2110

Ala Pro Lys Asp Ser Gly Arg Tyr Glu Cys Val Ala Ala Asn Leu Val
        2115                2120                2125

Gly Ser Ala Arg Arg Thr Val Gln Leu Asn Val Gln Arg Ala Ala Ala
    2130                2135                2140

Asn Ala Arg Ile Thr Gly Thr Ser Pro Arg Arg Thr Asp Val Arg Tyr
2145                2150                2155                2160

Gly Gly Thr Leu Lys Leu Asp Cys Ser Ala Ser Gly Asp Pro Trp Pro
                2165                2170                2175

Arg Ile Leu Trp Arg Leu Pro Ser Lys Arg Met Ile Asp Ala Leu Phe
            2180                2185                2190

Ser Phe Asp Ser Arg Ile Lys Val Phe Ala Asn Gly Thr Leu Val Val
        2195                2200                2205

Lys Ser Val Thr Asp Lys Asp Ala Gly Asp Tyr Leu Cys Val Ala Arg
    2210                2215                2220

Asn Lys Val Gly Asp Asp Tyr Val Val Leu Lys Val Asp Val Val Met
2225                2230                2235                2240

Lys Pro Ala Lys Ile Glu His Lys Glu Glu Asn Asp His Lys Val Phe
```

2245                2250                2255
Tyr Gly Gly Asp Leu Lys Val Asp Cys Val Ala Thr Gly Leu Pro Asn
            2260                2265                2270

Pro Glu Ile Ser Trp Ser Leu Pro Asp Gly Ser Leu Val Asn Ser Phe
        2275                2280                2285

Met Gln Ser Asp Asp Ser Gly Gly Arg Thr Lys Arg Tyr Val Val Phe
        2290                2295                2300

Asn Asn Gly Thr Leu Tyr Phe Asn Glu Val Gly Met Arg Glu Glu Gly
2305                2310                2315                2320

Asp Tyr Thr Cys Phe Ala Glu Asn Gln Val Gly Lys Asp Glu Met Arg
        2325                2330                2335

Val Arg Val Lys Val Val Thr Ala Pro Ala Thr Ile Arg Asn Lys Thr
        2340                2345                2350

Tyr Leu Ala Val Gln Val Pro Tyr Gly Asp Val Val Thr Val Ala Cys
        2355                2360                2365

Glu Ala Lys Gly Glu Pro Met Pro Lys Val Thr Trp Leu Ser Pro Thr
        2370                2375                2380

Asn Lys Val Ile Pro Thr Ser Ser Glu Lys Tyr Gln Ile Tyr Gln Asp
2385                2390                2395                2400

Gly Thr Leu Leu Ile Gln Lys Ala Gln Arg Ser Asp Ser Gly Asn Tyr
        2405                2410                2415

Thr Cys Leu Val Arg Asn Ser Ala Gly Glu Asp Arg Lys Thr Val Trp
        2420                2425                2430

Ile His Val Asn Val Gln Pro Pro Lys Ile Asn Gly Asn Pro Asn Pro
        2435                2440                2445

Ile Thr Thr Val Arg Glu Ile Ala Ala Gly Gly Ser Arg Lys Leu Ile
        2450                2455                2460

Asp Cys Lys Ala Glu Gly Ile Pro Thr Pro Arg Val Leu Trp Ala Phe
2465                2470                2475                2480

Pro Glu Gly Val Val Leu Pro Ala Pro Tyr Tyr Gly Asn Arg Ile Thr
        2485                2490                2495

Val His Gly Asn Gly Ser Leu Asp Ile Arg Ser Leu Arg Lys Ser Asp
        2500                2505                2510

Ser Val Gln Leu Val Cys Met Ala Arg Asn Glu Gly Gly Glu Ala Arg
        2515                2520                2525

Leu Ile Val Gln Leu Thr Val Leu Glu Pro Met Glu Lys Pro Ile Phe
        2530                2535                2540

His Asp Pro Ile Ser Glu Lys Ile Thr Ala Met Ala Gly His Thr Ile
2545                2550                2555                2560

Ser Leu Asn Cys Ser Ala Ala Gly Thr Pro Thr Pro Ser Leu Val Trp
        2565                2570                2575

Val Leu Pro Asn Gly Thr Asp Leu Gln Ser Gly Gln Gln Leu Gln Arg
        2580                2585                2590

Phe Tyr His Lys Ala Asp Gly Met Leu His Ile Ser Gly Leu Ser Ser
        2595                2600                2605

Val Asp Ala Gly Ala Tyr Arg Cys Val Ala Arg Asn Ala Ala Gly His
        2610                2615                2620

Thr Glu Arg Leu Val Ser Leu Lys Val Gly Leu Lys Pro Glu Ala Asn
2625                2630                2635                2640

Lys Gln Tyr His Asn Leu Val Ser Ile Ile Asn Gly Glu Thr Leu Lys
        2645                2650                2655

Leu Pro Cys Thr Pro Pro Gly Ala Gly Gln Gly Arg Phe Ser Trp Thr
        2660                2665                2670

| | | | | |
|---|---|---|---|---|
|Leu Pro Asn Gly Met His Leu Glu Gly Pro Gln Thr Leu Gly Arg Val| | | | |
| |2675| |2680| |2685|

Ser Leu Leu Asp Asn Gly Thr Leu Thr Val Arg Glu Ala Ser Val Phe
    2690            2695            2700

Asp Arg Gly Thr Tyr Val Cys Arg Met Glu Thr Glu Tyr Gly Pro Ser
2705            2710            2715            2720

Val Thr Ser Ile Pro Val Ile Val Ala Tyr Pro Pro Arg Ile Thr
        2725            2730            2735

Ser Glu Pro Thr Pro Val Ile Tyr Thr Arg Pro Gly Asn Thr Val Lys
        2740            2745            2750

Leu Asn Cys Met Ala Met Gly Ile Pro Lys Ala Asp Ile Thr Trp Glu
        2755            2760            2765

Leu Pro Asp Lys Ser His Leu Lys Ala Gly Val Gln Ala Arg Leu Tyr
        2770            2775            2780

Gly Asn Arg Phe Leu His Pro Gln Gly Ser Leu Thr Ile Gln His Ala
2785            2790            2795            2800

Thr Gln Arg Asp Ala Gly Phe Tyr Lys Cys Met Ala Lys Asn Ile Leu
            2805            2810            2815

Gly Ser Asp Ser Lys Thr Thr Tyr Ile His Val Phe
            2820            2825

<210> SEQ ID NO 55
<211> LENGTH: 6763
<212> TYPE: DNA
<213> ORGANISM: Homo sapiens

<400> SEQUENCE: 55

```
atggtgctga cgccctctga agagcagtcg ggtccttggg aactgtgcca gcttctctgt      60
aagcggggca catgcacatc ttgccagggc gtcctggtgc tgcccaccac atccttcgcc     120
agtgtgattt gggaggcacc aagaggacct tcccctggag aaggtgtgat gcttgtgcca     180
cacatggcta ctggtgacac caactctgca accaccatga gcttctcaac aagagctgct     240
acggagagag ctagggctac cgatccgaca gatggggtgc gaattctggc ttcggcttcc     300
tgctgtctgg ttttgagatg ttcccttagc ctttctgagc ctcacttctt tggtcagcag     360
atgggctgtg attgggtgcc ttcaaggatg gctgccaaat tggtgtccac agttataatg     420
gaggctggtc tggggatgg tggggcagct gcctgggta aggtcacggg gatagagatc      480
aggaccatct tgtgaagtt ggtggtcagc gcagtgggt gtcagatcgg tcagtgggac      540
aaaccagaca aattgcggct cttcaaggct gtagatgag tgaaacctca cattctgctg      600
ggaaaaaagg aagtgcccaa caagcccttg cgtgtgcgtg tccggtcctc agatgacagg     660
ctgtccgttg cgtggaaggc accacgcctg tctggagcca agagtccacg cagatcacgg     720
ggttttctcc tgggctacgg ggagagtggc cggaagatga attatgttcc actgacaaga     780
gatgaacgga cacacgaaat taaaaagcta gagcacttgc ttggacggaa gcccggcgag     840
cccacactcc taggcgctct gagagctcct aactctgagg aaggcacagc catgcatttc     900
ggagcctgga taagcagctc tgtgctcttc agtacctccg aggccagccc cctgggtcca     960
gttcttgggc tcgcccttca tagtcctcaa gaagtgggaa taccccccaga aagaggaaac    1020 ggaaaaaggg gaaggggagg aggaatgcag aaccccccgct ccagcccag ggatgtgtg      1080 ttcctgagaa atggaagtca gaatctcatc cctcactccc tggtccacag cctcggaatc    1140
cgtgtatgtg gtctccctgc agtccatgaa ctctcagggc cggagccaac cagtctacag    1200
ggctgcccta acaaagcgaa agatttcaga cagtacaccg tgcgctatcg agagaagggg    1260
```

```
gaattggcca ggtgggatta taagcagatc gctaacaggc gtgtgctgat tgagaacctg    1320
attccagaca ctgtgtatga atttgcagtc cgtatttcac agggtgaaag agatggcaaa    1380
tggagtacgt cagtcttcca aagaacacca gaatctgccc ctaccacagc tcctgaaaac    1440
ttgaacgtct ggccagtcaa tggcaaacct acagttgtcg ctgcatcttg ggatgcgcta    1500
ccagagactg aggggaaagt gaaagaatac attctttcat acgccccggc tctcaaacca    1560
tttggagcaa agtccctcac ctatcctgga gacactactt ctgccctggt ggatggtctg    1620
cagcctgggg aacgctatct tttcaaaatc cgggccacaa acaggagagg cctgggacct    1680
cactccaaag ccttcattgt cgctatgcca acaagcaatt cttaaaatc tgttgcagcc     1740 agtaaggcgg atgttcagca gaacacggag acaatggga aacccgaaaa acctgagcct    1800
tcctcacctt ctcccagagc tccagcttcc tcccaacacc cctctgtgcc tgcttctccc    1860
caagggagaa atgccaagga ccttcttctt gacttgaaga caaaatatt ggctaatggt     1920 ggggcgcccc gaaaacccca gcttcgcgcc aagaaggcag aggagctgga tcttcagtcg    1980
acagaaatca ctggggagga ggagctgggt tcccgggagg actcgcccat gtcaccctca    2040
gacacccaag accagaaacg gaccctgagg ccgccaagta gacacggcca ctcggtggtt    2100
gctcccggca ggactgcagt gagggcccgg atgccagcgc tgccccgaag ggaaggcgta    2160
gataagcctg gcttttccct ggccacgcag ccccgcccag gggcgccccc ctcggcttcg    2220
gcctctcctg cccaccacgc gtccacccag ggcacctctc atcgtccttc cctgcctgcc    2280
agcttgaatg acaacgactt ggtggactca gacgaagatg agcgcgctgt gggctccctc    2340 cacccccaagg gcgccttcgc ccagccccgg ccagccctgt cccccagccg ccagtccccg    2400
tccagcgttc tccgcgacag aagtctctgtg caccccggcg caaagccagc ctcgccggcg    2460
cggaggaccc cccattcagg ggccgcagag aagattcca gtgcctcagc cccaccctca     2520
agactttctc caccccatgg gggatcatct cggctgctgc ccaccagcc acacctgagc     2580 tctccacttt ccaagggcgg gaaggatggt gaggacgccc cagccaccaa ctccaatgcg    2640
ccatcacggt ccaccatgtc ctcctccgtc tcttctcatc tctcgtccag gacgcaggtc    2700
tctgagggag cggaggcttc tgatggtgaa agccacggtg acggcgatag ggaagacggc    2760
ggaaggcagg cggaggccac ggcccagacg ctgcgggccc ggcctgcctc tggacacttc    2820
catttgctca gacacaaacc ctttgctgcc aacgggaggc tccaagcag gttcagcatt     2880 gggcggggac ctcggctgca gccctccagc tccccacagt cgactgtgcc ctcccgagcc    2940 cacccccaggg ttccctctca ctctgattcc caccctaagc ttagctcagg tatccatgga   3000
gacgaggagg atgagaagcc gcttcctgcc accgttgtca atgaccacgt gccttcctcc    3060
tccaggcagc ccatctcccg gggctgggag gacttaagga gaagcccgca gagagggcc    3120 agcctgcatc ggaaggaacc catcccagag aaccccaaat ccacaggggc agatacacat    3180
cctcagggca gtactcctc cctggcctcc aaggctcagg atgttcaaca gagcacagac     3240
gcggacacgg agggtcattc tcccaaagca cagccagggt ccacagaccg ccacgcgtcc    3300
cctgctcgtc ctcccgcagc acggtcacag cagcatccca gtgttcccag aaggatgaca    3360
cccggccggg ccccagaaca gcagcccct cctcccgtcg ccacgtccca gcaccacccg    3420
ggaccccaga gcagagacgc gggtcggtca ccttcccagc ccaggctctc actgacccag    3480
gccgggcggc cccgcccac gtcgcagggc cgctcccact cctcctcgga cccttacacg    3540
gcgagctcca gagggatgct ccccacggcc ctccagaacc aggacgagga tgcccagggc    3600
agctacgacg acgacagcac agaagtcgag gcccaggatg tgcgggcccc cgcgcacgcc    3660
```

```
gcgcgcgcca aggaggcagc tgcgtcccct cccaagcacc agcaggtgga gtctcccaca    3720
ggcgcagggg caggtggcga ccacaggtcc cagcgcggac atgcggcctc ccccgccagg    3780
cccagccgac ccggcggccc ccagtcccgc gcccgggtcc ccagcagggc agcgccgggg    3840
aagtcggagc ctccttccaa gcggcccctg tcctccaagt cccagcagtc ggtctcagcc    3900
gaggacgagg aggaggagga cgcggggttt tttaaaggcg ggaaagaaga ccttctgtct    3960
tcctctgtgc caaagtggcc ctcttcctcc actcccaggg gcggcaaaga cgccgatggg    4020
agcctcgcca aggaagagag ggagcctgcc atcgcgcttg cccctcgcgg agggagcctg    4080
gctcctgtga agcgacctct ccccccaccct ccaggcagct cccccagggc ctcccacgtc    4140
ccttcccgac cgccgcctcg cagcgctgcc accgtgagcc ccgtcgcggg cacccacccc    4200
tggccgcagt acaccacgcg cgccccacct ggcgacttct ccaccacccc gatgctgtcc    4260
ttgcgccaga ggatgatgca tgccagattc cgtaaccctc tctcccgaca gcctgccaga    4320
ccctcttaca gacaaggtta taatggcaga ccaaatgtag aagggaaagt ccttcctggt    4380
agtaatggaa aaccgaatgg acagagaatt atcaatggcc ctcaaggaac aaagtgggtt    4440
gtggaccttg atcgtgggtt agtattgaat gcagaaggaa ggtacctcca agattccacat    4500 ggaaatcctc ttcggattaa actaggagga gatggtcgaa ccattgtaga tctggaaggg    4560 accccgtgg tgagtcctga cggcctccca ctctttgggc aggggcgaca tggcacacct    4620
ctggccaatg cccaagataa gccaattttg agtcttggag gaaagccgct ggtgggcttg    4680
gaggtcatca aaaaaccac ccatcccccct accactacca tgcagcccac cactactacg    4740
acgcccctgc ctaccactac aaccccgagg cccaccactg ccaccacccg ccgcacgacc    4800
accaggcgtc caacaaccac agtccgaacc actacgcgga caaccaccac caccaccccc    4860
aaacccacca ctcccatccc cacctgtccc cctgggacct tggaacggca cgacgatgat    4920
ggcaacctga taatgagctc caatgggatc ccagagtgct acgctgaaga agatgagttc    4980
tcaggcttgg agactgacac tgcagtacct acggaagagg cctacgttat atatgatgaa    5040
gattatgaat ttgagacgtc aaggccacca accaccactg agccttcgac cactgctacc    5100
acaccgaggg tgatcccaga ggaaggcgcc atcagttcct ttcctgaaga agaatttgat    5160
ctggctggaa ggaaacgatt tgttgctcct tacgtgacgt acctaaataa agacccatca    5220
gccccgtgct ctctgactga tgcactggat cacttccaag tggacagcct ggatgaaatc    5280
atccccaatg acctgaagaa gagtgatctg cctccccagc atgctccccg caacatcacc    5340
gtggtggccg tggaaggttg ccactcattt gtcattgtgg actgggacaa agccaccaca    5400
ggagatgtgg tcacaggtta cttggtttac agtgcatcct atgaagactt catcaggaac    5460
aagtggtcca ctcaagcttc atcagtaact cacttgccca ttgagaacct aaagcccaac    5520
acgaggtatt attttaaagt gcaagcacaa aatcctcatg gctacggacc tatcagccct    5580
tcggtctcat ttgtcaccga atcagataat cctctgcttg ttgtgaggcc cccaggcggt    5640
gagcctatct ggatcccatt cgctttcaaa catgatccca gctacacgga ctgccatgga    5700
cggcaatatg tgaagcgcac gtggtatcga aagttcgtgg gagttgttct ttgtaattca    5760
ctgaggtata aaatctacct cagtgacaac ctgaaagata cattctacag cattggagac    5820
agctggggaa gaggtgaaga ccattgccaa tttgtggatt cacaccttga tggaagaaca    5880
gggcctcagt cctatgtaga agccctccct actattcaag gctactatcg ccagtatcgt    5940
caggagcctg tcaggtttgg gaacatcggc ttcggaaccc cctactacta tgtgggctgg    6000
tacgagtgtg gggtctccat ccctggaaag tggtaatcac aggaccgtca tgctgcaagc    6060
```

-continued

```
ttgccctgcc cagccccacc aactaagtcg cactaggggc tgtgagcaaa gacagccagc      6120
atgctcagcc ccgctgccct aggtgccagg aaggtcacag atggacactg gccattctgg      6180
tcatctcagt ctggaactca gtcccacttc ttggcctgga caatgaacag gattcagttt      6240
tgctgttaac tttgcttctc tacttttttt tgtttgtttg taatagcaca tcccagagac      6300
atcagaaacc agcaactgat tcagtgtgat ttccagactt tttaggcatg aaattcggac      6360
acttcagtat ttccaggaat agcatatgca cgctgttctt gcttcatgga atgctacatg      6420
ctttctgttt ttctcatttt ggatttctcc aaaactaact gaatttaagc ttcaggtccc      6480
tttgtatgca gtagaaagga attattaaaa acaccaccaa agaaaataaa tatatcctac      6540
ttgaaattta ctctatggac ttacccactg ctagaataaa tgtatcaaat cttatttgta      6600
aattctcaat tttgatatat atatgtatat atgcatatac atatccacac ttgtctgcaa      6660
gaatattgat taaaattgct aaatttgtac ttgttcacca ggaaaaaaaa aaaaaaaaa       6720 aaaaggggc ggccrttccc tttaggaggg ttaattttag cgg                         6763
```

<210> SEQ ID NO 56
<211> LENGTH: 2011
<212> TYPE: PRT
<213> ORGANISM: Homo sapiens

<400> SEQUENCE: 56

```
Met Val Leu Thr Pro Ser Glu Glu Gln Ser Gly Pro Trp Glu Leu Cys
 1               5                  10                  15

Gln Leu Leu Cys Lys Arg Gly Thr Cys Thr Ser Cys Gln Gly Val Leu
            20                  25                  30

Val Leu Pro Thr Thr Ser Phe Ala Ser Val Ile Trp Glu Ala Pro Arg
        35                  40                  45

Gly Pro Ser Pro Gly Glu Gly Val Met Leu Val Pro His Met Ala Thr
    50                  55                  60

Gly Asp Thr Asn Ser Ala Thr Thr Met Ser Phe Ser Thr Arg Ala Ala
65                  70                  75                  80

Thr Glu Arg Ala Arg Ala Thr Asp Pro Thr Asp Gly Val Arg Ile Leu
                85                  90                  95

Ala Ser Ala Ser Cys Cys Leu Val Leu Arg Cys Ser Leu Ser Leu Ser
            100                 105                 110

Glu Pro His Phe Phe Gly Gln Gln Met Gly Cys Asp Trp Val Pro Ser
        115                 120                 125

Arg Met Ala Ala Lys Leu Val Ser Thr Val Ile Met Glu Ala Gly Ala
    130                 135                 140

Gly Asp Gly Gly Ala Ala Ala Trp Gly Lys Val Thr Gly Ile Glu Ile
145                 150                 155                 160

Arg Thr Ile Phe Val Lys Leu Val Val Ser Ala Val Gly Cys Gln Ile
                165                 170                 175

Gly Gln Trp Asp Lys Pro Asp Lys Leu Arg Leu Phe Lys Ala Val Asp
            180                 185                 190

Gly Val Lys Pro His Ile Leu Leu Gly Lys Lys Glu Val Pro Asn Lys
        195                 200                 205

Pro Leu Arg Val Arg Val Arg Ser Ser Asp Asp Arg Leu Ser Val Ala
    210                 215                 220

Trp Lys Ala Pro Arg Leu Ser Gly Ala Lys Ser Pro Arg Arg Ser Arg
225                 230                 235                 240

Gly Phe Leu Leu Gly Tyr Gly Ser Gly Arg Lys Met Asn Tyr Val
                245                 250                 255
```

-continued

Pro Leu Thr Arg Asp Glu Arg Thr His Glu Ile Lys Lys Leu Glu His
            260                 265                 270

Leu Leu Gly Arg Lys Pro Gly Glu Pro Thr Leu Leu Gly Ala Leu Arg
            275                 280                 285

Ala Pro Asn Ser Glu Glu Gly Thr Ala Met His Phe Gly Ala Trp Ile
            290                 295                 300

Ser Ser Ser Val Leu Phe Ser Thr Ser Glu Ala Ser Pro Leu Gly Pro
305                 310                 315                 320

Val Leu Gly Leu Ala Leu His Ser Pro Gln Glu Val Gly Ile Pro Pro
            325                 330                 335

Glu Arg Gly Asn Gly Lys Arg Gly Arg Gly Gly Met Gln Asn Pro
            340                 345                 350

Arg Ser Ser Pro Arg Gly Cys Val Phe Leu Arg Asn Gly Ser Gln Asn
            355                 360                 365

Leu Ile Pro His Ser Leu Val His Ser Leu Gly Ile Arg Val Cys Gly
            370                 375                 380

Leu Pro Ala Val His Glu Leu Ser Gly Pro Glu Pro Thr Ser Leu Gln
385                 390                 395                 400

Gly Cys Pro Asn Lys Ala Lys Asp Phe Arg Gln Tyr Thr Val Arg Tyr
            405                 410                 415

Arg Glu Lys Gly Glu Leu Ala Arg Trp Asp Tyr Lys Gln Ile Ala Asn
            420                 425                 430

Arg Arg Val Leu Ile Glu Asn Leu Ile Pro Asp Thr Val Tyr Glu Phe
            435                 440                 445

Ala Val Arg Ile Ser Gln Gly Glu Arg Asp Gly Lys Trp Ser Thr Ser
            450                 455                 460

Val Phe Gln Arg Thr Pro Glu Ser Ala Pro Thr Thr Ala Pro Glu Asn
465                 470                 475                 480

Leu Asn Val Trp Pro Val Asn Gly Lys Pro Thr Val Val Ala Ala Ser
            485                 490                 495

Trp Asp Ala Leu Pro Glu Thr Glu Gly Lys Val Lys Glu Tyr Ile Leu
            500                 505                 510

Ser Tyr Ala Pro Ala Leu Lys Pro Phe Gly Ala Lys Ser Leu Thr Tyr
            515                 520                 525

Pro Gly Asp Thr Thr Ser Ala Leu Val Asp Gly Leu Gln Pro Gly Glu
            530                 535                 540

Arg Tyr Leu Phe Lys Ile Arg Ala Thr Asn Arg Arg Gly Leu Gly Pro
545                 550                 555                 560

His Ser Lys Ala Phe Ile Val Ala Met Pro Thr Ser Asn Ser Leu Lys
            565                 570                 575

Ser Val Ala Ala Ser Lys Ala Asp Val Gln Gln Asn Thr Glu Asp Asn
            580                 585                 590

Gly Lys Pro Glu Lys Pro Glu Pro Ser Ser Pro Ser Pro Arg Ala Pro
            595                 600                 605

Ala Ser Ser Gln His Pro Ser Val Pro Ala Ser Pro Gln Gly Arg Asn
            610                 615                 620

Ala Lys Asp Leu Leu Asp Leu Lys Asn Lys Ile Leu Ala Asn Gly
625                 630                 635                 640

Gly Ala Pro Arg Lys Pro Gln Leu Arg Ala Lys Ala Glu Glu Leu
            645                 650                 655

Asp Leu Gln Ser Thr Glu Ile Thr Gly Glu Glu Leu Gly Ser Arg
            660                 665                 670

Glu Asp Ser Pro Met Ser Pro Ser Asp Thr Gln Asp Gln Lys Arg Thr
            675                 680                 685

-continued

Leu Arg Pro Pro Ser Arg His Gly His Ser Val Ala Pro Gly Arg
690                 695                 700

Thr Ala Val Arg Ala Arg Met Pro Ala Leu Pro Arg Arg Glu Gly Val
705                 710                 715                 720

Asp Lys Pro Gly Phe Ser Leu Ala Thr Gln Pro Arg Pro Gly Ala Pro
            725                 730                 735

Pro Ser Ala Ser Ala Ser Pro Ala His His Ala Ser Thr Gln Gly Thr
            740                 745                 750

Ser His Arg Pro Ser Leu Pro Ala Ser Leu Asn Asp Asn Asp Leu Val
            755                 760                 765

Asp Ser Asp Glu Asp Glu Arg Ala Val Gly Ser Leu His Pro Lys Gly
770                 775                 780

Ala Phe Ala Gln Pro Arg Pro Ala Leu Ser Pro Ser Arg Gln Ser Pro
785                 790                 795                 800

Ser Ser Val Leu Arg Asp Arg Ser Ser Val His Pro Gly Ala Lys Pro
                805                 810                 815

Ala Ser Pro Ala Arg Arg Thr Pro His Ser Gly Ala Ala Glu Glu Asp
            820                 825                 830

Ser Ser Ala Ser Ala Pro Pro Ser Arg Leu Ser Pro His Gly Gly
            835                 840                 845

Ser Ser Arg Leu Leu Pro Thr Gln Pro His Leu Ser Ser Pro Leu Ser
850                 855                 860

Lys Gly Gly Lys Asp Gly Glu Asp Ala Pro Ala Thr Asn Ser Asn Ala
865                 870                 875                 880

Pro Ser Arg Ser Thr Met Ser Ser Ser Val Ser Ser His Leu Ser Ser
                885                 890                 895

Arg Thr Gln Val Ser Glu Gly Ala Glu Ala Ser Asp Gly Glu Ser His
            900                 905                 910

Gly Asp Gly Asp Arg Glu Asp Gly Gly Arg Gln Ala Glu Ala Thr Ala
            915                 920                 925

Gln Thr Leu Arg Ala Arg Pro Ala Ser Gly His Phe His Leu Leu Arg
930                 935                 940

His Lys Pro Phe Ala Ala Asn Gly Arg Ser Pro Ser Arg Phe Ser Ile
945                 950                 955                 960

Gly Arg Gly Pro Arg Leu Gln Pro Ser Ser Pro Gln Ser Thr Val
                965                 970                 975

Pro Ser Arg Ala His Pro Arg Val Pro Ser His Ser Asp Ser His Pro
            980                 985                 990

Lys Leu Ser Ser Gly Ile His Gly Asp Glu Glu Asp Glu Lys Pro Leu
            995                 1000                1005

Pro Ala Thr Val Val Asn Asp His Val Pro Ser Ser Arg Gln Pro
    1010                1015                1020

Ile Ser Arg Gly Trp Glu Asp Leu Arg Arg Ser Pro Gln Arg Gly Ala
1025                1030                1035                1040

Ser Leu His Arg Lys Glu Pro Ile Pro Glu Asn Pro Lys Ser Thr Gly
            1045                1050                1055

Ala Asp Thr His Pro Gln Gly Lys Tyr Ser Ser Leu Ala Ser Lys Ala
            1060                1065                1070

Gln Asp Val Gln Gln Ser Thr Asp Ala Asp Thr Glu Gly His Ser Pro
            1075                1080                1085

Lys Ala Gln Pro Gly Ser Thr Asp Arg His Ala Ser Pro Ala Arg Pro
    1090                1095                1100

Pro Ala Ala Arg Ser Gln Gln His Pro Ser Val Pro Arg Arg Met Thr

```
            1105                1110                1115                1120
Pro Gly Arg Ala Pro Glu Gln Gln Pro Pro Pro Val Ala Thr Ser
                1125                1130                1135
Gln His His Pro Gly Pro Gln Ser Arg Asp Ala Gly Arg Ser Pro Ser
                1140                1145                1150
Gln Pro Arg Leu Ser Leu Thr Gln Ala Gly Arg Pro Arg Pro Thr Ser
                1155                1160                1165
Gln Gly Arg Ser His Ser Ser Ser Asp Pro Tyr Thr Ala Ser Ser Arg
                1170                1175                1180
Gly Met Leu Pro Thr Ala Leu Gln Asn Gln Asp Glu Asp Ala Gln Gly
1185                1190                1195                1200
Ser Tyr Asp Asp Asp Ser Thr Glu Val Glu Ala Gln Asp Val Arg Ala
                1205                1210                1215
Pro Ala His Ala Ala Arg Ala Lys Glu Ala Ala Ser Leu Pro Lys
                1220                1225                1230
His Gln Gln Val Glu Ser Pro Thr Gly Ala Gly Ala Gly Gly Asp His
                1235                1240                1245
Arg Ser Gln Arg Gly His Ala Ala Ser Pro Ala Arg Pro Ser Arg Pro
                1250                1255                1260
Gly Gly Pro Gln Ser Arg Ala Arg Val Pro Ser Arg Ala Ala Pro Gly
1265                1270                1275                1280
Lys Ser Glu Pro Pro Ser Lys Arg Pro Leu Ser Ser Lys Ser Gln Gln
                1285                1290                1295
Ser Val Ser Ala Glu Asp Glu Glu Glu Asp Ala Gly Phe Phe Lys
                1300                1305                1310
Gly Gly Lys Glu Asp Leu Leu Ser Ser Ser Val Pro Lys Trp Pro Ser
                1315                1320                1325
Ser Ser Thr Pro Arg Gly Gly Lys Asp Ala Asp Gly Ser Leu Ala Lys
                1330                1335                1340
Glu Glu Arg Glu Pro Ala Ile Ala Leu Ala Pro Arg Gly Gly Ser Leu
1345                1350                1355                1360
Ala Pro Val Lys Arg Pro Leu Pro Pro Pro Gly Ser Ser Pro Arg
                1365                1370                1375
Ala Ser His Val Pro Ser Arg Pro Pro Arg Ser Ala Ala Thr Val
                1380                1385                1390
Ser Pro Val Ala Gly Thr His Pro Trp Pro Gln Tyr Thr Thr Arg Ala
                1395                1400                1405
Pro Pro Gly Asp Phe Ser Thr Thr Pro Met Leu Ser Leu Arg Gln Arg
                1410                1415                1420
Met Met His Ala Arg Phe Arg Asn Pro Leu Ser Arg Gln Pro Ala Arg
1425                1430                1435                1440
Pro Ser Tyr Arg Gln Gly Tyr Asn Gly Arg Pro Asn Val Glu Gly Lys
                1445                1450                1455
Val Leu Pro Gly Ser Asn Gly Lys Pro Asn Gly Gln Arg Ile Ile Asn
                1460                1465                1470
Gly Pro Gln Gly Thr Lys Trp Val Val Asp Leu Asp Arg Gly Leu Val
                1475                1480                1485
Leu Asn Ala Glu Gly Arg Tyr Leu Gln Asp Ser His Gly Asn Pro Leu
                1490                1495                1500
Arg Ile Lys Leu Gly Gly Asp Gly Arg Thr Ile Val Asp Leu Glu Gly
1505                1510                1515                1520
Thr Pro Val Val Ser Pro Asp Gly Leu Pro Leu Phe Gly Gln Gly Arg
                1525                1530                1535
```

His Gly Thr Pro Leu Ala Asn Ala Gln Asp Lys Pro Ile Leu Ser Leu
            1540                1545                1550

Gly Gly Lys Pro Leu Val Gly Leu Glu Val Ile Lys Lys Thr Thr His
        1555                1560                1565

Pro Pro Thr Thr Thr Met Gln Pro Thr Thr Thr Thr Thr Pro Leu Pro
    1570                1575                1580

Thr Thr Thr Thr Pro Arg Pro Thr Thr Ala Thr Thr Arg Arg Thr Thr
1585                1590                1595                1600

Thr Arg Arg Pro Thr Thr Thr Val Arg Thr Thr Thr Arg Thr Thr Thr
                1605                1610                1615

Thr Thr Thr Pro Lys Pro Thr Thr Pro Ile Pro Thr Cys Pro Pro Gly
            1620                1625                1630

Thr Leu Glu Arg His Asp Asp Gly Asn Leu Ile Met Ser Ser Asn
            1635                1640                1645

Gly Ile Pro Glu Cys Tyr Ala Glu Glu Asp Glu Phe Ser Gly Leu Glu
        1650                1655                1660

Thr Asp Thr Ala Val Pro Thr Glu Glu Ala Tyr Val Ile Tyr Asp Glu
1665                1670                1675                1680

Asp Tyr Glu Phe Glu Thr Ser Arg Pro Pro Thr Thr Thr Glu Pro Ser
                1685                1690                1695

Thr Thr Ala Thr Thr Pro Arg Val Ile Pro Glu Glu Gly Ala Ile Ser
            1700                1705                1710

Ser Phe Pro Glu Glu Glu Phe Asp Leu Ala Gly Arg Lys Arg Phe Val
            1715                1720                1725

Ala Pro Tyr Val Thr Tyr Leu Asn Lys Asp Pro Ser Ala Pro Cys Ser
            1730                1735                1740

Leu Thr Asp Ala Leu Asp His Phe Gln Val Asp Ser Leu Asp Glu Ile
1745                1750                1755                1760

Ile Pro Asn Asp Leu Lys Lys Ser Asp Leu Pro Pro Gln His Ala Pro
                1765                1770                1775

Arg Asn Ile Thr Val Val Ala Val Glu Gly Cys His Ser Phe Val Ile
            1780                1785                1790

Val Asp Trp Asp Lys Ala Thr Pro Gly Asp Val Val Thr Gly Tyr Leu
            1795                1800                1805

Val Tyr Ser Ala Ser Tyr Glu Asp Phe Ile Arg Asn Lys Trp Ser Thr
        1810                1815                1820

Gln Ala Ser Ser Val Thr His Leu Pro Ile Glu Asn Leu Lys Pro Asn
1825                1830                1835                1840

Thr Arg Tyr Tyr Phe Lys Val Gln Ala Gln Asn Pro His Gly Tyr Gly
                1845                1850                1855

Pro Ile Ser Pro Ser Val Ser Phe Val Thr Glu Ser Asp Asn Pro Leu
            1860                1865                1870

Leu Val Val Arg Pro Pro Gly Gly Glu Pro Ile Trp Ile Pro Phe Ala
            1875                1880                1885

Phe Lys His Asp Pro Ser Tyr Thr Asp Cys His Gly Arg Gln Tyr Val
        1890                1895                1900

Lys Arg Thr Trp Tyr Arg Lys Phe Val Gly Val Val Leu Cys Asn Ser
1905                1910                1915                1920

Leu Arg Tyr Lys Ile Tyr Leu Ser Asp Asn Leu Lys Asp Thr Phe Tyr
                1925                1930                1935

Ser Ile Gly Asp Ser Trp Gly Arg Gly Glu Asp His Cys Gln Phe Val
            1940                1945                1950

Asp Ser His Leu Asp Gly Arg Thr Gly Pro Gln Ser Tyr Val Glu Ala
            1955                1960                1965

```
Leu Pro Thr Ile Gln Gly Tyr Tyr Arg Gln Tyr Arg Gln Glu Pro Val
        1970                1975                1980

Arg Phe Gly Asn Ile Gly Phe Gly Thr Pro Tyr Tyr Tyr Val Gly Trp
1985                1990                1995                2000

Tyr Glu Cys Gly Val Ser Ile Pro Gly Lys Trp
                2005                2010
```

```
<210> SEQ ID NO 57
<211> LENGTH: 1441
<212> TYPE: DNA
<213> ORGANISM: Homo sapiens

<400> SEQUENCE: 57
gtcgacccac gcgtccgccc ttacatcctc ctaggacccg gtcggtagtc gtcgcccag       60
cccgccgggg gcgcagcgcc cgagccgcgg ccctcgagac gggaccgaga gcatcatggg      120
cagcactgtc ccgcgctccg cctccgtgct gcttctgctg ctgctcctgc gccgggccga      180
gcagccctgc ggggccgagc tcaccttcga gctgccggac aacgccaagc agtgcttcca      240
cgaggaggtg gagcagggcg tgaagttctc cctggattac caggtcatca ctggaggcca      300
ctacgatgtt gactgctatg tagaggaccc ccaggggaac accatctaca gagaaacgaa      360
gaagcagtac gacagcttca cgtaccgggc tgaagtcaag ggcgtttatc agttttgctt      420
cagtaatgag ttttccacct tctctcacaa gaccgtctac tttgactttc aagtgggcga      480
tgagcctccc attctcccag acatggggaa cagggtcaca gctctcaccc agatggagtc      540
cgcctgcgtg accatccatg aggctctgaa acggtgatt gactcccaga cgcattaccg       600
gctgcgggag gcccaggacc gggcccgagc ggaagacctt aatagccgag tctcttactg      660
gtctgttggc gagacgattg ccctgttcgt ggtcagcttc agtcaggtgc tactgttgaa      720
aagcttcttc acagaaaaac gacccatcag cagggcagtc cactcctagc cccggcatcc      780
tgctctaggg cccctcatgc cccaggctgg agcagctctc ctaggtcaca gcctgctggg      840
ctgggtcgcg tagcccaggg tggaggcaga acgatgctgc tgtggtagcc ctttgccttt      900
catgcccatg cttgattctt gcacctcagc agctgaaggt ctcagagacc agtaatcaga      960
aggcatccga ctgcattaag tgtgcagcgc tgaaaagaca tttacaacta ggccagggat     1020
tagccactgt ggggagggtgg acaggcaatg gttcagtggc ctggctgttg caggaactc      1080
caagtgccca ggcctcttgg gcagcttagg gccctgcctc tgtttcatga tgcatgggtc     1140
atttgtcttg ggtgtcctat cccatatgga gaagaaaggg gctctaagtt ctggctcttc     1200
tttctttggg gttctctgta cctgaggaaa ccaggccctg ggtgactttg cagatctgct     1260
caccctcggt gagcaacagt gtcagccatg caagcaggac agaatggtga ctgggtgccc     1320
ttggtgagct gtgtatttcc tagaagtaga aaactgtggg aaactgtggc taataaaaac     1380
taagtgtgag cgtcaaaaaa aaaaaaaaaa aaaaaaaaaa aaaaaaaaaa agggcggccg     1440
c                                                                     1441

<210> SEQ ID NO 58
<211> LENGTH: 217
<212> TYPE: PRT
<213> ORGANISM: Homo sapiens

<400> SEQUENCE: 58

Met Gly Ser Thr Val Pro Arg Ser Ala Ser Val Leu Leu Leu Leu Leu
1               5                   10                  15

Leu Leu Arg Arg Ala Glu Gln Pro Cys Gly Ala Glu Leu Thr Phe Glu
```

```
                20                  25                  30
Leu Pro Asp Asn Ala Lys Gln Cys Phe His Glu Glu Val Glu Gln Gly
         35                  40                  45

Val Lys Phe Ser Leu Asp Tyr Gln Val Ile Thr Gly Gly His Tyr Asp
 50                  55                  60

Val Asp Cys Tyr Val Glu Asp Pro Gln Gly Asn Thr Ile Tyr Arg Glu
 65                  70                  75                  80

Thr Lys Lys Gln Tyr Asp Ser Phe Thr Tyr Arg Ala Glu Val Lys Gly
                 85                  90                  95

Val Tyr Gln Phe Cys Phe Ser Asn Glu Phe Ser Thr Phe Ser His Lys
            100                 105                 110

Thr Val Tyr Phe Asp Phe Gln Val Gly Asp Glu Pro Pro Ile Leu Pro
        115                 120                 125

Asp Met Gly Asn Arg Val Thr Ala Leu Thr Gln Met Glu Ser Ala Cys
    130                 135                 140

Val Thr Ile His Glu Ala Leu Lys Thr Val Ile Asp Ser Gln Thr His
145                 150                 155                 160

Tyr Arg Leu Arg Glu Ala Gln Asp Arg Ala Arg Ala Glu Asp Leu Asn
                165                 170                 175

Ser Arg Val Ser Tyr Trp Ser Val Gly Glu Thr Ile Ala Leu Phe Val
            180                 185                 190

Val Ser Phe Ser Gln Val Leu Leu Leu Lys Ser Phe Phe Thr Glu Lys
        195                 200                 205

Arg Pro Ile Ser Arg Ala Val His Ser
    210                 215

<210> SEQ ID NO 59
<211> LENGTH: 2316
<212> TYPE: DNA
<213> ORGANISM: Homo sapiens

<400> SEQUENCE: 59
ccacgcgtcc ggtctccccc agcactgagg agctcgcctg ctgccctctt gcgcgcggga      60
agcagcacca agttcacggc caacgccttg cactagggt ccagaatggc tacaacagtc     120
cctgatggtt gccgcaatgg cctgaaatcc aagtactaca gactttgtga taaggctgaa     180 gcttgggca tcgtcctaga aacggtggcc acagccgggg ttgtgacctc ggtgccttc      240 atgctcactc tcccgatcct cgtctgcaag gtgcaggact ccaacaggcg aaaaatgctg     300
cctactcagt ttctcttcct cctgggtgtg ttgggcatct ttggcctcac cttcgccttc     360
atcatcggac tggacgggag cacagggccc acacgcttct tcctctttgg gatcctcttt     420
tccatctgct tctcctgcct gctggctcat gctgtcagtc tgaccaagct cgtccggggg     480
aggaagcccc tttccctgtt ggtgattctg ggtctggccg tgggcttcag cctagtccag     540
gatgttatcg ctattgaata tattgtcctg accatgaata ggaccaacgt caatgtcttt     600
tctgagcttt ccgctcctcg tcgcaatgaa gactttgtcc tcctgctcac ctacgtcctc     660
ttcttgatgg cgctgacctt cctcatgtcc tccttcacct tctgtggttc cttcacgggc     720
tggaagagac atggggccca catctacctc acgatgctcc tctccattgc catctgggtg     780
gcctggatca ccctgctcat gcttcctgac tttgaccgca ggtgggatga ccatcctc      840 agctccgcct ggctgccaa tggctgggtg ttcctgttgg cttatgttag tcccgagttt     900
tggctgctca caaagcaacg aaaccccatg gattatcctg ttgaggatgc tttctgtaaa     960
cctcaactcg tgaagaagag ctatggtgtg gagaacagag cctactctca agaggaaatc    1020
```

```
actcaaggtt ttgaagagac aggggacacg ctctatgccc cctattccac acattttcag    1080
ctgcagaacc agcctcccca aaaggaattc tccatcccac gggcccacgc ttggccgagc    1140
ccttacaaag actatgaagt aaagaaagag ggcagctaac tctgtcctga agagtgggac    1200
aaatgcagcc gggcggcaga tctagcggga gctcaagggg atgtgggcga aatctgagtc    1260
ttctgagaaa actgtacaag acactacggg aacagtttgc ctccctccca gcctcaacca    1320
caattcttcc atgctgggggc tgatgtgggc tagtaagact ccagttctta gaggcgctgt    1380 agtattttt ttttttttgtc tcatcctttg gatacttctt ttaagtggga gtctcaggca    1440
actcaagttt agaccttac tcttttttgtt tgttttttga acaggatct tgctctgtca      1500 cccaggcttg agtgcagtgg tgcgatcaca gcccagtgca gcctcgacca cctgtgctca    1560
agcaatcctc ccatctccat ctcccaaagt gctgggatga caggcgtgag ccacagctcc    1620
cagcctaggc ccttaatctt gctgttattt tccatggact aaaggtctgg tcatctgagc    1680
tcacgctggc tcacacagct ctaggggcct gctcctctaa ctcacagtgg gttttgtgag    1740
gctctgtggc ccagagcaga cctgcatatc tgagcaaaaa tagcaaaagc ctctctcagc    1800
ccactggcct gaatctacac tggaagccaa cttgctggca ccccgctcc ccaacccttc     1860 ttgcctgggt aggagaggct aaagatcacc ctaaatttac tcatctctct agtgctgcct    1920
cacattgggc tcagcagct ccccagcacc aattcacagg tcaccctct cttcttgcac      1980 tgtccccaaa cttgctgtca attccgagat ctaatctccc cctacgctct gccaggaatt    2040
ctttcagacc tcactagcac aagcccggtt gctccttgtc aggagaattt gtagatcatt    2100
ctcacttcaa attcctgggg ctgatacttc tctcatcttg caccccaacc tctgtaaata    2160
gatttaccgc atttacggct gcattctgta agtgggcatg gtctcctaat ggaggagtgt    2220
tcattgtata ataagttatt cacctgagta tgcaataaag atgtggtggc cactctttca    2280
tggtggtggc agcaaaaaaa aaaaaaaaaa aaaaaa                              2316
```

<210> SEQ ID NO 60
<211> LENGTH: 357
<212> TYPE: PRT
<213> ORGANISM: Homo sapiens

<400> SEQUENCE: 60

Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
    50                  55                  60

Leu Pro Thr Gln Phe Leu Phe Leu Gly Val Leu Gly Ile Phe Gly
65                  70                  75                  80

Leu Thr Phe Ala Phe Ile Ile Gly Leu Asp Gly Ser Thr Gly Pro Thr
            85                  90                  95

Arg Phe Phe Leu Phe Gly Ile Leu Phe Ser Ile Cys Phe Ser Cys Leu
        100                 105                 110

Leu Ala His Ala Val Ser Leu Thr Lys Leu Val Arg Gly Arg Lys Pro
    115                 120                 125

Leu Ser Leu Leu Val Ile Leu Gly Leu Ala Val Gly Phe Ser Leu Val
130                 135                 140

Gln Asp Val Ile Ala Ile Glu Tyr Ile Val Leu Thr Met Asn Arg Thr

```
                145                 150                 155                 160
Asn Val Asn Val Phe Ser Glu Leu Ser Ala Pro Arg Arg Asn Glu Asp
                    165                 170                 175
Phe Val Leu Leu Leu Thr Tyr Val Leu Phe Leu Met Ala Leu Thr Phe
                    180                 185                 190
Leu Met Ser Ser Phe Thr Phe Cys Gly Ser Phe Thr Gly Trp Lys Arg
                    195                 200                 205
His Gly Ala His Ile Tyr Leu Thr Met Leu Leu Ser Ile Ala Ile Trp
                    210                 215                 220
Val Ala Trp Ile Thr Leu Leu Met Leu Pro Asp Phe Asp Arg Arg Trp
225                 230                 235                 240
Asp Asp Thr Ile Leu Ser Ser Ala Leu Ala Ala Asn Gly Trp Val Phe
                    245                 250                 255
Leu Leu Ala Tyr Val Ser Pro Glu Phe Trp Leu Leu Thr Lys Gln Arg
                    260                 265                 270
Asn Pro Met Asp Tyr Pro Val Glu Asp Ala Phe Cys Lys Pro Gln Leu
                    275                 280                 285
Val Lys Lys Ser Tyr Gly Val Glu Asn Arg Ala Tyr Ser Gln Glu Glu
                    290                 295                 300
Ile Thr Gln Gly Phe Glu Glu Thr Gly Asp Thr Leu Tyr Ala Pro Tyr
305                 310                 315                 320
Ser Thr His Phe Gln Leu Gln Asn Gln Pro Pro Gln Lys Glu Phe Ser
                    325                 330                 335
Ile Pro Arg Ala His Ala Trp Pro Ser Pro Tyr Lys Asp Tyr Glu Val
                    340                 345                 350
Lys Lys Glu Gly Ser
                    355

<210> SEQ ID NO 61
<211> LENGTH: 4651
<212> TYPE: DNA
<213> ORGANISM: Homo sapiens
<220> FEATURE:
<221> NAME/KEY: misc_feature
<222> LOCATION: 2270, 3639, 3724, 4265, 4638, 4644, 4645, 4647, 4649,
      4650, 4651
<223> OTHER INFORMATION: n = A,T,C or G

<400> SEQUENCE: 61 tttttagtt ttacctagtt ttatttgtct atttgagtat tgtccttgaa tttaaaattt    60
ttttcagccc caactgatac acacacatat acatacataa cacatgtgtg tgtgtgtagc   120
ttacagagtg tttataggaa actgattttg tatactttgg ctactttgtt gtaagttcta   180
gttttttttc ttttattatt aaactagtgc acgacatcaa tgctatatga ttggtgtttc   240
gttgacctag aaataatgca tgccatcttc ttttcacagc tgtgtgccaa ccacgatgca   300
aacatggtga atgtatcggg ccaaacaagt gcaagtgtca tcctggttat gctgaaaaa    360 ccttctaact cgtgtgaaga cgagcacatc ccagctcctc ttgaccaagg cagtgaacag   420
cctcttttcc aaccccctgga tcaccaagcc acaagtttgc cttcaaggga tctaaatgag   480
tgtggcctga agccccggcc ctgtaagcac aggtgcatga acacttacgg cagctacaag   540
tgctactgtc tcaacggata tatgctcatg ccggatggtt cctgctcaag tgccctgacc   600
tgctccatgg caaactgtca gtatggctgt gatgttgtta aaggacaaat acggtgccag   660
tgcccatccc ctggcctgca cctggctcct gatgggagga cctgtgtaga tgttgatgaa   720
tgtgctacag gaagagcctc ctgccctaga tttaggcaat gtgtcaacac ttttgggagc   780
```

```
tacatctgca agtgtcataa aggcttcgat ctcatgcata ttggaggcaa atatcaatgt    840
catgacatag acgaatgctc acttggtcag tatcagtgca gcagctttgc tcgatgttat    900
aacgtacgtg ggtcctacaa gtgcaaatgt aagaaggat accagggtga tggactgact    960
tgtgtgtata tcccaaaagt tatgattgaa ccttcaggtc caattcatgt accaaaggga   1020
aatggtacca ttttaaaggg tgacacagga ataataatt ggattcctga tgttggaagt   1080
acttggtggc ctccgaagac accatatatt cctcctatca ttaccaacag gcctacttct   1140
aagccaacaa caagacctac accaaagcca acaccaattc ctactccacc accaccacca   1200
cccctgccaa cagagctcag aacacctcta ccacctacaa ccccagaaag gccaaccacc   1260
ggactgacaa ctatagcacc agctgccagt acacctccag gagggattac agttgacaac   1320
agggtacaga cagaccctca gaaacccaga ggagatgtgt tcattccacg gcaaccttca   1380
aatgacttgt ttgaaatatt tgaaatagaa agaggagtca gtgcagacga tgaagcaaag   1440
gatgatccag tgttctggt acacagttgt aattttgacc atggactttg tggatggatc   1500
agggagaaag acaatgactt gcactgggaa ccaatcaggg acccagcagg tggacaatat   1560
ctgacagtgt cggcagccaa agccccaggg ggaaaagctg cacgcttggt gctacctctc   1620
ggccgcctca tgcattcagg ggacctgtgc ctgtcattca ggcacaaggt gacggggctg   1680
cactctggca cactccaggt gtttgtgaga aaacacggtg cccacggagc agccctgtgg   1740
ggaagaaatg gtggccatgg ctggaggcaa acacagatca ccttgcgagg ggctgacatc   1800
aagagcgtcg tcttcaaagg tgaaaaaagg cgtggtcaca ctggggagat tggattagat   1860
gatgtgagct tgaaaaaagg ccactgctct gaagaacgct aacaactcca gaactaacaa   1920
tgaactccta tgttgctcta tcctcttttt ccaattctca tcttctctcc tcttctccct   1980
tttatcaggc ctaggagaag agtgggtcag tgggtcagaa ggaagtctat ttggtgaccc   2040
aggtttttct ggcctgcttt tgtgcaatcc caatgaacag tgataccctc cttgaaatac   2100
aggggcatcg cagacacatc aaagccatct gtgggtgttg ccttccatcc tgtgtctctt   2160
tcaggaaggc attcagcatg cgtgagccat accatcctcc atcctgatta caaggtgctc   2220
cttgtagcaa attatgagag tgagttacgg gagcagtttt taaaagaaan tctttkcara   2280
kggstwtraw gtwwtkkgty cggkgttgkm cccawgrgkr gkwttgrcct tcccttgrra   2340
wawrawrwac aawagkgctk gkgaaawwra mwatmcccty ttcmytttaa rwwarwtytg   2400
gccygmccys aamatytkwy ttttaygtgs crkctcmytt twttaaaawa arggtgtgta   2460
acatatcaag atacatttat ttttatctgt tttttttttt cctgttaaag acaattatgt   2520
agagtgggca cgtaatccct ccttagtagt attgtgtttt gtgtaaatgt gctattgata   2580
ttaagtattt acatgttcca aatatttaca gactctagtt gcaaggtaaa gggcagcttg   2640
tgatctcaaa aaaatacatg gtgaaatgtc atccagttcc atgaccttat attggcagca   2700
gtaggaaatt ggcagaagtg ttgggttgtg gtaacggagt gatgaatttt ttttaatgg   2760
ccttgagttt gatctctgca aaggatagga aacctttagg aagacaagaa actgcagtta   2820
atttagaact gtcactgttt caagttacac tttaaaacca cagctttac catcataaca   2880
tggctctggt aatatgtagg aagctttata aaagttttgg ttgattcaga aaaaggatcc   2940
tgttgcagag tgagaggaag cataggggga aactccattg aacagatttt tcacacaacg   3000
ttttaaattg atataagttt aggcagttgt agttcataac ttatgttgct catgttgtgc   3060
tgtgtcagga tgggatagga agcaagtccc atgcttagag gcatgggatg tgttggaacg   3120
ggatttacac acactggagg agcagggcaa gttggaattc taagatccat gaacccccaa   3180
```

```
ctgtatttcc tccctgcata ttttaccaat atattaaaaa acaatgtaac ttttaaaagg    3240
catcattcct gaggtttgtc ttaatttctg attaagtaat cagaatattt tctgctattt    3300
ttgccaggaa tcacaaagat gattaaaggg ttggaaaaaa agatctatga tggaaaatta    3360
aaggaactgg gattattgag cctggagaag agaagactga ggggcaaacc attgatggtt    3420
ttcaagtata tgaagggttg gcacagagag ggtggcgacc agctgttctc catatgccac    3480
taagaataga acaagaggaa actggcttag actagagtat aagggagcat tcttggcag    3540 gggccattgt tagaatactt cataaaaaaa gaagtgtgaa aatctcagta tctctctctc    3600
tttctaaaaa attagataaa aatttgtcta tttaagatng gttaaagatg ttcttaccca    3660
aggaaaagta acaaattata gaatttccca aaagatgttt tgatcctact agtagtatgc    3720
agtngaaaat ctttagaact aaataatttg gacaaggctt aatttaggca tttccctctt    3780
gacctcctaa tggagaggga ttgaaagggg aagagcccac caaatgctga gctcactgaa    3840
atatctctcc cttatggcaa tcctagcagt attaaagaaa aaaggaaact atttattcca    3900
aatgagagta tgatggacag atatttagt atctcagtaa tgtcctagtg tggcggtggt    3960
tttcaatgtt tcttcatggt aaaggtataa gcctttcatt tgttcaatgg atgatgtttc    4020 ggatttttt ttttaagag atccttcaag gaacacagtt cagagagatt ttcatcgggt    4080
gcattctctc tgcttcgtgt gtgacaagtt atccttggctg ctgagaaaga gtgccctgcc    4140
ccacaccggc agacctttcc ttcacctcat cagtatgatt cagtttctct tatcaattgg    4200
actctcccag gttccacaga acagtaatat tttttgaaca ataggtacaa tagaaggtct    4260
tctgntcatt taacctggta aaggcagggc tggagggga aaataaatca ttaagccttt    4320
gagtaacggc agaatatatg gctgtagatc cattttaat ggttcatttc ctttatggtc    4380
atataactgc acagctgaag atgaaagggg aaaataaatg aaaattttac ttttcgatgc    4440
caatgataca ttgcactaaa ctgatggaag aagttatcca aagtactgta taacatcttg    4500
tttattattt aatgttttct aaaataaaaa atgttagtgg ttttccaaat ggcctaataa    4560
aaacaattat ttgtaaataa aaacactgtt agtaataaaa aaaaaaaaa aaaaaaaaa    4620 aarrrrmmra ammmmaancc gccnntngnn n                                4651

<210> SEQ ID NO 62
<211> LENGTH: 560
<212> TYPE: PRT
<213> ORGANISM: Homo sapiens

<400> SEQUENCE: 62

Met Leu Tyr Asp Trp Cys Phe Val Asp Leu Glu Ile Met His Ala Ile
1               5                   10                  15

Phe Phe Ser Gln Leu Cys Ala Asn His Asp Ala Asn Met Val Asn Val
            20                  25                  30

Ser Gly Gln Thr Ser Ala Ser Val Ile Leu Val Met Leu Glu Lys Pro
        35                  40                  45

Ser Asn Ser Cys Glu Asp Glu His Ile Pro Ala Pro Leu Asp Gln Gly
    50                  55                  60

Ser Glu Gln Pro Leu Phe Gln Pro Leu Asp His Gln Ala Thr Ser Leu
65                  70                  75                  80

Pro Ser Arg Asp Leu Asn Glu Cys Gly Leu Lys Pro Arg Pro Cys Lys
                85                  90                  95

His Arg Cys Met Asn Thr Tyr Gly Ser Tyr Lys Cys Tyr Cys Leu Asn
            100                 105                 110

Gly Tyr Met Leu Met Pro Asp Gly Ser Cys Ser Ser Ala Leu Thr Cys
```

```
                    115                 120                 125
Ser Met Ala Asn Cys Gln Tyr Gly Cys Asp Val Val Lys Gly Gln Ile
130                 135                 140

Arg Cys Gln Cys Pro Ser Pro Gly Leu His Leu Ala Pro Asp Gly Arg
145                 150                 155                 160

Thr Cys Val Asp Val Asp Glu Cys Ala Thr Gly Arg Ala Ser Cys Pro
                165                 170                 175

Arg Phe Arg Gln Cys Val Asn Thr Phe Gly Ser Tyr Ile Cys Lys Cys
                180                 185                 190

His Lys Gly Phe Asp Leu Met His Ile Gly Gly Lys Tyr Gln Cys His
                195                 200                 205

Asp Ile Asp Glu Cys Ser Leu Gly Gln Tyr Gln Cys Ser Ser Phe Ala
210                 215                 220

Arg Cys Tyr Asn Val Arg Gly Ser Tyr Lys Cys Lys Cys Lys Glu Gly
225                 230                 235                 240

Tyr Gln Gly Asp Gly Leu Thr Cys Val Tyr Ile Pro Lys Val Met Ile
                245                 250                 255

Glu Pro Ser Gly Pro Ile His Val Pro Lys Gly Asn Gly Thr Ile Leu
                260                 265                 270

Lys Gly Asp Thr Gly Asn Asn Asn Trp Ile Pro Asp Val Gly Ser Thr
                275                 280                 285

Trp Trp Pro Pro Lys Thr Pro Tyr Ile Pro Pro Ile Ile Thr Asn Arg
                290                 295                 300

Pro Thr Ser Lys Pro Thr Thr Arg Pro Thr Pro Lys Pro Thr Pro Ile
305                 310                 315                 320

Pro Thr Pro Pro Pro Pro Pro Leu Pro Thr Glu Leu Arg Thr Pro
                325                 330                 335

Leu Pro Pro Thr Thr Pro Glu Arg Pro Thr Thr Gly Leu Thr Thr Ile
                340                 345                 350

Ala Pro Ala Ala Ser Thr Pro Pro Gly Gly Ile Thr Val Asp Asn Arg
                355                 360                 365

Val Gln Thr Asp Pro Gln Lys Pro Arg Gly Asp Val Phe Ile Pro Arg
370                 375                 380

Gln Pro Ser Asn Asp Leu Phe Glu Ile Phe Glu Ile Glu Arg Gly Val
385                 390                 395                 400

Ser Ala Asp Asp Glu Ala Lys Asp Asp Pro Gly Val Leu Val His Ser
                405                 410                 415

Cys Asn Phe Asp His Gly Leu Cys Gly Trp Ile Arg Glu Lys Asp Asn
                420                 425                 430

Asp Leu His Trp Glu Pro Ile Arg Asp Pro Ala Gly Gly Gln Tyr Leu
                435                 440                 445

Thr Val Ser Ala Ala Lys Ala Pro Gly Gly Lys Ala Ala Arg Leu Val
450                 455                 460

Leu Pro Leu Gly Arg Leu Met His Ser Gly Asp Leu Cys Leu Ser Phe
465                 470                 475                 480

Arg His Lys Val Thr Gly Leu His Ser Gly Thr Leu Gln Val Phe Val
                485                 490                 495

Arg Lys His Gly Ala His Gly Ala Ala Leu Trp Gly Arg Asn Gly Gly
                500                 505                 510

His Gly Trp Arg Gln Thr Gln Ile Thr Leu Arg Gly Ala Asp Ile Lys
                515                 520                 525

Ser Val Val Phe Lys Gly Glu Lys Arg Gly His Thr Gly Glu Ile
530                 535                 540
```

Gly Leu Asp Asp Val Ser Leu Lys Lys Gly His Cys Ser Glu Glu Arg
545                 550                 555                 560

<210> SEQ ID NO 63
<211> LENGTH: 4461
<212> TYPE: DNA
<213> ORGANISM: Homo sapiens

<400> SEQUENCE: 63

| | | | | | |
|---|---|---|---|---|---|
| cgaccccgcg | tccggggggca | ttgcgtggtg | gaaagttgcg | tgcggcagag | aaccgaaggt | 60 |
| gcagcgccac | agcccagggg | acggtgtgtc | tgggagaaga | cgctgcccct | gcgtcgggac | 120 |
| ccgccagcgc | gcgggcaccg | cggggcccgg | gacgacgccc | cctcctgcgg | cgtggactcc | 180 |
| gtcagtggcc | caccaagaag | gaggaggaat | atggaatcca | aggggccag | ttcctgccgt | 240 |
| ctgctcttct | gcctcttgat | ctccgccacc | gtcttcaggc | caggccttgg | atggtatact | 300 |
| gtaaattcag | catatggaga | taccattatc | ataccttgcc | gacttgacgt | acctcagaat | 360 |
| ctcatgtttg | gcaaatggaa | atatgaaaag | ccccgatggct | ccccagtatt | tattgccttc | 420 |
| agatcctcta | caaagaaaag | tgtgcagtac | gacgatgtac | cagaatacaa | agacagattg | 480 |
| aacctctcag | aaaactacac | tttgtctatc | agtaatgcaa | ggatcagtga | tgaaaagaga | 540 |
| tttgtgtgca | tgctagtaac | tgaggacaac | gtgtttgagg | cacctacaat | agtcaaggtg | 600 |
| ttcaagcaac | catctaaacc | tgaaattgta | agcaaagcac | tgtttctcga | aacagagcag | 660 |
| ctaaaaaagt | tgggtgactg | catttcagaa | gacagttatc | cagatggcaa | tatcacatgg | 720 |
| tacaggaatg | gaaaagtgct | acatcccctt | gaaggagcgg | tggtcataat | ttttaaaaag | 780 |
| gaaatggacc | cagtgactca | gctctatacc | atgacttcca | ccctggagta | caagacaacc | 840 |
| aaggctgaca | tacaaatgcc | attcacctgc | tcggtgacat | attatggacc | atctggccag | 900 |
| aaaacaattc | attctgaaca | ggcagtattt | gatatttact | atcctacaga | gcaggtgaca | 960 |
| atacaagtgc | tgccaccaaa | aaatgccatc | aagaagggg | ataacatcac | tcttaaatgc | 1020 |
| ttagggaatg | gcaaccctcc | cccagaggaa | tttttgtttt | acttaccagg | acagcccgaa | 1080 |
| ggaataagaa | gctcaaatac | ttacacactg | atggatgtga | ggcgcaatgc | aacaggagac | 1140 |
| tacaagtgtt | ccctgataga | caaaaaaagc | atgattgctt | caacagccat | cacagttcac | 1200 |
| tatttggatt | tgtccttaaa | cccaagtgga | gaagtgacta | gacagattgg | tgatgcccta | 1260 |
| cccgtgtcat | gcacaatatc | tgctagcagg | aatgcaactg | tggtatggat | gaaagataac | 1320 |
| atcaggcttc | gatctagccc | gtcatttttct | agtcttcatt | atcaggatgc | tggaaactat | 1380 |
| gtctgcgaaa | ctgctctgca | ggaggttgaa | ggactaaaga | aaagagagtc | attgactctc | 1440 |
| attgtagaag | gcaaacctca | aataaaaatg | acaaagaaaa | ctgatcccag | tggactatct | 1500 |
| aaaacaataa | tctgccatgt | ggaaggtttt | ccaaagccag | ccattcagtg | gacaattact | 1560 |
| ggcagtggaa | gcgtcataaa | ccaaacagag | gaatctcctt | atattaatgg | caggtattat | 1620 |
| agtaaaatta | tcatttcccc | tgaagagaat | gttacattaa | cttgcacagc | agaaaaccaa | 1680 |
| ctggagagaa | cagtaaactc | cttgaatgtc | tctgctataa | gtattccaga | acacgatgag | 1740 |
| gcagacgaga | taagtgatga | aaacagagaa | aaggtgaatg | accaggcaaa | actaattgtg | 1800 |
| ggaatcgttg | ttggtctcct | ccttgctgcc | cttgttgctg | gtgtcgtcta | ctggctgtac | 1860 |
| atgaagaagt | caaagactgc | atcaaaacat | gtaaacaagg | acctcggtaa | tatggaagaa | 1920 |
| aacaaaaagt | tagaagaaaa | caatcacaaa | actgaagcct | aagagagaaa | ctgtcctagt | 1980 |
| tgtccagaga | taaaaatcat | atagaccaat | tgaagcatga | acgtggattg | tatttaagac | 2040 |
| ataaacaaag | acattgacag | caattcatgg | ttcaagtatt | aagcagttca | ttctaccaag | 2100 |

```
ctgtcacagg ttttcagaga attatctcaa gtaaaacaaa tgaaatttaa ttacaaacaa    2160
taagaacaag ttttggcagc catgataata ggtcatatgt tgtgtttggt tcaattttt    2220
ttccgtaaat gtctgcactg aggatttctt tttggtttgc cttttatgta aattttttac    2280
gtagctattt ttatacactg taagctttgt tctgggagtt gctgttaatc tgatgtataa    2340
tgtaatgttt ttatttcaat tgtttatatg gataatctga gcaggtacat ttctgattct    2400
gattgctatc agcaatgccc caaactttct cataagcacc taaacccaa aggtggcagc    2460
ttgtgaagat tggggacact catattgccc taattaaaaa ctgtgatttt tatcacaagg    2520
gaggggaggc cgagagtcag actgatagac accataggag ccgactcttt gatatgccac    2580
cagcgaactc tcagaaataa atcacagatg catatagaca cacatacata atggtactcc    2640
caaactgaca attttaccta ttctgaaaaa gacataaaac agaatttggt agcacttacc    2700
tctacagaca cctgctaata aattatttc tgtcaaaaga aaaacacaa gcatgtgtga    2760
gagacagttt ggaaaaatca tggtcaacat tcccatttc atagatcaca atgtaaatca    2820
ctataattac aaattggtgt taaatccttt gggttatcca ctgccttaaa attatcccta    2880
tttcatgttt aaaagatat caatcagaat tggagttttt aacagtggtc attatcaaag    2940
ctgtgttatt ttccacagaa tatagaatat atatttttt cgtgtgtgtt tttgttaact    3000
accctacaga tattgaatgc accttgagat aatttagtgt ttttaactga tacataattt    3060
atcaagcagt acatgaaagt gtaataataa aatgtctatg tatctttagt tacattcaaa    3120
tttgtaactt tataaacatg ttttatgctt gaggaaattt ttaaggtggt agtataaatg    3180
gaaactttt gaagtagacc ggatatgggc tacttgtgac tagacttta aactttgctc    3240
tttcaagcag aagcctggtt tctgggagaa cactgcacag cgatttcttt cccaggattt    3300
acacaacttt aagggaaga taaatgaaca tcagatttct aggtatagaa ctatgttatt    3360
gaaaggaaaa ggaaaactgg tgtttgtttc ttagactcat gaaataaaaa attatgaagg    3420
caatgaaaaa taaattgaaa attaaagtca gatgagaata ggaataatac tttgccactt    3480
ctgcattatt tagaaacata cgttattgta catttgtaaa ccattactg tctgggcaat    3540
agtgactccg tttaataaaa gcttccgtag tgcattggta tggattaaat gcataaaata    3600
ttcttagact cgatgctgta taaaatatta tgggaaaaaa aagaaaatac gttattttgc    3660
ctctaaactt ttattgaagt tttatttggc aggaaaaaaa attgaatctt ggtcaacatt    3720
taaaccaaag taaagggga aaaccaaag ttatttgttt tgcatggcta agccattctg    3780
ttatctctgt aaatactgtg atttcttttt tattttctct ttagaatttt gttaaagaaa    3840
ttctaaaatt tttaaacacc tgctctccac aataaatcac aaacactaaa ataaaattac    3900
ttccatataa atattatttt ctcttttggt gtgggagatc aaaggtttaa agtctaactt    3960
ctaagatata tttgcagaaa gaagcaacat gacaatagag agagttatgc tacaattatt    4020
tcttggtttc cacttgcaat ggttaattaa gtccaaaaac agctgtcaga acctcgagag    4080
cagaacatga gaaactcaga gctctggacc gaaagcagaa agtttgccag gaaaaaaaaa    4140
gacaacatta ttaccatcga ttcagtgcct ggataaagag gaaagcttac ttgtttaatg    4200
gcagccacat gcacgaagat gctaagaaga aaagaattc caaatcctca acttttgagg    4260
tttcggctct ccaatttaac tctttggcaa caggaaacag gttttgcaag ttcaaggttc    4320
actccctata tgtgattata ggaattgttt gtggaaatgg attaacatac ccgtctatgc    4380
ctaaagata ataaaactga aatatgtctt caaaaaaaaa aaaaaaaaa aaaaaaaaa    4440
aaaaaaaaaa gggcggccgc t                                                4461
```

<210> SEQ ID NO 64
<211> LENGTH: 583
<212> TYPE: PRT
<213> ORGANISM: Homo sapiens

<400> SEQUENCE: 64

```
Met Glu Ser Lys Gly Ala Ser Ser Cys Arg Leu Leu Phe Cys Leu Leu
 1               5                  10                  15

Ile Ser Ala Thr Val Phe Arg Pro Gly Leu Gly Trp Tyr Thr Val Asn
            20                  25                  30

Ser Ala Tyr Gly Asp Thr Ile Ile Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125

Lys Val Phe Lys Gln Pro Ser Lys Pro Glu Ile Val Ser Lys Ala Leu
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Ile Phe Lys Lys Glu Met
            180                 185                 190

Asp Pro Val Thr Gln Leu Tyr Thr Met Thr Ser Thr Leu Glu Tyr Lys
        195                 200                 205

Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270

Asn Gly Asn Pro Pro Pro Glu Glu Phe Leu Phe Tyr Leu Pro Gly Gln
        275                 280                 285

Pro Glu Gly Ile Arg Ser Ser Asn Thr Tyr Thr Leu Met Asp Val Arg
    290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
        355                 360                 365

Asp Asn Ile Arg Leu Arg Ser Ser Pro Ser Phe Ser Ser Leu His Tyr
    370                 375                 380
```

```
Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
            405                 410                 415

Gln Ile Lys Met Thr Lys Lys Thr Asp Pro Ser Gly Leu Ser Lys Thr
        420                 425                 430

Ile Ile Cys His Val Glu Gly Phe Pro Lys Pro Ala Ile Gln Trp Thr
    435                 440                 445

Ile Thr Gly Ser Gly Ser Val Ile Asn Gln Thr Glu Glu Ser Pro Tyr
450                 455                 460

Ile Asn Gly Arg Tyr Tyr Ser Lys Ile Ile Ile Ser Pro Glu Glu Asn
465                 470                 475                 480

Val Thr Leu Thr Cys Thr Ala Glu Asn Gln Leu Glu Arg Thr Val Asn
            485                 490                 495

Ser Leu Asn Val Ser Ala Ile Ser Ile Pro Glu His Asp Glu Ala Asp
        500                 505                 510

Glu Ile Ser Asp Glu Asn Arg Glu Lys Val Asn Asp Gln Ala Lys Leu
    515                 520                 525

Ile Val Gly Ile Val Val Gly Leu Leu Leu Ala Ala Leu Val Ala Gly
530                 535                 540

Val Val Tyr Trp Leu Tyr Met Lys Lys Ser Lys Thr Ala Ser Lys His
545                 550                 555                 560

Val Asn Lys Asp Leu Gly Asn Met Glu Glu Asn Lys Lys Leu Glu Glu
            565                 570                 575

Asn Asn His Lys Thr Glu Ala
        580

<210> SEQ ID NO 65
<211> LENGTH: 2174
<212> TYPE: DNA
<213> ORGANISM: Homo sapiens
<220> FEATURE:
<221> NAME/KEY: misc_feature
<222> LOCATION: 1910, 1941
<223> OTHER INFORMATION: n = A,T,C or G

<400> SEQUENCE: 65
agcaccacgc gtccgtgaag atggagacca acgagtctac ggagggatcg cggtcgcggt      60
cgcggtgaga gccgcagctc tggctgcagg cataagggga cgaggaaggt cagctgactt     120
cctctgctgc gcttttgaca gccatgtcgt gtttgctttc tttcagatct ttagacatac     180
agcccagctc cgaaggactg gggcccactt cggaaccgtt tccttcttca gatgacagtc     240
ccaggtcggc cctggcagct gcaaccgcag cagctgcagc ggctgcatca gctgctgcag     300
ctactgcagc cttcaccact gccaaagcag ctgcattatc tacaaagacc ccagcgccct     360
gttctgagtt catggagccg tcctctgacc ccagccttct ggggagccc tgtgcgggac      420 ccggctttac ccacaatata gcccatggga gtcttggctt tgagcccgtc tatgtttcct     480
gtattgctca ggacacttgc actacaactg accatagttc taatcctggc cctgttccag     540
gctctagctc tgggcctgtt cttggttcca gctcaggtgc tggccatggc tctggctctg     600
gctctggtcc tggctgtggc tctgtccctg gtctggctc tggtcctggt cctggctctg      660
gtcctggtca tggctctggc tctcatcctg gtcctgcctc tgggcctggt ccagacactg     720
gccctgactg tgagctcagc ccctgtattc ctccagggtt cagaaacctg gtggcagatc     780
gggtccctaa ctatacctcc tggagtcagc actgccctg gagcccag aaacaaccac        840
```

```
cttgggaatt tttgcaagtc ttagaaccgg gtgcccgagg actatggaaa ccccccagaca    900
ttaaagggaa gcttatggtt tgctatgaaa ctttgccacg gggccagtgc ctcctctaca    960
actgggagga agaggtatta aagttttggc ctgctcccct ttcttgaagg ctgccctcag   1020
tttcttaggg gaggcagtag tttacatgag ggtgggtacc agaagggata ttatagtcat   1080
tcaacttggg atccacagag agccaccaac cacctggatc aagtcccaag catgcaggat   1140
ggctctgaga gttttttctt ccgacacgga caccggggac tgctgactat gcaactaaag   1200
tcacccatgc cctccagcac cacccagaaa gactcgtacc agccaccagg aaacgtctat   1260
tggccacttc gagggaagcg tgaagccatg ctggagatgc tcctgcagca tcagatctgg   1320
taagggattg ggtaaagggg aagagggatg gggaggagaa aaattgggtg agaatggcct   1380
tgacacccct cgggctacat agtaaagagg tgcaggcaga acaggaaccc acaaggaagc   1440
tcttcgaggt tgagtctgtg acacaccatg actaccgaat ggagctggca caagcaggga   1500
ctcctgcccc aacaaaggtg agaacccacc ccccatcccc cgccacttgc accagctggg   1560
ctctgacagg ctgtggccaa gtaccaagcc cagaggttga gagagagggc tgaaggccag   1620
gagttactca gtaccctccc tcacagcctc acgactaccg ccaggagcaa cctgagacct   1680
tctggataca gagggcacca cagctgccgg tgtgtgaggg tgactaggtg ttgggggcag   1740
agcggggcag gaaaggtagg gcagagttgt tttgttctgg cttggggaga gtgggatcca   1800
tcctcatcct ggcactcctc cagggtgtca gtaacatcag gacattggac acaccattcc   1860
ggaagaactg cagcttctca cacccagta cccttgtctc tggggaaacn ttttgcccta    1920
tgaacctgag aattacccct naccaattgg gagaaaatat cttcccttcc ctgtcccgga   1980
ggaaggctgg gtggtggagg ggggagaatg actcctttct gaggggtgag gagggaagtg   2040
gggtatggaa tatggaatct atttctgtct gcactagaga ggtcgggagg aagttaattc   2100
tcactgymct tgaagaggct ttacataaag ggttctctct craaaaaaaa rawaraaaaa   2160
aaaagggcgg ccgs                                                    2174
```

<210> SEQ ID NO 66
<211> LENGTH: 287
<212> TYPE: PRT
<213> ORGANISM: Homo sapiens

<400> SEQUENCE: 66

```
Met Ser Cys Leu Leu Ser Phe Arg Ser Leu Asp Ile Gln Pro Ser Ser
 1               5                  10                  15

Glu Gly Leu Gly Pro Thr Ser Glu Pro Phe Pro Ser Ser Asp Asp Ser
            20                  25                  30

Pro Arg Ser Ala Leu Ala Ala Ala Thr Ala Ala Ala Ala Ala Ala Ala
        35                  40                  45

Ser Ala Ala Ala Ala Thr Ala Ala Phe Thr Thr Ala Lys Ala Ala Ala
    50                  55                  60

Leu Ser Thr Lys Thr Pro Ala Pro Cys Ser Glu Phe Met Glu Pro Ser
65                  70                  75                  80

Ser Asp Pro Ser Leu Leu Gly Glu Pro Cys Ala Gly Pro Gly Phe Thr
                85                  90                  95

His Asn Ile Ala His Gly Ser Leu Gly Phe Glu Pro Val Tyr Val Ser
            100                 105                 110

Cys Ile Ala Gln Asp Thr Cys Thr Thr Thr Asp His Ser Ser Asn Pro
        115                 120                 125

Gly Pro Val Pro Gly Ser Ser Ser Gly Pro Val Leu Gly Ser Ser Ser
    130                 135                 140
```

Gly Ala Gly His Gly Ser Gly Ser Gly Ser Gly Pro Gly Cys Gly Ser
145                 150                 155                 160

Val Pro Gly Ser Gly Ser Gly Pro Gly Pro Gly Ser Gly Pro Gly His
                165                 170                 175

Gly Ser Gly Ser His Pro Gly Pro Ala Ser Gly Pro Gly Pro Asp Thr
            180                 185                 190

Gly Pro Asp Ser Glu Leu Ser Pro Cys Ile Pro Pro Gly Phe Arg Asn
        195                 200                 205

Leu Val Ala Asp Arg Val Pro Asn Tyr Thr Ser Trp Ser Gln His Cys
    210                 215                 220

Pro Trp Glu Pro Gln Lys Gln Pro Pro Trp Glu Phe Leu Gln Val Leu
225                 230                 235                 240

Glu Pro Gly Ala Arg Gly Leu Trp Lys Pro Asp Ile Lys Gly Lys
                245                 250                 255

Leu Met Val Cys Tyr Glu Thr Leu Pro Arg Gly Gln Cys Leu Leu Tyr
            260                 265                 270

Asn Trp Glu Glu Glu Val Leu Lys Phe Trp Pro Ala Pro Phe Ser
        275                 280                 285

<210> SEQ ID NO 67
<211> LENGTH: 4305
<212> TYPE: DNA
<213> ORGANISM: Homo sapiens

<400> SEQUENCE: 67

```
cccttaataa gatttgccac gtacactcga gccatcgcga gtgtccttga gccgcgggtg        60
acggtggctc tcgctgctcg cgccccctcc tcccgcgggg ggagcctgat gccacgttcc       120
ctatgaatta tttatcgccg gcctaaaaat accccgaact tcacagcccg agtgaccctc       180
cggtggacat gggtgggcc ctggggccgg ccctgttgct cacctcgctc ttcggtgcct        240
gggcagggct gggtccgggg cagggcgagc agggcatgac ggtggccgtg gtgtttagca       300
gctcagggcc gccccaggcc cagttccgtg cccgcctcac ccccagagc ttcctggacc        360
taccccctgga gatccagccg ctcacagttg gggtcaacac caccaacccc agcagcctcc      420
tcacccagat ctgcggcctc ctgggtgctg cccacgtcca cggcattgtc tttgaggaca       480
acgtggacac cgaggcggtg gcccagatcc ttgacttcat ctcctcccag acccatgtgc       540
ccatcctcag catcagcgga ggctctgctg tggtcctcac ccccaaggag ccgggctccg       600
ccttcctgca gctgggcgtg tccctggagc agcagctgca ggtgctgttc aaggtgctgg       660
aagagtacga ctggagcgcc ttcgccgtca tcaccagcct gcacccgggc cacgcgctct       720
tcctggaggg cgtgcgcgcc gtcgccgacg ccagccacgt gagttggcgg ctgctggacg       780
tggtcacgct ggagctgggc ccggagggc gcgcgcgcg cacgcagcgc ctgctgcgcc         840
agctcgacgc gcccgtgttt gtggcctact gctcgcgcga ggaggccgag gtgctcttcg       900
ccgaggcggc gcaggccggt ctggtgggc ccggccacgt gtggctggtg cccaacctgg        960
cgctgggcag caccgatgcg ccccccgcca ccttccccgt gggcctcatc agcgtcgtca      1020
ccgagagctg gcgcctcagc ctgcgccaga aggtgcgcga cggcgtggcc attctggccc      1080
tgggcgccca cagctactgg cgccagcatg gaaccctgcc agccccggcc gggactgcc       1140
gtgttcaccc tgggcccgtc agccctgccc gggaggcctt ctacaggcac ctactgaatg      1200
tcacctggga gggccgagac ttctccttca gccctggtgg gtacctggtc cagcccacca      1260
tggtggtgat cgcccctcaac cggcaccgcc tctgggagat ggtggggcgc tgggagcatg     1320
```

```
gcgtcctata catgaagtac cctgtgtggc ctcgctacag tgcctctctg cagcccgtgg      1380
tggacagtcg gcacctgacg gtggccacgc tggaagagag gcccttttgtc atcgtggaga     1440 gccccgaccc tggcacagga ggctgcgtcc ccaacaccgt gccctgccgc aggcagagca      1500
accacacctt cagcagcggg gacgtggccc cctacaccaa gctctgttgt aagggattct      1560
gcatcgacat cctcaagaag ctggccagag tggtcaaatt ctcctacgac ctgtacctgg      1620
tgaccaacgg caagcatggc aagcgggtgc gcggcgtatg gaacggcatg attggggagg     1680
tgtactacaa gcgggcagac atggccatcg gctccctcac catcaatgag gaacgctccg      1740
agatcgtaga cttctctgta ccctttgtgg agacgggcat cagtgtgatg gtggctcgca     1800
gcaatggcac cgtctccccc tcggccttct ggagccata  tagccctgca gtgtgggtga     1860
tgatgtttgt catgtgcctc actgtggtgg ccatcaccgt cttcatgttc gagtacttca      1920
gccctgtcag ctacaaccag aacctcacca gaggcaagaa gtccgggggc ccagctttca     1980
ctatcggcaa gtccgtgtgg ctgctgtggg cgctggtctt caacaactca gtgcccatcg      2040
agaacccgcg gggcaccacc agcaagatca tggttctggt ctgggccttc tttgctgtca     2100
tcttcctcgc cagctacacg gccaacctgg ccgccttcat gatccaagag caatacatcg      2160
acactgtgtc gggcctcagt gacaagaagt ttcagcggcc tcaagatcag tacccaccttt    2220 tccgcttcgg cacggtgccc aacgcagca  cggagcggaa catccgcagt aactaccgtg      2280
acatgcacac ccacatggtc aagttcaacc agcgctcggt ggaggacgcg ctcaccagcc      2340
tcaagatggg gaagctggat gccttcatct atgatgctgc tgtcctcaac tacatggcag     2400
gcaaggacga gggctgcaag ctggtcacca ttgggtctgg caaggtcttt gctaccactg     2460
gctacggcat cgccatgcag aaggactccc actggaagcg ggccatagac ctggcgctct     2520
tgcagttcct gggggacgga gagacacaga aactggagac agtgtggctc tcagggatct     2580
gccagaatga agaacgag gtgatgagca gcaagctgga catcgacaac atggcaggcg       2640
tcttctacat gctgctggtg gccatggggc tggccctgct ggtcttcgcc tgggagcacc      2700
tggtctactg gaagctgcgc cactcggtgc ccaactcatc ccagctggac ttcctgctgg      2760 cttttcagcag gggcatctac agctgcttca gcggggtgca gagcctcgcc agcccaccgc     2820
ggcaggccag cccggacctc acggccagct cggcccaggc cagcgtgctc aagatgctgc     2880
aggcagcccg cgacatggtg accacggcgg gcgtaagcag ctcccctggac cgcgccactc    2940 gcaccatcga gaattggggt ggcggccgcc gtgcgccccc accgtccccc tgcccgaccc     3000
cgcggtctgg ccccagccca tgcctgccca cccccgaccc gccccagag ccgagccca       3060 cgggctgggg accgccagac gggggtcgcg cggcgcttgt gcgcagggct ccgcagcccc     3120
cgggccgccc ccgacgccg gggccgcccc tgtccgacgt ctcccgagtg tcgcgccgcc      3180
cagcctggga ggcgcggtgg ccggtgcgga ccgggcactg cgggaggcac ctctcggcct      3240
ccgagcggcc cctgtcgccc gcgcgctgtc actacagctc ctttcctcga gccgaccgat     3300
ccggccgccc cttcctcccg ctcttcccgg agccccggaa gctggaggac ctgccgctgc     3360
tcggtccgga gcagctggcc cggcgggagg ccctgctgca gcggcctggg cccggggct      3420 cgcgcccgcg tcacgcttcc ctgcccagct ccgtggccga ggcttcgct cggcccagct      3480 cgctgccccgc tgggtgcacc ggccccgcct gcgcccgccc cgacgccac tcggcctgca    3540 ggcgcttggc gcaggcgcag tcgatgtgct tgccgatcta ccgggaggcc tgccaggagg     3600
gcgagcaggc aggggccccc gcctggcagc acagacagca cgtctgcctg cacgcccacg     3660 cccaccctgcc attttgctgg gggctgtct  gtcctcacct tccaccctgt gccagccacg     3720
```

```
gctcctggct ctccggggcc tgggggcctc tggggcacag ggcaggact  ctggggctgg   3780 gcacaggcta cagagacagt gggggactgg acgagatcag cagtgtagcc cgtgggacgc   3840
aaggcttccc gggaccctgc acctggagac ggatctccag tctggagtca gaagtgtgag   3900
ttatcagcca ctcaggctcc gagccagctg gattctctgc ctgccactgt cagggttaag   3960
cggcaggcag gattgggctt ttctggcttc taccatgaaa tcctggccat gggaccccag   4020
tgacagatga tgtcttccat ggtcatcagt gacctcagta gcctcaaatc atggtgaggg   4080
ctgggctttt gctgtcctct ctcacgcag  agttctgcca ggagggtgtg ctgtggggt    4140 cagactcctg aggctctccc ttccctgggg ctagccagtt actggtcatg ctgctgtgg    4200 gcatggaggc tggaacttgt ggttgaggca gggccatccc gatccttgct ctacctggct   4260
agagtttctt ctcatcagag cactgggaca ttaaaccaac ctttt                   4305
```

<210> SEQ ID NO 68
<211> LENGTH: 1236
<212> TYPE: PRT
<213> ORGANISM: Homo sapiens

<400> SEQUENCE: 68

```
Met Gly Gly Ala Leu Gly Pro Ala Leu Leu Leu Thr Ser Leu Phe Gly
  1               5                  10                  15

Ala Trp Ala Gly Leu Gly Pro Gly Gln Gly Glu Gln Gly Met Thr Val
             20                  25                  30

Ala Val Val Phe Ser Ser Gly Pro Pro Gln Ala Gln Phe Arg Ala
         35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Gly Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
```

```
                275                 280                 285
Val Arg Asp Gly Val Ala Ile Leu Ala Leu Gly Ala His Ser Tyr Trp
290                 295                 300
Arg Gln His Gly Thr Leu Pro Ala Pro Ala Gly Asp Cys Arg Val His
305                 310                 315                 320
Pro Gly Pro Val Ser Pro Ala Arg Glu Ala Phe Tyr Arg His Leu Leu
                325                 330                 335
Asn Val Thr Trp Glu Gly Arg Asp Phe Ser Phe Ser Pro Gly Gly Tyr
                340                 345                 350
Leu Val Gln Pro Thr Met Val Val Ile Ala Leu Asn Arg His Arg Leu
            355                 360                 365
Trp Glu Met Val Gly Arg Trp Glu His Gly Val Leu Tyr Met Lys Tyr
370                 375                 380
Pro Val Trp Pro Arg Tyr Ser Ala Ser Leu Gln Pro Val Val Asp Ser
385                 390                 395                 400
Arg His Leu Thr Val Ala Thr Leu Glu Glu Arg Pro Phe Val Ile Val
                405                 410                 415
Glu Ser Pro Asp Pro Gly Thr Gly Cys Val Pro Asn Thr Val Pro
                420                 425                 430
Cys Arg Arg Gln Ser Asn His Thr Phe Ser Ser Gly Asp Val Ala Pro
435                 440                 445
Tyr Thr Lys Leu Cys Cys Lys Gly Phe Cys Ile Asp Ile Leu Lys Lys
450                 455                 460
Leu Ala Arg Val Val Lys Phe Ser Tyr Asp Leu Tyr Leu Val Thr Asn
465                 470                 475                 480
Gly Lys His Gly Lys Arg Val Arg Gly Val Trp Asn Gly Met Ile Gly
                485                 490                 495
Glu Val Tyr Tyr Lys Arg Ala Asp Met Ala Ile Gly Ser Leu Thr Ile
                500                 505                 510
Asn Glu Glu Arg Ser Glu Ile Val Asp Phe Ser Val Pro Phe Val Glu
                515                 520                 525
Thr Gly Ile Ser Val Met Val Ala Arg Ser Asn Gly Thr Val Ser Pro
                530                 535                 540
Ser Ala Phe Leu Glu Pro Tyr Ser Pro Ala Val Trp Val Met Met Phe
545                 550                 555                 560
Val Met Cys Leu Thr Val Val Ala Ile Thr Val Phe Met Phe Glu Tyr
                565                 570                 575
Phe Ser Pro Val Ser Tyr Asn Gln Asn Leu Thr Arg Gly Lys Lys Ser
                580                 585                 590
Gly Gly Pro Ala Phe Thr Ile Gly Lys Ser Val Trp Leu Leu Trp Ala
                595                 600                 605
Leu Val Phe Asn Asn Ser Val Pro Ile Glu Asn Pro Arg Gly Thr Thr
            610                 615                 620
Ser Lys Ile Met Val Leu Val Trp Ala Phe Phe Ala Val Ile Phe Leu
625                 630                 635                 640
Ala Ser Tyr Thr Ala Asn Leu Ala Ala Phe Met Ile Gln Glu Gln Tyr
                645                 650                 655
Ile Asp Thr Val Ser Gly Leu Ser Asp Lys Lys Phe Gln Arg Pro Gln
                660                 665                 670
Asp Gln Tyr Pro Pro Phe Arg Phe Gly Thr Val Pro Asn Gly Ser Thr
            675                 680                 685
Glu Arg Asn Ile Arg Ser Asn Tyr Arg Asp Met His Thr His Met Val
        690                 695                 700
```

-continued

```
Lys Phe Asn Gln Arg Ser Val Glu Asp Ala Leu Thr Ser Leu Lys Met
705                 710                 715                 720

Gly Lys Leu Asp Ala Phe Ile Tyr Asp Ala Val Leu Asn Tyr Met
            725                 730                 735

Ala Gly Lys Asp Glu Gly Cys Lys Leu Val Thr Ile Gly Ser Gly Lys
            740                 745                 750

Val Phe Ala Thr Thr Gly Tyr Gly Ile Ala Met Gln Lys Asp Ser His
        755                 760                 765

Trp Lys Arg Ala Ile Asp Leu Ala Leu Leu Gln Phe Leu Gly Asp Gly
    770                 775                 780

Glu Thr Gln Lys Leu Glu Thr Val Trp Leu Ser Gly Ile Cys Gln Asn
785                 790                 795                 800

Glu Lys Asn Glu Val Met Ser Ser Lys Leu Asp Ile Asp Asn Met Ala
            805                 810                 815

Gly Val Phe Tyr Met Leu Leu Val Ala Met Gly Leu Ala Leu Leu Val
            820                 825                 830

Phe Ala Trp Glu His Leu Val Tyr Trp Lys Leu Arg His Ser Val Pro
        835                 840                 845

Asn Ser Ser Gln Leu Asp Phe Leu Leu Ala Phe Ser Arg Gly Ile Tyr
    850                 855                 860

Ser Cys Phe Ser Gly Val Gln Ser Leu Ala Ser Pro Pro Arg Gln Ala
865                 870                 875                 880

Ser Pro Asp Leu Thr Ala Ser Ser Ala Gln Ala Ser Val Leu Lys Met
            885                 890                 895

Leu Gln Ala Ala Arg Asp Met Val Thr Thr Ala Gly Val Ser Ser Ser
            900                 905                 910

Leu Asp Arg Ala Thr Arg Thr Ile Glu Asn Trp Gly Gly Arg Arg
        915                 920                 925

Ala Pro Pro Ser Pro Cys Pro Thr Pro Arg Ser Gly Pro Ser Pro
930                 935                 940

Cys Leu Pro Thr Pro Asp Pro Pro Glu Pro Ser Pro Thr Gly Trp
945                 950                 955                 960

Gly Pro Pro Asp Gly Gly Arg Ala Ala Leu Val Arg Arg Ala Pro Gln
            965                 970                 975

Pro Pro Gly Arg Pro Pro Thr Pro Gly Pro Pro Leu Ser Asp Val Ser
            980                 985                 990

Arg Val Ser Arg Arg Pro Ala Trp Glu Ala Arg Trp Pro Val Arg Thr
        995                 1000                1005

Gly His Cys Gly Arg His Leu Ser Ala Ser Glu Arg Pro Leu Ser Pro
    1010                1015                1020

Ala Arg Cys His Tyr Ser Ser Phe Pro Arg Ala Asp Arg Ser Gly Arg
1025                1030                1035                1040

Pro Phe Leu Pro Leu Phe Pro Glu Pro Pro Glu Leu Glu Asp Leu Pro
            1045                1050                1055

Leu Leu Gly Pro Glu Gln Leu Ala Arg Arg Glu Ala Leu Leu His Ala
            1060                1065                1070

Ala Trp Ala Arg Gly Ser Arg Pro Arg His Ala Ser Leu Pro Ser Ser
        1075                1080                1085

Val Ala Glu Ala Phe Ala Arg Pro Ser Ser Leu Pro Ala Gly Cys Thr
    1090                1095                1100

Gly Pro Ala Cys Ala Arg Pro Asp Gly His Ser Ala Cys Arg Arg Leu
1105                1110                1115                1120

Ala Gln Ala Gln Ser Met Cys Leu Pro Ile Tyr Arg Glu Ala Cys Gln
            1125                1130                1135
```

```
Glu Gly Glu Gln Ala Gly Ala Pro Ala Trp Gln His Arg Gln His Val
        1140                1145                1150

Cys Leu His Ala His Ala His Leu Pro Phe Cys Trp Gly Ala Val Cys
    1155                1160                1165

Pro His Leu Pro Pro Cys Ala Ser His Gly Ser Trp Leu Ser Gly Ala
    1170                1175                1180

Trp Gly Pro Leu Gly His Arg Gly Arg Thr Leu Gly Leu Gly Thr Gly
1185                1190                1195                1200

Tyr Arg Asp Ser Gly Gly Leu Asp Glu Ile Ser Ser Val Ala Arg Gly
                1205                1210                1215

Thr Gln Gly Phe Pro Gly Pro Cys Thr Trp Arg Arg Ile Ser Ser Leu
            1220                1225                1230

Glu Ser Glu Val
        1235

<210> SEQ ID NO 69
<211> LENGTH: 1725
<212> TYPE: DNA
<213> ORGANISM: Homo sapiens

<400> SEQUENCE: 69
gtcgacccac gcgtccggct ggaaggaact ggtctgctca cacttgctgg cttgcgcatc      60
aggactggct ttatctcctg actcacggtg caaaggtgca ctctgcgaac gttaagtccg     120
tccccagcgc ttggaatcct acggccccca cagccggatc ccctcagcct tccaggtcct     180
caactcccgc ggacgctgaa caatggcctc catgggcta caggtaatgg gcatcgcgct      240
ggccgtcctg ggctggctgg ccgtcatgct gtgctgcgcg ctgcccatgt ggcgcgtgac     300
ggccttcatc ggcagcaaca ttgtcacctc gcagaccatc tgggagggcc tatggatgaa     360
ctgcgtggtg cagagcaccg gccagatgca gtgcaaggtg tacgactcgc tgctggcact     420
gccgcaggac ctgcaggcgg cccgcgccct cgtcatcatc agcatcatcg tggctgctct     480
gggcgtgctg ctgtccgtgg tgggggcaa gtgtaccaac tgcctggagg atgaaagcgc     540
caaggccaag accatgatcg tggcgggcgt ggtgttcctg ttggccggcc ttatggtgat     600
agtgccggtg tcctggacgg cccacaacat catccaagac ttctacaatc cgctggtggc     660
ctccgggcag aagcgggaga tgggtgcctc gctctacgtc ggctgggccg cctccggcct     720
gctgctcctt ggcggggggc tgctttgctg caactgtcca ccccgcacag acaagcctta     780
ctccgccaag tattctgctg cccgctctgc tgctgccagc aactacgtgt aaggtgccac     840
ggctccactc tgttcctctc tgctttgttc ttccctggac tgagctcagc gcaggctgtg     900
accccaggag ggccctgcca cgggccactg gctgctgggg actggggact gggcagagac     960
tgagccaggc aggaaggcag cagccttcag cctctctggc ccactcggac aacttcccaa    1020
ggccgcctcc tgctagcaag aacagagtcc accctcctct ggatattggg gagggacgga   1080
agtgacaggg tgtggtggtg gagtggggag ctggcttctg ctggccagga tggcttaacc    1140
ctgactttgg gatctgcctg catcggtgtt ggccactgtc cccatttaca ttttccccac   1200
tctgtctgcc tgcatctcct ctgttgcggg taggccttga tatcacctct gggactgtgc    1260
cttgctcacc gaaacccgcg cccaggagta tggctgaggc cttgcccacc cacctgcctg    1320
ggaagtgcag agtggatgga cgggtttaga ggggaggggc gaaggtgctg taaacaggtt    1380
tgggcagtgg tggggagggg ggccagagag gcggctcagg ttgcccagct ctgtggcctc    1440
aggactctct gcctcacccg cttcagccca gggcccctgg agactgatcc cctctgagtc    1500
```

| ctctgcccct tccaaggaca ctaatgagcc tgggagggtg gcagggagga ggggacagct | 1560 |
| tcacccttgg aagtcctggg gttttcctc ttccttcttt gtggtttctg ttttgtaatt | 1620 |
| taagaagagc tattcatcac tgtaattatt attattttct acaataaatg ggacctgtgc | 1680 |
| acaggaggaa aaaaaaaaaa aaaaaaaaa aaaaagggcg gccgc | 1725 |

<210> SEQ ID NO 70
<211> LENGTH: 206
<212> TYPE: PRT
<213> ORGANISM: Homo sapiens

<400> SEQUENCE: 70

Met Gly Leu Gln Val Met Gly Ile Ala Leu Ala Val Leu Gly Trp Leu
1               5                   10                  15

Ala Val Met Leu Cys Cys Ala Leu Pro Met Trp Arg Val Thr Ala Phe
            20                  25                  30

Ile Gly Ser Asn Ile Val Thr Ser Gln Thr Ile Trp Glu Gly Leu Trp
        35                  40                  45

Met Asn Cys Val Val Gln Ser Thr Gly Gln Met Gln Cys Lys Val Tyr
    50                  55                  60

Asp Ser Leu Leu Ala Leu Pro Gln Asp Leu Gln Ala Ala Arg Ala Leu
65                  70                  75                  80

Val Ile Ile Ser Ile Ile Val Ala Ala Leu Gly Val Leu Leu Ser Val
                85                  90                  95

Val Gly Gly Lys Cys Thr Asn Cys Leu Glu Asp Glu Ser Ala Lys Ala
            100                 105                 110

Lys Thr Met Ile Val Ala Gly Val Val Phe Leu Leu Ala Gly Leu Met
        115                 120                 125

Val Ile Val Pro Val Ser Trp Thr Ala His Asn Ile Ile Gln Asp Phe
    130                 135                 140

Tyr Asn Pro Leu Val Ala Ser Gly Gln Lys Arg Glu Met Gly Ala Ser
145                 150                 155                 160

Leu Tyr Val Gly Trp Ala Ala Ser Gly Leu Leu Leu Leu Gly Gly Gly
                165                 170                 175

Leu Leu Cys Cys Asn Cys Pro Pro Arg Thr Asp Lys Pro Tyr Ser Ala
            180                 185                 190

Lys Tyr Ser Ala Ala Arg Ser Ala Ala Ala Ser Asn Tyr Val
        195                 200                 205

<210> SEQ ID NO 71
<211> LENGTH: 5410
<212> TYPE: DNA
<213> ORGANISM: Homo sapiens

<400> SEQUENCE: 71

| gtcgacccac gcgtccggct accgccgcgt tctattctcc gaagccggcg accgccccac | 60 |
| ctcctccctc cctcccgccc gcttcctctg cccacagcgc cggccagagc gagctagaca | 120 |
| agggcacgcg gggcctcgcc tagacccgag aagactgcgg gcgcgcgcaa gcggcggcgt | 180 |
| ggaagctgtg agcgccccca tcccggaggt ctccgccggc tccgggtga atcagctccc | 240 |
| ggccgacttt aggattcttc tggattttaa attttttctt tttaaaaaaa cttggacgga | 300 |
| taaaagatgt gccatggcag gatagcacca agagcacct cagtgtttgc cgtggcctcc | 360 |
| gtgggacatg gagtgttcct tccgctagtg atcctttgca ccctgcttgg agacggactt | 420 |
| gcttccgtgt gccccctacc accggagcca gagaatggtg gctacatctg ccaccccgg | 480 |
| ccctgcagag accccctgac agcaggcagt gtcatcgaat acctgtgtgc tgaaggctac | 540 |

```
atgttgaagg gcgattacaa atacctgacg tgtaagaatg gcgagtggaa accagccatg    600
gagattagct gccgtctcaa cgaggataaa gacacccaca catcacttgg ggtccccacg    660
ctgtctatag tggcttctac tgccagctcc gtggcgctca ttctcctcct cgtggtgctg    720
tttgtgctgc tgcagccaaa gctgaagtct ttccatcata gcaggcgtga ccaggggta     780
tctggggacc aggtctccat catggtggat ggagtccagg ttgcactacc atcatacgag    840
gaggctgtat atggcagttc tggtcactgt gtgccacctg ctgaccccag agtacagatt    900
gtgctgtcag aagggtctgg gcccagtggg aggagcgtgc aaggagca acagctgccg      960
gaccaagggg cctgctcctc tgcaggtgga gaagatgagg ccccaggcca gtctggacta   1020
tgtgaagcct ggggctctcg ggcctcagag actgtgatgg tgcatcaggc aaccacctct   1080
tcctgggtgg ccggctcagg gaaccgccaa ctggcacaca aagaaactgc agattcagag   1140
aacagtgaca tacaaagcct tttatccctc acgtcagagg agtacacaga tgatattcca   1200
ctgttgaaag aagcatgagg gcagcggcca gcctttcctc tctgcgaggt tctctcagcc   1260
cttcctccct ctcccgtgtg gattgagcac cctgtactct ccagccacct tacctggata   1320
cctgagctgc cacctgtgta tctgtgtatc tctgagggcc ctataggccc ccttgctgg    1380
aaactcaagg aagattctcg ccatctgcct gttggacagc tggaggagct ggctctttgc   1440
ctggccccgc cttcccatct gtcagagaca tatttgaatg tgctggatca aaccctccct   1500
tttcctaagc ctctgggtcc cctccagcca gctctttggc ggcagcccc accagctcct    1560
gtgggcctga gtgctgctgt gtttacttgt gcctttcccc caccctgtcc agtttccctg   1620
tcatgcagac ttgttgctgt ccacaagcct tagtggctgc actgctgccc cctgccacac   1680
agggggccgg gcctgggtct gtcctgtttc ctttgagggt tgccctact gccctttgca    1740
ggaacagatc caggtgtgag agctcttgag tcaagagtgg cagaagtggc tctaattggg   1800
gtgagagtgt agtccctggg cttgccctgg gttgaccctg gtggcatatt tccttggctg   1860
aggatggaag atttggagaa tcatgtccat gctggcccag gacccagcca tctggcccaa   1920
aggcacaagc tcctggccct gttgagttga gagtttccaa gaagcatcca gaagatccca   1980
agggagagaa ggaaaatggc tgataatgat tgtcttccta atatgcaagt tctcacttcc   2040
tacttccagc atcggccttc ctggccttgt cttttttttg tttccctgga gtataatggg   2100
aagttgcatg ctgcctcctg ggttttatcc cagatagctc tggctttctt gctgcccaca   2160
ggggcctggg gcaggaagga gacttgctga gatgccatgg agtgcccatc tggtcactgg   2220
cagtctgggc aggttgcccc tttctgggtt tgtggtgacg gaggggaggc cgagaggcac   2280
agaccaagtc cccgggtggc tgcaggcagc tccagcccgg tcctgaggat cctcctcacc   2340
atggtcacgt gccttagtaa ctgtgcccag gaagtggcct gctgcttgct gtgctgctgc   2400
ttttcctact tctgcccttc cctgccaccc ctcgcatgtc acagctgaca agcaattcct   2460
tgtcttccct ggcccctggg ggaagggct gagaaacagt ccgtgtgcac cccaacctta    2520
atggcctgag gtgggcagag gggtgtggag cagcctggag tacagggccc tggggagga    2580
gcccactgat gaggggcgct ctcccatagc catgtgttga atgctaacta ggctggggtg   2640
gacgaactct gccaactgct gtcatcttag aagatagatg cagcagtaag gaatgtttgt   2700
tttgcttttt tctgaaattt tctgaagcac tgtggctggg aaacttcgaa gcggaccctg   2760
tgctgcatgt ctgctcctcc cctgagcctg tctgcttggg ggtggtaaaa ataaaaatcc   2820
cagtttattt tcagtacctt acctaacagg gttggctcca ggcgtgggtg cctagaaga    2880
tgaggggagt ggtcttctcc cagccttta ccctcttgcc tcctgcctcc gcgcttacac    2940
```

```
acgcacttta ccacccggtc attccctggc ctcttgctgc cacttgtagt cttccttcct   3000
tcctctcagg gtaagggcag tgcctgctgt gcctgttggc cactcccaca cttccctcc    3060
cccaggagcc ctcatctgct gtgctgagtc caggaaagca tagttaggta gggagctggt   3120
tggagaaggt gctagaacta aaggcagat gagactagca tgggcccacc tggagggctg    3180
tccctaatgg ccccagtcgc cttacctcac ccacagcagt gcccttgtct tcctccaaaa   3240
cagaaagcag tgacaaaagg gggaggggtg gtaatctgaa gtctcactgc tgagccttca   3300
gcttttattt ttcactgttt caaaacccgc attctattct agaatggttt ttaaaatgga   3360
agatcttacc ttttttctatc ttgttactct ggggttttgt cccctaaga gattgcactt    3420
tttgttttggg gtttattcag ctgcatagat gaccagcttg atccctggtg aaatgaaaag   3480
ccttccttct cctgaagcct cttccgccc tgccctccac taacaacact gaggagcaca    3540
agcccaggct tgcccacctg gtaggaaagg aagaaattag aacaatggga gccttggctc   3600
ccctctcgtc tcctccctc cttcttgtca ctggctttga tgaggccac ttcccagagg     3660
ctcctgggcc tgtgagtgca ggagctcatt ctcccctcac tgctgaagtc tgtgacagct   3720
tcttcctcca gttatgtctt tcttccaaag caatttctta accatcagcc atgtgctgct   3780
atttctaggg cttctgggct tgtccctta ctgagagatt agggactcca cagctgcctt    3840
gaggtagggt ctggctgaga gacaagggta gcagcaggtg gcaggctgtt aaaagacagg   3900
ctgcctgagg agcctggagc aggtggaaac aggtggaaga aaccggccac agccctgctt   3960
taccgggctc acctctaggg cattccagca agaggctgat gcaggagaat ggccagcacc   4020
aaaggacatt taaaagagtt tttgggtttt tttgtttgtt tgttgttggt gtttgttttt   4080
ttttttttt tttttttggca cacttgagct gactcagtgc aggtttaata tcctggtgac   4140
ttgcagtcac attctaatga ctttcaaggg ccagaatatg gtgaaaatca cttaaaatat   4200
ccgtcccttc catgccttag tttagcaggt aggctctatc ttttgccatt tctgtatttt   4260
atgtgctgtg ttcccgtttc actgggtatg aactgtgaaa tcgactgaat cctggccact   4320
ttatgagttt gtttggtttt ataaggcatt tcaatgtaca ttctataaat acaagcactc   4380
catttgcaaa cagatcttaa gctaatattt tctttcccat tcatcttgcc ctcccctcc    4440
tcccgccagc tttaaagttc agtggagaag ccagatggca attcagacaa aggtatactc   4500
ttcctgcttc atgggtggtg gcacgggaat agatagccct tagcccttc cctcccagtc    4560
ccagctgagc cctcagacca cttgcttccc acataacaat gtcgcctcca tttccgagga   4620
acatccttgc gtagagaatg aaatatgctg caatcatttc tgcatcctta ctcctcaccc   4680
ccaaagaaaa aaaaaaggcc tagcagggaa gcagcatgca ggcttcacag cttaatgcca   4740
aggacagcga gtgaggctgg gagcttctct tgggcctgct gggtctgtca gctctcggaa   4800
tagggacagt ccttactggt gccccaaggt gggacttgga gaatattttg cttggcatat   4860
gtttggtctg aatggtgtag ttgctggttc cctagagagg aaaaggtggc aggcccagct   4920
ttgctgggaa atggctctta atttccagtt gaaaccctag tagaattgtg aatgaaaacc   4980
tcaaggttga gcccctctgc caagcagcag agctagtaga aggggatgca ggggcaaagc   5040
actcagttgc caagcaagga ggagagatgt acgtgggctg tgtggcagtc cccacaccct   5100
gccctggctt cttcaggtta tcgcaccact atggaatcct ttgcagaatg gtactcatat   5160
aatggtttaa aacaacacat tcataattga ctctgtgcag gatgtcactc aatcagtttg   5220
ggtttgcttt attttatttt atatatatat ttttggtat cctgtacatt gcagtgggtg    5280
tgaagatagt atttaatat ttgtacaaag tttaatttaa ttttaattgt tctatgtata    5340
```

```
taactgcatt tctaaataat taaaaaaaag ttcttatgaa aaaaaaaaaa aaaaaaaaaa    5400
gggcggccgc                                                          5410
```

<210> SEQ ID NO 72
<211> LENGTH: 303
<212> TYPE: PRT
<213> ORGANISM: Homo sapiens

<400> SEQUENCE: 72

```
Met Cys His Gly Arg Ile Ala Pro Lys Ser Thr Ser Val Phe Ala Val
 1               5                  10                  15

Ala Ser Val Gly His Gly Val Phe Leu Pro Leu Val Ile Leu Cys Thr
            20                  25                  30

Leu Leu Gly Asp Gly Leu Ala Ser Val Cys Pro Leu Pro Pro Glu Pro
        35                  40                  45

Glu Asn Gly Gly Tyr Ile Cys His Pro Arg Pro Cys Arg Asp Pro Leu
    50                  55                  60

Thr Ala Gly Ser Val Ile Glu Tyr Leu Cys Ala Glu Gly Tyr Met Leu
65                  70                  75                  80

Lys Gly Asp Tyr Lys Tyr Leu Thr Cys Lys Asn Gly Glu Trp Lys Pro
                85                  90                  95

Ala Met Glu Ile Ser Cys Arg Leu Asn Glu Asp Lys Asp Thr His Thr
            100                 105                 110

Ser Leu Gly Val Pro Thr Leu Ser Ile Val Ala Ser Thr Ala Ser Ser
        115                 120                 125

Val Ala Leu Ile Leu Leu Leu Val Leu Phe Val Leu Leu Gln Pro
    130                 135                 140

Lys Leu Lys Ser Phe His His Ser Arg Arg Asp Gln Gly Val Ser Gly
145                 150                 155                 160

Asp Gln Val Ser Ile Met Val Asp Gly Val Gln Val Ala Leu Pro Ser
                165                 170                 175

Tyr Glu Glu Ala Val Tyr Gly Ser Ser Gly His Cys Val Pro Pro Ala
            180                 185                 190

Asp Pro Arg Val Gln Ile Val Leu Ser Glu Gly Ser Gly Pro Ser Gly
        195                 200                 205

Arg Ser Val Pro Arg Glu Gln Gln Leu Pro Asp Gln Gly Ala Cys Ser
    210                 215                 220

Ser Ala Gly Gly Glu Asp Glu Ala Pro Gly Gln Ser Gly Leu Cys Glu
225                 230                 235                 240

Ala Trp Gly Ser Arg Ala Ser Glu Thr Val Met Val His Gln Ala Thr
                245                 250                 255

Thr Ser Ser Trp Val Ala Gly Ser Gly Asn Arg Gln Leu Ala His Lys
            260                 265                 270

Glu Thr Ala Asp Ser Glu Asn Ser Asp Ile Gln Ser Leu Leu Ser Leu
        275                 280                 285

Thr Ser Glu Glu Tyr Thr Asp Asp Ile Pro Leu Leu Lys Glu Ala
    290                 295                 300
```

<210> SEQ ID NO 73
<211> LENGTH: 4392
<212> TYPE: DNA
<213> ORGANISM: Homo sapiens

<400> SEQUENCE: 73

```
gtcgacccac gcgtccgggc cgtccaggct agcggcggcc cgcaggcggc ggggagaaag    60
```

```
actctctcac ctggtcttgc ggctgtggcc accgccggcc aggggtgtgg agggcgtgct    120
gccggagacg tccgccgggc tctgcagttc cgccgggggt cgggcagcta tggagccgcg    180
gcccacggcg ccctcctccg gcgccccggg actggccggg gtcggggaga cgccgtcagc    240
cgctgcgctg gccgcagcca gggtggaact gcccggcacg gctgtgccct cggtgccgga    300
ggatgctgcg cccgcgagcc gggacggcgg cggggtccgc gatgagggcc ccgcggcggc    360
cggggacggg ctgggcagac ccttgggcc caccccgagc cagagccgtt ccaggtgga    420 cctggttcc gagaacgccg ggcgggccgc tgctgcggcg gcggcggcgg cggcggcagc    480
ggcggcggct ggtgctgggg cggggccaa gcagaccccc gcgacgggg aagccagcgg    540 cgagagcgag ccggctaaag gcagcgagga agccaagggc cgcttccgcg tgaacttcgt    600
ggacccagct gcctcctcgt cggctgaaga cagcctgtca gatgctgccg gggtcggagt    660
cgacgggccc aacgtgagct ccagaacgg cggggacacg gtgctgagcg agggcagcag    720
cctgcactcc ggcggcggcg gcggcagtgg gcaccaccag cactactatt atgatacca    780 caccaacacc tactacctgc gcaccttcgg ccacaacacc atggacgctg tgcccaggat    840
cgatcactac cggcacacag ccgcgcagct gggcgagaag ctgctccggc ctagcctggc    900
ggagctccac gacgagctgg aaaaggaacc ttttgaggat ggctttgcaa atggggaaga    960
aagtactcca accagagatg ctgtggtcac gtatactgca gaaagtaaag gagtcgtgaa    1020
gtttggctgg atcaagggtg tattagtacg ttgtatgtta acatttggg gtgtgatgct    1080 tttcattaga ttgtcatgga ttgtgggtca agctggaata ggtctatcag tccttgtaat    1140
aatgatggcc actgttgtga caactatcac aggattgtct acttcagcaa tagcaactaa    1200
tggatttgta agaggaggag gagcatatta tttaatatct agaagtcag ggccagaatt    1260 tggtggtgca attggtctaa tcttcgcctt tgccaacgct gttgcagttg ctatgtatgt    1320
ggttggattt gcagaaaccg tggtggagtt gcttaaggaa cattccatac ttatgataga    1380
tgaaatcaat gatatccgaa ttattggagc cattacagtc gtgattcttt taggtatctc    1440
agtagctgga atggagtggg aagcaaaagc tcagattgtt ctttggtga tcctacttct    1500 tgctattggt gatttcgtca taggaacatt tatcccactg gagagcaaga agccaaaagg    1560
gttttttggt tataaatctg aaatatttaa tgagaacttt gggcccgatt tcgagagga    1620 agagactttc tttttctgtat ttgccatctt ttttcctgct gcaactggta ttctggctgg    1680
agcaaatatc tcaggtgatc ttgcagatcc tcagtcagcc atacccaaag gaacactcct    1740
agccatttta attactacat tggtttacgt aggaattgca gtatctgtag ttcttgtgt    1800 tgttcgagat gccactggaa acgttaatga cactatcgta acagagctaa caaactgtac    1860
ttctgcagcc tgcaaattaa actttgattt ttcatcttgt gaaagcagtc cttgttccta    1920
tggcctaatg aacaacttcc aggtaatgag tatggtgtca ggatttacac cactaatttc    1980
tgcaggtata ttttcagcca ctctttcttc agcattagca tccctagtga gtgctcccaa    2040
aatatttcag gctctatgta aggacaacat ctacccagct ttccagatgt ttgctaaagg    2100
ttatgggaaa aataatgaac ctcttcgtgg ctacatctta acattcttaa ttgcacttgg    2160
attcatctta attgctgaac tgaatgttat tgcaccaatt atctcaaact tcttccttgc    2220
atcatatgca ttgatcaatt tttcagtatt ccatgcatca cttgcaaat ctccaggatg    2280 gcgtcctgca ttcaaatact acaacatgtg gatatcactt cttggagcaa ttcttgttg    2340 catagtaatg ttcgtcatta actggtgggc tgcattgcta acatatgtga tagtccttgg    2400
gctgtatatt tatgttacct acaaaaacc agatgtgaat tggggatcct ctacacaagc    2460
```

-continued

```
cctgacttac ctgaatgcac tgcagcattc aattcgtctt tctggagtgg aagaccacgt    2520
gaaaaacttt aggccacagt gtcttgttat gacaggtgct ccaaactcac gtccagcttc    2580
acttcatctt gttcatgatt tcacaaaaaa tgttggtttg atgatctgtg gccatgtaca    2640
tatgggtcct cgaagacaag ccatgaaaga gatgtccatc gatcaagcca aatatcagcg    2700
atggcttatt aagaacaaaa tgaaggcatt ttatgctcca gtacatgcag atgacttgag    2760
agaaggtgca cagtatttga tgcaggctgc tggtcttggt cgtatgaagc caaacacact    2820
tgtccttgga tttaagaaag attggttgca agcagatatg agggatgtgg atatgtatat    2880
aaacttattt catgatgctt ttgacataca atatggagta gtggttattc gcctaaaaga    2940
aggtctggat atatctcatc ttcaaggaca agaagaatta ttgtcatcac aagagaaatc    3000
tcctggcacc aaggatgtgg tagtaagtgt ggaatatagt aaaaagtccg atttagatac    3060
ttccaaacca ctcagtgaaa aaccaattac acacaaagtt gaggaagagg atggcaagac    3120
tgcaactcaa ccactgttga aaaagaatcc caaaggccct attgtgcctt taaatgtagc    3180
tgaccaaaag cttcttgaag ctagtacaca gtttcagaaa aacaaggaa agaatactat    3240 tgatgtctgg tggcttttg atgatggagg tttgacctta ttgataccttaccttctgac    3300 gaccaagaaa aaatggaaag actgtaagat cagagtattc attggtggaa agataaacag    3360
aatagaccat gaccggagag cgatggctac tttgcttagc aagttccgga tagacttttc    3420
tgatatcatg gttctaggag atatcaatac caaaccaaag aaagaaaata ttatagcttt    3480
tgaggaaatc attgagccat acagacttca tgaagatgat aaagagcaag atattgcaga    3540
taaaatgaaa gaagatgaac catggcgaat aacagataat gagcttgaac tttataagac    3600
caagacatac cggcagatca ggttaaatga gttattaaag aacattcaa gcacagctaa    3660 tattattgtc atgagtctcc cagttgcacg aaaaggtgct gtgtctagtg ctctctacat    3720 ggcatggta gaagctctat ctaaggacct accaccaatc ctcctagttc gtgggaatca    3780
tcagagtgtc cttaccttct attcataaat gttctataca gtggacagcc ctccagaatg    3840
gtacttcagt gcctagtgta gtaactgaaa tcttcaatga cacattaaca tcacaatggc    3900
gaatggtgac ttttctttca cgatttcatt aatttgaaag cacacaggaa agttgctcca    3960
ttgataacgt gtatggagac ttcggtttta gtcaattcca tatctcaatc ttaatggtga    4020
ttcttctctg ttgaactgaa gtttgtgaga gtagttttcc tttgctactt gaatagcaat    4080
aaaagcgtgt taactttttg attgatgaaa gaagtacaaa aagcctttag ccttgaggtg    4140
ccttctgaaa ttaaccaaat ttcatccata tatcctcttt tataaactta tagaatgtca    4200
aamwwwrmmw wmaamwrwww wwawwwmwar wmwmwwmmam wwwaaaamaa aawraamact    4260
gcttgtcttc ttccattgac catttagtgt tgagtactgt atgtgttttg ttaattctat    4320
aaaggtatct gttagatatt aaaggtgaga attagggcag gttaatcaaa aatggggaag    4380
gggaaatggt aa                                                        4392
```

<210> SEQ ID NO 74
<211> LENGTH: 1212
<212> TYPE: PRT
<213> ORGANISM: Homo sapiens

<400> SEQUENCE: 74

```
Met Glu Pro Arg Pro Thr Ala Pro Ser Ser Gly Ala Pro Gly Leu Ala
1               5                   10                  15

Gly Val Gly Glu Thr Pro Ser Ala Ala Ala Leu Ala Ala Ala Arg Val
            20                  25                  30
```

```
Glu Leu Pro Gly Thr Ala Val Pro Ser Val Pro Asp Ala Ala Pro
         35                  40                  45

Ala Ser Arg Asp Gly Gly Val Arg Asp Glu Gly Pro Ala Ala Ala
     50                  55                  60

Gly Asp Gly Leu Gly Arg Pro Leu Gly Pro Thr Pro Ser Gln Ser Arg
 65                  70                  75                  80

Phe Gln Val Asp Leu Val Ser Glu Asn Ala Gly Arg Ala Ala Ala
                 85                  90                  95

Ala Ala Ala Ala Ala Ala Ala Ala Ala Gly Ala Gly Ala Gly
            100                 105                 110

Ala Lys Gln Thr Pro Ala Asp Gly Glu Ala Ser Gly Glu Ser Glu Pro
            115                 120                 125

Ala Lys Gly Ser Glu Glu Ala Lys Gly Arg Phe Arg Val Asn Phe Val
    130                 135                 140

Asp Pro Ala Ala Ser Ser Ala Glu Asp Ser Leu Ser Asp Ala Ala
145                 150                 155                 160

Gly Val Gly Val Asp Gly Pro Asn Val Ser Phe Gln Asn Gly Gly Asp
                165                 170                 175

Thr Val Leu Ser Glu Gly Ser Ser Leu His Ser Gly Gly Gly Gly
                180                 185                 190

Ser Gly His His Gln His Tyr Tyr Tyr Asp Thr His Thr Asn Thr Tyr
        195                 200                 205

Tyr Leu Arg Thr Phe Gly His Asn Thr Met Asp Ala Val Pro Arg Ile
    210                 215                 220

Asp His Tyr Arg His Thr Ala Ala Gln Leu Gly Glu Lys Leu Leu Arg
225                 230                 235                 240

Pro Ser Leu Ala Glu Leu His Asp Glu Leu Glu Lys Glu Pro Phe Glu
                245                 250                 255

Asp Gly Phe Ala Asn Gly Glu Glu Ser Thr Pro Thr Arg Asp Ala Val
                260                 265                 270

Val Thr Tyr Thr Ala Glu Ser Lys Gly Val Val Lys Phe Gly Trp Ile
        275                 280                 285

Lys Gly Val Leu Val Arg Cys Met Leu Asn Ile Trp Gly Val Met Leu
            290                 295                 300

Phe Ile Arg Leu Ser Trp Ile Val Gly Gln Ala Gly Ile Gly Leu Ser
305                 310                 315                 320

Val Leu Val Ile Met Met Ala Thr Val Val Thr Thr Ile Thr Gly Leu
                325                 330                 335

Ser Thr Ser Ala Ile Ala Thr Asn Gly Phe Val Arg Gly Gly Gly Ala
            340                 345                 350

Tyr Tyr Leu Ile Ser Arg Ser Leu Gly Pro Glu Phe Gly Gly Ala Ile
        355                 360                 365

Gly Leu Ile Phe Ala Phe Ala Asn Ala Val Ala Val Ala Met Tyr Val
    370                 375                 380

Val Gly Phe Ala Glu Thr Val Val Glu Leu Leu Lys Glu His Ser Ile
385                 390                 395                 400

Leu Met Ile Asp Glu Ile Asn Asp Ile Arg Ile Ile Gly Ala Ile Thr
                405                 410                 415

Val Val Ile Leu Leu Gly Ile Ser Val Ala Gly Met Glu Trp Glu Ala
            420                 425                 430

Lys Ala Gln Ile Val Leu Leu Val Leu Leu Leu Ala Ile Gly Asp
        435                 440                 445

Phe Val Ile Gly Thr Phe Ile Pro Leu Glu Ser Lys Lys Pro Lys Gly
450                 455                 460
```

```
Phe Phe Gly Tyr Lys Ser Glu Ile Phe Asn Glu Asn Phe Gly Pro Asp
465                 470                 475                 480

Phe Arg Glu Glu Glu Thr Phe Phe Ser Val Phe Ala Ile Phe Phe Pro
            485                 490                 495

Ala Ala Thr Gly Ile Leu Ala Gly Ala Asn Ile Ser Gly Asp Leu Ala
            500                 505                 510

Asp Pro Gln Ser Ala Ile Pro Lys Gly Thr Leu Leu Ala Ile Leu Ile
            515                 520                 525

Thr Thr Leu Val Tyr Val Gly Ile Ala Val Ser Val Gly Ser Cys Val
            530                 535                 540

Val Arg Asp Ala Thr Gly Asn Val Asn Asp Thr Ile Val Thr Glu Leu
545                 550                 555                 560

Thr Asn Cys Thr Ser Ala Ala Cys Lys Leu Asn Phe Asp Phe Ser Ser
            565                 570                 575

Cys Glu Ser Ser Pro Cys Ser Tyr Gly Leu Met Asn Asn Phe Gln Val
            580                 585                 590

Met Ser Met Val Ser Gly Phe Thr Pro Leu Ile Ser Ala Gly Ile Phe
            595                 600                 605

Ser Ala Thr Leu Ser Ser Ala Leu Ala Ser Leu Val Ser Ala Pro Lys
            610                 615                 620

Ile Phe Gln Ala Leu Cys Lys Asp Asn Ile Tyr Pro Ala Phe Gln Met
625                 630                 635                 640

Phe Ala Lys Gly Tyr Gly Lys Asn Asn Glu Pro Leu Arg Gly Tyr Ile
            645                 650                 655

Leu Thr Phe Leu Ile Ala Leu Gly Phe Ile Leu Ile Ala Glu Leu Asn
            660                 665                 670

Val Ile Ala Pro Ile Ile Ser Asn Phe Phe Leu Ala Ser Tyr Ala Leu
            675                 680                 685

Ile Asn Phe Ser Val Phe His Ala Ser Leu Ala Lys Ser Pro Gly Trp
            690                 695                 700

Arg Pro Ala Phe Lys Tyr Tyr Asn Met Trp Ile Ser Leu Leu Gly Ala
705                 710                 715                 720

Ile Leu Cys Cys Ile Val Met Phe Val Ile Asn Trp Trp Ala Ala Leu
            725                 730                 735

Leu Thr Tyr Val Ile Val Leu Gly Leu Tyr Ile Tyr Val Thr Tyr Lys
            740                 745                 750

Lys Pro Asp Val Asn Trp Gly Ser Ser Thr Gln Ala Leu Thr Tyr Leu
            755                 760                 765

Asn Ala Leu Gln His Ser Ile Arg Leu Ser Gly Val Glu Asp His Val
770                 775                 780

Lys Asn Phe Arg Pro Gln Cys Leu Val Met Thr Gly Ala Pro Asn Ser
785                 790                 795                 800

Arg Pro Ala Leu Leu His Leu Val His Asp Phe Thr Lys Asn Val Gly
            805                 810                 815

Leu Met Ile Cys Gly His Val His Met Gly Pro Arg Arg Gln Ala Met
            820                 825                 830

Lys Glu Met Ser Ile Asp Gln Ala Lys Tyr Gln Arg Trp Leu Ile Lys
            835                 840                 845

Asn Lys Met Lys Ala Phe Tyr Ala Pro Val His Ala Asp Asp Leu Arg
850                 855                 860

Glu Gly Ala Gln Tyr Leu Met Gln Ala Ala Gly Leu Gly Arg Met Lys
865                 870                 875                 880

Pro Asn Thr Leu Val Leu Gly Phe Lys Lys Asp Trp Leu Gln Ala Asp
```

```
                    885                 890                 895
Met Arg Asp Val Asp Met Tyr Ile Asn Leu Phe His Asp Ala Phe Asp
                900                 905                 910

Ile Gln Tyr Gly Val Val Ile Arg Leu Lys Glu Gly Leu Asp Ile
            915                 920                 925

Ser His Leu Gln Gly Gln Glu Leu Leu Ser Ser Gln Glu Lys Ser
        930                 935                 940

Pro Gly Thr Lys Asp Val Val Ser Val Gly Tyr Ser Lys Lys Ser
945                 950                 955                 960

Asp Leu Asp Thr Ser Lys Pro Leu Ser Glu Lys Pro Ile Thr His Lys
                965                 970                 975

Val Glu Glu Glu Asp Gly Lys Thr Ala Thr Gln Pro Leu Leu Lys Lys
            980                 985                 990

Glu Ser Lys Gly Pro Ile Val Pro Leu Asn Val Ala Asp Gln Lys Leu
        995                 1000                1005

Leu Glu Ala Ser Thr Gln Phe Gln Lys Lys Gly Lys Asn Thr Ile
       1010                1015                1020

Asp Val Trp Trp Leu Phe Asp Asp Gly Gly Leu Thr Leu Leu Ile Pro
1025                1030                1035                1040

Tyr Leu Leu Thr Thr Lys Lys Lys Trp Lys Asp Cys Lys Ile Arg Val
                1045                1050                1055

Phe Ile Gly Gly Lys Ile Asn Arg Ile Asp His Asp Arg Arg Ala Met
            1060                1065                1070

Ala Thr Leu Leu Ser Lys Phe Arg Ile Asp Phe Ser Asp Ile Met Val
        1075                1080                1085

Leu Gly Asp Ile Asn Thr Lys Pro Lys Lys Glu Asn Ile Ile Ala Phe
   1090                1095                1100

Glu Glu Ile Ile Glu Pro Tyr Arg Leu His Glu Asp Asp Lys Glu Gln
1105                1110                1115                1120

Asp Ile Ala Asp Lys Met Lys Glu Asp Glu Pro Trp Arg Ile Thr Asp
                1125                1130                1135

Asn Glu Leu Glu Leu Tyr Lys Thr Lys Thr Tyr Arg Gln Ile Arg Leu
            1140                1145                1150

Asn Glu Leu Leu Lys Glu His Ser Ser Thr Ala Asn Ile Ile Val Met
        1155                1160                1165

Ser Leu Pro Val Ala Arg Lys Gly Ala Val Ser Ser Ala Leu Tyr Met
   1170                1175                1180

Ala Trp Leu Glu Ala Leu Ser Lys Asp Leu Pro Pro Ile Leu Leu Val
1185                1190                1195                1200

Arg Gly Asn His Gln Ser Val Leu Thr Phe Tyr Ser
                1205                1210

<210> SEQ ID NO 75
<211> LENGTH: 2778
<212> TYPE: DNA
<213> ORGANISM: Homo sapiens

<400> SEQUENCE: 75
gtcgacccac gcgtccggca agaagctgac gggtcgcctc atgctggccg tgggaggagc      60
agtgcttggc tccctgcagt ttggctacaa cactggagtc atcaatgccc ccagaaggt     120 gatcgaggag ttctacaacc agacatgggt ccaccgctat ggggagagca tcctgcccac     180
cacgctcacc acgctctggt ccctctcagt ggccatcttt tctgttgggg gcatgattgg     240
ctccttctct gtgggccttt tcgttaaccg ctttggccgg cggaattcaa tgctgatgat     300
```

```
gaacctgctg gccttcgtgt ccgccgtgct catgggcttc tcgaaactgg gcaagtcctt    360
tgagatgctg atcctgggcc gcttcatcat cggtgtgtac tgcggcctga ccacaggctt    420
cgtgcccatg tatgtgggtg aagtgtcacc cacagccctt cgtggggccc tgggcaccct    480
gcaccagctg ggcatcgtcg tcggcatcct catcgcccag gtgttcggcc tggactccat    540
catgggcaac aaggacctgt ggcccctgct gctgagcatc atcttcatcc cggccctgct    600
gcagtgcatc gtgctgccct tctgccccga gagtccccgc ttcctgctca tcaaccgcaa    660
cgaggagaac cgggccaaga gtgtgctaaa gaagctgcgc gggacagctg acgtgaccca    720
tgacctgcag gagatgaagg aagagagtcg gcagatgatg cggagaagaa aggtcaccat    780
cctggagctg ttccgctccc ccgcctaccg ccagcccatc ctcatcgctg tggtgctgca    840
gctgtcccag cagctgtctg gcatcaacgc tgtcttctat tactccacga gcatcttcga    900
gaaggcgggg gtgcagcagc ctgtgtatgc caccattggc tccggtatcg tcaacacggc    960
cttcactgtc gtgtcgctgt tgtggtggga gcgagcaggc cggcggaccc tgcacctcat   1020
aggcctcgct ggcatggcgg gttgtgccat actcatgacc atcgcgctag cactgctgga   1080
gcagctaccc tggatgtcct atctgagcat cgtggccatc tttggctttg tggccttctt   1140
tgaagtgggt cctggcccca tcccatggtt catcgtggct gaactcttca gccagggtcc   1200
acgtccagct gccattgccg ttgcaggctt ctccaactgg acctcaaatt tcattgtggg   1260
catgtgcttc cagtatgtgg agcaactgtg tggtccctac gtcttcatca tcttcactgt   1320
gctcctggtt ctgttcttca tcttcaccta cttcaaagtt cctgagacta aaggccggac   1380
cttcgatgag atcgcttccg gcttccggca gggggagcc agccaaagtg acaagacacc   1440
cgaggagctg ttccatcccc tggggctga ttcccaagtg tgagtcgccc cagatcacca   1500
gcccggcctg ctcccagcag ccctaaggat ctctcaggag cacaggcagc tggatgagac   1560
ttccaaacct gacagatgtc agccgagccg ggcctgggc tcctttctcc agccagcaat   1620
gatgtccaga agaatattca ggacttaacg gctccaggat tttaacaaaa gcaagactgt   1680
tgctcaaatc tattcagaca agcaacaggt tttataattt ttttattact gattttgtta   1740
tttttatatc agcctgagtc tcctgtgccc acatcccagg cttcaccctg aatggttcca   1800
tgcctgaggg tggagactaa gccctgtcga cacttgcc ttcttcaccc agctaatctg   1860
tagggctgga cctatgtcct aaggacacac taatcgaact atgaactaca aagcttctat   1920
cccaggaggt ggctatggcc acccgttctg ctggcctgga tctccccact ctagggtca   1980 ggctccatta ggatttgccc cttcccatct cttcctaccc aaccactcaa attaatcttt   2040
ctttacctga gaccagttgg gagcactgga gtgcaggag gagaggggaa gggccagtct   2100
gggctgccgg gttctagtct cctttgcact gagggccaca ctattaccat gagaagaggg   2160
cctgtgggag cctgcaaact cactgctcaa gaagacatgg agactcctgc cctgttgtgt   2220
atagatgcaa gatatttata tatatttttg gttgtcaata ttaaatacag acactaagtt   2280
atagtatatc tggacaagcc aacttgtaaa tacaccacct cactcctgtt acttacctaa   2340
acagatataa atggctggtt tttagaaaca tggttttgaa atgcttgtgg attgagggta   2400
ggaggtttgg atgggagtga gacagaagta agtggggttg caaccactgc aacggcttag   2460
acttcgactc aggatccagt cccttacacg tacctctcat cagtgtcctc ttgctcaaaa   2520
atctgtttga tccctgttac ccagagaata tatacattct ttatcttgac attcaaggca   2580
tttctatcac atatttgata gttggtgttc aaaaaaacac tagttttgtg ccagccgtga   2640
tgctcaggct tgaaatgcat tatttttgaat gtgaagtaaa tactgtaccct ttattggaca   2700
```

```
ggctcaaaaa aaaaaaaaaa aaaaaaaaaa aaaaaaaaaa aaaaaaaaaa aaaaaaaaaa    2760
aaaaaaaagg gcggccgc                                                   2778
```

<210> SEQ ID NO 76
<211> LENGTH: 480
<212> TYPE: PRT
<213> ORGANISM: Homo sapiens

<400> SEQUENCE: 76

```
Met Leu Ala Val Gly Gly Ala Val Leu Gly Ser Leu Gln Phe Gly Tyr
 1               5                   10                  15

Asn Thr Gly Val Ile Asn Ala Pro Gln Lys Val Ile Glu Glu Phe Tyr
            20                  25                  30

Asn Gln Thr Trp Val His Arg Tyr Gly Glu Ser Ile Leu Pro Thr Thr
        35                  40                  45

Leu Thr Thr Leu Trp Ser Leu Ser Val Ala Ile Phe Ser Val Gly Gly
    50                  55                  60

Met Ile Gly Ser Phe Ser Val Gly Leu Phe Val Asn Arg Phe Gly Arg
65                  70                  75                  80

Arg Asn Ser Met Leu Met Met Asn Leu Leu Ala Phe Val Ser Ala Val
                85                  90                  95

Leu Met Gly Phe Ser Lys Leu Gly Lys Ser Phe Glu Met Leu Ile Leu
            100                 105                 110

Gly Arg Phe Ile Ile Gly Val Tyr Cys Gly Leu Thr Thr Gly Phe Val
        115                 120                 125

Pro Met Tyr Val Gly Glu Val Ser Pro Thr Ala Leu Arg Gly Ala Leu
    130                 135                 140

Gly Thr Leu His Gln Leu Gly Ile Val Val Gly Ile Leu Ile Ala Gln
145                 150                 155                 160

Val Phe Gly Leu Asp Ser Ile Met Gly Asn Lys Asp Leu Trp Pro Leu
                165                 170                 175

Leu Leu Ser Ile Ile Phe Ile Pro Ala Leu Leu Gln Cys Ile Val Leu
            180                 185                 190

Pro Phe Cys Pro Glu Ser Pro Arg Phe Leu Leu Ile Asn Arg Asn Glu
        195                 200                 205

Glu Asn Arg Ala Lys Ser Val Leu Lys Lys Leu Arg Gly Thr Ala Asp
    210                 215                 220

Val Thr His Asp Leu Gln Glu Met Lys Glu Glu Ser Arg Gln Met Met
225                 230                 235                 240

Arg Glu Lys Lys Val Thr Ile Leu Glu Leu Phe Arg Ser Pro Ala Tyr
                245                 250                 255

Arg Gln Pro Ile Leu Ile Ala Val Val Leu Gln Leu Ser Gln Gln Leu
            260                 265                 270

Ser Gly Ile Asn Ala Val Phe Tyr Tyr Ser Thr Ser Ile Phe Glu Lys
        275                 280                 285

Ala Gly Val Gln Gln Pro Val Tyr Ala Thr Ile Gly Ser Gly Ile Val
    290                 295                 300

Asn Thr Ala Phe Thr Val Val Ser Leu Phe Val Val Glu Arg Ala Gly
305                 310                 315                 320

Arg Arg Thr Leu His Leu Ile Gly Leu Ala Gly Met Ala Gly Cys Ala
                325                 330                 335

Ile Leu Met Thr Ile Ala Leu Ala Leu Leu Glu Gln Leu Pro Trp Met
            340                 345                 350

Ser Tyr Leu Ser Ile Val Ala Ile Phe Gly Phe Val Ala Phe Phe Glu
        355                 360                 365
```

```
Val Gly Pro Gly Pro Ile Pro Trp Phe Ile Val Ala Glu Leu Phe Ser
    370                 375                 380

Gln Gly Pro Arg Pro Ala Ala Ile Ala Val Ala Gly Phe Ser Asn Trp
385                 390                 395                 400

Thr Ser Asn Phe Ile Val Gly Met Cys Phe Gln Tyr Val Glu Gln Leu
                405                 410                 415

Cys Gly Pro Tyr Val Phe Ile Phe Thr Val Leu Leu Val Leu Phe
                420                 425                 430

Phe Ile Phe Thr Tyr Phe Lys Val Pro Glu Thr Lys Gly Arg Thr Phe
            435                 440                 445

Asp Glu Ile Ala Ser Gly Phe Arg Gln Gly Gly Ala Ser Gln Ser Asp
            450                 455                 460

Lys Thr Pro Glu Glu Leu Phe His Pro Leu Gly Ala Asp Ser Gln Val
465                 470                 475                 480

<210> SEQ ID NO 77
<211> LENGTH: 2473
<212> TYPE: DNA
<213> ORGANISM: Homo sapiens

<400> SEQUENCE: 77
gtcgacccac gcgtccgcgc gaggcgcggg gagcctggga ccaggagcga gagccgccta      60
cctgcagccg ccgcccacgg cacggcagcc accatggcgc tcctgctgtg cttcgtgctc     120
ctgtgcggag tagtggattt cgccagaagt ttgagtatca ctactcctga agagatgatt     180
gaaaaagcca aggggaaac tgcctatctg ccatgcaaat ttacgcttag tcccgaagac      240
cagggaccgc tggacatcga gtggctgata tcaccagctg ataatcagaa ggtggatcaa     300
gtgattattt tatattctgg agacaaaatt tatgatgact actatccaga tctgaaaggc     360
cgagtacatt ttacgagtaa tgatctcaaa tctggtgatg catcaataaa tgtaacgaat     420
ttacaactgt cagatattgg cacatatcag tgcaaagtga aaaagctcc tggtgttgca     480 aataagaaga ttcatctggt agttcttgtt aagccttcag gtgcgagatg ttacgttgat     540
ggatctgaag aaattggaag tgactttaag ataaaatgtg aaccaaaaga aggttcactt     600
ccattacagt atgagtggca aaaattgtct gactcacaga aaatgcccac ttcatggtta     660
gcagaaatga cttcatctgt tatatctgta aaaaatgcct cttctgagta ctctgggaca     720
tacagctgta cagtcagaaa cagagtgggc tctgatcagt gcctgttgcg tctaaacgtt     780
gtccctcctt caaataaagc tggactaatt gcaggagcca ttataggaac tttgcttgct     840
ctagcgctca ttggtcttat catcttttgc tgtcgtaaaa agcgcagaga agaaaaatat     900
gaaaaggaag ttcatcacga tatcaggaa gatgtgccac ctccaaagag ccgtacgtcc      960
actgccagaa gctacatcgg cagtaatcat tcatccctgg ggtccatgtc tccttccaac    1020
atggaaggat attccaagac tcagtataac caagtaccaa gtgaagactt tgaacgcact    1080
cctcagagtc cgactctccc acctgctaag gtagctgccc ctaatctaag tcgaatgggt    1140
gcgattcctg tgatgattcc agcacagagc aaggatgggt ctatagtata gagcctccat    1200
atgtctcatc tgtgctctcc gtgttccttt ccttttttg atatatgaaa acctattctg     1260
gtctaaattg tgttactagc ctcaaaatac atcaaaaaat aagttaatca ggaactgtac    1320
ggaatatatt tttaaaaatt tttgtttggt tatatcaaaa tagttacagg cactaaagtt    1380
agtaaagaaa agtttaccat ctgaaaaagc tggattttct ttaagaggtt gattataaag    1440
ttttctaaat ttatcagtac ctaagtaaga tgtagcgctt tgaatatgaa atcataggtg    1500
```

-continued

```
aagacatggg tgaacttact tgcataccaa gttgatactt gaataaccat ctgaaagtgg    1560
tacttgatca ttttaccat tattttagg atgtgtattt catttattta tggcccacca     1620
gtctccccca aattagtaca gaaatatcca tgacaaaatt acttacgtat gtttgtactt    1680
ggttttacag ctcctttgaa aactctgtgt ttggaatatc tctaaaaaca tagaaaacac    1740
tacagtggtt tagaaattac taattttact tctaagtcat tcataaacct tgtctatgaa    1800
atgacttctt aaatatttag ttgatagact gctacaggta atagggactt agcaagctct    1860
tttatatgct aaaggagcat ctatcagatt aagttagaac atttgctgtc agccacatat    1920
tgagatgaca ctaggtgcaa tagcagggat agattttgtt ggtgagtagt ctcatgcctt    1980
gagatctgtg gtggtcttca aaatggtggc cagccagatc aaggatgtag tatctcatag    2040
ttcccaggtg atattttct tattagaaaa atattataac tcatttgttg tttgacactt     2100
atagattgaa atttcctaat ttattctaaa ttttaagtgg ttctttggtt ccagtgctttt   2160 atgttgttgt tgtttttgga tggtgttaca tattatatgt tctagaaaca tgtaatccta    2220 aatttacccct cttgaatata atccctggat gatattttt atcataaatg cagaataatc    2280
aaatacattt taagcaagtt aagtgtcctc catcaattct gtattccaga cttgggagga    2340
tgtacagttg ctgttgtgtg atcaaacatg tctctgtgta gttccagcaa atcaagctga    2400
gctttgaaaa agtttgtctt agttttgtga aggtgattta ttcttaaaaa aaaaaaaaa     2460 aaagggcggc cgc                                                       2473
```

<210> SEQ ID NO 78
<211> LENGTH: 365
<212> TYPE: PRT
<213> ORGANISM: Homo sapiens

<400> SEQUENCE: 78

```
Met Ala Leu Leu Leu Cys Phe Val Leu Leu Cys Gly Val Val Asp Phe
  1               5                  10                  15

Ala Arg Ser Leu Ser Ile Thr Thr Pro Glu Glu Met Ile Glu Lys Ala
                 20                  25                  30

Lys Gly Glu Thr Ala Tyr Leu Pro Cys Lys Phe Thr Leu Ser Pro Glu
             35                  40                  45

Asp Gln Gly Pro Leu Asp Ile Glu Trp Leu Ile Ser Pro Ala Asp Asn
         50                  55                  60

Gln Lys Val Asp Gln Val Ile Ile Leu Tyr Ser Gly Asp Lys Ile Tyr
 65                  70                  75                  80

Asp Asp Tyr Tyr Pro Asp Leu Lys Gly Arg Val His Phe Thr Ser Asn
                 85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205
```

```
Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
            260                 265                 270

Val His His Asp Ile Arg Glu Asp Val Pro Pro Lys Ser Arg Thr
    275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
            340                 345                 350

Val Met Ile Pro Ala Gln Ser Lys Asp Gly Ser Ile Val
            355                 360                 365

<210> SEQ ID NO 79
<211> LENGTH: 1588
<212> TYPE: DNA
<213> ORGANISM: Homo sapiens

<400> SEQUENCE: 79
gtcgacccac gcgtccggca gcagcagcca ggtgtggcag tgacagggag gtgtgaatga      60
ggcaggatga actggacagg tttgtacacc ttgctcagtg gcgtgaaccg gcattctact     120
gccattggcc gagtatggct ctcggtcatc ttcatcttca gaatcatggt gctggtggtg     180
gctgcagaga gtgtgtgggg tgatgagaaa tcttccttca tctgcaacac actccagcct     240
ggctgcaaca cgctttgcta tgaccaattc ttccccatct cccatgtgcg gctgtggtcc     300
ctgcagctca tcctagtttc caccccagct ctcctcgtgg ccatgcacgt ggctcaccag     360
caacacatag agaagaaaat gctacggctt gagggccatg ggacccccct acacctggag     420
gaggtgaaga ggcacaaggt ccacatctca gggacactgt ggtggaccta tgtcatcagc     480
gtggtgttcc ggctgttgtt tgaggccgtc ttcatgtatg tcttttatct gctctaccct     540
ggctatgcca tggtgcggct ggtcaagtgc gacgtctacc cctgccccaa cacagtggac     600
tgcttcgtgt cccgccccac cgagaaaacc gtcttcaccg tcttcatgct agctgcctct     660
ggcatctgca tcatcctcaa tgtggccgag gtggtgtacc tcatcatccg gcctgtgcc      720
cgccgagccc agcgccgctc caatccacct tcccgcaagg gctcgggctt cggccaccgc     780
ctctcacctg aatacaagca gaatgagatc aacaagctgc tgagtgagca ggatggctcc     840
ctgaaagaca tactcgcgcc cagccctggc accggggctg gctggctga aaagagcgac     900
cgctgctcgg cctgctgatg ccacatacca ggcaacctcc catcccaccc ccgaccctgc     960
cctgggcgag cccctccttc tcccctgccg gtgcacaggc ctctgcctgc tggggattac    1020
tcgatcaaaa ccttccttcc ctggctactt cccttcctcc cggggccttc cttttgagga    1080
gctggagggg tggggagcta gaggccacct atgccagtgc tcaaggttac tgggagtgtg    1140
ggctgccctt gttgctgca  cccttccctc ttccctctcc ctctctctgg gaccactggg    1200
tacaagagat gggatgctcc gacagcgtct ccaattatga aactaatctt aaccctgtgc    1260
```

```
tgtcagatac cctgtttctg gagtcacatc agtgaggagg gatgtgggta agaggagcag    1320
agggcagggg tgctgtggac atgtgggtgg agaagggagg gtggccagca ctagtaaagg    1380
aggaatagtg cttgctggcc acaaggaaaa ggaggaggtg tctggggtga gggagttagg    1440
gagagagaag caggcagata agttggagca ggggttggtc aaggccacct ctgcctctag    1500
tccccaaggc ctctctctgc ctgaaatgtt acacattaaa caggatttta cagtaaatga    1560
aaaaaaaaaa aaaaaaaagg gcggccgc                                       1588
```

<210> SEQ ID NO 80
<211> LENGTH: 283
<212> TYPE: PRT
<213> ORGANISM: Homo sapiens

<400> SEQUENCE: 80

```
Met Asn Trp Thr Gly Leu Tyr Thr Leu Leu Ser Gly Val Asn Arg His
  1               5                  10                  15

Ser Thr Ala Ile Gly Arg Val Trp Leu Ser Val Ile Phe Ile Phe Arg
             20                  25                  30

Ile Met Val Leu Val Val Ala Ala Glu Ser Val Trp Gly Asp Glu Lys
         35                  40                  45

Ser Ser Phe Ile Cys Asn Thr Leu Gln Pro Gly Cys Asn Ser Val Cys
     50                  55                  60

Tyr Asp Gln Phe Phe Pro Ile Ser His Val Arg Leu Trp Ser Leu Gln
 65                  70                  75                  80

Leu Ile Leu Val Ser Thr Pro Ala Leu Leu Val Ala Met His Val Ala
                 85                  90                  95

His Gln Gln His Ile Glu Lys Lys Met Leu Arg Leu Glu Gly His Gly
            100                 105                 110

Asp Pro Leu His Leu Glu Glu Val Lys Arg His Lys Val His Ile Ser
        115                 120                 125

Gly Thr Leu Trp Trp Thr Tyr Val Ile Ser Val Val Phe Arg Leu Leu
    130                 135                 140

Phe Glu Ala Val Phe Met Tyr Val Phe Tyr Leu Leu Tyr Pro Gly Tyr
145                 150                 155                 160

Ala Met Val Arg Leu Val Lys Cys Asp Val Tyr Pro Cys Pro Asn Thr
                165                 170                 175

Val Asp Cys Phe Val Ser Arg Pro Thr Glu Lys Thr Val Phe Thr Val
            180                 185                 190

Phe Met Leu Ala Ala Ser Gly Ile Cys Ile Ile Leu Asn Val Ala Glu
        195                 200                 205

Val Val Tyr Leu Ile Ile Arg Ala Cys Ala Arg Arg Ala Gln Arg Arg
    210                 215                 220

Ser Asn Pro Pro Ser Arg Lys Gly Ser Gly Phe Gly His Arg Leu Ser
225                 230                 235                 240

Pro Glu Tyr Lys Gln Asn Glu Ile Asn Lys Leu Leu Ser Glu Gln Asp
                245                 250                 255

Gly Ser Leu Lys Asp Ile Leu Arg Arg Ser Pro Gly Thr Gly Ala Gly
            260                 265                 270

Leu Ala Glu Lys Ser Asp Arg Cys Ser Ala Cys
        275                 280
```

<210> SEQ ID NO 81
<211> LENGTH: 3337
<212> TYPE: DNA
<213> ORGANISM: Homo sapiens

```
<400> SEQUENCE: 81
gtcgacccac gcgtccggag ccagctctcc cgagcccgta accttcgcat cccaagagct      60
gcagtttcag ccgcgacagc aagaacggca gagccggcga ccgcggcggc ggcggcggcg     120
gaggcaggag cagcctgggc gggtcgcagg gtctccgcgg gcgcaggaag gcgagcagag     180
atatcctctg agagccaagc aaagaacatt aaggaaggaa ggaggaatga ggctggatac     240
ggtgcagtga aaaaggcact tccaagagtg gggcactcac tacgcacaga ctcgacggtg     300
ccatcagcat gagaacttac cgctacttct tgctgctctt ttgggtgggc cagccctacc     360
caactctctc aactccacta tcaaagagga ctagtggttt cccagcaaag aaaagggccc     420
tggagctctc tggaaacagc aaaaatgagc tgaaccgttc aaaaaggagc tggatgtgga     480
atcagttctt tctcctggag aatacacag gatccgatta tcagtatgtg ggcaagttac     540
attcagacca ggatagagga gatggatcac ttaaatatat cctttcagga gatggagcag     600
gagatctctt cattattaat gaaaacacag gcgacataca ggccaccaag aggctggaca     660
gggaagaaaa acccgtttac atccttcgag ctcaagctat aaacagaagg acaggagac     720
ccgtggagcc cgagtctgaa ttcatcatca agatccatga catcaatgac aatgaaccaa     780
tattcaccaa ggaggtttac acagccactg tccctgaaat gtctgatgtc ggtacatttg     840
ttgtccaagt cactgcgacg gatgcagatg atccaacata tgggaacagt gctaaagttg     900
tctacagtat tctacaggga cagccctatt tttcagttga atcagaaaca ggtattatca     960
agacagcttt gctcaacatg gatcgagaaa cagggagca gtaccaagtg gtgattcaag    1020
ccaaggatat gggcggccag atgggaggat tatctgggac caccaccgtg aacatcacac    1080
tgactgatgt caacgacaac cctccccgat ccccccagag tacataccag tttaaaactc    1140
ctgaatcttc tccaccgggg acaccaattg gcagaatcaa agccagcgac gctgatgtgg    1200
gagaaaatgc tgaaattgag tacagcatca cagacggtga ggggctggat atgtttgatg    1260
tcatcaccga ccaggaaacc caggaaggga ttataactgt caaaaagctc ttggactttg    1320
aaaagaagaa agtgtatacc cttaaagtgg aagcctccaa tccttatgtt gagccacgat    1380
ttctctactt ggggcctttc aaagattcag ccacggttag aattgtggtg gaggatgtag    1440
atgagccacc tgtcttcagc aaactggcct acatcttaca aataagagaa gatgctcaga    1500
taaacaccac aataggctcc gtcacagccc aagatccaga tgctgccagg aatcctgtca    1560
agtactctgt agatcgacac acagatatgg acagaatatt caacattgat tctggaaatg    1620
gttcgatttt tacatcgaaa cttcttgacc gagaaacact gctatggcac aacattacag    1680
tgatagcaac agagatcaat aatccaaagc aaagtagtcg agtacctcta tatattaaag    1740
ttctagatgt caatgacaac gccccagaat tgctgagtt ctatgaaact tttgtctgtg    1800
aaaaagcaaa ggcagatcag ttgattcaga ccctgcatgc tgttgacaag gatgacccctt   1860
atagtggaca ccaattttcg ttttccttgg cccctgaagc agccagtggc tcaaacttta    1920
ccattcaaga caacaaagac aacacggcgg gaatcttaac tcggaaaaat ggctataata    1980
gacacgagat gagcacctat ctcttgcctg tggtcatttc agacaacgac tacccagttc    2040
aaagcagcac tgggacagtg actgtccggg tctgtgcatg tgaccaccac gggaacatgc    2100
aatcctgcca tgcggaggcg ctcatccacc ccacgggact gagcacgggg gctctggttg    2160
ccatccttct gtgcatcgtg atcctactag tgacagtggt gctgtttgca gctctgaggc    2220
ggcagcgaaa aaaagagcct ttgatcattt ccaaagagga catcagagat aacattgtca    2280
gttacaacga cgaaggtggt ggagaggagg acacccaggc ttttgatatc ggcaccctga    2340
```

-continued

```
ggaatcctga agccatagag acaacaaat tacgaaggga cattgtgccc gaagcccttt      2400
tcctaccccg acggactcca acagctcgcg acaacaccga tgtcagagat ttcattaacc      2460
aaaggttaaa ggaaaatgac acggacccca ctgccccgcc atacgactcc ttggccactt      2520
acgcctatga aggcactggc tccgtggcgg attccctgag ctcgctggag tcagtgacca      2580
cggatgcaga tcaagactat gattaccta gtgactgggg acctcgattc aaaaagcttg      2640
cagatatgta tggaggagtg acagtgaca aagactccta atctgttgcc tttttcattt      2700
tccaatacga cactgaaata tgtgaagtgg ctatttcttt atatttatcc actactccgt      2760
gaaggcttct ctgttctacc cgttccaaaa gccaatggct gcagtccgtg tggatccaat      2820
gttagagact tttttctagt acacttttat gagcttccaa ggggcaaatt tttatttttt      2880
agtgcatcca gttaaccaag tcagcccaac aggcaggtgc cggaggggag gacagggaac      2940
agtatttcca cttgttctca gggcagcgtg cccgcttccg ctgtcctggt gttttactac      3000
actccatgtc aggtcagcca actgccctaa ctgtacattt cacaggctaa tgggataaag      3060
gactgtgctt taaagataaa aatatcatca tagtaaaaga aatgagggca tatcggctca      3120
caaagagata aactacatag gggtgtttat ttgtgtcaca aagaatttaa aataacactt      3180
gcccatgcta tttgttcttc aagaactttc tctgccatca actactattc aaaacctcaa      3240
atccacccat atgttaaaat tctcattact cttaaggaat agaagcaaat taaacggtaa      3300
catccaaaag caaaaaaaaa aaaaaaaggg cggccgc                                3337
```

<210> SEQ ID NO 82
<211> LENGTH: 790
<212> TYPE: PRT
<213> ORGANISM: Homo sapiens

<400> SEQUENCE: 82

```
Met Arg Thr Tyr Arg Tyr Phe Leu Leu Leu Phe Trp Val Gly Gln Pro
  1               5                  10                  15

Tyr Pro Thr Leu Ser Thr Pro Leu Ser Lys Arg Thr Ser Gly Phe Pro
             20                  25                  30

Ala Lys Lys Arg Ala Leu Glu Leu Ser Gly Asn Ser Lys Asn Glu Leu
         35                  40                  45

Asn Arg Ser Lys Arg Ser Trp Met Trp Asn Gln Phe Phe Leu Leu Glu
     50                  55                  60

Glu Tyr Thr Gly Ser Asp Tyr Gln Tyr Val Gly Lys Leu His Ser Asp
 65                  70                  75                  80

Gln Asp Arg Gly Asp Gly Ser Leu Lys Tyr Ile Leu Ser Gly Asp Gly
                 85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
    130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
```

```
              195                 200                 205
Ser Val Glu Ser Glu Thr Gly Ile Ile Lys Thr Ala Leu Leu Asn Met
210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
        275                 280                 285

Arg Ile Lys Ala Ser Asp Ala Asp Val Gly Glu Asn Ala Glu Ile Glu
        290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

Tyr Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
        370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
                405                 410                 415

Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
        435                 440                 445

Glu Thr Leu Leu Trp His Asn Ile Thr Val Ile Ala Thr Glu Ile Asn
        450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
        530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
        610                 615                 620
```

```
Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
            645                 650                 655

Val Ser Tyr Asn Asp Glu Gly Gly Glu Glu Asp Thr Gln Ala Phe
        660                 665                 670

Asp Ile Gly Thr Leu Arg Asn Pro Glu Ala Ile Glu Asp Asn Lys Leu
            675                 680                 685

Arg Arg Asp Ile Val Pro Glu Ala Leu Phe Leu Pro Arg Arg Thr Pro
690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Ala Asp Gln Asp Tyr Asp Tyr Leu Ser
            755                 760                 765

Asp Trp Gly Pro Arg Phe Lys Lys Leu Ala Asp Met Tyr Gly Gly Val
770                 775                 780

Asp Ser Asp Lys Asp Ser
785             790

<210> SEQ ID NO 83
<211> LENGTH: 1070
<212> TYPE: DNA
<213> ORGANISM: Homo sapiens

<400> SEQUENCE: 83
gtcgacccac gcgtccgctt tgggtgaccg gaaaactcca cctcaagttt tctttttgtgg      60 ggctgccccc caagtgtcgt ttgtttact gtagggtctc ccgcccggcg cccccagtgt      120
tttctgaggg cggaaatggc caattcgggc ctgcagttgc tgggcttctc catggccctg      180
ctgggctggg tgggtctggt ggcctgcacc gccatcccgc agtggcagat gagctcctat      240
gcgggtgaca acatcatcac ggcccaggcc atgtacaagg gctgtggat ggactgcgtc      300 acgcagagca cggggatgat gagctgcaaa atgtacgact cggtgctcgc cctgtccgcg      360
gccttgcagg ccactcgagc cctaatggtg gtctccctgg tgctgggctt cctggccatg      420
tttgtggcca cgatgggcat gaagtgcacg cgctgtgggg gagacgacaa agtgaagaag      480
gcccgtatag ccatgggtgg aggcataatt ttcatcgtgg caggtcttgc cgccttggta      540
gcttgctcct ggtatggcca tcagattgtc acagactttt ataacccttt gatccctacc      600
aacattaagt atgagtttgg ccctgccatc tttattggct gggcagggtc tgccctagtc      660
atcctgggag gtgcactgct ctcctgttcc tgtcctggga atgagagcaa ggctgggtac      720
cgtgcacccc gctcttaccc taagtccaac tcttccaagg agtatgtgtg acctgggatc      780
tccttgcccc agcctgacag gctatgggag tgtctagatg cctgaaaggg cctggggctg      840
agctcagcct gtgggcaggg tgccggacaa aggcctcctg gtcactctgt ccctgcactc      900
catgtatagt cctcttgggt tgggggtggg gggtgccgt tggtgggaga gacaaaaaga      960
gggagagtgt gcttttttgta cagtaataaa aaataagtat tgggaagcag gcaaaaaaaa      1020
aaaaaaaaaa aaaaaaaaaa aaaaaaaaaa aaaaaaaaa gggcggccgc      1070

<210> SEQ ID NO 84
<211> LENGTH: 211
```

```
<212> TYPE: PRT
<213> ORGANISM: Homo sapiens

<400> SEQUENCE: 84

Met Ala Asn Ser Gly Leu Gln Leu Leu Gly Phe Ser Met Ala Leu Leu
 1               5                  10                  15

Gly Trp Val Gly Leu Val Ala Cys Thr Ala Ile Pro Gln Trp Gln Met
            20                  25                  30

Ser Ser Tyr Ala Gly Asp Asn Ile Ile Thr Ala Gln Ala Met Tyr Lys
        35                  40                  45

Gly Leu Trp Met Asp Cys Val Thr Gln Ser Thr Gly Met Met Ser Cys
 50                  55                  60

Lys Met Tyr Asp Ser Val Leu Ala Leu Ser Ala Ala Leu Gln Ala Thr
65                  70                  75                  80

Arg Ala Leu Met Val Val Ser Leu Val Leu Gly Phe Leu Ala Met Phe
                85                  90                  95

Val Ala Thr Met Gly Met Lys Cys Thr Arg Cys Gly Gly Asp Asp Lys
            100                 105                 110

Val Lys Lys Ala Arg Ile Ala Met Gly Gly Gly Ile Ile Phe Ile Val
        115                 120                 125

Ala Gly Leu Ala Ala Leu Val Ala Cys Ser Trp Tyr Gly His Gln Ile
130                 135                 140

Val Thr Asp Phe Tyr Asn Pro Leu Ile Pro Thr Asn Ile Lys Tyr Glu
145                 150                 155                 160

Phe Gly Pro Ala Ile Phe Ile Gly Trp Ala Gly Ser Ala Leu Val Ile
                165                 170                 175

Leu Gly Gly Ala Leu Leu Ser Cys Ser Cys Pro Gly Asn Glu Ser Lys
            180                 185                 190

Ala Gly Tyr Arg Ala Pro Arg Ser Tyr Pro Lys Ser Asn Ser Ser Lys
        195                 200                 205

Glu Tyr Val
    210

<210> SEQ ID NO 85
<211> LENGTH: 1733
<212> TYPE: DNA
<213> ORGANISM: Homo sapiens

<400> SEQUENCE: 85
gtcgacccac gcgtccgctg ggtcctgcct tcgacaccac cccaaggctt cctaccttgc     60
gtgcctggag tctgccccag gggcccttgt cctgggccat ggcccagaag ggggtcctgg    120
ggcctgggca gctgggggct gtggccattc tgctctatct tggattactc cggtcaggga    180
caggagcgga aggggcagaa gctccctgcg gtgtggcccc caagcacgc  atcacaggtg    240 gcagcagtgc agtcgccggt cagtggccct ggcaggtcag catcacctat gaaggcgtcc    300
atgtgtgtgg tggctctctc gtgtctgagc agtgggtgct gtcagctgct cactgcttcc    360
ccagcgagca ccacaaggaa gcctatgagg tcaagctggg ggcccaccag ctagactcct    420
actccgagga cgccaaggtc agcaccctga aggacatcat ccccacccc  agctacctcc    480 aggagggctc ccagggcgac attgcactcc tccaactcag cagacccatc accttctccc    540
gctacatccg gccatctgc  ctccctgcag ccaacgcctc cttccccaac ggcctccact    600
gcactgtcac tggctgggt  catgtggccc cctcagtgag cctcctgacg cccaagccac    660
tgcagcaact cgaggtgcct ctgatcagtc gtgagacgtg taactgcctg tacaacatcg    720
acgccaagcc tgaggagccg cactttgtcc aagaggacat ggtgtgtgct ggctatgtgg    780
```

```
agggggggcaa ggacgcctgc cagggtgact ctgggggccc actctcctgc cctgtggagg    840
gtctctggta cctgacgggc attgtgagct ggggagatgc ctgtggggcc cgcaacaggc    900
ctggtgtgta cactctggcc tccagctatg cctcctggat ccaaagcaag gtgacagaac    960
tccagcctcg tgtggtgccc caaacccagg agtcccagcc cgacagcaac ctctgtggca   1020
gccacctggc cttcagctct gccccagccc agggcttgct gaggcccatc cttttcctgc   1080
ctctgggcct ggctctgggc ctcctctccc catggctcag cgagcactga gctggcccta   1140
cttccaggat ggatgcatca cactcaagga caggagcctg gtccttccct gatggccttt   1200
ggacccaggg cctgacttga gccactcctt ccttcaggac tctgcgggag ctggggccc    1260 catcttgatc tttgagccca ttcttctggg tgtgcttttt gggaccatca ctgagagtca   1320
ggagttttac tgcctgtagc aatggccaga gcctctggcc cctcacccac catggaccag   1380
cccattggcc gagctcctgg ggagctcctg gacccttggg ctatgaaaat gagccctggc   1440
tcccacctgt ttctggaaga ctgctcccgg cccgcctgcc cagactgatg agcacatctc   1500
tctgccctct ccctgtgttc tgggctgggg ccacctttgt gcagcttcga ggacaggaaa   1560
ggccccaatc ttgcccactg gccgctgagc gcccccgagc cctgactcct ggactccgga   1620
ggactgagcc cccaccggaa ctgggctggc gcttggatct ggggtgggag taacagggca   1680
gaaatgatta aatgtttga gcacaaaaaa aaaaaaaaaa aaagggcggc cgc            1733
```

<210> SEQ ID NO 86
<211> LENGTH: 343
<212> TYPE: PRT
<213> ORGANISM: Homo sapiens

<400> SEQUENCE: 86

```
Met Ala Gln Lys Gly Val Leu Gly Pro Gly Gln Leu Gly Ala Val Ala
 1               5                  10                  15

Ile Leu Leu Tyr Leu Gly Leu Leu Arg Ser Gly Thr Gly Ala Glu Gly
             20                  25                  30

Ala Glu Ala Pro Cys Gly Val Ala Pro Gln Ala Arg Ile Thr Gly Gly
         35                  40                  45

Ser Ser Ala Val Ala Gly Gln Trp Pro Trp Gln Val Ser Ile Thr Tyr
     50                  55                  60

Glu Gly Val His Val Cys Gly Gly Ser Leu Val Ser Glu Gln Trp Val
 65                  70                  75                  80

Leu Ser Ala Ala His Cys Phe Pro Ser Glu His His Lys Glu Ala Tyr
                 85                  90                  95

Glu Val Lys Leu Gly Ala His Gln Leu Asp Ser Tyr Ser Glu Asp Ala
            100                 105                 110

Lys Val Ser Thr Leu Lys Asp Ile Ile Pro His Pro Ser Tyr Leu Gln
        115                 120                 125

Glu Gly Ser Gln Gly Asp Ile Ala Leu Leu Gln Leu Ser Arg Pro Ile
    130                 135                 140

Thr Phe Ser Arg Tyr Ile Arg Pro Ile Cys Leu Pro Ala Ala Asn Ala
145                 150                 155                 160

Ser Phe Pro Asn Gly Leu His Cys Thr Val Thr Gly Trp Gly His Val
                165                 170                 175

Ala Pro Ser Val Ser Leu Leu Thr Pro Lys Pro Leu Gln Gln Leu Glu
            180                 185                 190

Val Pro Leu Ile Ser Arg Glu Thr Cys Asn Cys Leu Tyr Asn Ile Asp
        195                 200                 205
```

```
Ala Lys Pro Glu Glu Pro His Phe Val Gln Glu Asp Met Val Cys Ala
    210                 215                 220
Gly Tyr Val Glu Gly Lys Asp Ala Cys Gln Gly Asp Ser Gly Gly
225                 230                 235                 240
Pro Leu Ser Cys Pro Val Glu Gly Leu Trp Tyr Leu Thr Gly Ile Val
                245                 250                 255
Ser Trp Gly Asp Ala Cys Gly Ala Arg Asn Arg Pro Gly Val Tyr Thr
            260                 265                 270
Leu Ala Ser Ser Tyr Ala Ser Trp Ile Gln Ser Lys Val Thr Glu Leu
        275                 280                 285
Gln Pro Arg Val Val Pro Gln Thr Gln Glu Ser Gln Pro Asp Ser Asn
    290                 295                 300
Leu Cys Gly Ser His Leu Ala Phe Ser Ser Ala Pro Ala Gln Gly Leu
305                 310                 315                 320
Leu Arg Pro Ile Leu Phe Leu Pro Leu Gly Leu Ala Leu Gly Leu Leu
                325                 330                 335
Ser Pro Trp Leu Ser Glu His
            340

<210> SEQ ID NO 87
<211> LENGTH: 4188
<212> TYPE: DNA
<213> ORGANISM: Homo sapiens
<220> FEATURE:
<221> NAME/KEY: misc_feature
<222> LOCATION: 3457, 3481, 3707, 3716, 3723, 3733, 3736, 3746, 3751,
      3828, 3853, 3857, 3863, 3883, 3890, 4126
<223> OTHER INFORMATION: n = A,T,C or G

<400> SEQUENCE: 87
ggctccttac ccacccggag acttttttttt gaaaggaaac tagggaggga gggagaggga      60
gagagggaga aaacgaaggg gagctcgtcc atccattgaa gcacagttca ctatgatctt     120
actcacattc agcactggaa gacggttgga tttcgtgcat cattcggggg tgttttctct     180
gcaaaccttg ctttggatttt tatgtgctac agtctgcgga acggagcagt atttcaatgt    240 ggaggttttgg ttacaaaagt acggctacct tccaccgact gaccccagaa tgtcagtgct   300
gcgctctgca gagaccatgc agtctgccct agctgccatg cagcagttct atggcattaa    360
catgacagga aaagtggaca gaaacacaat tgactggatg aagaagcccc gatgcggtgt    420
acctgaccag acaagaggta gctccaaatt tcatattcgt cgaaagcgat atgcattgac    480
aggacagaaa tggcagcaca gcacatcac ttacagtata aagaacgtaa ctccaaaagt     540
aggagaccct gagactcgta aagctattcg ccgtgccttt gatgtgtggc agaatgtaac    600
tcctctgaca tttgaagaag ttccctacag tgaattagaa aatggcaaac gtgatgtgga    660
tataaccatt attttttgcat ctggtttcca tggggacagc tctcccttttg atggagaggg  720 aggattttttg gcacatgcct acttccctgg accaggaatt ggaggagata cccatttttga  780 ctcagatgag ccatggacac taggaaatcc taatcatgat ggaaatgact tatttcttgt    840
agcagtccat gaactgggac atgctctggg attggagcat tccaatgacc ccactgccat    900
catggctcca ttttaccagt acatggaaac agacaacttc aaactaccta atgatgattt    960
acagggcatc cagaagatat atggtccacc tgacaagatt cctccaccta caagacctct   1020
accgacagtg cccccacacc gctctattcc tccggctgac ccaaggaaaa atgacaggcc   1080
aaaacctcct cggcctccaa ccggcagacc ctcctatccc ggagccaaac ccaacatctg   1140
tgatgggaac tttaacactc tagctattct tcgtcgtgag atgtttgttt tcaaggacca  1200
```

```
gtggttttgg cgagtgagaa acaacagggt gatggatgga tacccaatgc aaattactta    1260
cttctggcgg ggcttgcctc ctagtatcga tgcagtttat gaaaatagcg acgggaattt    1320
tgtgttcttt aaaggtaaca atattgggt gttcaaggat acaactcttc aacctggtta     1380
ccctcatgac ttgataaccc ttggaagtgg aattccccct catggtattg attcagccat    1440
ttggtgggag gacgtcggga aaacctattt cttcaaggga gacagatatt ggagatatag    1500
tgaagaaatg aaaacaatgg accctggcta tcccaagcca atcacagtct ggaaagggat    1560
ccctgaatct cctcagggag catttgtaca caaagaaaat ggctttacgt atttctacaa    1620
aggaaaggag tattggaaat tcaacaacca gatactcaag gtagaacctg gatatccaag    1680
atccatcctc aaggatttta tgggctgtga tggaccaaca gacagagtta agaaggaca    1740 cagcccacca gatgatgtag acattgtcat caaactggac aacacagcca gcactgtgaa    1800
agccatagct attgtcattc cctgcatctt ggccttatgc ctccttgtat ggtttacac    1860 tgtgttccag ttcaagagga aaggaacacc ccgccacata ctgtactgta acgctctat    1920 gcaagagtgg gtgtgatgta gggttttttc ttctttcttt cttttgcagg agtttgtggt    1980
aacttgagat tcaagacaag agctgttatg ctgtttccta gctaggagca ggcttgtggc    2040
agcctgattc ggggctgacc tttcaaacca gagggttgct ggtcctgcac atgagtggaa    2100
atacactcat ggggaagctt ccatgatgca cagtatctgc tgttcttcag tcctttgtct    2160
ttctttgtca ttcagttcta ggcctttcct ctgcacgctc aatgcccagt aaaatttcag    2220
gattaactaa agaagaggag aaaagaaga aagattctt tcttaaaagt ttctaatgtt     2280
attttccttc tgaagtctga gcccatttct gggggagaa aaaaaagca atcagaaaa       2340 cccacggttt ttcttttttt cttttttttct ttttttcttt tttggcttta aaacaaaggg   2400
aaaaaagagt ttaaacaaaa aacccacaat tgaacttcca ggaaagtgtg aagacccaaa    2460
acagctttgt ctccaaagaa gatagctctc tgactgcttt ggatagtctc ctacgcacca    2520
ttttgtcagg tgggagattt ggaatacaca tgcaggacgt tagactgttg ggacagccat    2580
tttccaacaa ccaaggggcc aaaatatctg caatatagta acagccttaa taatacatcc    2640 attttttcgtt ttatacagct gttctcagct atgtcctcag tgtttcatcg catttatatt   2700
catagctatt ttcaaacacg acctttaat tgttttgaa gtattctaa accccttctt        2760 tccaccttac tcctccatca ttgtgataat cttcccaagt tgtattaggc cattgcccca    2820
ggccttccat gggtctgtca ggaatattcg ttacaaagca gagcaagaag gcagtatgtc    2880
tctgaagtgg attacagtgg cagttatttt acaaggattt tgtgacactag ttacataccc   2940 gtgttaccct ttgagaacta tcagaccagc tytcagagtc ttaggattgt cgstcttgcg    3000
atctgataaa ttatagaact gggcaatggt aaaaacagtc acaagttcaa gaagttcagg   3060
tttttaaaac agatatccta taatgtcata taatttttaa atgatttaca agactacata    3120
aatgtgttta taacaaacag aaatgatgtt acttgccaaa attttctgg caaataaaaa     3180 aggtatttta ttaagattct cataaatctg aaattttatt tgaaaaaact gataatagcc    3240
taagtcttcc tttctttttt ttaggcatac tgaattctg ttttaaaatc cattgcatga     3300
aaattcaatt tgccttggta tatgcagtta gcattgccat tttaaaaatg aattaaaacg    3360
gtgactctga agttgcatga atatcctcca gtgcattacc tattgcatgt ccaccatagt    3420
tctcaaaggg ttagtgtggc ttctggcatt tagccgncca tttgatcact gacagagcca    3480
ngagaccacc aaagcatttc attgttgagt gtaatttgtc ctaacagcag tatttgtcatt   3540 ttcatgtgac ctgcagagca ggtttgtatc aatattttt tcctagagaa aagtcagcaa     3600
```

-continued

```
ctgacagacc tctttattga ttttaggag ctgcttcttg cagtgaaagg ctttacagcc    3660
actgggctgt gaacttatta gagatggtca gaatgaatgc accccantga gtcagnamca    3720
ttnggctttg tgntgnaaag cccagncttt ngaggggatt agccttttgg aaaacaaatg    3780
aaccagcctt gcccttgaaa cttgaattaa ttgatcctat tgactgtnca ttaacaacaa    3840
cttaaacatt gtncttnctg tgnaaaattt tccttgaaga gtncctgttn ctatgtcttt    3900 gcccttttgac ctttaacttg caaactggca caaactgaag gaaatctggt gttgcttctc    3960
cattggatta gttgttctct aaaacctagt aagcatgagc tgtttcctta gagtggagag    4020
agtggtgatg gcagatctgc agatggacac tttgctcttt acatgcacac tctgaaaatg    4080
ccctataggt agaagtgaat tttaatttca ttttaatata atttcnaagt ctaaattcat    4140
cattttagta caaattacaa aaactatagg aaaaaaaaaa aaaaaaaa                 4188
```

<210> SEQ ID NO 88
<211> LENGTH: 607
<212> TYPE: PRT
<213> ORGANISM: Homo sapiens

<400> SEQUENCE: 88

```
Met Ile Leu Leu Thr Phe Ser Thr Gly Arg Arg Leu Asp Phe Val His
 1               5                   10                  15

His Ser Gly Val Phe Leu Gln Thr Leu Leu Trp Ile Leu Cys Ala
             20                  25                  30

Thr Val Cys Gly Thr Glu Gln Tyr Phe Asn Val Glu Val Trp Leu Gln
         35                  40                  45

Lys Tyr Gly Tyr Leu Pro Pro Thr Asp Pro Arg Met Ser Val Leu Arg
     50                  55                  60

Ser Ala Glu Thr Met Gln Ser Ala Leu Ala Ala Met Gln Gln Phe Tyr
 65                  70                  75                  80

Gly Ile Asn Met Thr Gly Lys Val Asp Arg Asn Thr Ile Asp Trp Met
                 85                  90                  95

Lys Lys Pro Arg Cys Gly Val Pro Asp Gln Thr Arg Gly Ser Ser Lys
            100                 105                 110

Phe His Ile Arg Arg Lys Arg Tyr Ala Leu Thr Gly Gln Lys Trp Gln
        115                 120                 125

His Lys His Ile Thr Tyr Ser Ile Lys Asn Val Thr Pro Lys Val Gly
    130                 135                 140

Asp Pro Glu Thr Arg Lys Ala Ile Arg Arg Ala Phe Asp Val Trp Gln
145                 150                 155                 160

Asn Val Thr Pro Leu Thr Phe Glu Glu Val Pro Tyr Ser Glu Leu Glu
                165                 170                 175

Asn Gly Lys Arg Asp Val Asp Ile Thr Ile Ile Phe Ala Ser Gly Phe
            180                 185                 190

His Gly Asp Ser Ser Pro Phe Asp Gly Glu Gly Gly Phe Leu Ala His
        195                 200                 205

Ala Tyr Phe Pro Gly Pro Gly Ile Gly Gly Asp Thr His Phe Asp Ser
    210                 215                 220

Asp Glu Pro Trp Thr Leu Gly Asn Pro Asn His Asp Gly Asn Asp Leu
225                 230                 235                 240

Phe Leu Val Ala Val His Glu Leu Gly His Ala Leu Gly Leu Glu His
                245                 250                 255

Ser Asn Asp Pro Thr Ala Ile Met Ala Pro Phe Tyr Gln Tyr Met Glu
            260                 265                 270

Thr Asp Asn Phe Lys Leu Pro Asn Asp Asp Leu Gln Gly Ile Gln Lys
```

```
              275                 280                 285
Ile Tyr Gly Pro Pro Asp Lys Ile Pro Pro Thr Arg Pro Leu Pro
290                 295                 300

Thr Val Pro Pro His Arg Ser Ile Pro Pro Ala Asp Pro Arg Lys Asn
305                 310                 315                 320

Asp Arg Pro Lys Pro Arg Pro Pro Thr Gly Arg Pro Ser Tyr Pro
                325                 330                 335

Gly Ala Lys Pro Asn Ile Cys Asp Gly Asn Phe Asn Thr Leu Ala Ile
                340                 345                 350

Leu Arg Arg Glu Met Phe Val Phe Lys Asp Gln Trp Phe Trp Arg Val
                355                 360                 365

Arg Asn Asn Arg Val Met Asp Gly Tyr Pro Met Gln Ile Thr Tyr Phe
370                 375                 380

Trp Arg Gly Leu Pro Pro Ser Ile Asp Ala Val Tyr Glu Asn Ser Asp
385                 390                 395                 400

Gly Asn Phe Val Phe Lys Gly Asn Lys Tyr Trp Val Phe Lys Asp
                405                 410                 415

Thr Thr Leu Gln Pro Gly Tyr Pro His Asp Leu Ile Thr Leu Gly Ser
                420                 425                 430

Gly Ile Pro Pro His Gly Ile Asp Ser Ala Ile Trp Trp Glu Asp Val
                435                 440                 445

Gly Lys Thr Tyr Phe Phe Lys Gly Asp Arg Tyr Trp Arg Tyr Ser Glu
                450                 455                 460

Glu Met Lys Thr Met Asp Pro Gly Tyr Pro Lys Pro Ile Thr Val Trp
465                 470                 475                 480

Lys Gly Ile Pro Glu Ser Pro Gln Gly Ala Phe Val His Lys Glu Asn
                485                 490                 495

Gly Phe Thr Tyr Phe Tyr Lys Gly Lys Glu Tyr Trp Lys Phe Asn Asn
                500                 505                 510

Gln Ile Leu Lys Val Glu Pro Gly Tyr Pro Arg Ser Ile Leu Lys Asp
                515                 520                 525

Phe Met Gly Cys Asp Gly Pro Thr Asp Arg Val Lys Glu Gly His Ser
530                 535                 540

Pro Pro Asp Asp Val Asp Ile Val Ile Lys Leu Asp Asn Thr Ala Ser
545                 550                 555                 560

Thr Val Lys Ala Ile Ala Ile Val Ile Pro Cys Ile Leu Ala Leu Cys
                565                 570                 575

Leu Leu Val Leu Val Tyr Thr Val Phe Gln Phe Lys Arg Lys Gly Thr
                580                 585                 590

Pro Arg His Ile Leu Tyr Cys Lys Arg Ser Met Gln Glu Trp Val
                595                 600                 605

<210> SEQ ID NO 89
<211> LENGTH: 3438
<212> TYPE: DNA
<213> ORGANISM: Homo sapiens

<400> SEQUENCE: 89
atccccgggc cgagctcga  attccaggtg  ccccagtagc  cgaccgccg   agatgcccag     60 cccgccgggg ctccgggcgc tatggctttg gccgcgctg   tgcgcttccc  ggagggccgg    120
cggcgccccc cagcccggcc cggggcccac cgcctgcccg  gccccctgcc  actgccagga    180
ggacggcatc atgctgtctg ccgactgctc tgagctcggg  ctgtccgccg  ttccggggga    240
cctggacccc ctgacggctt acctggacct cagcatgaac  aacctcacag  agcttcagcc    300
```

-continued

```
tggcctcttc caccacctgc gcttcttgga ggagctgcgt ctctctggga accatctctc    360
acacatccca ggacaagcat tctctggtct ctacagcctg aaaatcctga tgctgcagaa    420
caatcagctg ggaggaatcc ccgcagaggc gctgtgggag ctgccgagcc tgcagtcgct    480
gcgcctagat gccaacctca tctccctggt cccggagagg agctttgagg ggctgtcctc    540
cctccgccac ctctggctgg acgacaatgc actcacggag atccctgtca gggccctcaa    600
caacctccct gccctgcagg ccatgaccct ggccctcaac cgcatcagcc acatccccga    660
ctacgcgttc cagaatctca ccagccttgt ggtgctgcat ttgcataaca accgcatcca    720
gcatctgggg acccacagct cgagggggct gcacaatctg gagacactag acctgaatta    780
taacaagctg caggagttcc ctgtggccat ccggaccctg gcagactgca ggaactggg    840 gttccataac aacaacatca aggccatccc agaaaaggcc ttcatgggga ccctctgct    900 acagacgata cacttttatg ataacccaat ccagtttgtg gaagatcgg cattccagta    960 cctgcctaaa ctccacacac tatctctgaa tggtgccatg gacatccagg agtttccaga   1020
tctcaaaggc accaccagcc tggagatcct gaccctgacc cgcgcaggca tccggctgct   1080
cccatcgggg atgtgccaac agctgcccag gctccgagtc ctggaactgt ctcacaatca   1140
aattgaggag ctgcccagcc tgcacaggtg tcagaaattg aggaaatcg gcctccaaca   1200 caaccgcatc tgggaaattg gagctgacac cttcagccag ctgagctccc tgcaagccct   1260
ggatcttagc tggaacgcca tccggtccat ccaccctgag gccttctcca ccctgcactc   1320
cctggtcaag ctggacctga cagacaacca gctgaccaca ctgccctgg ctggacttgg   1380 gggcttgatg catctgaagc tcaaagggaa ccttgctctc tcccaggcct tctccaagga   1440
cagtttccca aaactgagga tcctggaggt gccttatgcc taccagtgct gtccctatgg   1500
gatgtgtgcc agcttcttca aggcctctgg gcagtgggag gctgaagacc ttcaccttga   1560
tgatgaggag tcttcaaaaa ggcccctggg cctccttgcc agacaagcag agaaccacta   1620
tgaccaggac ctggatgagc tccagctgga gatggaggac tcaaagccac accccagtgt   1680
ccagtgtagc cctactccag gccccttcaa gccctgtgag tacctctttg aaagctgggg   1740
catccgcctg gccgtgtggg ccatcgtgtt gctctccgtg ctctgcaatg gactggtgct   1800
gctgaccgtg ttcgctggcg ggcctgcccc cctgcccccg gtcaagtttg tggtaggtgc   1860
gattgcaggc gccaacacct tgactggcat ttcctgtggc cttctagcct cagtcgatgc   1920 cctgacctt ggtcagttct ctgagtacgg agcccgctgg gagacggggc taggctgccg   1980
ggccactggc ttcctggcag tacttgggtc ggaggcatcg gtgctgctgc tcactctggc   2040
cgcagtgcag tgcagcgtct ccgtctcctg tgtccgggcc tatgggaagt cccctcct   2100 gggcagcgtt cgagcagggg tcctaggctg cctggcactg gcagggctgg ccgccgcact   2160 gccctggc tcagtgggag aatacggggc ctccccactc tgcctgccct acgcgccacc   2220
tgagggtcag ccagcagccc tgggcttcac cgtggccctg gtgatgatga actccttctg   2280
tttcctggtc gtggccggtg cctacatcaa actgtactgt gacctgccgc ggggcgactt   2340
tgaggccgtg tgggactgcg ccatggtgag gcacgtggcc tggctcatct cgcagacgg   2400 gctcctctac tgtcccgtgg ccttcctcag cttcgcctcc atgctgggcc tcttccctgt   2460
cacgcccgag gccgtcaagt ctgtcctgct ggtggtgctg cccctgcctg cctgcctcaa   2520
cccactgctg tacctgctct tcaaccccca cttccgggat gaccttcggc ggcttcggcc   2580
ccgcgcaggg gactcagggc ccctagccta tgctgcggcc gggagctgg agaagagctc   2640 ctgtgattct acccaggccc tggtagcctt ctctgatgtg gatctcattc tggaagcttc   2700
```

-continued

```
tgaagctggg cggccccctg ggctggagac ctatggcttc ccctcagtga ccctcatctc   2760
ctgtcagcag ccaggggccc ccaggctgga gggcagccat tgtgtagagc cagaggggaa   2820
ccactttggg aaccccccaac cctccatgga tggagaactg ctgctgaggg cagagggatc   2880
tacgccagca ggtggaggct tgtcaggggg tggcggcttt cagccctctg gcttggcctt   2940
tgcttcacac gtgctcgagc aaaagttgat ttctgaagaa gatttgaacg gtgaacaaaa   3000
gctaatctcc gaggaagact tgaacggtga acaaaaatta atctcagaag aagacttgaa   3060
cggatcatag atctctaatt ccggttattt tccaccatat tgccgtcttt tggcaatgtg   3120
agggcccgga aacctggccc tgtcttcttg acgagcattc ctaggggtct ttcccctctc   3180
gccaaaggaa tgcaaggtct gttgaatgtc gtgaaggaag cagttcctct ggaagcttct   3240
tgaagacaaa caacgtctgt agcgaccctt tgcaggcagc ggaaccccc acctggcgac   3300 aggtgcctct gcggccaaaa gccacgtgta taagatacac ctgcaaaggc ggcacaaccc   3360
cagtgccacg ttgtgagttg gatagttgtg gaaagagtca aatggctctc ctcaagcgta   3420
ttcaacaagg ggctgaag                                                  3438
```

<210> SEQ ID NO 90
<211> LENGTH: 1005
<212> TYPE: PRT
<213> ORGANISM: Homo sapiens

<400> SEQUENCE: 90

```
Met Pro Ser Pro Pro Gly Leu Arg Ala Leu Trp Leu Cys Ala Ala Leu
 1               5                  10                  15

Cys Ala Ser Arg Arg Ala Gly Gly Ala Pro Gln Pro Gly Pro Gly Pro
                20                  25                  30

Thr Ala Cys Pro Ala Pro Cys His Cys Gln Glu Asp Gly Ile Met Leu
            35                  40                  45

Ser Ala Asp Cys Ser Glu Leu Gly Leu Ser Ala Val Pro Gly Asp Leu
        50                  55                  60

Asp Pro Leu Thr Ala Tyr Leu Asp Leu Ser Met Asn Asn Leu Thr Glu
65                  70                  75                  80

Leu Gln Pro Gly Leu Phe His His Leu Arg Phe Leu Glu Glu Leu Arg
                85                  90                  95

Leu Ser Gly Asn His Leu Ser Ile Pro Gly Gln Ala Phe Ser Gly
                100                 105                 110

Leu Tyr Ser Leu Lys Ile Leu Met Leu Gln Asn Asn Gln Leu Gly Gly
            115                 120                 125

Ile Pro Ala Glu Ala Leu Trp Glu Leu Pro Ser Leu Gln Ser Leu Arg
        130                 135                 140

Leu Asp Ala Asn Leu Ile Ser Leu Val Pro Glu Arg Ser Phe Glu Gly
145                 150                 155                 160

Leu Ser Ser Leu Arg His Leu Trp Leu Asp Asp Asn Ala Leu Thr Glu
                165                 170                 175

Ile Pro Val Arg Ala Leu Asn Asn Leu Pro Ala Leu Gln Ala Met Thr
            180                 185                 190

Leu Ala Leu Asn Arg Ile Ser His Ile Pro Asp Tyr Ala Phe Gln Asn
        195                 200                 205

Leu Thr Ser Leu Val Val Leu His Leu His Asn Arg Ile Gln His
    210                 215                 220

Leu Gly Thr His Ser Phe Glu Gly Leu His Asn Leu Glu Thr Leu Asp
225                 230                 235                 240

Leu Asn Tyr Asn Lys Leu Gln Glu Phe Pro Val Ala Ile Arg Thr Leu
```

```
                    245                 250                 255
Gly Arg Leu Gln Glu Leu Gly Phe His Asn Asn Asn Ile Lys Ala Ile
            260                 265                 270
Pro Glu Lys Ala Phe Met Gly Asn Pro Leu Leu Gln Thr Ile His Phe
        275                 280                 285
Tyr Asp Asn Pro Ile Gln Phe Val Gly Arg Ser Ala Phe Gln Tyr Leu
    290                 295                 300
Pro Lys Leu His Thr Leu Ser Leu Asn Gly Ala Met Asp Ile Gln Glu
305                 310                 315                 320
Phe Pro Asp Leu Lys Gly Thr Thr Ser Leu Glu Ile Leu Thr Leu Thr
                325                 330                 335
Arg Ala Gly Ile Arg Leu Leu Pro Ser Gly Met Cys Gln Gln Leu Pro
            340                 345                 350
Arg Leu Arg Val Leu Glu Leu Ser His Asn Gln Ile Glu Glu Leu Pro
        355                 360                 365
Ser Leu His Arg Cys Gln Lys Leu Glu Glu Ile Gly Leu Gln His Asn
    370                 375                 380
Arg Ile Trp Glu Ile Gly Ala Asp Thr Phe Ser Gln Leu Ser Ser Leu
385                 390                 395                 400
Gln Ala Leu Asp Leu Ser Trp Asn Ala Ile Arg Ser Ile His Pro Glu
                405                 410                 415
Ala Phe Ser Thr Leu His Ser Leu Val Lys Leu Asp Leu Thr Asp Asn
            420                 425                 430
Gln Leu Thr Thr Leu Pro Leu Ala Gly Leu Gly Gly Leu Met His Leu
        435                 440                 445
Lys Leu Lys Gly Asn Leu Ala Leu Ser Gln Ala Phe Ser Lys Asp Ser
    450                 455                 460
Phe Pro Lys Leu Arg Ile Leu Glu Val Pro Tyr Ala Tyr Gln Cys Cys
465                 470                 475                 480
Pro Tyr Gly Met Cys Ala Ser Phe Phe Lys Ala Ser Gly Gln Trp Glu
                485                 490                 495
Ala Glu Asp Leu His Leu Asp Asp Glu Glu Ser Ser Lys Arg Pro Leu
            500                 505                 510
Gly Leu Leu Ala Arg Gln Ala Glu Asn His Tyr Asp Gln Asp Leu Asp
        515                 520                 525
Glu Leu Gln Leu Glu Met Glu Asp Ser Lys Pro His Pro Ser Val Gln
    530                 535                 540
Cys Ser Pro Thr Pro Gly Pro Phe Lys Pro Cys Glu Tyr Leu Phe Glu
545                 550                 555                 560
Ser Trp Gly Ile Arg Leu Ala Val Trp Ala Ile Val Leu Leu Ser Val
                565                 570                 575
Leu Cys Asn Gly Leu Val Leu Thr Val Phe Ala Gly Gly Pro Ala
            580                 585                 590
Pro Leu Pro Pro Val Lys Phe Val Val Gly Ala Ile Ala Gly Ala Asn
        595                 600                 605
Thr Leu Thr Gly Ile Ser Cys Gly Leu Leu Ala Ser Val Asp Ala Leu
    610                 615                 620
Thr Phe Gly Gln Phe Ser Glu Tyr Gly Ala Arg Trp Glu Thr Gly Leu
625                 630                 635                 640
Gly Cys Arg Ala Thr Gly Phe Leu Ala Val Leu Gly Ser Glu Ala Ser
                645                 650                 655
Val Leu Leu Leu Thr Leu Ala Ala Val Gln Cys Ser Val Ser Val Ser
            660                 665                 670
```

Cys Val Arg Ala Tyr Gly Lys Ser Pro Ser Leu Gly Ser Val Arg Ala
            675                 680                 685
Gly Val Leu Gly Cys Leu Ala Leu Ala Gly Leu Ala Ala Leu Pro
        690                 695                 700
Leu Ala Ser Val Gly Glu Tyr Gly Ala Ser Pro Leu Cys Leu Pro Tyr
705                 710                 715                 720
Ala Pro Pro Glu Gly Gln Pro Ala Ala Leu Gly Phe Thr Val Ala Leu
                725                 730                 735
Val Met Met Asn Ser Phe Cys Phe Leu Val Ala Gly Ala Tyr Ile
            740                 745                 750
Lys Leu Tyr Cys Asp Leu Pro Arg Gly Asp Phe Glu Ala Val Trp Asp
                755                 760                 765
Cys Ala Met Val Arg His Val Ala Trp Leu Ile Phe Ala Asp Gly Leu
770                 775                 780
Leu Tyr Cys Pro Val Ala Phe Leu Ser Phe Ala Ser Met Leu Gly Leu
785                 790                 795                 800
Phe Pro Val Thr Pro Glu Ala Val Lys Ser Val Leu Leu Val Val Leu
                805                 810                 815
Pro Leu Pro Ala Cys Leu Asn Pro Leu Leu Tyr Leu Leu Phe Asn Pro
                820                 825                 830
His Phe Arg Asp Asp Leu Arg Arg Leu Arg Pro Arg Ala Gly Asp Ser
            835                 840                 845
Gly Pro Leu Ala Tyr Ala Ala Gly Glu Leu Glu Lys Ser Ser Cys
        850                 855                 860
Asp Ser Thr Gln Ala Leu Val Ala Phe Ser Asp Val Asp Leu Ile Leu
865                 870                 875                 880
Glu Ala Ser Glu Ala Gly Arg Pro Pro Gly Leu Glu Thr Tyr Gly Phe
                885                 890                 895
Pro Ser Val Thr Leu Ile Ser Cys Gln Gln Pro Gly Ala Pro Arg Leu
                900                 905                 910
Glu Gly Ser His Cys Val Glu Pro Glu Gly Asn His Phe Gly Asn Pro
            915                 920                 925
Gln Pro Ser Met Asp Gly Glu Leu Leu Leu Arg Ala Glu Gly Ser Thr
            930                 935                 940
Pro Ala Gly Gly Gly Leu Ser Gly Gly Gly Gly Phe Gln Pro Ser Gly
945                 950                 955                 960
Leu Ala Phe Ala Ser His Val Leu Glu Gln Lys Leu Ile Ser Glu Glu
                965                 970                 975
Asp Leu Asn Gly Glu Gln Lys Leu Ile Ser Glu Glu Asp Leu Asn Gly
            980                 985                 990
Glu Gln Lys Leu Ile Ser Glu Glu Asp Leu Asn Gly Ser
            995                 1000                1005

<210> SEQ ID NO 91
<211> LENGTH: 2196
<212> TYPE: DNA
<213> ORGANISM: Homo sapiens
<220> FEATURE:
<221> NAME/KEY: misc_feature
<222> LOCATION: 1952, 1960
<223> OTHER INFORMATION: n = A,T,C or G

<400> SEQUENCE: 91
aaacacactc agcccttgca ctgacctgcc ttctgattgg aggctggttg cttcggataa    60
tgacctccag gaccccactg ttggttacag cctgtttgta ttattcttac tgcaactcaa   120
gacacctgca gcagggcgtg agaaaaagta aaagaccagt attttcacat tgccaggtac   180

```
cagaaacaca gaagactgac acccgccact taagtggggc cagggctggt gtctgcccat    240
gttgccatcc tgatgggctg cttgccacaa tgagggatct tcttcaatac atcgcttgct    300
tctttgcctt tttctctgct gggtttttga ttgtggccac ctggactgac tgttggatgg    360
tgaatgctga tgactctctg gaggtgagca caaaatgccg aggcctctgg tgggaatgcg    420
tcacaaatgc ttttgatggg attcgcacct gtgatgagta cgattccata cttgcggagc    480
atcccttgaa gctggtggta actcgagcgt tgatgattac tgcagatatt ctagctgggt    540
ttggatttct caccctgctc cttggtcttg actgcgtgaa attcctccct gatgagccgt    600
acattaaagt ccgcatctgc tttgttgctg agccacgtt  actaatagca ggtacccag     660 gaatcattgg ctctgtgtgg tatgctgttg atgtgtatgt ggaacgttct actttggttt    720
tgcacaatat atttcttggt atccaatata aatttggttg gtcctgttgg ctcggaatgg    780
ctgggtctct gggttgcttt ttggctggag ctgttctgac ctgctgctta tatctttta     840 aagatgttgg acctgagaga aactatcctt attccttgag gaaagcctat tcagccgcgg    900
gtgtttccat ggccaagtca tactcagccc ctcgcacaga gacggccaaa atgtatgctg    960
tagacacaag ggtgtaaaat gcacgtttca gggtgtgttt gcatatgatt taatcaatca   1020
gtatggttac attgataaaa tagtaagtca atccaggaac agttatttag aattcatatt   1080
gaattaaatt aattgctagc ttaatcaaaa tgtttgattc tcctatactt tttctttcta   1140
ttactcttat attttcccgt cattctctct gctaaccttc caccttatgc acacactttc   1200
cctatatttt aagataagtc tgctaggatg tagaaatatt tgtttgtgat ttctatatag   1260
ctattagaga ttatgacata gtaatattaa aatgaaatga tacttaaaca gaaagcaatt   1320
tccaaagagg ccagggaccc taatctttga agagatgaag aaacttactt ttctccctgg   1380
cttttggttc acttttttgta cttttaacaa gtgggtgaat tatttgataa ttttgaggaa   1440
gattattctt ttaaattcaa actagtatgt caatgcctac cattactctg attatattaa   1500
aacagaaaaa ggaaataaca acttcgtata ccagccactg gtgagagtta aagacaagag   1560
ctgccccccc accccaaat  gtcaaaggca aatgctaaat tgatactgga gctcgtggtg   1620
actttctacc tcactaacaa cataagggat ctccatatta tttcaccact attctagctt   1680
tgctgagata ttgccaaatg attagactac acaatagttc aaccagagaa tttactcatt   1740
tattgattaa acatccaaat actattgtaa tatactatgt taaaattcat caattcaagt   1800
gcccacacac cactgaatca tcagcaccaa gcaatatatt agacatatgg caaaattcaa   1860
caaatatatt ttgatataaa taaataaacg ttcacgactt tacttaaaaa atcaatgttg   1920
cggctgggca cggtagctcg cgtctgtaat cnccgcactn tgggaggcca aggcgggtgg   1980
atcacgaggt caagagacgg agaccatcct ggctaacatg gtgaaaccct gtctctacta   2040
aaaatacaaa aattagccgg gcgtggtggc ggtgcctgta gtcccagcta ctcgggaggc   2100
tgaggcagga gaatcgtttg aacccaggag gtggaggttg cagtgagcgg agatcgcacc   2160
attgcactcc agtctggcaa cagagcgaga ctccat                              2196
```

<210> SEQ ID NO 92
<211> LENGTH: 305
<212> TYPE: PRT
<213> ORGANISM: Homo sapiens

<400> SEQUENCE: 92

```
Met Thr Ser Arg Thr Pro Leu Leu Val Thr Ala Cys Leu Tyr Tyr Ser
 1               5                  10                  15
```

```
Tyr Cys Asn Ser Arg His Leu Gln Gln Gly Val Arg Lys Ser Lys Arg
         20                  25                  30

Pro Val Phe Ser His Cys Gln Val Pro Glu Thr Gln Lys Thr Asp Thr
             35                  40                  45

Arg His Leu Ser Gly Ala Arg Ala Gly Val Cys Pro Cys Cys His Pro
 50                      55                  60

Asp Gly Leu Leu Ala Thr Met Arg Asp Leu Leu Gln Tyr Ile Ala Cys
 65                  70                  75                  80

Phe Phe Ala Phe Phe Ser Ala Gly Phe Leu Ile Val Ala Thr Trp Thr
                 85                  90                  95

Asp Cys Trp Met Val Asn Ala Asp Asp Ser Leu Glu Val Ser Thr Lys
                100                 105                 110

Cys Arg Gly Leu Trp Trp Glu Cys Val Thr Asn Ala Phe Asp Gly Ile
            115                 120                 125

Arg Thr Cys Asp Glu Tyr Asp Ser Ile Leu Ala Glu His Pro Leu Lys
130                 135                 140

Leu Val Val Thr Arg Ala Leu Met Ile Thr Ala Asp Ile Leu Ala Gly
145                 150                 155                 160

Phe Gly Phe Leu Thr Leu Leu Leu Gly Leu Asp Cys Val Lys Phe Leu
                165                 170                 175

Pro Asp Glu Pro Tyr Ile Lys Val Arg Ile Cys Phe Val Ala Gly Ala
            180                 185                 190

Thr Leu Leu Ile Ala Gly Thr Pro Gly Ile Ile Gly Ser Val Trp Tyr
            195                 200                 205

Ala Val Asp Val Tyr Val Glu Arg Ser Thr Leu Val Leu His Asn Ile
            210                 215                 220

Phe Leu Gly Ile Gln Tyr Lys Phe Gly Trp Ser Cys Trp Leu Gly Met
225                 230                 235                 240

Ala Gly Ser Leu Gly Cys Phe Leu Ala Gly Ala Val Leu Thr Cys Cys
                245                 250                 255

Leu Tyr Leu Phe Lys Asp Val Gly Pro Glu Arg Asn Tyr Pro Tyr Ser
            260                 265                 270

Leu Arg Lys Ala Tyr Ser Ala Ala Gly Val Ser Met Ala Lys Ser Tyr
            275                 280                 285

Ser Ala Pro Arg Thr Glu Thr Ala Lys Met Tyr Ala Val Asp Thr Arg
    290                 295                 300

Val
305

<210> SEQ ID NO 93
<211> LENGTH: 7460
<212> TYPE: DNA
<213> ORGANISM: Homo sapiens

<400> SEQUENCE: 93
cgtccgggag aacgctgcag aaattctcat cctggccgac ctccacagtg cagatcagtt    60
gaaaactcag gcagtggatt tcatcaacta tcatgcttcg gatgtcttgg agacctctgg   120
gtggaagtca atggtggtgt cacatcccca cttggtggct gaggcatacc gctctctggc   180
ttcagcacag tgcccttttc tgggaccccc acgcaaacgc tgaagcaat cctaagatcc   240 tgcttgttgt aagactccgt ttaatttcca gaagcagcag ccactgttgc tgccactgac   300
caccaggtag acagcgcaat ctgtggagct tttactctgt tgtgagggga agagactgca   360
ttgtggcccc agactttaa aacagcacta ataacttggg ggaaacgggg ggagggaaa    420 atgaaatgaa aaccctgttg ctgcgtcact gtgttccctt tggcctggct gagtttgata   480
```

```
ctgtggggat tcagtttagg cgctggcccg aggatatccc agcggtggta cttcggagac    540
acctgtctgc atctgactga gccggctctc ctggcctcgc gctgcacatt ctctcctggc    600
ggcggcgcca cctgcagtag cgttcgcccg aacatggcga cacggagcag caggagggag    660
tcgcgactcc cgttcctatt caccctggtc gcactgctgc cgcccggagc tctctgcgaa    720
gtctggacgc agaggctgca cggcggcagc gcgcccttgc cccaggaccg gggcttcctc    780
gtggtgcagg gcgacccgcg cgagctgcgg ctgtgggcgc gcgggatgc caggggggcg     840
agccgcgcgg acgagaagcc gctccggagg aaacggagcg ctgccctgca gcccgagccc    900
atcaaggtgt acggacaggt tagtctgaat gattcccaca atcagatggt ggtgcactgg    960
gctggagaga aaagcaacgt gatcgtggcc ttggcccgag atagcctggc attggcgagg   1020
cccaagagca gtgatgtgta cgtgtcttac gactatggaa atcattcaa gaaaatttca    1080
gacaagttaa actttggctt gggaaatagg agtgaagctg ttatcgccca gttctaccac   1140
agccctgcgg acaacaagcg gtacatcttt gcagacgctt atgcccagta cctctggatc   1200
acgtttgact tctgcaacac tcttcaaggc ttttccatcc catttcgggc agctgatctc   1260
ctcctacaca gtaaggcctc caaccttctc ttgggctttg acaggtccca ccccaacaag   1320
cagctgtgga agtcagatga ctttggccag acctggatca tgattcagga acatgtcaag   1380
tcctttctt ggggaattga tcccatgac aaaccaaata ccatctacat gaacgacac     1440
gaaccctctg ctactccac tgtcttccga agtacagatt tcttccagtc ccgggaaaac   1500
caggaagtga tccttgagga agtgagagat tttcagcttc gggacaagta catgtttgct   1560
acaaaggtgg tgcatctctt gggcagtgaa cagcagtctt ctgtccagct ctgggtctcc   1620
tttggccgga agcccatgag agcagcccag tttgtcacaa gacatcctat taatgaatat   1680
tacatcgcag atgcctccga ggaccaggtg tttgtgtgtg tcagccacag taacaaccgc   1740
accaatttat acatctcaga ggcagagggg ctgaagttct ccctgtcctt ggagaacgtg   1800
ctctattaca gcccaggagg ggccggcagt gacaccttgg tgaggtattt tgcaaatgaa   1860
ccatttgctg acttccaccg agtggaagga ttgcaaggag tctacattgc tactctgatt   1920
aatggttcta tgaatgagga gaacatgaga tcggtcatca cctttgacaa aggggaacc    1980
tgggagtttc ttcaggctcc agccttcacg ggatatggag agaaaatcaa ttgtgagctt   2040
tcccagggct gttcccttca tctggctcag cgcctcagtc agctcctcaa cctccagctc   2100
cggagaatgc ccatcctgtc caaggagtcg gctccaggcc tcatcatcgc cactggctca   2160
gtgggaaaga acttggctag caagacaaac gtgtacatct ctagcagtgc tggagccagg   2220
tggcgagagg cacttcctgg acctcactac tacacatggg gagaccacgg cggaatcatc   2280
acggccattg cccagggcat ggaaaccaac gagctaaaat acagtaccaa tgaaggggag   2340
acctggaaaa cattcatctt ctctgagaag ccagtgtttg tgtatggcct cctcacagaa   2400
cctggggaga agagcactgt cttcaccatc tttggctcga caaagagaa tgtccacagc   2460
tggctgatcc tccaggtcaa tgccacggat gccttgggag ttccctgcac agagaatgac   2520
tacaagctgt ggtcaccatc tgatgagcgg gggaatgagt gtttgctggg acacaagact   2580
gttttcaaac ggcggacccc ccatgccaca tgcttcaatg agagggactt tgacaggccg   2640
gtggtcgtgt ccaactgctc ctgcacccgg gaggactatg agtgtgactt cggttttcaag   2700
atgagtgaag atttgtcatt agaggtttgt gttccagatc cggaattttc tggaaagtca   2760
tactcccctc ctgtgccttg ccctgtgggt tctacttaca ggagaacgag aggctaccgg   2820
aagatttctg gggacacttg tagcggagga gatgttgaag cgcgactgga aggagagctg   2880
```

```
gtcccctgtc ccctggcaga agagaacgag ttcattctgt atgctgtgag gaaatccatc    2940
taccgctatg acctggcctc gggagccacc gagcagttgc ctctcaccgg gctacgggca    3000
gcagtggccc tggactttga ctatgagcac aactgtttgt attggtccga cctggccttg    3060
gacgtcatcc agcgcctctg tttgaatgga agcacagggc aagaggtgat catcaattct    3120
ggcctggaga cagtgaaagc tttggctttt gaacccctca gccagctgct ttactgggta    3180
gatgcaggct tcaaaaagat tgaggtagct aatccagatg gcgacttccg actcacaatc    3240
gtcaattcct ctgtgcttga tcgtcccagg gctctggtcc tcgtgcccca gaggggtg     3300 atgttctgga cagactgggg agacctgaag cctgggattt atcggagcaa tatggatggt    3360
tctgctgcct atcacctggt gtctgaggat gtgaagtggc ccaatggcat ctctgtggac    3420
gaccagtgga tttactggac ggatgcctac ctggagtgca tagagcggat cacgttcagt    3480
ggccagcagc gctctgtcat tctggacaac ctcccgcacc cctatgccat tgctgtcttt    3540
aagaatgaaa tctactggga tgactggtca cagctcagca tattccgagc ttccaaatac    3600
agtgggtccc agatggagat tctggcaaac cagctcacgg ggctcatgga catgaagatt    3660
ttctacaagg ggaagaacac tggaagcaat gcctgtgtgc ccaggccatg cagcctgctg    3720
tgcctgccca aggccaacaa cagtagaagc tgcaggtgtc cagaggatgt gtccagcagt    3780
gtgcttccat caggggacct gatgtgtgac tgccctcagg gctatcagct caagaacaat    3840
acctgtgtca agaagagaa cacctgtctt cgcaaccagt atcgctgcag caacgggaac    3900
tgtatcaaca gcatttggtg gtgtgacttt gacaacgact gtggagacat gagcgatgag    3960
agaaactgcc ctaccaccat ctgtgacctg acacccagt ttcgttgcca ggagtctggg    4020
acttgtatcc cactgtccta taaatgtgac cttgaggatg actgtggaga caacagtgat    4080
gaaagtcatt gtgaaatgca ccagtgccgg agtgacgagt acaactgcag ttccggcatg    4140
tgcatccgct cctcctgggt atgtgacggg acaacgact gcagggactg gtctgatgaa    4200
gccaactgta ccgccatcta tcacacctgt gaggcctcca acttccagtg ccgaaacggg    4260
cactgcatcc cccagcggtg ggcgtgtgac ggggatacgg actgccagga tggttccgat    4320
gaggatccag tcaactgtga agaagtgc aatggattcc gctgcccaaa cggcacttgc    4380
atcccatcca gcaaacattg tgatggtctg cgtgattgct ctgatggctc cgatgaacag    4440
cactgcgagc ccctctgtac gcacttcatg gactttgtgt gtaagaaccg ccagcagtgc    4500
ctgttccact ccatggtctg tgacggaatc atccagtgcc gcgacgggtc cgatgaggat    4560
gcggcgtttg caggatgctc ccaagatcct gagttccaca aggtatgtga tgagttcggt    4620
ttccagtgtc agaatggagt gtgcatcagt ttgatttgga agtgcgacgg gatggatgat    4680
tgcggcgatt attctgatga agccaactgc gaaaacccca cagaagcccc aaactgctcc    4740
cgctacttcc agtttcggtg tgagaatggc cactgcatcc ccaacagatg gaaatgtgac    4800
agggagaacg actgtgggga ctggtctgat gagaaggatt gtggagattc acatattctt    4860
cccttctcga ctcctgggcc ctccacgtgt ctgcccaatt actaccgctg cagcagtggg    4920
acctgcgtga tggacacctg ggtgtgcgac gggtaccgag attgtgcaga tggctctgac    4980
gaggaagcct gcccccttgct tgcaaacgtc actgctgcct ccactcccac ccaacttggg    5040
cgatgtgacc gatttgagtt cgaatgccac caaccgaaga cgtgtattcc caactggaag    5100
cgctgtgacg gccaccaaga ttgccaggat ggccgggacg aggccaattg ccccacacac    5160
agcaccttga cttgcatgag caggggagttc cagtgcgagg acgggggaggc ctgcattgtg    5220 ctctcggagc gctgcgacgg cttcctggac tgctcggacg agagcgatga aaaggcctgc    5280
```

```
agtgatgagt tgactgtgta caaagtacag aatcttcagt ggacagctga cttctctggg    5340
gatgtgactt tgacctggat gaggcccaaa aaaatgccct ctgcatcttg tgtatataat    5400
gtctactaca gggtggttgg agagagcata tggaagactc tggagaccca cagcaataag    5460
acaaacactg tattaaaagt cttgaaacca gataccacgt atcaggttaa agtacaggtt    5520
cagtgtctca gcaaggcaca caacaccaat gactttgtga ccctgaggac cccagaggga    5580
ttgccagatg cccctcgaaa tctccagctg tcactcccca gggaagcaga aggtgtgatt    5640
gtaggccact gggctcctcc catccacacc catggcctca tccgtgagta cattgtagaa    5700
tacagcagga gtggttccaa gatgtgggcc tcccagaggg ctgctagtaa ctttacagaa    5760
atcaagaact tattggtcaa cactctatac accgtcagag tggctgcggt gactagtcgt    5820
ggaataggaa actggagcga ttctaaatcc attaccacca taaaaggaaa agtgatccca    5880
ccaccagata tccacattga cagctatggt gaaaattatc taagcttcac cctgaccatg    5940
gagagtgata tcaaggtgaa tggctatgtg gtgaaccttt tctgggcatt tgacacccac    6000
aagcaagaga ggagaacttt gaacttccga ggaagcatat tgtcacacaa agttggcaat    6060
ctgcagactc atacatccta tgagatttct gcctgggcca agactgactt gggggatagc    6120
cctctggcat ttgagcatgt tatgaccaga ggggttcgcc cacctgcacc tagcctcaag    6180
gccaaagcca tcaaccagac tgcagtggaa tgtacctgga ccggccccg gaatgtggtt    6240 tatggtatt tctatgccac gtcctttctt gacctctatc gcaacccgaa gagcttgact    6300
acttcactcc acaacaagac ggtcattgtc agtaaggatg agcagtattt gtttctggtc    6360
cgtgtagtgg taccctacca ggggccatcc tctgactacg ttgtagtgaa gatgatcccg    6420
gacagcaggc ttccacccg tcacctgcat gtggttcata cgggcaaaac ctccgtggtc    6480
atcaagtggg aatcaccgta tgactctcct gaccaggact tgttgtatgc aattgcagtc    6540
aaagatctca agaaagac tgacaggagc tacaaagtaa aatcccgtaa cagcactgtg    6600
gaatacaccc ttaacaagtt ggagcctggc gggaaatacc acatcattgt ccaactgggg    6660
aacatgagca agattccag cataaaaatt accacagttt cattatcagc acctgatgcc    6720 ttaaaatca taacagaaaa tgatcatgtt cttctgtttt ggaaaagcct ggctttaaag    6780
gaaaagcatt ttaatgaaag caggggctat gagatacaca tgtttgatag tgccatgaat    6840
atcacagctt accttgggaa tactactgac aatttcttta aaatttccaa cctgaagatg    6900
ggtcataatt acacgttcac cgtccaagca agatgccttt ttggcaacca gatctgtggg    6960
gagcctgcca tcctgctgta cgatgagctg gggtctggtg cagatgcatc tgcaacgcag    7020
gctgccagat ctacggatgt tgctgctgtg gtggtgccca tcttattcct gatactgctg    7080
agcctggggg tggggtttgc catcctgtac acgaagcacc ggaggctgca gagcagcttc    7140
accgccttcg ccaacagcca ctacagctcc aggctgggt ccgcaatctt ctcctctggg    7200
gatgacctgg gggaagatga tgaagatgcc cctatgataa ctggattttc agatgacgtc    7260
cccatggtga tagcctgaaa gagctttcct cactagaaac caaatggtgt aaatatttta    7320
tttgataaag atagttgatg gtttatttta aaagatgcac tttgagttgc aatatgttat    7380
ttttatatgg gccaaaaaca aaaaacaaaa aaaaaaaaaa agggcggccg cgaatgaata    7440
aactttgtag taatcaactg                                               7460
```

<210> SEQ ID NO 94
<211> LENGTH: 2214
<212> TYPE: PRT
<213> ORGANISM: Homo sapiens

<400> SEQUENCE: 94

```
Met Ala Thr Arg Ser Ser Arg Arg Glu Ser Arg Leu Pro Phe Leu Phe
 1               5                  10                  15

Thr Leu Val Ala Leu Leu Pro Pro Gly Ala Leu Cys Glu Val Trp Thr
             20                  25                  30

Gln Arg Leu His Gly Gly Ser Ala Pro Leu Pro Gln Asp Arg Gly Phe
         35                  40                  45

Leu Val Val Gln Gly Asp Pro Arg Glu Leu Arg Leu Trp Ala Arg Gly
     50                  55                  60

Asp Ala Arg Gly Ala Ser Arg Ala Asp Glu Lys Pro Leu Arg Arg Lys
 65                  70                  75                  80

Arg Ser Ala Ala Leu Gln Pro Glu Pro Ile Lys Val Tyr Gly Gln Val
                 85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Gly Phe Asp Arg
    210                 215                 220

Ser His Pro Asn Lys Gln Leu Trp Lys Ser Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                405                 410                 415
```

-continued

```
Val Glu Gly Leu Gln Gly Val Tyr Ile Ala Thr Leu Ile Asn Gly Ser
            420                 425                 430

Met Asn Glu Glu Asn Met Arg Ser Val Ile Thr Phe Asp Lys Gly Gly
            435                 440                 445

Thr Trp Glu Phe Leu Gln Ala Pro Ala Phe Thr Gly Tyr Gly Glu Lys
    450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
            500                 505                 510

Asn Leu Ala Ser Lys Thr Asn Val Tyr Ile Ser Ser Ala Gly Ala
            515                 520                 525

Arg Trp Arg Glu Ala Leu Pro Gly Pro His Tyr Tyr Thr Trp Gly Asp
    530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
    595                 600                 605

Ser Trp Leu Ile Leu Gln Val Asn Ala Thr Asp Ala Leu Gly Val Pro
610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
            660                 665                 670

Ser Asn Cys Ser Cys Thr Arg Glu Asp Tyr Glu Cys Asp Phe Gly Phe
    675                 680                 685

Lys Met Ser Glu Asp Leu Ser Leu Glu Val Cys Val Pro Asp Pro Glu
690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
            740                 745                 750

Pro Leu Ala Glu Glu Asn Glu Phe Ile Leu Tyr Ala Val Arg Lys Ser
    755                 760                 765

Ile Tyr Arg Tyr Asp Leu Ala Ser Gly Ala Thr Glu Gln Leu Pro Leu
770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                805                 810                 815

Leu Asn Gly Ser Thr Gly Gln Glu Val Ile Ile Asn Ser Gly Leu Glu
            820                 825                 830

Thr Val Glu Ala Leu Ala Phe Glu Pro Leu Ser Gln Leu Leu Tyr Trp
```

-continued

```
                835                 840                 845
Val Asp Ala Gly Phe Lys Lys Ile Glu Val Ala Asn Pro Asp Gly Asp
    850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
            900                 905                 910

Tyr His Leu Val Ser Glu Asp Val Lys Trp Pro Asn Gly Ile Ser Val
        915                 920                 925

Asp Asp Gln Trp Ile Tyr Trp Thr Asp Ala Tyr Leu Glu Cys Ile Glu
    930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
                965                 970                 975

Asp Trp Ser Gln Leu Ser Ile Phe Arg Ala Ser Lys Tyr Ser Gly Ser
            980                 985                 990

Gln Met Glu Ile Leu Ala Asn Gln Leu Thr Gly Leu Met Asp Met Lys
        995                 1000                1005

Ile Phe Tyr Lys Gly Lys Asn Thr Gly Ser Asn Ala Cys Val Pro Arg
    1010                1015                1020

Pro Cys Ser Leu Leu Cys Leu Pro Lys Ala Asn Asn Ser Arg Ser Cys
1025                1030                1035                1040

Arg Cys Pro Glu Asp Val Ser Ser Val Leu Pro Ser Gly Asp Leu
                1045                1050                1055

Met Cys Asp Cys Pro Gln Gly Tyr Gln Leu Lys Asn Asn Thr Cys Val
            1060                1065                1070

Lys Glu Glu Asn Thr Cys Leu Arg Asn Gln Tyr Arg Cys Ser Asn Gly
        1075                1080                1085

Asn Cys Ile Asn Ser Ile Trp Trp Cys Asp Phe Asp Asn Asp Cys Gly
    1090                1095                1100

Asp Met Ser Asp Glu Arg Asn Cys Pro Thr Thr Ile Cys Asp Leu Asp
1105                1110                1115                1120

Thr Gln Phe Arg Cys Gln Glu Ser Gly Thr Cys Ile Pro Leu Ser Tyr
                1125                1130                1135

Lys Cys Asp Leu Glu Asp Asp Cys Gly Asp Asn Ser Asp Glu Ser His
            1140                1145                1150

Cys Glu Met His Gln Cys Arg Ser Asp Glu Tyr Asn Cys Ser Ser Gly
        1155                1160                1165

Met Cys Ile Arg Ser Ser Trp Val Cys Asp Gly Asp Asn Asp Cys Arg
    1170                1175                1180

Asp Trp Ser Asp Glu Ala Asn Cys Thr Ala Ile Tyr His Thr Cys Glu
1185                1190                1195                1200

Ala Ser Asn Phe Gln Cys Arg Asn Gly His Cys Ile Pro Gln Arg Trp
                1205                1210                1215

Ala Cys Asp Gly Asp Thr Asp Cys Gln Asp Gly Ser Asp Glu Asp Pro
            1220                1225                1230

Val Asn Cys Glu Lys Lys Cys Asn Gly Phe Arg Cys Pro Asn Gly Thr
        1235                1240                1245

Cys Ile Pro Ser Ser Lys His Cys Asp Gly Leu Arg Asp Cys Ser Asp
    1250                1255                1260
```

```
Gly Ser Asp Glu Gln His Cys Glu Pro Leu Cys Thr His Phe Met Asp
1265                1270                1275                1280

Phe Val Cys Lys Asn Arg Gln Gln Cys Leu Phe His Ser Met Val Cys
            1285                1290                1295

Asp Gly Ile Ile Gln Cys Arg Asp Gly Ser Asp Glu Asp Ala Ala Phe
        1300                1305                1310

Ala Gly Cys Ser Gln Asp Pro Glu Phe His Lys Val Cys Asp Glu Phe
    1315                1320                1325

Gly Phe Gln Cys Gln Asn Gly Val Cys Ile Ser Leu Ile Trp Lys Cys
1330                1335                1340

Asp Gly Met Asp Asp Cys Gly Asp Tyr Ser Asp Glu Ala Asn Cys Glu
1345                1350                1355                1360

Asn Pro Thr Glu Ala Pro Asn Cys Ser Arg Tyr Phe Gln Phe Arg Cys
            1365                1370                1375

Glu Asn Gly His Cys Ile Pro Asn Arg Trp Lys Cys Asp Arg Glu Asn
        1380                1385                1390

Asp Cys Gly Asp Trp Ser Asp Glu Lys Asp Cys Gly Asp Ser His Ile
    1395                1400                1405

Leu Pro Phe Ser Thr Pro Gly Pro Ser Thr Cys Leu Pro Asn Tyr Tyr
1410                1415                1420

Arg Cys Ser Ser Gly Thr Cys Val Met Asp Thr Trp Val Cys Asp Gly
1425                1430                1435                1440

Tyr Arg Asp Cys Ala Asp Gly Ser Asp Glu Glu Ala Cys Pro Leu Leu
            1445                1450                1455

Ala Asn Val Thr Ala Ala Ser Thr Pro Thr Gln Leu Gly Arg Cys Asp
        1460                1465                1470

Arg Phe Glu Phe Glu Cys His Gln Pro Lys Thr Cys Ile Pro Asn Trp
    1475                1480                1485

Lys Arg Cys Asp Gly His Gln Asp Cys Gln Asp Gly Arg Asp Glu Ala
1490                1495                1500

Asn Cys Pro Thr His Ser Thr Leu Thr Cys Met Ser Arg Glu Phe Gln
1505                1510                1515                1520

Cys Glu Asp Gly Glu Ala Cys Ile Val Leu Ser Glu Arg Cys Asp Gly
            1525                1530                1535

Phe Leu Asp Cys Ser Asp Glu Ser Asp Glu Lys Ala Cys Ser Asp Glu
        1540                1545                1550

Leu Thr Val Tyr Lys Val Gln Asn Leu Gln Trp Thr Ala Asp Phe Ser
    1555                1560                1565

Gly Asp Val Thr Leu Thr Trp Met Arg Pro Lys Lys Met Pro Ser Ala
1570                1575                1580

Ser Cys Val Tyr Asn Val Tyr Tyr Arg Val Val Gly Glu Ser Ile Trp
1585                1590                1595                1600

Lys Thr Leu Glu Thr His Ser Asn Lys Thr Asn Thr Val Leu Lys Val
            1605                1610                1615

Leu Lys Pro Asp Thr Thr Tyr Gln Val Lys Val Gln Val Gln Cys Leu
        1620                1625                1630

Ser Lys Ala His Asn Thr Asn Asp Phe Val Thr Leu Arg Thr Pro Glu
    1635                1640                1645

Gly Leu Pro Asp Ala Pro Arg Asn Leu Gln Leu Ser Leu Pro Arg Glu
1650                1655                1660

Ala Glu Gly Val Ile Val Gly His Trp Ala Pro Pro Ile His Thr His
1665                1670                1675                1680

Gly Leu Ile Arg Glu Tyr Ile Val Glu Tyr Ser Arg Ser Gly Ser Lys
            1685                1690                1695
```

```
Met Trp Ala Ser Gln Arg Ala Ala Ser Asn Phe Thr Glu Ile Lys Asn
            1700                1705                1710

Leu Leu Val Asn Thr Leu Tyr Thr Val Arg Val Ala Ala Val Thr Ser
            1715                1720                1725

Arg Gly Ile Gly Asn Trp Ser Asp Ser Lys Ser Ile Thr Thr Ile Lys
            1730                1735                1740

Gly Lys Val Ile Pro Pro Asp Ile His Ile Asp Ser Tyr Gly Glu
1745                1750                1755                1760

Asn Tyr Leu Ser Phe Thr Leu Thr Met Glu Ser Asp Ile Lys Val Asn
            1765                1770                1775

Gly Tyr Val Val Asn Leu Phe Trp Ala Phe Asp Thr His Lys Gln Glu
            1780                1785                1790

Arg Arg Thr Leu Asn Phe Arg Gly Ser Ile Leu Ser His Lys Val Gly
            1795                1800                1805

Asn Leu Thr Ala His Thr Ser Tyr Glu Ile Ser Ala Trp Ala Lys Thr
            1810                1815                1820

Asp Leu Gly Asp Ser Pro Leu Ala Phe Glu His Val Met Thr Arg Gly
1825                1830                1835                1840

Val Arg Pro Pro Ala Pro Ser Leu Lys Ala Lys Ala Ile Asn Gln Thr
            1845                1850                1855

Ala Val Glu Cys Thr Trp Thr Gly Pro Arg Asn Val Val Tyr Gly Ile
            1860                1865                1870

Phe Tyr Ala Thr Ser Phe Leu Asp Leu Tyr Arg Asn Pro Lys Ser Leu
            1875                1880                1885

Thr Thr Ser Leu His Asn Lys Thr Val Ile Val Ser Lys Asp Glu Gln
            1890                1895                1900

Tyr Leu Phe Leu Val Arg Val Val Val Pro Tyr Gln Gly Pro Ser Ser
1905                1910                1915                1920

Asp Tyr Val Val Val Lys Met Ile Pro Asp Ser Arg Leu Pro Pro Arg
            1925                1930                1935

His Leu His Val Val His Thr Gly Lys Thr Ser Val Val Ile Lys Trp
            1940                1945                1950

Glu Ser Pro Tyr Asp Ser Pro Asp Gln Asp Leu Leu Tyr Ala Ile Ala
            1955                1960                1965

Val Lys Asp Leu Ile Arg Lys Thr Asp Arg Ser Tyr Lys Val Lys Ser
            1970                1975                1980

Arg Asn Ser Thr Val Glu Tyr Thr Leu Asn Lys Leu Glu Pro Gly Gly
1985                1990                1995                2000

Lys Tyr His Ile Ile Val Gln Leu Gly Asn Met Ser Lys Asp Ser Ser
            2005                2010                2015

Ile Lys Ile Thr Thr Val Ser Leu Ser Ala Pro Asp Ala Leu Lys Ile
            2020                2025                2030

Ile Thr Glu Asn Asp His Val Leu Leu Phe Trp Lys Ser Leu Ala Leu
            2035                2040                2045

Lys Glu Lys His Phe Asn Glu Ser Arg Gly Tyr Glu Ile His Met Phe
            2050                2055                2060

Asp Ser Ala Met Asn Ile Thr Ala Tyr Leu Gly Asn Thr Thr Asp Asn
2065                2070                2075                2080

Phe Phe Lys Ile Ser Asn Leu Lys Met Gly His Asn Tyr Thr Phe Thr
            2085                2090                2095

Val Gln Ala Arg Cys Leu Phe Gly Asn Gln Ile Cys Gly Glu Pro Ala
            2100                2105                2110

Ile Leu Leu Tyr Asp Glu Leu Gly Ser Gly Ala Asp Ala Ser Ala Thr
```

```
                2115                2120                2125
Gln Ala Ala Arg Ser Thr Asp Val Ala Ala Val Val Pro Ile Leu
    2130                2135                2140

Phe Leu Ile Leu Leu Ser Leu Gly Val Gly Phe Ala Ile Leu Tyr Thr
2145                2150                2155                2160

Lys His Arg Arg Leu Gln Ser Ser Phe Thr Ala Phe Ala Asn Ser His
            2165                2170                2175

Tyr Ser Ser Arg Leu Gly Ser Ala Ile Phe Ser Ser Gly Asp Asp Leu
            2180                2185                2190

Gly Glu Asp Asp Glu Asp Ala Pro Met Ile Thr Gly Phe Ser Asp Asp
            2195                2200                2205

Val Pro Met Val Ile Ala
    2210

<210> SEQ ID NO 95
<211> LENGTH: 5980
<212> TYPE: DNA
<213> ORGANISM: Homo sapiens

<400> SEQUENCE: 95
gccatgctgt catgagaaag tggcttcttc tcaatgaccc ggaagatacc agttcaggtt      60
ctaaaggtta tatgaaagtc agcatgtttg tcctgggaac cggagatgag cctcctcctg     120
agagacgaga tcgtgataat gacagtgatg atgtggagag taatttgtta ctccctgctg     180
gcattgccct gggaaccgga gatgagcctc ctcctgagag acgagatcgt gataatgaca     240
gtgatgatgt ggagagtaat tgttactcc ctgctggcat tgccctccgg tgggtgacct      300
tcttgctgaa atctaccga gctgaggaca tcccccagat ggatgatgcc ttctcacaga      360
cagtaaagga atatttgga ggcaatgcag ataagaaaaa tctcgtggat cctttttgtag    420 aagtttcctt tgctggaaaa aaggtttgta caaacataat tgagaaaaat gcaaacccag     480
agtggaatca ggtcgtcaat cttcagatca gtttccttc agtgtgtgaa aaaataaaac      540
taacaatata tgactgggac cgtcttacta aaaatgatgt agttggaaca acatatctac     600
acctctctaa aattgctgcc tctggtgggg aagtggaaga tttctcatct tcgggaactg     660 ggctgcatc atatacagta aacacaggag aaacagaggt aggctttgtt ccaacgtttg      720
gaccttgtta cctgaatctt tatggaagcc ccagagagta cacgggattc ccagaccct      780 atgatgagct gaatactgga aagggggaag gagttgccta cagaggcagg atcttggttg     840
aattagccac ttttcttgag aagacaccac cagataaaaa gcttgagccc atttcaaatg     900
atgacctgct ggttgttgag aaataccagc gaaggcggaa gtacagcctg tctgccgtgt     960
ttcattcagc caccatgttg caagatgttg gtgaggccat tcagtttgaa gtcagcattg    1020
ggaactatgg caacaagttt gacaccacct gtaagccttt ggcatcaaca actcagtaca    1080
gccgtgctgt atttgatggc aactactatt attacttgcc ttgggcccac accaagccag    1140
ttgttaccct gacttcatac tgggaggata ttagtcatcg cctggatgcg tgaacactc     1200 tcctagctat ggcagaacgg ctgcaaacaa atatagaagc tctaaaatca gggatacaag    1260
gtaaaattcc tgcaaaccag ctggctgaat tgtggctgaa gctgatagat gaagttatag    1320
aagacacgag atacacgttg cctctcacag aaggaaaagc caacgtcaca gttctcgata    1380
ctcagatccg aaagctgcgg tccaggtctc tctcccaaat acatgaggcg ctgtgagga     1440 tgaggtcgga agccacagat gtgaagtcca cactggcaga aattgaggac tggcttgata    1500
aattaatgca gctgactgaa gagccacaga acagcatgcc tgacatcatc atctggatga    1560
```

```
tccggggaga gaagagactg gcctatgcac gaattcccgc acatcaggtc ttgtactcca   1620
ccagtggtga gaatgcatct ggaaaatact gtgggaaaac ccaaaccatc tttctgaagt   1680
atccacagga gaaaacaac gggccaaagg tgcctgtgga gttgcgagtg aacatctggc    1740
taggcttaag tgctgtggag aagaagttta acagcttcgc agaaggaact ttcaccgtct   1800
ttgctgaaat gtatgaaaat caagctctca tgtttggaaa atggggtact tctggattag   1860
taggacgtca taagttttct gatgtcacag gaaaaataaa actcaagagg gaattttttc   1920
tgcctccaaa aggctgggaa tgggaaggag agtggatagt tgatcctgaa agaagcttgc   1980
tgactgaggc agatgcaggt cacacggagt tcactgatga agtctatcag aacgagagcc   2040
gctaccccgg gggcgactgg aagccggccg aggacaccta cacggatgcg aacggcgata   2100
aagcagcatc acccagcgag ttgacttgtc ctccaggttg ggaatgggaa gatgatgcat   2160
ggtcttatga cataaatcga gcggtggatg agaaggctg gaatatgga atcaccattc     2220
ctcctgatca taagcccaaa tcctgggttg cagcagagaa aatgtaccac actcatagac   2280
ggcgaaggct ggtccgaaaa cgcaagaaag atttaacaca gactgcttca agcaccgcaa   2340
gggccatgga ggaattgcaa gaccaagagg gctgggaata tgcttctcta attggctgga   2400
aatttcactg gaaacaacgt agttcagata ccttccgccg cagacgctgg aggagaaaaa   2460
tggctccttc agaaacacat ggtgcagctg ccatctttaa acttgaaggt gcccttgggg   2520
cagacactac cgaagatggg gatgagaaga gcctggagaa acagaagcac agtgccacca   2580
ctgtgttcgg agcaaacacc cccattgttt cctgcaattt tgacagagtc tacatctacc   2640
atctgcgctg ctatgtctat caagccagaa acctcttggc tttagataag gatagctttt   2700
cagatccata tgctcatatc tgtttcctcc atcggagcaa aaccactgag atcatccatt   2760
caaccctgaa tcccacgtgg gaccaaacaa ttatattcga tgaagttgaa atctatgggg   2820
aaccccaaac agttctacag aatccaccca aagttatcat ggaactttt gacaatgacc    2880
aagtgggcaa agatgaattt ttaggacgaa gcatttctc tcctgtggtg aaactgaact    2940
cagaaatgga catcacaccc aaacttctct ggcacccagt aatgaatgga acaaagcct    3000
gcggggatgt tcttgtaact gcagagctga ttctgagggg caaggatggc tccaaccttc   3060
ccattcttcc ccctcaaagg gcgccaaatc tatacatggt ccccaggggg atcaggcctg   3120
tggtccagct cactgccatt gagattctag cttgggggctt aagaaatatg aaaaacttcc   3180
agatggcttc tatcacatcc cccagtcttg ttgtggagtg tggaggagaa agggtggaat   3240
cggtggtgat caaaaacctt aagaagacac ccaactttcc aagttctgtt ctcttcatga   3300
aagtgttctt gcccaaggag gaattgtaca tgcccccact ggtgatcaag gtcatcgacc   3360
acaggcagtt tgggcggaag cctgtcgtcg gccagtgcac catcgagcgc ctggaccgct   3420
ttcgctgtga cccttatgca gggaaagagg acatcgtccc acagctcaaa gcctccttc    3480
tgtctgcccc accatgccgg gacatcgtta tcgaaatgga agacaccaaa ccattactgg   3540
cttctaagct gacagaaaag gaggaagaaa tcgtggactg gtggagtaaa ttttatgctt   3600
cctcagggga acatgaaaaa tgcggacagt atattcagaa aggctattcc aagctcaaga   3660
tatataattg cgaactagaa aatgtagcag aatttgaggg cctgacagac ttctcagata   3720
cgttcaagtt gtaccgaggc aagtcggatg aaaaatgaaga tccttctgtg gttggagagt   3780
ttaagggctc ctttcggatc taccctctgc cggatgaccc cagcgtgcca gcccctccca   3840
gacagtttcg ggaattacct gacagcgtcc cacaggaatg cacggttagg atttacattg   3900
ttcgaggctt agagctccag ccccaggaca acaatggcct gtgtgaccct tacataaaaa   3960
```

```
taacactggg caaaaaagtc attgaagacc gagatcacta cattcccaac actctcaacc    4020
cagtctttgg caggatgtac gaactgagct gctacttacc tcaagaaaaa gacctgaaaa    4080
tttctgtcta tgattatgac acctttaccc gggatgaaaa agtaggagaa acaattattg    4140
atctggaaaa ccgattcctt tcccgctttg ggtcccactg cggcatacca gaggagtact    4200
gtgtttctgg agtcaatacc tggcgagatc aactgagacc aacacagctg cttcaaaatg    4260
tcgccagatt caaaggcttc ccacaaccca tcctttccga agatgggagt agaatcagat    4320
atggaggacg agactacagc ttggatgaat ttgaagccaa caaaatcctg caccagcacc    4380
tcggggcccc tgaagagcgg cttgctcttc acatcctcag gactcagggg ctggtccctg    4440
agcacgtgga acaaggact ttgcacagca ccttccagcc caacatttcc cagggaaaac    4500
ttcagatgtg ggtggatgtt ttccccaaga gtttggggcc accaggccct cctttcaaca    4560
tcacaccccg gaaagccaag aaatactacc tgcgtgtgat catctggaac accaaggacg    4620
ttatcttgga cgagaaaagc atcacaggag aggaaatgag tgacatctac gtcaaaggct    4680
ggattcctgg caatgaagaa acaaacaga aaacagatgt ccattacaga tctttggatg    4740
gtgaagggaa ttttaactgg cgatttgttt tcccgtttga ctaccttcca gccgaacaac    4800
tctgtatcgt tgcgaaaaaa gagcatttct ggagtattga ccaaacggaa tttcgaatcc    4860
cacccaggct gatcattcag atatgggaca atgacaagtt ttctctggat gactacttgg    4920
gtttcctaga acttgacttg cgtcacacga tcattcctgc aaaatcacca gagaaatgca    4980
ggttggacat gattccggac ctcaaagcca tgaaccccct taaagccaag acagcctccc    5040
tctttgagca gaagtccatg aaaggatggt ggccatgcta cgcagagaaa gatggcgccc    5100
gcgtaatggc tgggaaagtg gagatgacat tggaaatcct caacgagaag gaggccgacg    5160
agaggccagc cgggaagggg cgggacgaac ccaacatgaa ccccaagctg gacttaccaa    5220
atcgaccaga aacctccttc ctctggttca ccaacccatg caagaccatg aagttcatcg    5280
tgtggcgccg ctttaagtgg gtcatcatcg gcttgctgtt cctgcttatc ctgctgctct    5340
tcgtggccgt gctcctctac tctttgccga actatttgtc aatgaagatt gtaaagccaa    5400
atgtgtaaca aaggcaaagg cttcatttca agagtcatcc agcaatgaga gaatcctgcc    5460
tctgtagacc aacatccagt gtgattttgt gtctgagacc acccccagt agcaggttac    5520
gccatgtcac cgagccccat tgattcccag aggktcttag tcctgggaaa gtcaggccaa    5580
caagcaacgt ttgcatcatg ttatctctta agtattaaaa gttttatttt ctaaagttta    5640
aatcatggtt tttymaaata tttttcaagg tggctggttc catttaaaaa tcatcttttt    5700
atatgtgtct tcggttctag acttcagctt ttggaaattg ctaaatagaa ttcaaaaatc    5760
tctgcatcct gaggtgatat acttcatatt tgtaatcaac tgaaagagct gtgcattata    5820
aaatcagtta gaatagttag acaattctt atttatgccc acaaccattg ctatattttg    5880
tatggatgtc ataaagtct atttaacctc tgtaatgaaa ctaaataaaa atgtttcacc    5940
tttaaagaca aaaaaaaaa gattgagagg acggccgatc                          5980
```

```
<210> SEQ ID NO 96
<211> LENGTH: 1798
<212> TYPE: PRT
<213> ORGANISM: Homo sapiens

<400> SEQUENCE: 96

Met Arg Lys Trp Leu Leu Leu Asn Asp Pro Glu Asp Thr Ser Ser Gly
1               5                   10                  15

Ser Lys Gly Tyr Met Lys Val Ser Met Phe Val Leu Gly Thr Gly Asp
```

```
                    20                  25                  30
Glu Pro Pro Pro Glu Arg Arg Asp Arg Asp Asn Asp Ser Asp Val
                 35                  40                  45

Glu Ser Asn Leu Leu Leu Pro Ala Gly Ile Ala Leu Gly Thr Gly Asp
 50                  55                  60

Glu Pro Pro Pro Glu Arg Arg Asp Arg Asp Asn Asp Ser Asp Val
 65                  70                  75                  80

Glu Ser Asn Leu Leu Leu Pro Ala Gly Ile Ala Leu Arg Trp Val Thr
                 85                  90                  95

Phe Leu Leu Lys Ile Tyr Arg Ala Glu Asp Ile Pro Gln Met Asp Asp
                100                 105                 110

Ala Phe Ser Gln Thr Val Lys Glu Ile Phe Gly Gly Asn Ala Asp Lys
                115                 120                 125

Lys Asn Leu Val Asp Pro Phe Val Glu Val Ser Phe Ala Gly Lys Lys
                130                 135                 140

Val Cys Thr Asn Ile Ile Glu Lys Asn Ala Asn Pro Glu Trp Asn Gln
145                 150                 155                 160

Val Val Asn Leu Gln Ile Lys Phe Pro Ser Val Cys Glu Lys Ile Lys
                165                 170                 175

Leu Thr Ile Tyr Asp Trp Asp Arg Leu Thr Lys Asn Asp Val Val Gly
                180                 185                 190

Thr Thr Tyr Leu His Leu Ser Lys Ile Ala Ala Ser Gly Gly Glu Val
                195                 200                 205

Glu Asp Phe Ser Ser Ser Gly Thr Gly Ala Ala Ser Tyr Thr Val Asn
                210                 215                 220

Thr Gly Glu Thr Glu Val Gly Phe Val Pro Thr Phe Gly Pro Cys Tyr
225                 230                 235                 240

Leu Asn Leu Tyr Gly Ser Pro Arg Glu Tyr Thr Gly Phe Pro Asp Pro
                245                 250                 255

Tyr Asp Glu Leu Asn Thr Gly Lys Gly Glu Gly Val Ala Tyr Arg Gly
                260                 265                 270

Arg Ile Leu Val Glu Leu Ala Thr Phe Leu Glu Lys Thr Pro Pro Asp
                275                 280                 285

Lys Lys Leu Glu Pro Ile Ser Asn Asp Asp Leu Leu Val Val Glu Lys
                290                 295                 300

Tyr Gln Arg Arg Lys Tyr Ser Leu Ser Ala Val Phe His Ser Ala
305                 310                 315                 320

Thr Met Leu Gln Asp Val Gly Glu Ala Ile Gln Phe Glu Val Ser Ile
                325                 330                 335

Gly Asn Tyr Gly Asn Lys Phe Asp Thr Thr Cys Lys Pro Leu Ala Ser
                340                 345                 350

Thr Thr Gln Tyr Ser Arg Ala Val Phe Asp Gly Asn Tyr Tyr Tyr Tyr
                355                 360                 365

Leu Pro Trp Ala His Thr Lys Pro Val Val Thr Leu Thr Ser Tyr Trp
                370                 375                 380

Glu Asp Ile Ser His Arg Leu Asp Ala Val Asn Thr Leu Leu Ala Met
385                 390                 395                 400

Ala Glu Arg Leu Gln Thr Asn Ile Glu Ala Leu Lys Ser Gly Ile Gln
                405                 410                 415

Gly Lys Ile Pro Ala Asn Gln Leu Ala Glu Leu Trp Leu Lys Leu Ile
                420                 425                 430

Asp Glu Val Ile Glu Asp Thr Arg Tyr Thr Leu Pro Leu Thr Glu Gly
                435                 440                 445
```

```
Lys Ala Asn Val Thr Val Leu Asp Thr Gln Ile Arg Lys Leu Arg Ser
    450                 455                 460

Arg Ser Leu Ser Gln Ile His Glu Ala Ala Val Arg Met Arg Ser Glu
465                 470                 475                 480

Ala Thr Asp Val Lys Ser Thr Leu Ala Glu Ile Glu Asp Trp Leu Asp
                485                 490                 495

Lys Leu Met Gln Leu Thr Glu Glu Pro Gln Asn Ser Met Pro Asp Ile
            500                 505                 510

Ile Ile Trp Met Ile Arg Gly Glu Lys Arg Leu Ala Tyr Ala Arg Ile
        515                 520                 525

Pro Ala His Gln Val Leu Tyr Ser Thr Ser Gly Glu Asn Ala Ser Gly
    530                 535                 540

Lys Tyr Cys Gly Lys Thr Gln Thr Ile Phe Leu Lys Tyr Pro Gln Glu
545                 550                 555                 560

Lys Asn Asn Gly Pro Lys Val Pro Val Glu Leu Arg Val Asn Ile Trp
                565                 570                 575

Leu Gly Leu Ser Ala Val Glu Lys Lys Phe Asn Ser Phe Ala Glu Gly
            580                 585                 590

Thr Phe Thr Val Phe Ala Glu Met Tyr Glu Asn Gln Ala Leu Met Phe
        595                 600                 605

Gly Lys Trp Gly Thr Ser Gly Leu Val Gly Arg His Lys Phe Ser Asp
    610                 615                 620

Val Thr Gly Lys Ile Lys Leu Lys Arg Glu Phe Phe Leu Pro Pro Lys
625                 630                 635                 640

Gly Trp Glu Trp Glu Gly Glu Trp Ile Val Asp Pro Glu Arg Ser Leu
                645                 650                 655

Leu Thr Glu Ala Asp Ala Gly His Thr Glu Phe Thr Asp Glu Val Tyr
            660                 665                 670

Gln Asn Glu Ser Arg Tyr Pro Gly Gly Asp Trp Lys Pro Ala Glu Asp
        675                 680                 685

Thr Tyr Thr Asp Ala Asn Gly Asp Lys Ala Ala Ser Pro Ser Glu Leu
    690                 695                 700

Thr Cys Pro Pro Gly Trp Glu Trp Glu Asp Asp Ala Trp Ser Tyr Asp
705                 710                 715                 720

Ile Asn Arg Ala Val Asp Glu Lys Gly Trp Glu Tyr Gly Ile Thr Ile
                725                 730                 735

Pro Pro Asp His Lys Pro Lys Ser Trp Val Ala Ala Glu Lys Met Tyr
            740                 745                 750

His Thr His Arg Arg Arg Leu Val Arg Lys Arg Lys Asp Leu
        755                 760                 765

Thr Gln Thr Ala Ser Ser Thr Ala Arg Ala Met Glu Glu Leu Gln Asp
    770                 775                 780

Gln Glu Gly Trp Glu Tyr Ala Ser Leu Ile Gly Trp Lys Phe His Trp
785                 790                 795                 800

Lys Gln Arg Ser Ser Asp Thr Phe Arg Arg Arg Trp Arg Arg Lys
                805                 810                 815

Met Ala Pro Ser Glu Thr His Gly Ala Ala Ile Phe Lys Leu Glu
            820                 825                 830

Gly Ala Leu Gly Ala Asp Thr Thr Glu Asp Gly Asp Glu Lys Ser Leu
        835                 840                 845

Glu Lys Gln Lys His Ser Ala Thr Thr Val Phe Gly Ala Asn Thr Pro
    850                 855                 860

Ile Val Ser Cys Asn Phe Asp Arg Val Tyr Ile Tyr His Leu Arg Cys
865                 870                 875                 880
```

```
Tyr Val Tyr Gln Ala Arg Asn Leu Leu Ala Leu Asp Lys Asp Ser Phe
                885                 890                 895
Ser Asp Pro Tyr Ala His Ile Cys Phe Leu His Arg Ser Lys Thr Thr
            900                 905                 910
Glu Ile Ile His Ser Thr Leu Asn Pro Thr Trp Asp Gln Thr Ile Ile
        915                 920                 925
Phe Asp Glu Val Glu Ile Tyr Gly Pro Gln Thr Val Leu Gln Asn
    930                 935                 940
Pro Pro Lys Val Ile Met Glu Leu Phe Asp Asn Asp Gln Val Gly Lys
945                 950                 955                 960
Asp Glu Phe Leu Gly Arg Ser Ile Phe Ser Pro Val Val Lys Leu Asn
                965                 970                 975
Ser Glu Met Asp Ile Thr Pro Lys Leu Leu Trp His Pro Val Met Asn
            980                 985                 990
Gly Asp Lys Ala Cys Gly Asp Val Leu Val Thr Ala Glu Leu Ile Leu
        995                 1000                1005
Arg Gly Lys Asp Gly Ser Asn Leu Pro Ile Leu Pro Pro Gln Arg Ala
    1010                1015                1020
Pro Asn Leu Tyr Met Val Pro Gln Gly Ile Arg Pro Val Val Gln Leu
1025                1030                1035                1040
Thr Ala Ile Glu Ile Leu Ala Trp Gly Leu Arg Asn Met Lys Asn Phe
                1045                1050                1055
Gln Met Ala Ser Ile Thr Ser Pro Ser Leu Val Val Glu Cys Gly Gly
            1060                1065                1070
Glu Arg Val Glu Ser Val Val Ile Lys Asn Leu Lys Lys Thr Pro Asn
        1075                1080                1085
Phe Pro Ser Ser Val Leu Phe Met Lys Val Phe Leu Pro Lys Glu Glu
    1090                1095                1100
Leu Tyr Met Pro Pro Leu Val Ile Lys Val Ile Asp His Arg Gln Phe
1105                1110                1115                1120
Gly Arg Lys Pro Val Val Gly Gln Cys Thr Ile Glu Arg Leu Asp Arg
                1125                1130                1135
Phe Arg Cys Asp Pro Tyr Ala Gly Lys Glu Asp Ile Val Pro Gln Leu
            1140                1145                1150
Lys Ala Ser Leu Leu Ser Ala Pro Pro Cys Arg Asp Ile Val Ile Glu
        1155                1160                1165
Met Glu Asp Thr Lys Pro Leu Leu Ala Ser Lys Leu Thr Glu Lys Glu
    1170                1175                1180
Glu Glu Ile Val Asp Trp Trp Ser Lys Phe Tyr Ala Ser Ser Gly Glu
1185                1190                1195                1200
His Glu Lys Cys Gly Gln Tyr Ile Gln Lys Gly Tyr Ser Lys Leu Lys
                1205                1210                1215
Ile Tyr Asn Cys Glu Leu Glu Asn Val Ala Glu Phe Glu Gly Leu Thr
            1220                1225                1230
Asp Phe Ser Asp Thr Phe Lys Leu Tyr Arg Gly Lys Ser Asp Glu Asn
        1235                1240                1245
Glu Asp Pro Ser Val Val Gly Glu Phe Lys Gly Ser Phe Arg Ile Tyr
    1250                1255                1260
Pro Leu Pro Asp Asp Pro Ser Val Pro Ala Pro Pro Arg Gln Phe Arg
1265                1270                1275                1280
Glu Leu Pro Asp Ser Val Pro Gln Glu Cys Thr Val Arg Ile Tyr Ile
                1285                1290                1295
Val Arg Gly Leu Glu Leu Gln Pro Gln Asp Asn Asn Gly Leu Cys Asp
```

```
                       1300                1305                1310

Pro Tyr Ile Lys Ile Thr Leu Gly Lys Lys Val Ile Glu Asp Arg Asp
            1315                1320                1325

His Tyr Ile Pro Asn Thr Leu Asn Pro Val Phe Gly Arg Met Tyr Glu
            1330                1335                1340

Leu Ser Cys Tyr Leu Pro Gln Glu Lys Asp Leu Lys Ile Ser Val Tyr
1345                1350                1355                1360

Asp Tyr Asp Thr Phe Thr Arg Asp Glu Lys Val Gly Thr Ile Ile
            1365                1370                1375

Asp Leu Glu Asn Arg Phe Leu Ser Arg Phe Gly Ser His Cys Gly Ile
            1380                1385                1390

Pro Glu Glu Tyr Cys Val Ser Gly Val Asn Thr Trp Arg Asp Gln Leu
            1395                1400                1405

Arg Pro Thr Gln Leu Leu Gln Asn Val Ala Arg Phe Lys Gly Phe Pro
            1410                1415                1420

Gln Pro Ile Leu Ser Glu Asp Gly Ser Arg Ile Arg Tyr Gly Gly Arg
1425                1430                1435                1440

Asp Tyr Ser Leu Asp Glu Phe Glu Ala Asn Lys Ile Leu His Gln His
            1445                1450                1455

Leu Gly Ala Pro Glu Glu Arg Leu Ala Leu His Ile Leu Arg Thr Gln
            1460                1465                1470

Gly Leu Val Pro Glu His Val Glu Thr Arg Thr Leu His Ser Thr Phe
            1475                1480                1485

Gln Pro Asn Ile Ser Gln Gly Lys Leu Gln Met Trp Val Asp Val Phe
            1490                1495                1500

Pro Lys Ser Leu Gly Pro Pro Gly Pro Pro Phe Asn Ile Thr Pro Arg
1505                1510                1515                1520

Lys Ala Lys Lys Tyr Tyr Leu Arg Val Ile Ile Trp Asn Thr Lys Asp
            1525                1530                1535

Val Ile Leu Asp Glu Lys Ser Ile Thr Gly Glu Glu Met Ser Asp Ile
            1540                1545                1550

Tyr Val Lys Gly Trp Ile Pro Gly Asn Glu Glu Asn Lys Gln Lys Thr
            1555                1560                1565

Asp Val His Tyr Arg Ser Leu Asp Gly Glu Gly Asn Phe Asn Trp Arg
            1570                1575                1580

Phe Val Phe Pro Phe Asp Tyr Leu Pro Ala Glu Gln Leu Cys Ile Val
1585                1590                1595                1600

Ala Lys Lys Glu His Phe Trp Ser Ile Asp Gln Thr Glu Phe Arg Ile
            1605                1610                1615

Pro Pro Arg Leu Ile Ile Gln Ile Trp Asp Asn Asp Lys Phe Ser Leu
            1620                1625                1630

Asp Asp Tyr Leu Gly Phe Leu Glu Leu Asp Leu Arg His Thr Ile Ile
            1635                1640                1645

Pro Ala Lys Ser Pro Glu Lys Cys Arg Leu Asp Met Ile Pro Asp Leu
            1650                1655                1660

Lys Ala Met Asn Pro Leu Lys Ala Lys Thr Ala Ser Leu Phe Glu Gln
1665                1670                1675                1680

Lys Ser Met Lys Gly Trp Trp Pro Cys Tyr Ala Glu Lys Asp Gly Ala
            1685                1690                1695

Arg Val Met Ala Gly Lys Val Glu Met Thr Leu Glu Ile Leu Asn Glu
            1700                1705                1710

Lys Glu Ala Asp Glu Arg Pro Ala Gly Lys Gly Arg Asp Glu Pro Asn
            1715                1720                1725
```

```
Met Asn Pro Lys Leu Asp Leu Pro Asn Arg Pro Glu Thr Ser Phe Leu
    1730                1735                1740

Trp Phe Thr Asn Pro Cys Lys Thr Met Lys Phe Ile Val Trp Arg Arg
1745                1750                1755                1760

Phe Lys Trp Val Ile Ile Gly Leu Leu Phe Leu Leu Ile Leu Leu Leu
            1765                1770                1775

Phe Val Ala Val Leu Leu Tyr Ser Leu Pro Asn Tyr Leu Ser Met Lys
        1780                1785                1790

Ile Val Lys Pro Asn Val
        1795

<210> SEQ ID NO 97
<211> LENGTH: 3724
<212> TYPE: DNA
<213> ORGANISM: Homo sapiens

<400> SEQUENCE: 97
```

| | | | | | |
|---|---|---|---|---|---|
| gaattccggc | ccggcatccc | gatggccgcc | gctgggcccc | ggcgctccgt | gcgcggagcc | 60 |
| gtctgcctgc | atctgctgct | gaccctcgtg | atcttcagtc | gtgatggtga | agcctgcaaa | 120 |
| aaggtgatac | ttaatgtacc | ttctaaacta | gaggcagaca | aaataattgg | cagagttaat | 180 |
| ttggaagagt | gcttcaggtc | tgcagacctc | atccggtcaa | gtgatcctga | tttcagagtt | 240 |
| ctaaatgatg | ggtcagtgta | cacagccagg | gctgttgcgc | tgtctgataa | gaaaagatca | 300 |
| tttaccatat | ggcttttctga | caaaaggaaa | cagacacaga | aagaggttac | tgtgctgcta | 360 |
| gaacatcaga | agaaggtatc | gaagacaaga | cacactagaa | aaactgttct | caggcgtgcc | 420 |
| aagaggagat | gggcacctat | tccttgctct | atgcaagaga | attccttggg | cccttttcca | 480 |
| ttgtttcttc | aacaagttga | atctgatgca | gcacagaact | atactgtctt | ctactcaata | 540 |
| agtggacgtg | gagttgataa | agaaccttta | aatttgtttt | atatagaaag | agacactgga | 600 |
| aatctatttt | gcactcggcc | tgtggatcgt | gaagaatatg | atgtttttga | tttgattgct | 660 |
| tatgcgtcaa | ctgcagatgg | atattcagca | gatctgcccc | tcccactacc | catcagggta | 720 |
| gaggatgaaa | atgacaacca | ccctgttttc | acagaagcaa | tttataattt | tgaagttttg | 780 |
| gaaagtagta | gacctggtac | tacagtgggg | gtggtttgtg | ccacagacag | agatgaaccg | 840 |
| gacacaatgc | atacgcgcct | gaaatacagc | attttgcagc | agacaccaag | gtcacctggg | 900 |
| ctcttttctg | tgcatcccag | cacaggcgta | atcaccacag | tctctcatta | tttggacaga | 960 |
| gaggttgtag | acaagtactc | attgataatg | aaagtacaag | acatggatgg | ccagtttttt | 1020 |
| ggattgatag | gcacatcaac | ttgtatcata | acagtaacag | attcaaatga | taatgcaccc | 1080 |
| actttcagac | aaaatgctta | tgaagcattt | gtagaggaaa | atgcattcaa | tgtgaaaatc | 1140 |
| ttacgaatac | ctatagaaga | taaggattta | attaacactg | ccaattggag | agtcaatttt | 1200 |
| accattttaa | agggaaatga | aaatggacat | tcaaaaatca | gcacagacaa | agaaactaat | 1260 |
| gaaggtgttc | tttctgttgt | aaagccactg | aattatgaag | aaaaccgtca | agtgaacctg | 1320 |
| gaaattggag | taaacaatga | agcgccattt | gctagagata | ttcccagagt | gacagccttg | 1380 |
| aacagagcct | tggttacagt | tcatgtgagg | gatctggatg | aggggcctga | atgcactcct | 1440 |
| gcagcccaat | atgtgcggat | taaagaaaac | ttagcagtgg | ggtcaaagat | caacggctat | 1500 |
| aaggcatatg | accccgaaaa | tagaaatggc | aatggtttaa | ggtacaaaaa | attgcatgat | 1560 |
| cctaaaggtt | ggatcaccat | tgatgaaatt | tcagggtcaa | tcataacttc | caaaatcctg | 1620 |
| gataggagg | ttgaaactcc | caaaaatgag | ttgtataata | ttacagtcct | ggcaatagac | 1680 |
| aaagatgata | gatcatgtac | tggaacactt | gctgtgaaca | ttgaagatgt | aaatgataat | 1740 |

| | | |
|---|---|---|
| ccaccagaaa tacttcaaga atatgtagtc atttgcaaac caaaaatggg gtataccgac | 1800 | |
| attttagctg ttgatcctga tgaacctgtc catggagctc cattttattt cagtttgccc | 1860 | |
| aatacttctc cagaaatcag tagactgtgg agcctcacca aagttaatga tacagctgcc | 1920 | |
| cgtctttcat atcagaaaaa tgctggattt caagaatata ccattcctat tactgtaaaa | 1980 | |
| gacagggccg gccaagctgc aacaaaatta ttgagagtta atctgtgtga atgtactcat | 2040 | |
| ccaactcagt gtcgtgcgac ttcaaggagt acaggagtaa tacttggaaa atgggcaatc | 2100 | |
| cttgcaatat tactgggtat agcactgctc ttttctgtat tgctaacttt agtatgtgga | 2160 | |
| gtttttggtg caactaaagg gaaacgtttt cctgaagatt tagcacagca aaacttaatt | 2220 | |
| atatcaaaca cagaagcacc tggagacgat agagtgtgct ctgccaatgg atttatgacc | 2280 | |
| caaactacca acaactctag ccaaggtttt tgtggtacta tgggatcagg aatgaaaaat | 2340 | |
| ggagggcagg aaaccattga aatgatgaaa ggaggaaacc agaccttgga atcctgccgg | 2400 | |
| ggggctgggc atcatcatac cctggactcc tgcaggggag acacacggga ggtggacaac | 2460 | |
| tgcagataca cttactcgga gtggcacagt tttactcagc cccgtctcgg tgaaaaattg | 2520 | |
| catcgatgta atcagaatga agaccgcatg ccatcccaag attatgtcct cacttataac | 2580 | |
| tatgagggaa gaggatctcc agctggttct gtgggctgct gcagtgaaaa gcaggaagaa | 2640 | |
| gatggccttg acttttttaaa taatttggaa cccaaattta ttacattagc agaagcatgc | 2700 | |
| agtgctacaa ttaggtcttt gtcagacatt ctggaggttt ccaaaaataa tattgtaaag | 2760 | |
| ttcaatttca acatgtatgt atatgatgat ttttttctca attttgaatt atgctactca | 2820 | |
| ccaattatat ttttaaagca agttgttgct tatctttttcc aaaaagtgaa aaatgttaaa | 2880 | |
| acagacaact ggtaaatctc aaactccagc actggaatta aggtctctaa agcatctgct | 2940 | |
| cttttttttt ttacggatat tttagtaata aatatgctgg ataaatatta gtccaacaat | 3000 | |
| agctaagtta tgctaatatc acattattat gtattcactt aagtgatag tttaaaaaat | 3060 | |
| aaacaagaaa tattgagtat cactatgtga agaaagtttt ggaaagaaa caatgaagac | 3120 | |
| tgaattaaat taaaaatgtt gcagctcata aagaattggg actcacccct actgcactac | 3180 | |
| caaattcatt tgactttgga ggcaaaatgt gttgaagtgc cctatgaagt agcaattttc | 3240 | |
| tataggaata tagttggaaa taatgtgtg tgtgtatatt attattaatc aatgcaatat | 3300 | |
| ttaaaatgaa atgagaacaa agaggaagat ggtaaaaact tgaaatgagg ctggggtata | 3360 | |
| gtttgttcta caatgaaaaa agagagagct ttctaggcct gggctcttaa atgctgcatt | 3420 | |
| ataactgagt ctatgaggaa ataagtcctg ttcaaattgt gtaatttgtt taaaatgtaa | 3480 | |
| ataaataaac ttttctggtt tctgtgggaa ggaaataggg aatccaatgg aacagtagct | 3540 | |
| ttgctttgca gtctgtttca agatttctgc atccacaagt tagtagcaaa ctggggaata | 3600 | |
| ctcgctgcag ctggggttcc ctgcttttg gtagcaaggg tccagagatg agggtgtttt | 3660 | |
| tttcggggag ctaataacaa aaacatttta aaacttacct ttactgaagt taaatcctta | 3720 | |
| ttgc | 3724 | |

<210> SEQ ID NO 98
<211> LENGTH: 896
<212> TYPE: PRT
<213> ORGANISM: Homo sapiens

<400> SEQUENCE: 98

Met Ala Ala Ala Gly Pro Arg Arg Ser Val Arg Gly Ala Val Cys Leu
1               5                   10                  15

-continued

```
His Leu Leu Leu Thr Leu Val Ile Phe Ser Arg Asp Gly Glu Ala Cys
         20                  25                  30

Lys Lys Val Ile Leu Asn Val Pro Ser Lys Leu Glu Ala Asp Lys Ile
         35                  40                  45

Ile Gly Arg Val Asn Leu Glu Glu Cys Phe Arg Ser Ala Asp Leu Ile
 50                  55                  60

Arg Ser Ser Asp Pro Asp Phe Arg Val Leu Asn Asp Gly Ser Val Tyr
 65                  70                  75                  80

Thr Ala Arg Ala Val Ala Leu Ser Asp Lys Lys Arg Ser Phe Thr Ile
                 85                  90                  95

Trp Leu Ser Asp Lys Arg Lys Gln Thr Gln Lys Glu Val Thr Val Leu
                100                 105                 110

Leu Glu His Gln Lys Lys Val Ser Lys Thr Arg His Thr Arg Glu Thr
            115                 120                 125

Val Leu Arg Arg Ala Lys Arg Arg Trp Ala Pro Ile Pro Cys Ser Met
130                 135                 140

Gln Glu Asn Ser Leu Gly Pro Phe Pro Leu Phe Leu Gln Gln Val Glu
145                 150                 155                 160

Ser Asp Ala Ala Gln Asn Tyr Thr Val Phe Tyr Ser Ile Ser Gly Arg
                165                 170                 175

Gly Val Asp Lys Glu Pro Leu Asn Leu Phe Tyr Ile Glu Arg Asp Thr
            180                 185                 190

Gly Asn Leu Phe Cys Thr Arg Pro Val Asp Arg Glu Glu Tyr Asp Val
        195                 200                 205

Phe Asp Leu Ile Ala Tyr Ala Ser Thr Ala Asp Gly Tyr Ser Ala Asp
210                 215                 220

Leu Pro Leu Pro Leu Pro Ile Arg Val Glu Asp Glu Asn Asp Asn His
225                 230                 235                 240

Pro Val Phe Thr Glu Ala Ile Tyr Asn Phe Glu Val Leu Glu Ser Ser
                245                 250                 255

Arg Pro Gly Thr Thr Val Gly Val Val Cys Ala Thr Asp Arg Asp Glu
            260                 265                 270

Pro Asp Thr Met His Thr Arg Leu Lys Tyr Ser Ile Leu Gln Gln Thr
        275                 280                 285

Pro Arg Ser Pro Gly Leu Phe Ser Val His Pro Ser Thr Gly Val Ile
290                 295                 300

Thr Thr Val Ser His Tyr Leu Asp Arg Glu Val Val Asp Lys Tyr Ser
305                 310                 315                 320

Leu Ile Met Lys Val Gln Asp Met Asp Gly Gln Phe Phe Gly Leu Ile
                325                 330                 335

Gly Thr Ser Thr Cys Ile Ile Thr Val Thr Asp Ser Asn Asp Asn Ala
            340                 345                 350

Pro Thr Phe Arg Gln Asn Ala Tyr Glu Ala Phe Val Glu Glu Asn Ala
        355                 360                 365

Phe Asn Val Glu Ile Leu Arg Ile Pro Ile Glu Asp Lys Asp Leu Ile
370                 375                 380

Asn Thr Ala Asn Trp Arg Val Asn Phe Thr Ile Leu Lys Gly Asn Glu
385                 390                 395                 400

Asn Gly His Phe Lys Ile Ser Thr Asp Lys Glu Thr Asn Glu Gly Val
                405                 410                 415

Leu Ser Val Val Lys Pro Leu Asn Tyr Glu Glu Asn Arg Gln Val Asn
            420                 425                 430

Leu Glu Ile Gly Val Asn Asn Glu Ala Pro Phe Ala Arg Asp Ile Pro
        435                 440                 445
```

```
Arg Val Thr Ala Leu Asn Arg Ala Leu Val Thr Val His Val Arg Asp
    450                 455                 460

Leu Asp Glu Gly Pro Glu Cys Thr Pro Ala Ala Gln Tyr Val Arg Ile
465                 470                 475                 480

Lys Glu Asn Leu Ala Val Gly Ser Lys Ile Asn Gly Tyr Lys Ala Tyr
                    485                 490                 495

Asp Pro Glu Asn Arg Asn Gly Asn Gly Leu Arg Tyr Lys Lys Leu His
                500                 505                 510

Asp Pro Lys Gly Trp Ile Thr Ile Asp Glu Ile Ser Gly Ser Ile Ile
                515                 520                 525

Thr Ser Lys Ile Leu Asp Arg Glu Val Glu Thr Pro Lys Asn Glu Leu
            530                 535                 540

Tyr Asn Ile Thr Val Leu Ala Ile Asp Lys Asp Asp Arg Ser Cys Thr
545                 550                 555                 560

Gly Thr Leu Ala Val Asn Ile Glu Asp Val Asn Asp Asn Pro Pro Glu
                    565                 570                 575

Ile Leu Gln Glu Tyr Val Val Ile Cys Lys Pro Lys Met Gly Tyr Thr
                580                 585                 590

Asp Ile Leu Ala Val Asp Pro Asp Glu Pro Val His Gly Ala Pro Phe
                595                 600                 605

Tyr Phe Ser Leu Pro Asn Thr Ser Pro Glu Ile Ser Arg Leu Trp Ser
610                 615                 620

Leu Thr Lys Val Asn Asp Thr Ala Ala Arg Leu Ser Tyr Gln Lys Asn
625                 630                 635                 640

Ala Gly Phe Gln Glu Tyr Thr Ile Pro Ile Thr Val Lys Asp Arg Ala
                    645                 650                 655

Gly Gln Ala Ala Thr Lys Leu Leu Arg Val Asn Leu Cys Glu Cys Thr
                660                 665                 670

His Pro Thr Gln Cys Arg Ala Thr Ser Arg Ser Thr Gly Val Ile Leu
                675                 680                 685

Gly Lys Trp Ala Ile Leu Ala Ile Leu Leu Gly Ile Ala Leu Leu Phe
            690                 695                 700

Ser Val Leu Leu Thr Leu Val Cys Gly Val Phe Gly Ala Thr Lys Gly
705                 710                 715                 720

Lys Arg Phe Pro Glu Asp Leu Ala Gln Gln Asn Leu Ile Ile Ser Asn
                    725                 730                 735

Thr Glu Ala Pro Gly Asp Asp Arg Val Cys Ser Ala Asn Gly Phe Met
                740                 745                 750

Thr Gln Thr Thr Asn Asn Ser Ser Gln Gly Phe Cys Gly Thr Met Gly
                755                 760                 765

Ser Gly Met Lys Asn Gly Gly Gln Glu Thr Ile Glu Met Met Lys Gly
            770                 775                 780

Gly Asn Gln Thr Leu Glu Ser Cys Arg Gly Ala Gly His His His Thr
785                 790                 795                 800

Leu Asp Ser Cys Arg Gly Gly His Thr Glu Val Asp Asn Cys Arg Tyr
                    805                 810                 815

Thr Tyr Ser Glu Trp His Ser Phe Thr Gln Pro Arg Leu Gly Glu Lys
                820                 825                 830

Leu His Arg Cys Asn Gln Asn Glu Asp Arg Met Pro Ser Gln Asp Tyr
                835                 840                 845

Val Leu Thr Tyr Asn Tyr Glu Gly Arg Gly Ser Pro Ala Gly Ser Val
850                 855                 860

Gly Cys Cys Ser Glu Lys Gln Glu Glu Asp Gly Leu Asp Phe Leu Asn
```

|   |   |   |   |   |   |   |   |   |   |   |   |   |   |   |   |
|---|---|---|---|---|---|---|---|---|---|---|---|---|---|---|---|
| | | 865 | | | | 870 | | | | 875 | | | | 880 | |
| Asn | Leu | Glu | Pro | Lys | Phe | Ile | Thr | Leu | Ala | Glu | Ala | Cys | Thr | Lys | Arg |
| | | | | 885 | | | | | 890 | | | | | 895 | |

<210> SEQ ID NO 99
<211> LENGTH: 2391
<212> TYPE: DNA
<213> ORGANISM: Homo sapiens

<400> SEQUENCE: 99

| | | | | | |
|---|---|---|---|---|---|
| gtcgacccac | gcgtccgccg | ctacgaggcc | ctgcgtgggg | agcagccccc | ggaccttgag | 60 |
| acaacagtca | ttctgcctga | gtctgtcttc | agagagacgc | cccccgtggt | caggcccgca | 120 |
| ggccccggag | aggcccagga | gccagaggag | ctggcacggc | gacagcgacg | gcacccggag | 180 |
| ctgagccagg | gtgaggctgt | ggccagcgtc | atcatctacc | gcaccctggc | cgggctactg | 240 |
| cctcataact | atgaccctga | caagcgcagc | ttgagagtcc | ccaaacgccc | gatcatcaac | 300 |
| acacccgtgg | tgagcatcag | cgtccatgat | gatgaggagc | ttctgccccg | ggccctggac | 360 |
| aaacccgtca | cggtgcagtt | ccgcctgctg | gagacagagg | agcggaccaa | gcccatctgt | 420 |
| gtcttctgga | accattcaat | cctggtcagt | ggcacaggtg | gctggtcggc | cagaggctgt | 480 |
| gaagtcgtct | ccgcaatga | gagccacgtc | agctgccagt | gcaaccacat | gacgagcttc | 540 |
| gctgtgctca | tggacgtttc | tcggcgggag | aatggggaga | tcctgccact | gaagacactg | 600 |
| acatacgtgg | ctctaggtgt | caccttggct | gcccttctgc | tcaccttctt | cttcctcact | 660 |
| ctcttgcgta | tcctgcgctc | caaccaacac | ggcatccgac | gtaacctgac | agctgccctg | 720 |
| ggcctggctc | agctggtctt | cctcctggga | atcaaccagg | ctgacctccc | ttttgcctgc | 780 |
| acagtcattg | ccatcctgct | gcacttcctg | tacctctgca | ccttttcctg | ggctctgctg | 840 |
| gaggccttgc | acctgtaccg | ggcactcact | gaggtgcgcg | atgtcaacac | cggccccatg | 900 |
| cgcttctact | acatgctggg | ctggggcgtg | cctgccttca | tcacagggct | agccgtgggc | 960 |
| ctggaccccg | agggctacgg | gaaccctgac | ttctgctggc | tctccatcta | tgacacgctc | 1020 |
| atctggagtt | ttgctggccc | ggtggccttt | gccgtctcga | tgagtgtctt | cctgtacatc | 1080 |
| ctggcggccc | gggcctcctg | tgctgcccag | cggcagggct | ttgagaagaa | aggtcctgtc | 1140 |
| tcgggcctgc | agccctcctt | cgccgtcctc | tgctgctga | cgccacgtg | gctgctggca | 1200 |
| ctgctctctg | tcaacagcga | caccctcctc | ttccactacc | tctttgctac | ctgcaattgc | 1260 |
| atccagggcc | ccttcatctt | cctctcctat | gtggtgctta | gcaaggaggt | ccggaaagca | 1320 |
| ctcaagcttg | cctgcagccg | caagcccagc | cctgaccctg | ctctgaccac | caagtccacc | 1380 |
| ctgacctcgt | cctacaactg | ccccagcccc | tacgcagatg | gcggctgta | ccagccctac | 1440 |
| ggagactcgg | ccggctctct | gcacagcacc | agtcgctcgg | gcaagagtca | gcccagctac | 1500 |
| atccccttct | tgctgaggga | ggagtccgca | ctgaaccctg | gccaagggcc | cctggcctg | 1560 |
| ggggatccag | gcagcctgtt | cctggaaggt | caagaccagc | agcatgatcc | tgacacggac | 1620 |
| tccgacagtg | acctgtcctt | agaagacgac | cagagtggct | cctatgcctc | tacccactca | 1680 |
| tcagacagtg | aggaggaaga | agaggaggag | gaagagaggagg | ccgccttccc | tggagagcag | 1740 |
| ggctgggata | gctgctgggg | gctggagca | gagagactgc | cctgcacag | tactcccaag | 1800 |
| gatggggcc | cagggcctgg | caaggccccc | tggccaggaa | ctttgggac | cacagcaaaa | 1860 |
| gagagtagtg | gcaacgggc | cctgaggag | cggctgcggg | agaatggaga | tgccctgtct | 1920 |
| cgagagggt | ccctaggccc | ccttccaggc | tcttctgccc | agcctcacaa | aggcatcctt | 1980 |
| aagaagaagt | gtctgcccac | catcagcgag | aagagcagcc | tcctgcggct | cccctggag | 2040 |

-continued

```
caatgcacag ggtcttcccg gggctcctcc gctagtgagg gcagccgggg cggccccct      2100 ccccgcccac cgccccggca gagcctccag gagcagctga acggggtcat gcccatcgcc      2160
atgagcatca aggcaggcac ggtggatgag gactcgtcag gctccgacag cgacgaaacg      2220
tccatctgag gagcctgggc cttgccggga ggggtactca ccccacctaa ggccatctag      2280
tgccaactcc cccccacca ttcccctcac tgcactttgg acccctgggg ccaacatctc      2340
caagacaaag tttttcagaa aagaggaaaa aaaaaaaaaa agggcggccg c              2391

<210> SEQ ID NO 100
<211> LENGTH: 565
<212> TYPE: PRT
<213> ORGANISM: Homo sapiens

<400> SEQUENCE: 100

Met Thr Ser Phe Ala Val Leu Met Asp Val Ser Arg Arg Glu Asn Gly
  1               5                  10                  15

Glu Ile Leu Pro Leu Lys Thr Leu Thr Tyr Val Ala Leu Gly Val Thr
             20                  25                  30

Leu Ala Ala Leu Leu Leu Thr Phe Phe Phe Leu Thr Leu Leu Arg Ile
         35                  40                  45

Leu Arg Ser Asn Gln His Gly Ile Arg Arg Asn Leu Thr Ala Ala Leu
 50                  55                  60

Gly Leu Ala Gln Leu Val Phe Leu Leu Ile Asn Gln Ala Asp Leu Pro
 65                  70                  75                  80

Phe Ala Cys Thr Val Ile Ala Ile Leu Leu His Phe Leu Tyr Leu Cys
                 85                  90                  95

Thr Phe Ser Trp Ala Leu Leu Glu Ala Leu His Leu Tyr Arg Ala Leu
            100                 105                 110

Thr Glu Val Arg Asp Val Asn Thr Gly Pro Met Arg Phe Tyr Tyr Met
        115                 120                 125

Leu Gly Trp Gly Val Pro Ala Phe Ile Thr Gly Leu Ala Val Gly Leu
    130                 135                 140

Asp Pro Glu Gly Tyr Gly Asn Pro Asp Phe Cys Trp Leu Ser Ile Tyr
145                 150                 155                 160

Asp Thr Leu Ile Trp Ser Phe Ala Gly Pro Val Ala Phe Ala Val Ser
                165                 170                 175

Met Ser Val Phe Leu Tyr Ile Leu Ala Ala Arg Ala Ser Cys Ala Ala
            180                 185                 190

Gln Arg Gln Gly Phe Glu Lys Lys Gly Pro Val Ser Gly Leu Gln Pro
        195                 200                 205

Ser Phe Ala Val Leu Leu Leu Ser Ala Thr Trp Leu Leu Ala Leu
    210                 215                 220

Leu Ser Val Asn Ser Asp Thr Leu Leu Phe His Tyr Leu Phe Ala Thr
225                 230                 235                 240

Cys Asn Cys Ile Gln Gly Pro Phe Ile Phe Leu Ser Tyr Val Val Leu
                245                 250                 255

Ser Lys Glu Val Arg Lys Ala Leu Lys Leu Ala Cys Ser Arg Lys Pro
            260                 265                 270

Ser Pro Asp Pro Ala Leu Thr Thr Lys Ser Thr Leu Thr Ser Ser Tyr
        275                 280                 285

Asn Cys Pro Ser Pro Tyr Ala Asp Gly Arg Leu Tyr Gln Pro Tyr Gly
    290                 295                 300

Asp Ser Ala Gly Ser Leu His Ser Thr Ser Arg Ser Gly Lys Ser Gln
305                 310                 315                 320
```

```
Pro Ser Tyr Ile Pro Phe Leu Leu Arg Glu Glu Ser Ala Leu Asn Pro
            325                 330                 335

Gly Gln Gly Pro Pro Gly Leu Gly Asp Pro Gly Ser Leu Phe Leu Glu
            340                 345                 350

Gly Gln Asp Gln Gln His Asp Pro Asp Thr Asp Ser Asp Ser Asp Leu
            355                 360                 365

Ser Leu Glu Asp Asp Gln Ser Gly Ser Tyr Ala Ser Thr His Ser Ser
        370                 375                 380

Asp Ser Glu Glu Glu Glu Glu Glu Glu Glu Ala Ala Phe Pro
385                 390                 395                 400

Gly Glu Gln Gly Trp Asp Ser Leu Leu Gly Pro Ala Glu Arg Leu
            405                 410                 415

Pro Leu His Ser Thr Pro Lys Asp Gly Pro Gly Pro Gly Lys Ala
            420                 425                 430

Pro Trp Pro Gly Asp Phe Gly Thr Thr Ala Lys Glu Ser Ser Gly Asn
            435                 440                 445

Gly Ala Pro Glu Glu Arg Leu Arg Glu Asn Gly Asp Ala Leu Ser Arg
        450                 455                 460

Glu Gly Ser Leu Gly Pro Leu Pro Gly Ser Ser Ala Gln Pro His Lys
465                 470                 475                 480

Gly Ile Leu Lys Lys Lys Cys Leu Pro Thr Ile Ser Gly Lys Ser Ser
            485                 490                 495

Leu Leu Arg Leu Pro Leu Glu Gln Cys Thr Gly Ser Ser Arg Gly Ser
            500                 505                 510

Ser Ala Ser Glu Gly Ser Arg Gly Gly Pro Pro Arg Pro Pro Pro
            515                 520                 525

Arg Gln Ser Leu Gln Glu Gln Leu Asn Gly Val Met Pro Ile Ala Met
            530                 535                 540

Ser Ile Lys Ala Gly Thr Val Asp Glu Asp Ser Ser Gly Ser Asp Ser
545                 550                 555                 560

Asp Glu Thr Ser Ile
            565

<210> SEQ ID NO 101
<211> LENGTH: 3748
<212> TYPE: DNA
<213> ORGANISM: Homo sapiens

<400> SEQUENCE: 101
gggaacccag gcatgaatga ccatgcccct cacattctgt accctacctc aaccaactcg      60
tcagcagcct tcgagatggt gcctcgaact gccctgctg gctacctggt caccaaagtc     120
atagctatgg actcagactc tgggcaaaat gcttggcttt ttaccatct agcccagact     180 tctgacctgg acctctttaa ggtagagctg cacacaggag aaattaggac taccaggaag     240
atgggagatg agagtggtag cactttcaac ctgaccgtgg tggtccgaga taatggagag     300
ccatcactat cagcctctgt ggccattaca gtagctgtgg tggatagggt ttccaaaatc     360
ctccctgaca ctcagaggca tgttaagagc cctcggacat actctgaaat tacccttat     420 ctaataatag cattaagcac agtgtctttt atatttcttt tgacaatcat cattttgagc     480
atcatcaagt gctaccgcta cactgcgtat ggcactgcat gctgtggagg cttctgtgga     540
gtaagggaaa ggtcccctgc agaactgtac aaacaagcca acaacaatat tgatgccagg     600
ataccgcatg gcctcaaagt gcagcctcac ttcattgaag ttcgagggaa tggctccctc     660
accaagacct actgctacaa ggcctgtctg acagcaggct cagggagtga cacttcatg     720
```

```
ttttacaata cagggcccca gacaggacca gggccttcgg gagcccaagc agcagtgact    780
gacagcagga atctcacagg ccaaagtggt cagaatgctg ggaacctgat tattctcaaa    840
aatgaggctg tttctcaaaa tgagccacga cagcccaacc ctgactggcg ttactctgcc    900
tccctgagag caggcatgca cagctctgtg cacctagagg aggctggcat tctacgggct    960
ggtccaggag ggcctgatca gcagtggcca acagtatcca gtgcaacacc agaaccagag   1020
gcaggagaag tgtcccctcc agtcggtgcg ggtgtcaaca gcaacagctg gacctttaaa   1080
tacggaccag gcaaccccaa acaatccggt cccggtgagt tgcccgacaa attcattatc   1140
ccaggatctc ctgcaatcat ctccatccgg caggagccta ctaacagcca aattgacaaa   1200
agtgacttca taaccttcgg caaaaaggag gagaccaaga aaagaagaa aaagaagaag    1260
ggtaacaaga cccaggagaa aaaagagaaa gggaacagca cgactgacaa cagtgaccag   1320
tgaggtcctc aaatggaaac aagccactta gccagttttt gtaataatgg caaatctctc   1380
ccatgtagca attccctgct cctttttcct atctacatga gccctcttag agacctcaga   1440
aatctgcaga aagttccctg tgtctgtcta gaacgcattt aacaggtttt gtcgtaaaag   1500
ctttactaag tctggtgtta actctttctc tccactctgg cttgttttca gaacctaaaa   1560
agcagaccca gtttcctttt ctcctccgcc gcaaaggaga ggcttcccag ccccgccagt   1620
gagaggttgg actctctgcc ctgtgctccg ggatcctgt cttgatgaca cttgcagggc    1680
aggctgaaaa gttttgagat tgagcagctt gggagtttgt ggccactggg tatgtgtggc   1740
taccgcgggt atgcgagtgc cagatattgg ctgagacgag ccagcttaga ctaattggta   1800
caaggaaggc aagaaaacaa agacaaataa acagcggaag ttatcagtat ggaggggaag   1860
tgtaaactta aagggaccag actttctaaa tcttacaact caagaggtgg cagccaccct   1920
ctaggagaca aaactacccc cactgacaag gctttaggag accctaaagt ctgatggctg   1980
tgacgtcatt atacctaaaa tctgcatcat acctgcaagc caacagttca gtgttttaac   2040
agagaaccac cctgggaaac agaagcagat ctgatgtgtt tcctatacat gtcctgtgct   2100
cactttatta aaaattcttt tgcacacaat gtttatgaaa aggccagatc cttttccaat   2160
acttatgcaa aagcaaaaga aaaccccgac acctcacctt tcgctgtttg ttgtttcata   2220
gatttattta aaaaaagaga aagtctatag ctataaatct ttaaagagaa atatgaatac   2280
aattccccta aactctcctc aaaagagaat tcagtctaca gccatttaaa tgatcattgc   2340
tgctacagaa gtgctttaag agaattgcct gaaacatctg tattatatcg gccacctgcc   2400
aatcacagct ttactctttc aggtcactct ggggctgcct cttgcatgta ttactaaata   2460
aaatgatctc tctttctctc tctctctctc ttttctaaga acaattatg tgcactttga    2520
tacacaacct tctctaacca actatatatc aagcccaaa aattgaagaa aaatattgtt    2580
ttctcataca gtgagcagat ttttcaatct actaattctg tgacttgtct tggtgtgcta   2640
gcctacacct tctctttggt ttagttttcc ttttctataa cactctgaat tgctaatctt   2700
actaacacct atgatgttac ctgaaatcaa tctcccatat gtatgctgta tgctatgcta   2760
agactcctga aatatactta ctctgtgctt gtgtatgtga atgttaatgc aactattacc   2820
tagagtgaac tttaagcttt attgttgaat gtaattccat tatatttcct tttgtacacc   2880
tgtgaaaaag tggagtagtg tttttttaac cattgttaat cagcttttgt gtatgaaaga   2940
cacagtaaaa tttctttctt aaatcaagat actggtgatt caaggaattt tatttatggt   3000
ccagccaaga gccatctcgt gccaagactt ctgctggcaa gggaatggat aaagctgttt   3060
tgttctagta acaatttgg aatgaatact gacaatattc catgagggtg tgcaagcaca    3120
```

```
aattttacca atctgacctc tttgaagttg cagaatgctt tgaaattcta atggtatctg    3180
aaatatcagc tcatagaaag taacaaaatt tgctgtcacc ttaaataaga catttttaatt   3240 ttgttataat gtacaattta gaagtttgat taattatatt atctatttag cattaatat    3300 aaaagaggta ggagtctgtt atttaaaaaa agcattaaat ttaaaaaaaa actgtcttgt   3360
ctacttttag cttcattctc ccatattttg aagggtgtgt aacttcagct ctgcaggatt   3420
gccatggggt aaaacttgtt acccaacaca tgtgaaccat tgcctacatt gtaggttgtg   3480
atcattttgc cccactgaag cccatgtatc tgaccttacg tgccttttga actaggagaa   3540
tcgggctaat ttattaatga tgataattat aatgtatctg tacagcactt tttacatttg   3600
cgaagtgctt tccaatccat gttagttact agttattaca gctgtaagga taaaacacgt   3660
catgtggatt cattttgaat tggtgctatt ggtatttcct ctgttattgc taataaatga   3720
aaatggtggt atgaaaaaaa aaaaaaaa                                      3748

<210> SEQ ID NO 102
<211> LENGTH: 436
<212> TYPE: PRT
<213> ORGANISM: Homo sapiens

<400> SEQUENCE: 102

Met Asn Asp His Ala Pro His Ile Leu Tyr Pro Thr Ser Thr Asn Ser
  1               5                  10                  15

Ser Ala Ala Phe Glu Met Val Pro Arg Thr Ala Pro Ala Gly Tyr Leu
             20                  25                  30

Val Thr Lys Val Ile Ala Met Asp Ser Asp Ser Gly Gln Asn Ala Trp
         35                  40                  45

Leu Phe Tyr His Leu Ala Gln Thr Ser Asp Leu Asp Leu Phe Lys Val
     50                  55                  60

Glu Leu His Thr Gly Glu Ile Arg Thr Arg Lys Met Gly Asp Glu
 65                  70                  75                  80

Ser Gly Ser Thr Phe Asn Leu Thr Val Val Arg Asp Asn Gly Glu
                 85                  90                  95

Pro Ser Leu Ser Ala Ser Val Ala Ile Thr Val Ala Val Val Asp Arg
            100                 105                 110

Val Ser Lys Ile Leu Pro Asp Thr Gln Arg His Val Lys Ser Pro Arg
        115                 120                 125

Thr Tyr Ser Glu Ile Thr Leu Tyr Leu Ile Ile Ala Leu Ser Thr Val
    130                 135                 140

Ser Phe Ile Phe Leu Leu Thr Ile Ile Ile Leu Ser Ile Ile Lys Cys
145                 150                 155                 160

Tyr Arg Tyr Thr Ala Tyr Gly Thr Ala Cys Cys Gly Gly Phe Cys Gly
                165                 170                 175

Val Arg Glu Arg Ser Pro Ala Glu Leu Tyr Lys Gln Ala Asn Asn Asn
            180                 185                 190

Ile Asp Ala Arg Ile Pro His Gly Leu Lys Val Gln Pro His Phe Ile
        195                 200                 205

Glu Val Arg Gly Asn Gly Ser Leu Thr Lys Thr Tyr Cys Tyr Lys Ala
    210                 215                 220

Cys Leu Thr Ala Gly Ser Gly Ser Asp Thr Phe Met Phe Tyr Asn Thr
225                 230                 235                 240

Gly Ala Gln Thr Gly Pro Gly Pro Ser Gly Ala Gln Ala Ala Val Thr
                245                 250                 255

Asp Ser Arg Asn Leu Thr Gly Gln Ser Gly Gln Asn Ala Gly Asn Leu
```

```
                     260                 265                 270
Ile Ile Leu Lys Asn Glu Ala Val Ser Gln Asn Glu Pro Arg Gln Pro
            275                 280                 285

Asn Pro Asp Trp Arg Tyr Ser Ala Ser Leu Arg Ala Gly Met His Ser
        290                 295                 300

Ser Val His Leu Glu Glu Ala Gly Ile Leu Arg Ala Gly Pro Gly Gly
305                 310                 315                 320

Pro Asp Gln Gln Trp Pro Thr Val Ser Ser Ala Thr Pro Glu Pro Glu
                325                 330                 335

Ala Gly Glu Val Ser Pro Pro Val Gly Ala Gly Val Asn Ser Asn Ser
            340                 345                 350

Trp Thr Phe Lys Tyr Gly Pro Gly Asn Pro Lys Gln Ser Gly Pro Gly
        355                 360                 365

Glu Leu Pro Asp Lys Phe Ile Ile Pro Gly Ser Pro Ala Ile Ile Ser
        370                 375                 380

Ile Arg Gln Glu Pro Thr Asn Ser Gln Ile Asp Lys Ser Asp Phe Ile
385                 390                 395                 400

Thr Phe Gly Lys Lys Glu Glu Thr Lys Lys Lys Lys Lys Lys Lys Lys
                405                 410                 415

Gly Asn Lys Thr Gln Glu Lys Lys Glu Lys Gly Asn Ser Thr Thr Asp
            420                 425                 430

Asn Ser Asp Gln
        435

<210> SEQ ID NO 103
<211> LENGTH: 2429
<212> TYPE: DNA
<213> ORGANISM: Homo sapiens

<400> SEQUENCE: 103
gtcgacccac gcgtccgcgg acgcgtgggc ggctgagcgc tggcggtcgg tgcggcgtca      60
ggtgcgcccg ccaggtgagc gcgctccctg gcaccgttgg cccccggagg gtcgggccca     120
gttgcggcga gcggattggt ttatcttgga agctaaaggg cattgctcat cctgaagatc     180
agctgaccat tgacaatcag ccatgtcatc caggcctctt gaaagtccac ctccttacag     240
gcctgatgaa ttcaaaccga atcattatgc accaagcaat gacatatatg gtggagagat     300
gcatgttcga ccaatgctct ctcagccagc ctactctttt tacccagaag atgaaattct     360
tcacttctac aaatggacct ctcctccagg agtgattcgg atcctgtcta tgctcattat     420
tgtgatgtgc attgccatct ttgcctgtgt ggcctccacg cttgcctggg acagaggcta     480
tggaacttcc cttttaggag gtagtgtagg ctacccttat ggaggaagtg gctttggtag     540
ctacggaagt ggctatggct atggctatgg ttatggctat ggctacggag ctatacaga     600 cccaagagca gcaaagggct tcatgttggc catggctgcc ttttgtttca ttgccgcgtt     660
ggtgatcttt gttaccagtg ttataagatc tgaaatgtcc agaacaagaa gatactactt     720
aagtgtgata atagtgagtg ctatcctggg catcatggtg tttattgcca caattgtcta     780
tataatggga gtgaacccaa ctgctcagtc ttctggatct ctatatggtt cacaaatata     840
tgccctctgc aaccaatttt atacacctgc agctactgga ctctacgtgg atcagtattt     900
gtatcactac tgtgttgtgg atccccagga ggccattgcc attgtactgg ggttcatgat     960
tattgtggct tttgctttaa taatttttctt gctgtgaaa actcgaagaa agatggacag    1020
gtatgacaag tccaatattt tgtgggacaa ggaacacatt tatgatgagc agccccccaa    1080
tgtcgaggag tgggttaaaa atgtgtctgc aggcacacag gacgtgcctt caccccatc     1140
```

```
tgactatgtg gaaagagttg acagtcccat ggcatactct tccaatggca aagtgaatga    1200
caagcggttt tatccagagt cttcctataa atccacgccg gttcctgaag tggttcagga    1260
gcttccatta acttcgcctg tggatgactt caggcagcct cgttacagca gcggtggtaa    1320
ctttgagaca ccttcaaaaa gagcacctgc aaagggaaga gcaggaaggt caaagagaac    1380
agagcaagat cactatgaga cagactacac aactggcggc gagtcctgtg atgagctgga    1440
ggaggactgg atcagggaat atccacctat cacttcagat caacaaagac aactgtacaa    1500
gaggaatttt gacactggcc tacaggaata caagagctta caatcagaac ttgatgagat    1560
caataaagaa ctctcccgtt tggataaaga attggatgac tatagagaag aaagtgaaga    1620
gtacatggct gctgctgatg aatacaatag actgaagcaa gtgaagggat ctgcagatta    1680
caaaagtaag aagaatcatt gcaagcagtt aaagagcaaa ttgtcacaca tcaagaagat    1740
ggttggagac tatgatagac agaaaacata aaggctgat gccaagttgt ttgagaaatt    1800
aagtatctga catctctgca atcttctcag aaggcaaatg actttggacc ataaccccgg    1860
aagccaaacc tctgtgagca tcacaaagtt ttggttgctt taacatcatc agtattgaag    1920
cattttataa atcgcttttg ataatcaact gggctgaaca ctccaattaa ggattttatg    1980
ctttaaacat tggttcttgt attaagaatg aaatactgtt tgaggttttt aagccttaaa    2040
ggaaggttct ggtgtgaact aaactttcac accccagacg atgtcttcat acctacatgt    2100
atttgtttgc ataggtgatc tcatttaatc ctctcaacca cctttcagat aactgttatt    2160
tataatcact ttttttccaca taaggaaact gggttcctgc aatgaagtct ctgaagtgaa    2220
actgcttgtt tcctagcaca cacttttggt taagtctgtt ttatgacttc attaataata    2280
aattccctgg cctttcatat tttagctact atatatgtga tgatctacca gcctccctat    2340 ttttttttctg ttatataaat ggttaaaaga ggtttttctt aaataataaa gatcatgtaa    2400
aagtaaaaaa aaaaaaaaag ggcggccgc                                       2429
```

<210> SEQ ID NO 104
<211> LENGTH: 522
<212> TYPE: PRT
<213> ORGANISM: Homo sapiens

<400> SEQUENCE: 104

```
Met Ser Ser Arg Pro Leu Glu Ser Pro Pro Tyr Arg Pro Asp Glu
 1               5                  10                  15

Phe Lys Pro Asn His Tyr Ala Pro Ser Asn Asp Ile Tyr Gly Gly Glu
            20                  25                  30

Met His Val Arg Pro Met Leu Ser Gln Pro Ala Tyr Ser Phe Tyr Pro
        35                  40                  45

Glu Asp Glu Ile Leu His Phe Tyr Lys Trp Thr Ser Pro Pro Gly Val
    50                  55                  60

Ile Arg Ile Leu Ser Met Leu Ile Val Met Cys Ile Ala Ile Phe
65                  70                  75                  80

Ala Cys Val Ala Ser Thr Leu Ala Trp Asp Arg Gly Tyr Gly Thr Ser
                85                  90                  95

Leu Leu Gly Gly Ser Val Gly Tyr Pro Tyr Gly Gly Ser Gly Phe Gly
            100                 105                 110

Ser Tyr Gly Ser Gly Tyr Gly Tyr Gly Tyr Gly Tyr Gly Tyr
        115                 120                 125

Gly Gly Tyr Thr Asp Pro Arg Ala Ala Lys Gly Phe Met Leu Ala Met
    130                 135                 140
```

```
Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
            165                 170                 175

Ile Val Ser Ala Ile Leu Gly Ile Met Val Phe Ile Ala Thr Ile Val
        180                 185                 190

Tyr Ile Met Gly Val Asn Pro Thr Ala Gln Ser Ser Gly Ser Leu Tyr
    195                 200                 205

Gly Ser Gln Ile Tyr Ala Leu Cys Asn Gln Phe Tyr Thr Pro Ala Ala
210                 215                 220

Thr Gly Leu Tyr Val Asp Gln Tyr Leu Tyr His Tyr Cys Val Val Asp
225                 230                 235                 240

Pro Gln Glu Ala Ile Ala Ile Val Leu Gly Phe Met Ile Ile Val Ala
                245                 250                 255

Phe Ala Leu Ile Ile Phe Phe Ala Val Lys Thr Arg Arg Lys Met Asp
            260                 265                 270

Arg Tyr Asp Lys Ser Asn Ile Leu Trp Asp Lys Glu His Ile Tyr Asp
                275                 280                 285

Glu Gln Pro Pro Asn Val Glu Glu Trp Val Lys Asn Val Ser Ala Gly
290                 295                 300

Thr Gln Asp Val Pro Ser Pro Ser Asp Tyr Val Glu Arg Val Asp
305                 310                 315                 320

Ser Pro Met Ala Tyr Ser Ser Asn Gly Lys Val Asn Asp Lys Arg Phe
                325                 330                 335

Tyr Pro Glu Ser Ser Tyr Lys Ser Thr Pro Val Pro Glu Val Val Gln
            340                 345                 350

Glu Leu Pro Leu Thr Ser Pro Val Asp Asp Phe Arg Gln Pro Arg Tyr
                355                 360                 365

Ser Ser Gly Gly Asn Phe Glu Thr Pro Ser Lys Arg Ala Pro Ala Lys
370                 375                 380

Gly Arg Ala Gly Arg Ser Lys Arg Thr Glu Gln Asp His Tyr Glu Thr
385                 390                 395                 400

Asp Tyr Thr Thr Gly Gly Glu Ser Cys Asp Glu Leu Glu Glu Asp Trp
                405                 410                 415

Ile Arg Glu Tyr Pro Pro Ile Thr Ser Asp Gln Gln Arg Gln Leu Tyr
            420                 425                 430

Lys Arg Asn Phe Asp Thr Gly Leu Gln Glu Tyr Lys Ser Leu Gln Ser
                435                 440                 445

Glu Leu Asp Glu Ile Asn Lys Glu Leu Ser Arg Leu Asp Lys Glu Leu
450                 455                 460

Asp Asp Tyr Arg Glu Glu Ser Glu Glu Tyr Met Ala Ala Ala Asp Glu
465                 470                 475                 480

Tyr Asn Arg Leu Lys Gln Val Lys Gly Ser Ala Asp Tyr Lys Ser Lys
                485                 490                 495

Lys Asn His Cys Lys Gln Leu Lys Ser Lys Leu Ser His Ile Lys Lys
                500                 505                 510

Met Val Gly Asp Tyr Asp Arg Gln Lys Thr
                515                 520

<210> SEQ ID NO 105
<211> LENGTH: 2985
<212> TYPE: DNA
<213> ORGANISM: Homo sapiens
<220> FEATURE:
<221> NAME/KEY: misc_feature
<222> LOCATION: 15
```

<223> OTHER INFORMATION: n = A,T,C or G

<400> SEQUENCE: 105

```
cccgcgtccg gattnttttg ataagtacgg gacgttattg atggtagaga atattttat      60
agactgttgg agttggaagt cttcttgctt ggcattaagg aagagactga taaaggtaat    120
gggtgtgaac cactcttaaa gatgtaggca atgaaaaaat agcctggaga gagaacaagg    180
ccaagtgaag tttgtcattc cccacctccc cccaccctcc atcttccaaa ccaaggagaa    240
ggagccagtg gagaacaaag gagcttaagg aacattcgag taaagttcct caagattcag    300
tagtagatct taaaaatgaa atgtattagg atatattaca tatggactgt ttctataata    360
tactcttcct ttctcctctc agctttgaca tctttatata atagcatgat attttactta    420
catatatctt taaaaaatca ttctatagga gtgtccctag ttgtaacaga aactgtcgat    480
gcaggtttat ttggagaagg attggggaga gttttgattc atgcatggga gcatttactt    540
ttacagccaa agaccaaagg tgaaagtgct aattgtgaaa agtatgggaa agttatacca    600
gcaagtgctg ttatatttgg gatggcagta gaatgtgcag agataagaag acatcataga    660
gtgggtatta aggacattgc tggtatccat ttgccaacaa atgtgaaatt tcagagtccg    720
gcttattctt ctgtagatac tgaagaaaca attgaacctt atacaactga aaagatgagt    780
cgagttcctg gaggatattt ggctttgaca gagtgctttg aaattatgac agtagatttc    840
aacaaccttc aggaattaaa aagtcttgca actaaaaagc ctgataagat tggtattcct    900
gttattaaag aaggcatact agatgctatt atggtttggt ttgtgctcca gcttgatgat    960
gaacatagtt tatccacaag tcctagtgag gaaacatgtt gggaacaggc tgtctacccc   1020
gtacaggacc ttgcagacta ctggataaag cctggagacc atgtgatgat ggaagtatct   1080
tgtcaagact gttacttaag aatccagagt attagtgtct gggtttgga atgtgaaatg   1140
gatgttgcaa aaagttttac ccagaataaa gacttgttat cgttaggaaa tgaggctgaa   1200
ctttgtagtg ccctcgctaa ccttcagacc agtaaaccag atgctgtaga gcagacatgt   1260
atattggaat ctacagaaat tgctttgctt aacaacatcc catatcatga aggctttaaa   1320
atggcaatga gcaaagtttt gtcttcactg actccagaga aactgtatca gaccatggat   1380
actcactgtc agaatgagat gagctctgga actggacaga gtaatactgt acagaacatc   1440
cttgaacctt tctacgtgtt agatgtgtcc gaaggcttct ctgttctgcc tgttattgct   1500
ggcacacttg ggcaggttaa accatacagt tctgtggaga agaccagca tcgtattgct   1560
ctggacctca tatctgaagc caatcacttt cctaaagaaa cacttgagtt ttggctgaga   1620
catgtggagg atgaatctgc tatgttacaa aggccaaaat cagacaagtt atggagcata   1680
attatattgg atgtcattga gccatctggg ctcattcagc aggaaataat ggaaaaagct   1740
gcaatatcca ggtgtttact acaatctgga ggcaagatct ttcctcagta tgtgctgatg   1800
tttgggttgc ttgtggaatc acagacactc ctagaggaga atgctgttca aggaacagaa   1860
gtactcttgg attaaatata gcaccttta ttaaccagtt tcaggtacct atacgtgtat   1920
ttttggacct atcctcattg ccctgtatac ctttaagcaa gccagtggaa ctcttaagac   1980
tagatttaat gactccgtat ttgaacacct ctaacagaga agtaaaggta tacgtttgta   2040
aatctggaag actgactgct attccatttt ggtatcatat gtaccttgat gaagagatta   2100
ggttggatac ttcaagtgaa gcctcccact ggaaacaagc tgcagttgtt ttagataatc   2160
ccatccaggt tgaaatggga gaggaacttg tactcagcat tcagcatcac aaaagcaatg   2220
tcagcatcac agtaaagcaa tgaagagcag ttttccaatg aaaactgtgt aaatagagca   2280
```

```
tcaacaagta caaaattctt gtcttaatta gtggggtat ataaaaattc cttgtaatgg   2340
tcaaatattt tttaaaattg acattaataa agcatatttt aaaagattct aaaaaaaaaa   2400
aaaamgsayk mkkrkmgamw ymctgctgca gatttgcttt ctggaaaagg atacatcact   2460
agttttttaa attaggaaac ttcttttgct cgattttaca gaatagggat tttaaaagtc   2520
ttatcgttat tgacatgtgt aagtaaagca aaacttact tttgtaggca tcttggcctt   2580
ttttcttaaa tccaaacttg taattgggaa acactgaaag gcttccactg aagactgagg   2640
gttatggtta cctgtaaatt ccaatcttgc ttcctttaaa tactcagtgt acatctgaaa   2700
catctcaggt tttgttttga gaatgcaagc ttgaaaaaga atttaagcta taagctaaat   2760
gtaattaaaa cagtaaagga gttagggaat aaatcttcag gaggcagcat ttttcttggt   2820
ctactttggc aaaagaacat ttaaaagctg gtaacaaaac aaagttaaat tgaaggaaga   2880
cttaatccta tactattttt caaagttttg atttggatgt acaataagta cattaattga   2940
tccattttta caaaccttt gaataaggag atcataatat gcctc              2985
```

<210> SEQ ID NO 106
<211> LENGTH: 519
<212> TYPE: PRT
<213> ORGANISM: Homo sapiens

<400> SEQUENCE: 106

```
Met Lys Cys Ile Arg Ile Tyr Tyr Ile Trp Thr Val Ser Ile Ile Tyr
  1               5                  10                  15

Ser Ser Phe Leu Leu Ser Ala Leu Thr Ser Leu Tyr Asn Ser Met Ile
                 20                  25                  30

Phe Tyr Leu His Ile Ser Leu Lys Asn His Ser Ile Gly Val Ser Leu
             35                  40                  45

Val Val Thr Glu Thr Val Asp Ala Gly Leu Phe Gly Glu Gly Leu Gly
         50                  55                  60

Arg Val Leu Ile His Ala Trp Glu His Leu Leu Gln Pro Lys Thr
 65                  70                  75                  80

Lys Gly Glu Ser Ala Asn Cys Glu Lys Tyr Gly Lys Val Ile Pro Ala
                 85                  90                  95

Ser Ala Val Ile Phe Gly Met Ala Val Glu Cys Ala Glu Ile Arg Arg
                100                 105                 110

His His Arg Val Gly Ile Lys Asp Ile Ala Gly Ile His Leu Pro Thr
            115                 120                 125

Asn Val Lys Phe Gln Ser Pro Ala Tyr Ser Ser Val Asp Thr Glu Glu
        130                 135                 140

Thr Ile Glu Pro Tyr Thr Thr Glu Lys Met Ser Arg Val Pro Gly Gly
145                 150                 155                 160

Tyr Leu Ala Leu Thr Glu Cys Phe Glu Ile Met Thr Val Asp Phe Asn
                165                 170                 175

Asn Leu Gln Glu Leu Lys Ser Leu Ala Thr Lys Lys Pro Asp Lys Ile
            180                 185                 190

Gly Ile Pro Val Ile Lys Glu Gly Ile Leu Asp Ala Ile Met Val Trp
        195                 200                 205

Phe Val Leu Gln Leu Asp Asp Glu His Ser Leu Ser Thr Ser Pro Ser
    210                 215                 220

Glu Glu Thr Cys Trp Glu Gln Ala Val Tyr Pro Val Gln Asp Leu Ala
225                 230                 235                 240

Asp Tyr Trp Ile Lys Pro Gly Asp His Val Met Met Glu Val Ser Cys
                245                 250                 255
```

```
Gln Asp Cys Tyr Leu Arg Ile Gln Ser Ile Ser Val Leu Gly Leu Glu
            260                 265                 270

Cys Glu Met Asp Val Ala Lys Ser Phe Thr Gln Asn Lys Asp Leu Leu
        275                 280                 285

Ser Leu Gly Asn Glu Ala Glu Leu Cys Ser Ala Leu Ala Asn Leu Gln
    290                 295                 300

Thr Ser Lys Pro Asp Ala Val Glu Gln Thr Cys Ile Leu Glu Ser Thr
305                 310                 315                 320

Glu Ile Ala Leu Leu Asn Asn Ile Pro Tyr His Gly Phe Lys Met
                325                 330                 335

Ala Met Ser Lys Val Leu Ser Ser Leu Thr Pro Glu Lys Leu Tyr Gln
            340                 345                 350

Thr Met Asp Thr His Cys Gln Asn Glu Met Ser Ser Gly Thr Gly Gln
        355                 360                 365

Ser Asn Thr Val Gln Asn Ile Leu Glu Pro Phe Tyr Val Leu Asp Val
    370                 375                 380

Ser Glu Gly Phe Ser Val Leu Pro Val Ile Ala Gly Thr Leu Gly Gln
385                 390                 395                 400

Val Lys Pro Tyr Ser Ser Val Glu Lys Asp Gln His Arg Ile Ala Leu
                405                 410                 415

Asp Leu Ile Ser Glu Ala Asn His Phe Pro Lys Glu Thr Leu Glu Phe
            420                 425                 430

Trp Leu Arg His Val Glu Asp Glu Ser Ala Met Leu Gln Arg Pro Lys
        435                 440                 445

Ser Asp Lys Leu Trp Ser Ile Ile Leu Asp Val Ile Glu Pro Ser
    450                 455                 460

Gly Leu Ile Gln Gln Glu Ile Met Glu Lys Ala Ala Ile Ser Arg Cys
465                 470                 475                 480

Leu Leu Gln Ser Gly Gly Lys Ile Phe Pro Gln Tyr Val Leu Met Phe
                485                 490                 495

Gly Leu Leu Val Glu Ser Gln Thr Leu Leu Glu Glu Asn Ala Val Gln
            500                 505                 510

Gly Thr Glu Val Leu Leu Asp
        515

<210> SEQ ID NO 107
<211> LENGTH: 2467
<212> TYPE: DNA
<213> ORGANISM: Homo sapiens
<220> FEATURE:
<221> NAME/KEY: misc_feature
<222> LOCATION: 2453, 2454, 2455, 2456, 2457, 2458, 2459, 2460, 2461,
      2462, 2463, 2464, 2465, 2466, 2467
<223> OTHER INFORMATION: n = A,T,C or G

<400> SEQUENCE: 107
cgaccacgcg tccgcccgca gcggccgagc tgcagcccgg gctcagtctc cgccgccgcc      60
gtgaacatgg agccccggga cgcaccggcc caggcgcgcg ggccccgcg gctgctgttg     120 ctcgcagtcc tgctggcggc gcacccagat gcccaggcgg aggtgcgctt gtctgtaccc     180
ccgctggtgg aggtgatgcg aggaaagtct gtcattctgg actgcacccc tacgggaacc     240
cacgaccatt atatgctgga atggttcctt accgaccgct cgggagctcg ccccgccta     300 gcctcggctg agatgcaggg ctctgagctc caggtcacaa tgcacgacac ccggggccgc     360
agtcccccat accagctgga ctcccagggg gcctggtgc tggctgaggc ccaggtgggc     420
gacgagcgag actacgtgtg cgtggtgagg gcaggggcgg caggcactgc tgaggccact     480
```

```
gcgcggctca acgtgtttgc aaagccagag gccactgagg tctcccccaa caaagggaca    540
ctgtctgtga tggaggactc tgcccaggag atcgccacct gcaacagccg aacgggaac     600
ccggcccca  agatcacgtg gtatcgcaac gggcagcgcc tggaggtgcc cgtagagatg    660
aacccagagg gctacatgac cagccgcacg gtccgggagg cctcgggcct gctctccctc    720
accagcaccc tctacctgcg gctccgcaag gatgaccgag acgccagctt ccactgcgcc    780
gcccactaca gctgcccga  gggccgccac ggccgcctgg acagcccac  cttccacctc    840
accctgcact atcccacgga gcacgtgcag ttctgggtgg gcagcccgtc caccccagca    900
ggctgggtac gcgagggtga cactgtccag ctgctctgcc gggggacgg  cagccccagc    960
ccggagtata cgcttttccg ccttcaggat gagcaggagg aagtgctgaa tgtgaatctc   1020
gagggaact  tgaccctgga gggagtgacc cgggccaga  gcgggaccta tggctgcaga   1080
gtggaggatt acgacgcggc agatgacgtg cagctctcca agacgctgga gctgcgcgtg   1140
gcctatctgg acccctgga  gctcagcgag gggaaggtgc tttccttacc tctaaacagc   1200
agtgcagtcg tgaactgctc cgtgcacggc ctgcccaccc ctgccctacg ctggaccaag   1260
gactccactc ccctgggcga tggccccatg ctgtcgctca gttctatcac cttcgattcc   1320
aatggcacct acgtatgtga ggcctccctg cccacagtcc cggtcctcag ccgcacccag   1380
aacttcacgc tgctggtcca aggctcgcca gagctaaaga cagcggaaat agagcccaag   1440
gcagatggca gctggaggga aggagacgaa gtcacactca tctgctctgc ccgcggccat   1500
ccagacccca aactcagctg gagccaattg ggggcagcc  ccgcagagcc aatccccgga   1560
cggcagggtt gggtgagcag ctctctgacc ctgaaagtga ccagcgccct gagccgcgat   1620
ggcatctcct gtgaagcctc caacccccac gggaacaagc gccatgtctt ccacttcggc   1680
gccgtgagcc cccagacctc ccaggctgga gtggccgtca tggccgtggc cgtcagcgtg   1740
ggcctcctgc tcctcgtcgt tgctgtcttc tactgcgtga cacgcaaagg gggcccctgc   1800
tgccgccagc ggcgggagaa gggggctccg ccgccagggg agccagggct gagccactcg   1860
gggtcggagc aaccagagca gaccggcctt ctcatgggag gtgcctccgg aggagccagg   1920
ggtggcagcg ggggcttcgg agacgagtgc tgagccaaga acctcctaga ggctgtccct   1980
ggacctggag ctgcaggcat cagagaacca gccctgctca cgccatgccc gcccccgcct   2040
tccctcttcc ctcttccctc tccctgccca gccctccctt ccttcctctg ccggcaaggc   2100
agggacccac agtggctgcc tgcctccggg agggaaggag agggagggtg ggtgggtggg   2160
aggggcctt  cctccaggga atgtgactct cccaggcccc agaatagctc ctggacccaa   2220
gcccaaggcc cagcctggga caaggctccg agggtcggct ggccggagct attttttacct  2280
cccgcctccc ctgctggtcc ccccacctga cgtcttgctg cagagtctga cactggattc   2340
ccccccctca ccccgcccct ggtcccactc ctgccccgc  cctacctccg ccccaccca    2400
tcatctgtgg acactggagt ctggaataaa tgctgtttgt cacatcaaca ccnnnnnnnn   2460
nnnnnn                                                              2467
```

<210> SEQ ID NO 108
<211> LENGTH: 628
<212> TYPE: PRT
<213> ORGANISM: Homo sapiens

<400> SEQUENCE: 108

Met Glu Pro Pro Asp Ala Pro Ala Gln Ala Arg Gly Ala Pro Arg Leu
 1               5                  10                  15

Leu Leu Leu Ala Val Leu Leu Ala Ala His Pro Asp Ala Gln Ala Glu

-continued

```
                 20                  25                  30
Val Arg Leu Ser Val Pro Pro Leu Val Glu Val Met Arg Gly Lys Ser
             35                  40                  45
Val Ile Leu Asp Cys Thr Pro Thr Gly Thr His Asp His Tyr Met Leu
             50                  55                  60
Glu Trp Phe Leu Thr Asp Arg Ser Gly Ala Arg Pro Arg Leu Ala Ser
65                  70                  75                  80
Ala Glu Met Gln Gly Ser Glu Leu Gln Val Thr Met His Asp Thr Arg
                 85                  90                  95
Gly Arg Ser Pro Pro Tyr Gln Leu Asp Ser Gln Gly Arg Leu Val Leu
                100                 105                 110
Ala Glu Ala Gln Val Gly Asp Glu Arg Asp Tyr Val Cys Val Val Arg
                115                 120                 125
Ala Gly Ala Ala Gly Thr Ala Glu Ala Thr Ala Arg Leu Asn Val Phe
                130                 135                 140
Ala Lys Pro Glu Ala Thr Glu Val Ser Pro Asn Lys Gly Thr Leu Ser
145                 150                 155                 160
Val Met Glu Asp Ser Ala Gln Glu Ile Ala Thr Cys Asn Ser Arg Asn
                165                 170                 175
Gly Asn Pro Ala Pro Lys Ile Thr Trp Tyr Arg Asn Gly Gln Arg Leu
                180                 185                 190
Glu Val Pro Val Glu Met Asn Pro Glu Gly Tyr Met Thr Ser Arg Thr
                195                 200                 205
Val Arg Glu Ala Ser Gly Leu Leu Ser Leu Thr Ser Thr Leu Tyr Leu
                210                 215                 220
Arg Leu Arg Lys Asp Asp Arg Asp Ala Ser Phe His Cys Ala Ala His
225                 230                 235                 240
Tyr Ser Leu Pro Glu Gly Arg His Gly Arg Leu Asp Ser Pro Thr Phe
                245                 250                 255
His Leu Thr Leu His Tyr Pro Thr Glu His Val Gln Phe Trp Val Gly
                260                 265                 270
Ser Pro Ser Thr Pro Ala Gly Trp Val Arg Glu Gly Asp Thr Val Gln
                275                 280                 285
Leu Leu Cys Arg Gly Asp Gly Ser Pro Ser Pro Glu Tyr Thr Leu Phe
                290                 295                 300
Arg Leu Gln Asp Glu Gln Glu Val Leu Asn Val Asn Leu Glu Gly
305                 310                 315                 320
Asn Leu Thr Leu Glu Gly Val Thr Arg Gly Gln Ser Gly Thr Tyr Gly
                325                 330                 335
Cys Arg Val Glu Asp Tyr Asp Ala Ala Asp Asp Val Gln Leu Ser Lys
                340                 345                 350
Thr Leu Glu Leu Arg Val Ala Tyr Leu Asp Pro Leu Glu Leu Ser Glu
                355                 360                 365
Gly Lys Val Leu Ser Leu Pro Leu Asn Ser Ser Ala Val Val Asn Cys
                370                 375                 380
Ser Val His Gly Leu Pro Thr Pro Ala Leu Arg Trp Thr Lys Asp Ser
385                 390                 395                 400
Thr Pro Leu Gly Asp Gly Pro Met Leu Ser Leu Ser Ser Ile Thr Phe
                405                 410                 415
Asp Ser Asn Gly Thr Tyr Val Cys Glu Ala Ser Leu Pro Thr Val Pro
                420                 425                 430
Val Leu Ser Arg Thr Gln Asn Phe Thr Leu Leu Val Gln Gly Ser Pro
                435                 440                 445
```

| | | | | | | | | | | | | | | |
|---|---|---|---|---|---|---|---|---|---|---|---|---|---|---|
|Glu|Leu|Lys|Thr|Ala|Glu|Ile|Glu|Pro|Lys|Ala|Asp|Gly|Ser|Trp|Arg|
| |450| | | | |455| | | |460| | | | |

Glu Gly Asp Glu Val Thr Leu Ile Cys Ser Ala Arg Gly His Pro Asp
465                 470                 475                 480

Pro Lys Leu Ser Trp Ser Gln Leu Gly Gly Ser Pro Ala Glu Pro Ile
            485                 490                 495

Pro Gly Arg Gln Gly Trp Val Ser Ser Ser Leu Thr Leu Lys Val Thr
            500                 505                 510

Ser Ala Leu Ser Arg Asp Gly Ile Ser Cys Glu Ala Ser Asn Pro His
        515                 520                 525

Gly Asn Lys Arg His Val Phe His Phe Gly Ala Val Ser Pro Gln Thr
        530                 535                 540

Ser Gln Ala Gly Val Ala Val Met Ala Val Ala Val Ser Val Gly Leu
545                 550                 555                 560

Leu Leu Leu Val Val Ala Val Phe Tyr Cys Val Arg Arg Lys Gly Gly
                565                 570                 575

Pro Cys Cys Arg Gln Arg Arg Glu Lys Gly Ala Pro Pro Pro Gly Glu
            580                 585                 590

Pro Gly Leu Ser His Ser Gly Ser Glu Gln Pro Glu Gln Thr Gly Leu
            595                 600                 605

Leu Met Gly Gly Ala Ser Gly Gly Ala Arg Gly Gly Ser Gly Gly Phe
610                 615                 620

Gly Asp Glu Cys
625

```
<210> SEQ ID NO 109
<211> LENGTH: 3825
<212> TYPE: DNA
<213> ORGANISM: Homo sapiens

<400> SEQUENCE: 109
```

| | |
|---|---|
|ccaagttcta cctcatgttt ggaggatctt gctagctatg ccctcgtac tcggctccct|60|
|gttgctgctg gggctgtgcg ggaactcctt ttcaggaggg cagccttcat ccacagatgc|120|
|tcctaaggct tggaattatg aattgcctgc aacaaattat gagacccaag actcccataa|180|
|agctggaccc attggcattc tctttgaact agtgcatatc tttctctatg tggtacagcc|240|
|gcgtgatttc ccagaagata ctttgagaaa attcttacag aaggcatatg aatccaaaat|300|
|tgattatgac aagccagaaa ctgtaatctt aggtctaaag attgtctact atgaagcagg|360|
|gattattcta tgctgtgtcc tggggctgct gtttattatt ctgatgcctc tggtgggta|420|
|tttcttttgt atgtgtcgtt gctgtaacaa atgtggtgga gaaatgcacc agcgacagaa|480|
|ggaaaatggg cccttcctga ggaaatgctt tgcaatctcc ctgttggtga tttgtataat|540|
|aataagcatt ggcatcttct atggttttgt ggcaaatcac caggtaagaa cccggatcaa|600|
|aaggagtcgg aaactggcag atagcaattt caaggacttg cgaactctct tgaatgaaac|660|
|tccagagcaa atcaaatata tattggccca gtacaacact accaaggaca aggcgttcac|720|
|agatctgaac agtatcaatt cagtgctagg aggcggaatt cttgaccgac tgagacccaa|780|
|catcatccct gttcttgatg agattaagtc catggcaaca gcgatcaagg agaccaaaga|840|
|ggcgttggag aacatgaaca gcaccttgaa gagcttgcac caacaaagta cacagcttag|900|
|cagcagtctg accagcgtga aaactagcct gcggtcatct ctcaatgacc ctctgtgctt|960|
|ggtgcatcca tcaagtgaaa cctgcaacag catcagattg tctctaagcc agctgaatag|1020|
|caaccctgaa ctgaggcagc ttccacccgt ggatgcagaa cttgacaacg ttaataacgt|1080|

```
tcttaggaca gatttggatg gcctggtcca acagggctat caatccctta atgatatacc    1140
tgacagagta caacgccaaa ccacgactgt cgtagcaggt atcaaaaggg tcttgaattc    1200
cattggttca gatatcgaca atgtaactca gcgtcttcct attcaggata tactctcagc    1260
attctctgtt tatgttaata acactgaaag ttacatccac agaaatttac ctacattgga    1320
agagtatgat tcatactggt ggctgggtgg cctggtcatc tgctctctgc tgaccctcat    1380
cgtgattttt tactacctgg gcttactgtg tggcgtgtgc ggctatgaca ggcatgccac    1440
cccgaccacc cgaggctgtg tctccaacac cggaggcgtc ttcctcatgg ttggagttgg    1500
attaagtttc ctcttttgct ggatattgat gatcattgtg gttcttacct ttgtctttgg    1560
tgcaaatgtg gaaaaactga tctgtgaacc ttacacgagc aaggaattat tccgggtttt    1620
ggatacaccc tacttactaa atgaagactg gaatactat ctctctggga agctatttaa     1680
taaatcaaaa atgaagctca cttttgaaca agtttacagt gactgcaaaa aaaatagagg    1740
cacttacggc actcttcacc tgcagaacag cttcaatatc agtgaacatc tcaacattaa    1800
tgagcatact ggaagcataa gcagtgaatt ggaaagtctg aaggtaaatc ttaatatctt    1860
tctgttgggt gcagcaggaa gaaaaaacct tcaggatttt gctgcttgtg gaatagacag    1920
aatgaattat gacagctact ggctcagac tggtaaatcc ccgcaggag tgaatctttt       1980
atcatttgca tatgatctag aagcaaaagc aaacagtttg ccccaggaa atttgaggaa      2040
ctccctgaaa agagatgcac aaactattaa aacaattcac cagcaacgag tccttcctat    2100
agaacaatca ctgagcactc tataccaaag cgtcaagata cttcaacgca cagggaatgg    2160
attgttggag agagtaacta ggattctagc ttctctggat tttgctcaga acttcatcac    2220
aaacaatact tcctctgtta ttattgagga aactaagaag tatgggagaa caataatagg    2280
atattttgaa cattatctgc agtggatcga gttctctatc agtgagaaag tggcatcgtg    2340
caaacctgtg gccaccgctc tagatactgc tgttgatgtc tttctgtgta gctacattat    2400
cgacccttg aatttgtttt ggtttggcat aggaaaagct actgtatttt tacttccggc     2460
tctaattttt gcggtaaaac tggctaagta ctatcgtcga atggattcgg aggacgtgta    2520
cgatgatgtt gaaactatac ccatgaaaaa tatggaaaat ggtaataatg ttatcataa     2580
agatcatgta tatggtattc acaatcctgt tatgacaagc ccatcacaac attgatagct    2640
gatgttgaaa ctgcttgagc atcaggatac tcaaagtgga aaggatcaca gattttggt    2700
agtttctggg tctacaagga ctttccaaat ccaggagcaa cgccagtggc aacgtagtga    2760
ctcaggcggg caccaaggca acggcaccat tggtctctgg gtagtgcttt aagaatgaac    2820
acaatcacgt tatagtccat ggtccatcac tattcaagga tgactccctc ccttcctgtc    2880
tatttttgtt ttttactttt ttacactgag tttctattta gacactacaa catatggggt    2940
gtttgttccc attggatgca tttctatcaa aactctatca aatgtgatgg ctagattcta    3000
acatattgcc atgtgtggag tgtgctgaac acacaccagt ttacaggaaa gatgcatttt    3060
gtgtacagta aacggtgtat ataccttttg ttaccacaga gttttttaaa caaatgagta    3120
ttataggact ttcttctaaa tgagctaaat aagtcaccat tgacttcttg gtgctgttga    3180
aaataatcca ttttcactaa aagtgtgtga aacctacagc atattcttca cgcagagatt    3240
ttcatctatt atactttatc aaagattggc catgttccac ttggaaatgg catgcaaaag    3300
ccatcataga gaaacctgcg taactccatc tgacaaattc aaaagagaga gagagatctt    3360
gagagagaaa tgctgtycgt tccaaaagtg gagttgtttt taaaccagat gcccaattac    3420
ggtgtaccag tttaaccaga gttttcctgt tgccattagg ataaacatta attggagtgc    3480
```

-continued

```
cagcctaaca tgagtatcca tccagaccta gtatcaagtg ttcctaaaat gaaatatgag    3540
aagatccctg tcacaattcc ttagatctgg tgtcccagca tggatgaaac ctttgagttt    3600
ggtccctaaa tttgcatgaa agcacaaggt aaatattcat ttgcttcagg agtttcatgt    3660
tggatctgtc attatcaaaa gtgatcagca atgaagaact ggtcggacaa aatttaacgt    3720
tgatgtaatg raattccaga tgtaggcatt ccccccaggt cttttcatgt gcagattgca    3780
gttctgattc atttgaataa aaaggaactt ggaaaacaaa aaaaa                    3825

<210> SEQ ID NO 110
<211> LENGTH: 865
<212> TYPE: PRT
<213> ORGANISM: Homo sapiens

<400> SEQUENCE: 110

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320
```

-continued

```
Leu Ser Leu Ser Gln Leu Asn Ser Asn Pro Glu Leu Arg Gln Leu Pro
            325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
            355                 360                 365

Asp Arg Val Gln Arg Gln Thr Thr Thr Val Val Ala Gly Ile Lys Arg
            370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
            405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
            485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Leu Phe Arg Val Leu
            515                 520                 525

Asp Thr Pro Tyr Leu Leu Asn Glu Asp Trp Glu Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
            565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
            610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
            645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
            675                 680                 685

Glu Gln Ser Leu Ser Thr Leu Tyr Gln Ser Val Lys Ile Leu Gln Arg
            690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Thr Ser Ser Val Ile Ile
            725                 730                 735

Glu Glu Thr Lys Lys Tyr Gly Arg Thr Ile Ile Gly Tyr Phe Glu His
            740                 745                 750
```

```
Tyr Leu Gln Trp Ile Glu Phe Ser Ile Ser Glu Lys Val Ala Ser Cys
            755                 760                 765

Lys Pro Val Ala Thr Ala Leu Asp Thr Ala Val Asp Val Phe Leu Cys
        770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

Asp His Val Tyr Gly Ile His Asn Pro Val Met Thr Ser Pro Ser Gln
850                 855                 860

His
865

<210> SEQ ID NO 111
<211> LENGTH: 673
<212> TYPE: DNA
<213> ORGANISM: Homo sapiens

<400> SEQUENCE: 111
ttgaattcgc caaggctggg tttccctcat gtatggcaag agctctactc gtgcggtgct      60
tcttctcctt ggcatacagc tcacagctct tggcctata  gcagctgtgg aaatttatac     120
ctcccgggtg ctggaggctg ttaatgggac agatgctcgg ttaaaatgca ctttctccag     180
ctttgcccct gtgggtgatg ctctaacagt gacctggaat tttcgtcctc tagacggggg     240
acctgagcag tttgtattct actaccacat agatcccttc caacccatga gtgggcggtt     300
taaggaccgg gtgtcttggg atgggaatcc tgagcggtac gatgcctcca tccttctctg     360
gaaactgcag ttcgacgaca atgggacata cacctgccag gtgaagaacc cacctgatgt     420
tgatggggtg ataggggaga tccggctcag cgtcgtgcac actgtacgct tctctgagat     480
ccacttcctg gctctggcca ttggctctgc ctgtgcactg atgatcataa tagtaattgt     540
agtggtcctc ttccagcatt accggaaaaa gcgatgggcc gaaagagctc ataaagtggt     600
ggagataaaa tcaaaagaag aggaaaggct caaccaagag aaaaaggtct ctgtttattt     660
agaagacaca gac                                                        673

<210> SEQ ID NO 112
<211> LENGTH: 215
<212> TYPE: PRT
<213> ORGANISM: Homo sapiens

<400> SEQUENCE: 112

Met Tyr Gly Lys Ser Ser Thr Arg Ala Val Leu Leu Leu Leu Gly Ile
1               5                   10                  15

Gln Leu Thr Ala Leu Trp Pro Ile Ala Ala Val Glu Ile Tyr Thr Ser
            20                  25                  30

Arg Val Leu Glu Ala Val Asn Gly Thr Asp Ala Arg Leu Lys Cys Thr
        35                  40                  45

Phe Ser Ser Phe Ala Pro Val Gly Asp Ala Leu Thr Val Thr Trp Asn
    50                  55                  60

Phe Arg Pro Leu Asp Gly Gly Pro Glu Gln Phe Val Phe Tyr Tyr His
65                  70                  75                  80
```

-continued

```
Ile Asp Pro Phe Gln Pro Met Ser Gly Arg Phe Lys Asp Arg Val Ser
             85              90              95

Trp Asp Gly Asn Pro Glu Arg Tyr Asp Ala Ser Ile Leu Leu Trp Lys
            100             105             110

Leu Gln Phe Asp Asp Asn Gly Thr Tyr Thr Cys Gln Val Lys Asn Pro
        115             120             125

Pro Asp Val Asp Gly Val Ile Gly Glu Ile Arg Leu Ser Val Val His
    130             135             140

Thr Val Arg Phe Ser Glu Ile His Phe Leu Ala Leu Ala Ile Gly Ser
145             150             155             160

Ala Cys Ala Leu Met Ile Ile Ile Val Ile Val Val Val Leu Phe Gln
            165             170             175

His Tyr Arg Lys Lys Arg Trp Ala Glu Arg Ala His Lys Val Val Glu
            180             185             190

Ile Lys Ser Lys Glu Glu Glu Arg Leu Asn Gln Glu Lys Lys Val Ser
        195             200             205

Val Tyr Leu Glu Asp Thr Asp
    210             215
```